United States Patent
Nakagawa et al.

[11] Patent Number: 5,550,121
[45] Date of Patent: Aug. 27, 1996

[54] AMINOALKYLPYRROLIDINYL-THIOCARBAPENEM DERIVATIVES

[75] Inventors: Susumu Nakagawa; Shinji Kato; Satoshi Murase; Osamu Okamoto; Ryuji Mitomo; Katsumi Yamamoto; Koji Yamada; Hiroshi Fukatsu, all of Tsukuba, Japan

[73] Assignee: Banyu Pharmaceutical Co., Ltd., Tokyo, Japan

[21] Appl. No.: 312,619

[22] Filed: Sep. 27, 1994

Related U.S. Application Data

[63] Continuation of Ser. No. 982,585, Nov. 27, 1992, abandoned.

[30] Foreign Application Priority Data

Nov. 27, 1991 [JP] Japan ................. 3-335888
Jul. 21, 1992 [JP] Japan ................. 4-215613

[51] Int. Cl.$^6$ ............... C07D 487/04; A61K 31/40
[52] U.S. Cl. ............................... 514/210; 540/350
[58] Field of Search .................... 514/210; 540/350

[56] References Cited

U.S. PATENT DOCUMENTS

| | | | |
|---|---|---|---|
| 4,740,507 | 4/1988 | Sunagawa et al. | 540/350 |
| 5,093,328 | 3/1992 | Sunagawa et al. | 540/350 |
| 5,449,672 | 9/1995 | Nakagawa et al. | 540/350 |

*Primary Examiner*—Nicholas Rizzo
*Attorney, Agent, or Firm*—Oblon, Spivak, McClelland, Maier & Neustadt, P.C.

[57] ABSTRACT

A compound of the formula:

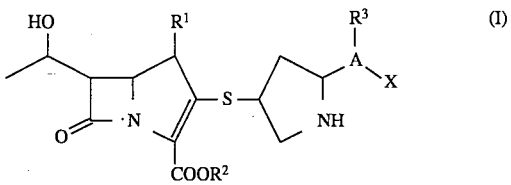

wherein $R^1$ is a hydrogen atom or a methyl group, $R^2$ is a hydrogen atom or a negative charge, $R^3$ is a hydrogen atom, a halogen atom, a hydroxyl group, a lower alkoxy group, a lower alkanoyloxy group, an amino group, an N-lower alkylamino group, an N,N-di-lower alkylamino group, a lower alkanoylamino group, an aroylamino group, a (lower alkylsulfonyl)amino group, a sulfamoylamino group, a cyano group, a nitro group, a group of —COOR$^4$ (wherein $R^4$ is a hydrogen atom or a lower alkyl group) or a group of —CON($R^5$)$R^6$ (wherein each of $R^5$ and $R^6$ which may be the same or different, is a hydrogen atom or a lower alkyl group, or $R^5$ and $R^6$ form together with the adjacent nitrogen atom a heterocyclic group selected from the group consisting of an aziridinyl group, an azetidinyl group, a pyrrolidinyl group, a piperidyl group, a piperazinyl group, a 4-lower alkyl piperazinyl group and a morpholino group), A is a linear or branched lower alkylene group, X is a group of —N($R^7$)$R^8$ (wherein each of $R^7$ and $R^8$ which may be the same or different, is a hydrogen atom or a lower alkyl group) or a group of —N$^+$($R^9$)($R^{10}$)$R^{11}$ (wherein each of $R^9$, $R^{10}$ and $R^{11}$ which may be the same or different, is a lower alkyl group), provided that when A is a linear lower alkylene group, $R^3$ is other than a hydrogen atom; or a pharmaceutically acceptable salt or ester thereof.

21 Claims, 1 Drawing Sheet

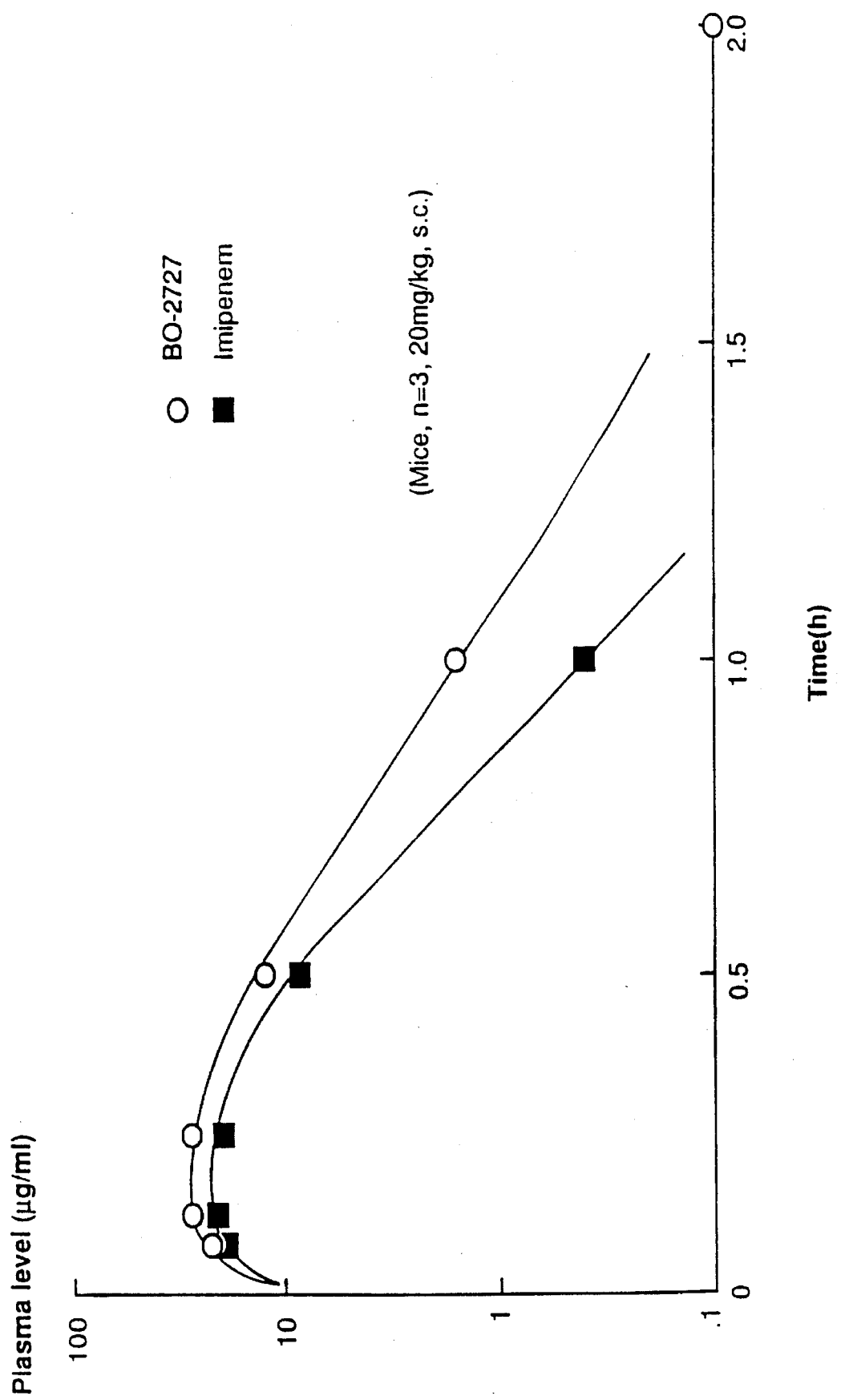

AMINOALKYLPYRROLIDINYL-THIOCARBAPENEM DERIVATIVES

This is a continuation of application Ser. No. 07/982,585, filed on Nov. 27, 1992, now abandoned.

The present invention relates to novel carbapenem (7-oxo-1-azabicyclo[3.2.0]hept-2-en-2-carboxylic acid) compounds, antibacterial agents containing such compounds as active ingredients, and a process for producing such compounds.

In recent years, new β-lactam antibiotic substances have been found in nature which have the same β-lactam rings as penicillin derivatives and as cephalosporin derivatives, but which have different basic structures.

For example, naturally derived carbapenem compounds such as thienamycin isolated from the fermentation of *Streptomyces cattleya* (J. Am. Chem. Soc., vol. 100, p. 6491 (1978)), may be mentioned. Thienamycin has an excellent antibacterial spectrum and strong antibacterial activities over a wide range against gram positive bacteria and gram negative bacteria. Therefore, its development as a highly useful β-lactam agent has been expected. However, thienamycin itself is chemically unstable, and it has been reported that it is likely to be decomposed by a certain enzyme in vivo such as renal dehydropeptidase I (hereinafter referred to simply as DHP-I), whereby the antibacterial activities tend to decrease, and the recovery rate in the urine is low (Antimicrob. Agents Chemother., vol. 22, p.62 (1982); ditto, vol. 23, p.300 (1983)).

Merck & Co., Inc. have synthesized many thienamycin analogues with an aim to maintain the excellent antibacterial activities of thienamycin and to secure chemical stability. As a result, imipenem, (5R,6S,8R)-3 -[[2-(formimidoylamino)ethyl]thio]-6-(1-hydroxyethyl)-7 -oxo-1-azabicyclo[3.2.0]hept-2-en-2-carboxylic acid monohydrate, obtained by formimidation of the amino group of thienamycin, has been practically developed as a pharmaceutical product (J. Med. Chem., vol. 22, p. 1435 (1979)). Imipenem has antibacterial activities of an equal or higher level than thienamycin against various types of bacteria and has β-lactamase resistance. Especially against *Pseudomonas aeruginosa*, its antibacterial activities are superior to thienamycin by from 2 to 4 times. Further, the stability of imipenem in the solid form or in an aqueous solution is remarkably improved over thienamycin.

However, like thienamycin, imipenem is likely to be decomposed by DHP-I in the human kidney. Therefore, it can not be used for treatment of the urinary-tract infection. Further, it presents toxicity against the kidney due to the decomposition products. Therefore, imipenem can not be administered alone and is required to be used in combination with a DHP-I inhibitor like cilastatin (J. Antimicrob. Chemother., vol. 12 (Suppl. D), p. 1 (1983)). In recent years, imipenem has been frequently used for the treatment and prevention of infectious diseases. Consequently, highly methicillin resistant *Staphylococcus aureus* which is resistant to imipenem and imipenem resistant *Pseudomonas aeruginosa* are increasing in the clinical field. Imipenem does not show adequate treating effects against these resistant bacteria.

As the prior art closest to the present invention, European Patent Publication No. 182213 may be mentioned. This publication generally describes in its claims carbapenem compounds including those wherein the side chain at the 2-position of the carbapenem structure is a 2-(substituted) pyrrolidin-4-ylthio group, and the substituent is an amino-$C_{1-6}$ alkyl group which may be protected. These compounds are characterized in that they have a linear $C_{1-6}$ alkylene group. Whereas, the compounds of the present invention are characterized in that they either have a substituent on a linear lower alkylene group or have a branched lower alkylene group. Namely, in the compounds disclosed in the above publication, the side chain at the 2-position of the pyrrolidinyl group is restricted to the one substituted on the pyrrolidinyl group via a linear $C_{1-6}$ alkylene group, and furthermore, the compound having an aminoalkyl group at the 2-position of the pyrrolidinyl group is limited to a compound having an (acetylamino)methyl group the compound of specific example 24 in European Patent Publication No. 182213 (p. 116) (the compound of REFERENCE EXAMPLE 13 in this specification) or the compound of specific example 23 (EXAMPLE 19)]. Therefore, carbapenem compounds wherein, as a feature of the present invention, the lower alkylene group of the side chain at the 2-position of the pyrrolidinyl group substituted at the 2-position of the carbapenem structure has a primary, secondary or tertiary amino group or an ammonio group at its terminal and has a branched structure (a structure having a branched lower alkylene group or a structure in which a linear lower alkylene group has a substituent) are novel compounds not disclosed or suggested in any prior art literatures or patent specifications.

β-Lactam antibiotics exhibit selective toxicity against bacteria and show no substantial effects against animal cells. Therefore, they are widely used for treatment of infectious diseases caused by bacteria, as rare antibiotics having little side effects, and thus are highly useful drugs.

However, in recent years, highly methicillin resistant *Staphylococcus aureus* and resistant *Pseudomonas aeruginosa* have been isolated frequently from patients with the immunity decreased, as bacteria causing hardly curable infectious diseases. This is regarded as a clinically serious problem. Accordingly, it is strongly desired to develop an antibacterial agent having improved antibacterial activities against such resistant bacteria. Especially with respect to carbapenem compounds, it is desired to improve the antibacterial activities, to improve the stability against DHP-I, to reduce the toxicity against the kidney and to reduce side effects against the central nervous system.

The compounds disclosed in the above-mentioned European Patent Publication No. 182213 show good antibacterial activities, but their antibacterial activities particularly against the above-mentioned highly methicillin resistant *Staphylococcus aureus* and resistant *Pseudomonas aeruginosa* are not adequate. Accordingly, a carbapenem compound having superior antibacterial activities, is still desired.

The present inventors have made extensive researches with an aim to provide novel carbapenem compounds which have excellent antibacterial activities and which are resistant against DHP-I. As a result, they have found that carbapenem compounds of the present invention having, at the 2-position of the carbapenem structure, a group of the formula:

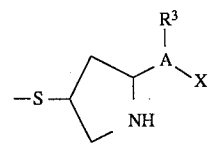

wherein $R^3$ is a hydrogen atom, a halogen atom, a hydroxyl group, a lower alkoxy group, a lower alkanoyloxy group, an amino group, an N-lower alkylamino group, an N,N-di-lower alkylamino group, a lower alkanoylamino group, an aroylamino group, a (lower alkylsulfonyl)amino group, a sulfamoylamino group, a cyano group, a nitro group, a group of —COOR⁴ (wherein R⁴ is a hydrogen atom or a lower alkyl group) or a group of —CON(R⁵)R⁶ (wherein each of R⁵ and R⁶ which may be the same or different, is a hydrogen atom or a lower alkyl group, or R⁵ and R⁶ form together with the adjacent nitrogen atom a heterocyclic group selected from the group consisting of an aziridinyl group, an azetidinyl group, a pyrrolidinyl group, a piperidyl group, a piperazinyl group, a 4-lower alkyl piperazinyl group and a morpholino group), A is a linear or branched lower alkylene group, X is a group of —N(R⁷)R⁸ (wherein each of R⁷ and R⁸ which may be the same or different, is a hydrogen atom or a lower alkyl group) or a group of —N⁺(R⁹)(R¹⁰)R¹¹ (wherein each of R⁹, R¹⁰ and R¹¹ which may be the same or different, is a lower alkyl group), provided that when A is a linear lower alkylene group, R³ is other than a hydrogen atom, are novel compounds not disclosed in any literatures, and that such compounds have strong antibacterial activities against gram positive bacteria such as *Staphylococcus aureus* and against gram negative bacteria including *Pseudomonas aeruginosa* and further exhibit excellent stability against DHP-I. The present invention has been accomplished on the basis of this discovery.

The present invention provides a compound of the formula:

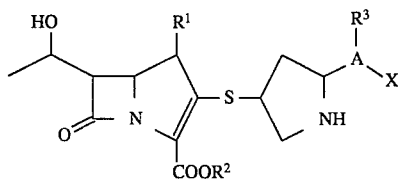

wherein R¹ is a hydrogen atom or a methyl group, R² is a hydrogen atom or a negative charge, R³ is a hydrogen atom, a halogen atom, a hydroxyl group, a lower alkoxy group, a lower alkanoyloxy group, an amino group, an N-lower alkylamino group, an N,N-di-lower alkylamino group, a lower alkanoylamino group, an aroylamino group, a (lower alkylsulfonyl)amino group, a sulfamoylamino group, a cyano group, a nitro group, a group of —COOR⁴ (wherein R⁴ is a hydrogen atom or a lower alkyl group) or a group of —CON(R⁵)R⁶ (wherein each of R⁵ and R⁶ which may be the same or different, is a hydrogen atom or a lower alkyl group, or R⁵ and R⁶ form together with the adjacent nitrogen atom a heterocyclic group selected from the group consisting of an aziridinyl group, an azetidinyl group, a pyrrolidinyl group, a piperidyl group, a piperazinyl group, a 4-lower alkyl piperazinyl group and a morpholino group), A is a linear or branched lower alkylene group, X is a group of —N(R⁷)R⁸ (wherein each of R⁷ and R⁸ which may be the same or different, is a hydrogen atom or a lower alkyl group) or a group of —N⁺(R⁹)(R¹⁰)R¹¹ (wherein each of R⁹, R¹⁰ and R¹¹ which may be the same or different, is a lower alkyl group), provided that when A is a linear lower alkylene group, R³ is other than a hydrogen atom; or a pharmaceutically acceptable salt or ester thereof.

The present invention also provides a process for producing the compound of the formula (I) or a pharmaceutically acceptable salt or ester thereof, which comprises reacting a compound of the formula:

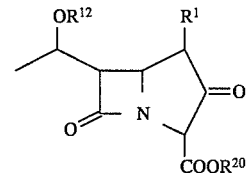

wherein R¹ is as defined above, R¹² is a hydrogen atom or a hydroxyl-protecting group, and R²⁰ is a hydrogen atom or a carboxyl-protecting group, or a reactive derivative thereof, with a compound of the formula:

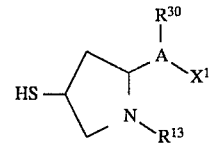

wherein R¹³ is a hydrogen atom or an imino-protecting group, R³⁰ is a hydrogen atom, a halogen atom, a hydroxyl group which may be protected, a lower alkoxy group, a lower alkanoyloxy group, an amino or N-lower alkylamino group which may be protected, an N,N-di-lower alkylamino group, a lower alkanoylamino group, an aroylamino group, a (lower alkylsulfonyl)amino group, a sulfamoylamino group which may be protected, a cyano group, a nitro group, a group of —COOR⁴⁰ (wherein R⁴⁰ is a hydrogen atom, a lower alkyl group or a carboxyl-protecting group) or a group of —CON(R⁵⁰)R⁶⁰ (wherein each of R⁵⁰ and R⁶⁰ which may be the same or different, is a hydrogen atom, a lower alkyl group or an amino- or imino-protecting group, or R⁵⁰ and R⁶⁰ form together with the adjacent nitrogen atom a heterocyclic group selected from the group consisting of an aziridinyl group, an azetidinyl group, a pyrrolidinyl group, a piperidyl group, a piperazinyl group which may be protected, a 4-lower alkyl piperazinyl group and a morpholino group), A is a linear or branched lower alkylene group, X¹ is a group of —N(R⁷⁰)R⁸⁰ (wherein each of R⁷⁰ and R⁸⁰ which may be the same or different, is a hydrogen atom, a lower alkyl group or an amino- or imino-protecting group) or a group of —N⁺(R⁹)(R¹⁰)R¹¹ (wherein each of R⁹, R¹⁰ and R¹¹ which may be the same or different, is a lower alkyl group), provided that when A is a linear lower alkylene group, R³⁰ is other than a hydrogen atom, to obtain a compound of the formula:

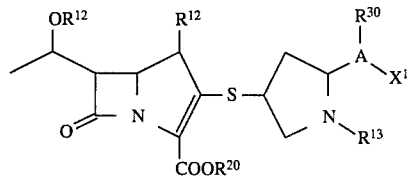

wherein R¹, R¹², R¹³, R²⁰, R³⁰, A and X¹ are as defined above, and if necessary, removing any protecting groups of the compound of the formula (IV).

Further, the present invention provides an antibacterial agent comprising an antibacterially effective amount of the compound of the formula (I) or a pharmaceutically acceptable salt or ester thereof, and a pharmaceutically acceptable carrier or diluent.

Now, the present invention will be described in detail with reference to the preferred embodiments. Firstly, the symbols and terms used in this specification will be explained.

The compound of the present invention has a basic structure of the formula:

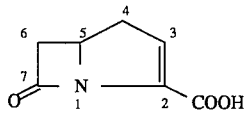

which is systematically referred to as a 7-oxo-1-azabicyclo[3.2.0]hept-2-en-2-carboxylic acid. For the convenience sake, in this specification, this basic structure will be referred to as a 1-carbapen-2-em-3-carboxylic acid by putting the numbers based on a commonly widely used carbapenem of the formula:

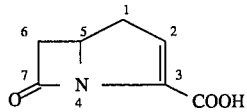

The present invention includes optical isomers based on the asymmetrical carbon atoms at the 1-position, 5-position, 6-position and 8-position of the carbapenem structure and stereoisomers. Among these isomers, preferred is a compound of a (5R,6S,8R) configuration i.e. a compound having a steric configuration of (5R,6S) (5,6-trans) like thienamycin and in which the carbon atom at the 8-position takes a R-configuration, or a compound of a (1R,5S,6S,8R) configuration in a case where a methyl group is present at the 1-position.

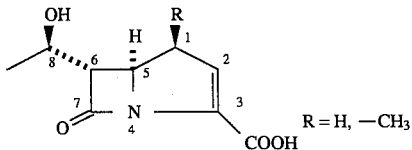

Also with respect to the 2-substituted pyrrolidin-4-ylthio group of the side chain at the 2-position, the present invention includes isomers based on the asymmetrical carbon atoms at the 2-position and 4-position of the pyrrolidine structure and in the side chain at the 2-position. Among these isomers, preferred are compounds of the formula:

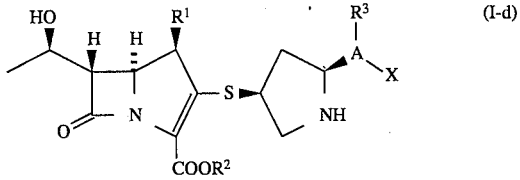

wherein $R^1$, $R^2$, $R^3$, A and X are as defined above, and compounds of the formula:

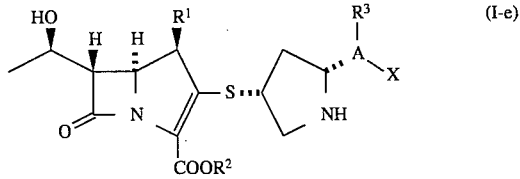

wherein $R^1$, $R^2$, $R^3$, A and X are as defined above.

Further, with respect to the side chain substituted at the 2-position of the pyrrolidine structure, there exist isomers based on asymmetrical carbons, and the present invention includes such isomers as well.

The lower alkyl group means a linear or branched alkyl group having from 1 to 6 carbon atoms, such as a methyl group, an ethyl group, a propyl group, an isopropyl group, a butyl group, a sec-butyl group, a tert-butyl group, a pentyl group or a hexyl group, preferably a methyl group, an ethyl group or a tert-butyl group.

The lower alkoxy group means an alkoxy group having from 1 to 6 carbon atoms with the above lower alkyl group substituted on a hydroxyl group, such as a methoxy group, an ethoxy group, a propoxy group, an isopropoxy group, a butoxy group, a sec-butoxy group or a tert-butoxy group, preferably a methoxy group, an ethoxy group or a tert-butoxy group.

The lower alkanoyloxy group means an alkanoyloxy group having from 1 to 6 carbon atoms with a lower alkanoyl group substituted on a hydroxyl group, such as a formyloxy group, an acetoxy group, a propionyloxy group, a butyryloxy group, an isobutyryloxy group, a valeryloxy group or a pivaloyloxy group, preferably a formyloxy group or an acetoxy group.

The N-lower alkylamino group means an N-alkylamino group having from 1 to 6 carbon atoms with the above lower alkyl group mono-substituted on an amino group, such as an N-methylamino group, an N-ethylamino group, an N-propylamino group, an N-isopropylamino group or an N-butylamino group, preferably an N-methylamino group or an N-ethylamino group.

The N,N-di-lower alkylamino group means an N,N-dialkylamino group having from 2 to 12 carbon atoms with the above-mentioned two lower alkyl groups substituted on an amino group, such as an N,N-dimethylamino group, an N,N-diethylamino group, an N,N-dipropylamino group, an N,N-diisopropylamino group, an N,N-dibutylamino group, an N-ethyl-N-methylamino group, an N-methyl-N-propylamino group or an N-ethyl-N-propylamino group, preferably an N,N-dimethylamino group or an N,N-diethylamino group.

The lower alkanoylamino group means an alkanoylamino group having from 1 to 6 carbon atoms with a lower alkanoyl group substituted on an amino group, such as a formylamino group, an acetylamino group, a propionylamino group, a butyrylamino group, an isobutyrylamino group, a valerylamino group, an isovalerylamino group or a pivaloylamino group, preferably a formylamino group or an acetylamino group.

The aroylamino group means an aroylamino group having from 7 to 11 carbon atoms, such as a benzoylamino group.

The (lower alkylsulfonyl)amino group means an (alkylsulfonyl)amino group having from 1 to 6 carbon atoms with the above lower alkyl-substituted sulfonyl group substituted on an amino group, such as a (methylsulfonyl)amino group, an (ethylsulfonyl)amino group, a (propylsulfonyl)amino group, an (isopropylsulfonyl)amino group, a (butylsulfonyl)amino group, a (sec-butylsulfonyl)amino group, a (tert-butylsulfonyl)amino group or a (pentylsulfonyl)amino group, preferably a (methylsulfonyl)amino group.

The linear or branched lower alkylene group means a linear or branched alkylene group having from 1 to 6 carbon atoms, such as a methylene group, an ethylene group, a propylene group, a butylene group, a methylmethylene group, an ethylmethylene group, a dimethylmethylene group, a 1-methylethylene group, a 2-methylethylene group, a 1-ethylethylene group, a 2-ethylethylene group, a 1,1-dimethylethylene group, a 1,2-dimethylethylene group, a 2,2-dimethylethylene group, a 1-methylpropylene group, a 2-methylpropylene group, a 3-methylpropylene group, a 1-ethylpropylene group, a 2-ethylpropylene group, a 3-ethylpropylene group, a 1,1-dimethylpropylene group, a 2,2-dimethylpropylene group or a 3,3-dimethylpropylene group, preferably a methylmethylene group, a 1,1-dimethylethylene group, a 2,2-dimethylethylene group or a 2-methylpropylene group.

The halogen atom may, for example, be a fluorine atom, a chlorine atom, a bromine atom or an iodine atom.

The carboxyl-protecting group may, for example, be a lower alkyl group such as a methyl group, an ethyl group, a propyl group, an isopropyl group or a tert-butyl group; a halogenated lower alkyl group such as a 2,2,2-trichloroethyl group or a 2,2,2-trifluoroethyl group; a lower alkanoyloxyalkyl group such as an acetoxymethyl group, a propionyloxymethyl group, a pivaloyloxymethyl group, a 1-acetoxyethyl group or a 1-propionyloxyethyl group; a lower alkoxycarbonyloxyalkyl group such as a 1-(methoxycarbonyloxy)ethyl group, a 1-(ethoxycarbonyloxy)ethyl group or a 1-(isopropoxycarbonyloxy)ethyl group; a lower alkenyl group such as a 2-propenyl group, a 2-chloro-2-propenyl group, a 3-methoxycarbonyl-2-propenyl group, a 2-methyl-2-propenyl group, a 2-butenyl group or a cinnamyl group; an aralkyl group such as a benzyl group, a p-methoxybenzyl group, a 3,4-dimethoxybenzyl group, an o-nitrobenzyl group, a p-nitrobenzyl group, a benzhydryl group or a bis(p-methoxyphenyl)methyl group; a (5-substituted 2-oxo-1,3-dioxol-4-yl)methyl group such as a (5-methyl-2-oxo-1,3-dioxol-4-yl)methyl group; a lower alkylsilyl group such as a trimethylsilyl group or a tert-butyldimethylsilyl group; an indanyl group, a phthalidyl group or a methoxymethyl group. Particularly preferred are a 2-propenyl group, a p-nitrobenzyl group, a p-methoxybenzyl group, a benzhydryl group and a tert-butyldimethylsilyl group.

The hydroxyl-protecting group may, for example, be a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a 2,4-dimethoxybenzyl group, an o-nitrobenzyl group, a p-nitrobenzyl group or a trityl group; an acyl group such as a formyl group or an acetyl group; a lower alkoxycarbonyl group such as a tert-butoxycarbonyl group, a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; or an aralkyloxycarbonyl group such as a benzyloxycarbonyl group, a p-methoxybenzyloxycarbonyl group, an o-nitrobenzyloxycarbonyl group or a p-nitrobenzyloxycarbonyl group. Particularly preferred are a 2-propenyloxycarbonyl group, a p-nitrobenzyloxycarbonyl group and a tert-butyldimethylsilyl group.

The amino- or imino-protecting group may, for example, be an aralkylidene group such as a benzylidene group, a p-chlorobenzylidene group, a p-nitrobenzylidene group, a salicylidene group, an α-naphthylidene group or a β-naphthylidene group; an aralkyl group such as a benzyl group, a p-methoxybenzyl group, a 3,4-dimethoxybenzyl group, an o-nitrobenzyl group, a p-nitrobenzyl group, a benzhydryl group, a bis(p-methoxyphenyl)methyl group or a trityl group; a lower alkanoyl group such as a formyl group, an acetyl group, a propionyl group, a butyryl group, an oxalyl group, a succinyl group or a pivaloyl group; a halogenated lower alkanoyl group such as a chloroacetyl group, a dichloroacetyl group, a trichloroacetyl group or a trifluoroacetyl group; an arylalkanoyl group such as a phenylacetyl group or a phenoxyacetyl group; a lower alkoxycarbonyl group such as a methoxycarbonyl group, an ethoxycarbonyl group, a propoxycarbonyl group or a tert-butoxycarbonyl group; a halogenated lower alkoxycarbonyl group such as a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; an aralkyloxycarbonyl group such as a benzyloxycarbonyl group, an o-nitrobenzyloxycarbonyl group, a p-nitrobenzyloxycarbonyl group or a phenethyloxycarbonyl group; or a lower alkylsilyl group such as a trimethylsilyl group or a tert-butyldimethylsilyl group. Particularly preferred are a 2-propenyloxycarbonyl group, a tert-butoxycarbonyl group and a p-nitrobenzyloxycarbonyl group.

$R^3$ is a hydrogen atom, a halogen atom, a hydroxyl group, a lower alkoxy group, a lower alkanoyloxy group, an amino group, an N-lower alkylamino group, an N,N-di-lower alkylamino group, a lower alkanoylamino group, an aroylamino group, a (lower alkylsulfonyl)amino group, a sulfamoylamino group, a cyano group, a nitro group, a group of —$COOR^4$ (wherein $R^4$ is a hydrogen atom or a lower alkyl group) or a group of —$CON(R^5)R^6$ (wherein each of $R^5$ and $R^6$ which may be the same or different, is a hydrogen atom or a lower alkyl group, or $R^5$ and $R^6$ form together with the adjacent nitrogen atom a heterocyclic group selected from the group consisting of an aziridinyl group, an azetidinyl group, a pyrrolidinyl group, a piperidyl group, a piperazinyl group, a 4-lower alkyl piperazinyl group and a morpholino group). However, when A is a linear lower alkylene group, $R^3$ is other than a hydrogen atom. $R^3$ may be substituted at an optional position on the linear or branched lower alkylene group represented by A. $R^3$ is preferably a hydrogen atom, a halogen atom, a hydroxyl group, a lower alkoxy group, a lower alkanoyloxy group, an amino group, a lower alkanoylamino group, a (lower alkylsulfonyl)amino group, a cyano group or a carbamoyl group, particularly preferably a hydroxyl group.

X is a group of —$N(R^7)R^8$ (wherein each of $R^7$ and $R^8$ which may be the same or different, is a hydrogen atom or a lower alkyl group) or a group of —$N^+(R^9)(R^{10})R^{11}$ (wherein each of $R^9$, $R^{10}$ and $R^{11}$ which may be the same or different, is a lower alkyl group). X may, for example, be an amino group, an N-methylamino group, an N-ethylamino group, an N-propylamino group, an N-isopropyl amino group, an N-butylamino group, an N,N-dimethylamino group, an N,N-diethylamino group, an N,N-dipropylamino group, an N,N-diisopropylamino group, an N,N-dibutylamino group, an N-ethyl-N-methylamino group, an N-methyl-N-propylamino group, an N-ethyl-N-propylamino group, an N,N,N-trimethylammonio group, an N,N,N-triethylammonio group, an N,N-dimethyl-N-ethylammonio group or an N,N-diethyl-N-methylammonio group, preferably an amino group, an N-methylamino group, an N-ethylamino group, an N,N-dimethylamino group, an N,N-diethylamino group or an N,N,N-trimethylammonio group.

$R^2$ is a hydrogen atom or a negative charge. When the side chain at the 2-position of the pyrrolidinyl group forms an ammonio group, $R^2$ is a negative charge and forms a pair together with the ammonium ion, whereby the compound of the formula (I) forms an intramolecular salt.

The salt of the compound of the formula (I) is a common pharmaceutically acceptable salt and may, for example, be a salt at the carboxyl group at the 3-position of the carbapenem structure, or at the pyrrolidine base or the base on the side chain substituted on the pyrrolidine ring.

The basic addition salt at said carboxyl group includes, for example, an alkali metal salt such as a sodium salt or a potassium salt; an alkaline earth metal salt such as a calcium salt or a magnesium salt; an ammonium salt; an aliphatic amine salt such as a trimethylamine salt, a triethylamine salt, a dicyclohexylamine salt, an ethanolamine salt, a diethanolamine salt, a triethanolamine salt or a procaine salt; an aralkylamine salt such as an N,N'-dibenzylethylenediamine salt; an aromatic heterocyclic amine salt such as a pyridine salt, a picoline salt, a quinoline salt or an isoquinoline salt; a quaternary ammonium salt such as a tetramethylammonium salt, a tetraethylammonium salt, a benzyltrimethylammonium salt, a benzyltriethylammonium salt, a benzyltributylammonium salt, a methyltrioctylammonium salt or a tetrabutylammonium salt; and a basic amino acid salt such as an arginine salt or a lysine salt.

The acid addition salt at the pyrrolidine base or at the base on the side chain substituted on the pyrrolidine ring includes, for example, an inorganic salt such as a hydrochloride, a sulfate, a nitrate, a phosphate, a carbonate, a hydrogencarbonate or a perchlorate; an organic salt such as an acetate, a propionate, a lactate, a maleate, a fumarate, a tartrate, a malate, a succinate or an ascorbate; a sulfonate such as a methanesulfonate, an isethionate, a benzenesulfonate or a p-toluenesulfonate; and an acidic amino acid salt such as an aspartate or a glutamate.

The non-toxic ester of the compound of the formula (I) means a common pharmaceutically acceptable ester at the carboxyl group at the 3-position of the carbapenem structure. For example, it includes an ester with an alkanoyloxymethyl group such as an acetoxymethyl group or a pivaloyloxymethyl group, an ester with an alkoxycarbonyloxyalkyl group such as a 1-(ethoxycarbonyloxy)ethyl group, an ester with a phthalidyl group and an ester with a (5-substituted-2-oxo-1,3-dioxol-4-yl)methyl group such as a (5-methyl-2-oxo-1,3-dioxol-4-yl)methyl group.

Among the compounds of the formula (I), preferred is a compound of the formula:

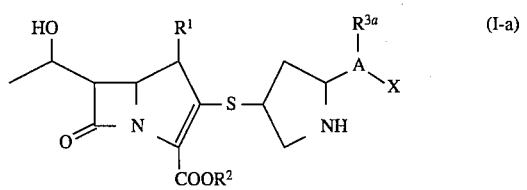

(I-a)

wherein $R^1$ is a hydrogen atom or a methyl group, $R^2$ is a hydrogen atom or a negative charge, $R^{3a}$ is a hydrogen atom, a halogen atom, a hydroxyl group, a lower alkoxy group, a lower alkanoyloxy group, an amino group, an N-lower alkylamino group, a lower alkanoylamino group, a (lower alkylsulfonyl)amino group, a cyano group or a carbamoyl group, A is a linear or branched lower alkylene group, X is a group of —$N(R^7)R^8$ (wherein each of $R^7$ and $R^8$ which may be the same or different, is a hydrogen atom or a lower alkyl group) or a group of —$N^+(R^9)(R^{10})R^{11}$ (wherein each of $R^9$, $R^{10}$ and $R^{11}$ which may be the same or different, is a lower alkyl group), provided that when A is a linear lower alkylene group, $R^{3a}$ is other than a hydrogen atom; or a pharmaceutically acceptable salt or ester thereof.

More preferred are a compound of the formula:

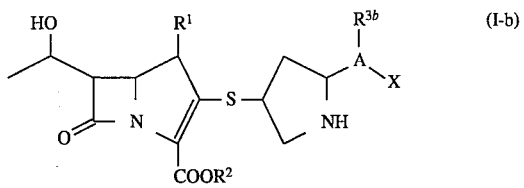

(I-b)

wherein $R^1$ is a hydrogen atom or a methyl group, $R^2$ is a hydrogen atom or a negative charge, $R^{3b}$ is a hydrogen atom, a hydroxyl group, an amino group, a lower alkanoylamino group, a (lower alkylsulfonyl)amino group, a cyano group or a carbamoyl group, A is a linear or branched lower alkylene group, X is a group of —$N(R^7)R^8$ (wherein each of $R^7$ and $R^8$ which may be the same or different, is a hydrogen atom or a lower alkyl group) or a group of —$N^+(R^9)(R^{10})R^{11}$ (wherein each of $R^9$, $R^{10}$ and $R^{11}$ which may be the same or different, is a lower alkyl group), provided that when A is a linear lower alkylene group, $R^{3b}$ is other than a hydrogen atom; or a pharmaceutically acceptable salt or ester thereof; and a compound of the formula:

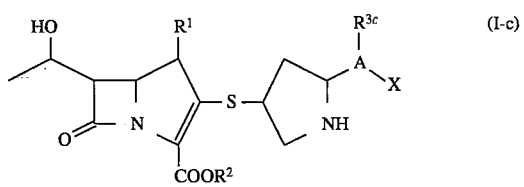

(I-c)

wherein $R^1$ is a hydrogen atom or a methyl group, $R^2$ is a hydrogen atom or a negative charge, $R^{3c}$ is a halogen atom, a lower alkoxy group, an N-lower alkylamino group or a lower alkanoyloxy group, A is a linear or a branched lower alkylene group, X is a group of —$N(R^7)R^8$ (wherein each of $R^7$ and $R^8$ which may be the same or different, is a hydrogen atom or a lower alkyl group) or a group of —$N^+(R^9)(R^{10})R^{11}$ (wherein each of $R^9$, $R^{10}$ and $R^{11}$ which may be the same or different, is a lower alkyl group), provided that when A is a linear lower alkylene group, $R^{3c}$ is other than a hydrogen atom; or a pharmaceutically acceptable salt or ester thereof.

The compound of the present invention is characterized in that the terminal of the lower alkylene group as the side chain at the 2-position of the pyrrolidinyl group substituted at the 2-position of the carbapenem structure is a primary, secondary or tertiary amino group or an ammonio group, and the lower alkylene group has a branched structure.

Here, the "branched structure" means that the lower alkylene group of the compound of the formula (I) has a substituent or is branched. Specifically, it includes a case where the lower alkylene group is a linear lower alkylene group which has a substituent, and a case where the lower alkylene group is a branched lower alkylene group. The branched lower alkylene group may or may not have a substituent.

When the lower alkylene group is a linear lower alkylene group, the substituent ($R^3$) is preferably a halogen atom, a hydroxyl group, a lower alkoxy group, a lower alkanoyloxy group, an amino group, a lower alkanoylamino group, a (lower alkylsulfonyl)amino group, a cyano group or a carbamoyl group.

When the lower alkylene group is a branched lower alkylene group, the substituent ($R^3$) is preferably a hydrogen atom, a hydroxyl group or a carbamoyl group.

Specific examples of the compound of the formula (I) include, for example, the following compounds. The following abbreviations in the table have the following meanings.

Ac: Acetyl group
Et: Ethyl group
Me: Methyl group

| No. | R¹ | R² | $-A\begin{smallmatrix}R^3\\X\end{smallmatrix}$ |
|---|---|---|---|
| 1 | H | H | Me, NH₂ (isopropylamine) |
| 2 | H | H | Et, NH—Me |
| 3 | H | H | Et, NH—Et |
| 4 | H | Negative Charge | Me, N⁺(Me)(Me)(Me) |
| 5 | H | H | OH, NH—Me |
| 6 | H | H | Cl, NH—Et |
| 7 | H | H | NH—Ac, NH₂ |
| 8 | H | H | NH—SO₂Me, NH—Me |
| 9 | H | H | CONH₂, NH₂ |
| 10 | H | H | OH, NH₂ |
| 11 | H | H | OH, NH—Me |
| 12 | H | H | Me, Me, NH₂ |
| 13 | Me | H | Me, NH—Et |
| 14 | Me | H | CN, NH₂ |
| 15 | Me | H | Et, NH₂ |
| 16 | Me | H | OH, NH₂ |
| 17 | Me | H | OH, NH—Me |
| 18 | Me | H | OH, NH—Et |
| 19 | Me | H | OH, N(Me)(Me) |
| 20 | Me | Negative Charge | OH, N⁺(Me)(Me)(Me) |
| 21 | Me | H | OMe, NH—Me |
| 22 | Me | H | Cl, NH—Me |
| 23 | Me | H | Cl, N(Me)(Me) |
| 24 | Me | H | NO₂, NH₂ |
| 25 | Me | H | NH—Ac, NH₂ |
| 26 | Me | H | NH—SO₂Me, NH₂ |
| 27 | Me | H | NH—SO₂Me, NH—Me |
| 28 | Me | H | NH₂, CONH₂ |

-continued

[Structure: carbapenem core with HO-CH(Me)- group, β-lactam, COOR² at C3, S linkage at C4 to pyrrolidine bearing R¹, NH, and substituent -A(R³)-X]

| No. | R¹ | R² | -A(R³)X |
|-----|----|----|---------|
| 29 | Me | H | -CH(CONH₂)-CH(Me)-CH₂-NH-Me |
| 30 | Me | H | -CH(CONH₂)-CH(Me)-CH₂-NH₂ |
| 31 | Me | H | -CH(CONH₂)-CH(Me)-CH₂-NH-Me |
| 32 | Me | H | -CH(CON(piperazinyl-N-Et))-CH(Me)-CH₂-NH-Me |
| 33 | Me | H | -CH(NO₂)-CH(Me)-CH₂-N(Et)₂ |
| 34 | Me | H | -CH(CON(pyrrolidinyl))-CH(Me)-CH₂-NH₂ |
| 35 | Me | H | -CH(CON(morpholinyl))-CH(Me)-CH₂-N(Me)₂ |
| 36 | Me | H | -CH(CON(piperazinyl-NH))-CH(Me)-NH-Me |
| 37 | Me | H | -CH(NH-SO₂NH₂)-CH(Me)-CH₂-NH-Me |
| 38 | Me | H | -CH(NH-Me)-CH(Me)-CH₂-NH-Me |
| 39 | Me | H | -CH(Me)-CH(Me)-CH₂-NH₂ |

-continued

[Structure: same carbapenem core as above]

| No. | R¹ | R² | -A(R³)X |
|-----|----|----|---------|
| 40 | Me | H | -CH(Me)-CH(Me)-CH₂-NH-Me |
| 41 | Me | H | -CH(Me)-CH(Me)-CH₂-N(Me)₂ |
| 42 | Me | Negative Charge | -CH(Me)-CH(Me)-CH₂-N⁺(Me)₃ |
| 43 | Me | H | -CH(NH₂)-CH(Et)-Me |
| 44 | Me | H | -CH(NH-Me)-CH(Et)-Me |
| 45 | Me | H | -CH(Et)-CH(Me)-N(Me)₂ |
| 46 | Me | Negative Charge | -CH(Et)-CH(Me)-N⁺(Me)₃ |
| 47 | Me | H | -CH(Et)-CH(Me)-CH₂-NH-Me |
| 48 | Me | H | -CH(NH₂)-C(Me)₂-Me |
| 49 | Me | H | -CH(NH-Me)-C(Me)₂-Me |
| 50 | Me | H | -CH(Et)-C(Me)₂-N(Me)₂ |
| 51 | Me | Negative Charge | -CH(Et)-C(Me)₂-N⁺(Me)₃ |
| 52 | Me | H | -CH₂-CH(Me)-CH₂-NH₂ |
| 53 | Me | H | -CH₂-CH(Me)-CH₂-NH-Me |

15
-continued

| No. | R¹ | R² | -A(R³)(X) |
|---|---|---|---|
| 54 | Me | H | isobutyl-CH2-N(Me)2 |
| 55 | Me | Negative Charge | isobutyl-CH2-N+(Me)3 |
| 56 | Me | H | CH(OH)-CH2CH2-NH2 |
| 57 | Me | H | CH(OH)-CH2CH2-NHMe |
| 58 | Me | H | CH(OH)-CH2CH2-N(Me)2 |
| 59 | Me | Negative Charge | CH(OH)-CH2CH2-N+(Me)3 |
| 60 | Me | H | CH(OMe)-CH2CH2-NHMe |
| 61 | Me | H | CH(Cl)-CH2CH2-NHMe |
| 62 | Me | H | CH2-CH(OH)-CH2-NH2 |
| 63 | Me | H | CH2-CH(OH)-CH2-NHMe |
| 64 | Me | H | CH2-CH(OH)-CH2-N(Me)2 |
| 65 | Me | H | CH2-CH(OMe)-CH2-NH2 |
| 66 | Me | H | CH2-CH(OMe)-CH2-NHMe |
| 67 | Me | H | CH2-CH(OAc)-CH2-NH2 |
| 68 | Me | H | CH2-CH(OAc)-CH2-NHMe |
| 69 | Me | H | CH2-CH(Cl)-CH2-NHMe |
| 70 | Me | H | CH(CH2OH)-NH2 (2-amino-CH2OH) |
| 71 | Me | H | CH(CH2OH)-NHMe |
| 72 | Me | H | CH(CH2OH)-N(Me)2 |
| 73 | Me | Negative Charge | CH(CH2OH)-N+(Me)3 |
| 74 | Me | H | CH(NHMe)-CH2CH2-NHMe |
| 75 | Me | H | CH(NHAc)-CH2CH2-NHMe |
| 76 | Me | H | CH(NHSO2Me)-CH2CH2-NHMe |
| 77 | Me | H | CH(CONH2)-CH2CH2-NHMe |
| 78 | Me | H | CH(CON(piperazinyl-N-Et))-CH2-NH2 |
| 79 | Me | H | CH(CON(morpholinyl))-CH2CH2-NHMe |

(Table 15/16 continued showing carbapenem structures with HO-CH(Me)- group on β-lactam, R¹ at C-4, COOR² at C-3, and S-linked side chain with -A(R³)(X) substituent.)

17
-continued

Structure: carbapenem core with HO-CH(Me)- group, R¹, COOR², S-linked pyrrolidine with NH, and substituent –A(R³)–X

| No. | R¹ | R² | –A(R³)–X |
|---|---|---|---|
| 80 | Me | H | CH(NH₂)CH₂CH₂NH₂ (3-aminobutyl with NH₂) |
| 81 | Me | H | CH(NH₂)CH₂CH₂NH—Me |
| 82 | Me | H | CH(NH₂)CH₂CH₂N(Me)Me |
| 83 | Me | Negative Charge | CH(NH₂)CH₂CH₂N⁺(Me)(Me)Me |
| 84 | Me | H | C(Me)(Me)CH₂NH₂ with Me substituent |
| 85 | Me | H | C(Me)(Me)... NH—Me |
| 86 | Me | H | C(Me)(Me)... N(Me)(Me)Me |
| 87 | Me | Negative Charge | C(Me)(Me)... N⁺(Me)(Me)Me |
| 88 | Me | H | CH₂C(Me)(Me)CH₂NH₂ |
| 89 | Me | H | CH₂C(Me)(Me)CH₂NH—Me |
| 90 | Me | H | CH₂C(Me)(Me)CH₂N(Me)(Me)Me |
| 91 | Me | Negative Charge | CH₂C(Me)(Me)CH₂N⁺(Me)(Me)Me |
| 92 | Me | H | CH(Me)CH₂NH₂ |
| 93 | Me | H | CH(Me)CH₂CH₂NH₂ |

18
-continued

| No. | R¹ | R² | –A(R³)–X |
|---|---|---|---|
| 94 | Me | H | CH(Me)CH₂CH₂CH₂NH—Me |
| 95 | Me | H | CH(Et)CH₂CH₂CH₂NH₂ |
| 96 | Me | H | CH(Et)CH₂CH₂CH₂NH—Me |
| 97 | Me | H | CH(CN)CH₂CH₂NH—Me |
| 98 | Me | H | CH(NO₂)CH₂CH₂NH—Me |
| 99 | Me | H | CH₂CH(Me)CH₂C(O)N(piperazinyl-N-Et)... NH—Me |
| 100 | Me | H | CH(CH₂Et)(CH₂NH—Me)CH₂C(O)N(pyrrolidinyl) |
| 101 | Me | H | CH₂CH₂CH₂C(Me)(Me)NH—Me |
| 102 | Me | H | CH₂CH₂CH₂CH(Et)NH₂ |
| 103 | Me | H | CH(CH₂F)CH₂NH₂ (with F) |
| 104 | Me | H | CH(CH₂F)CH₂NH—Me |
| 105 | Me | H | CH(F)CH₂CH₂NH—Me |
| 106 | Me | H | CH(F)CH₂CH₂N(Me)Me |
| 107 | Me | H | CH(CH₂OH)CH(Me)CH₂NH₂ |

[Structure: carbapenem core with HO-CH(Me)-, R¹, S-link to pyrrolidine with -A(R³)(X)-NH, COOR² group]

| No. | R¹ | R² | -A(R³)(X) |
|---|---|---|---|
| 108 | Me | H | CH₂OH branch; NH—Me |
| 109 | Me | H | CH₂OH branch; N(Me)(Me) |
| 110 | Me | Negative Charge | CH₂OH branch; N⁺(Me)(Me)(Me) |
| 111 | Me | H | CH₂Cl branch; NH—Me |
| 112 | Me | H | CH₂F branch; N(Me)(Me) |
| 113 | Me | H | CH₂NH—SO₂Me branch; NH—Me |
| 114 | Me | H | CH₂OH branch; NH₂ |
| 115 | Me | H | CH₂OH branch; NH—Me |
| 116 | Me | H | CH₂OH branch; N(Me)(Me) |
| 117 | Me | Negative Charge | CH₂OH branch; N⁺(Me)(Me)(Me) |

Among the above compounds, preferred are compounds identified by compound Nos. 2, 4, 5, 6, 9, 11, 12, 13, 14, 16, 17, 18, 19, 20, 22, 23, 25, 26, 27, 28, 29, 30, 31, 32, 35, 36, 37, 38, 41, 43, 44, 48, 49, 53, 56, 57, 58, 59, 61, 62, 63, 64, 67, 70, 71, 72, 73, 74, 75, 76, 78, 79, 80, 84, 88, 89, 90, 91, 92, 94, 95, 99, 101, 102, 104, 105, 107, 108, 109, 110, 111, 112, 113, 114, 115, 116 and 117. Among them, particularly preferred are as follows:

5 (5R,6S)-6-[(1R)-1-hydroxyethyl]-2-[(2S,4S)-2-[(1 -hydroxy-2-N-methylamino)ethyl]pyrrolidin-4-ylthio]-1-carbapen-2-em-3-carboxylic acid, 6 (5R,6S)-2-[(2S,4S)-2-[(1-chloro-2-N-ethylamino)ethyl] pyrrolidin-4-ylthio]-6-[(1R)-1 -hydroxyethyl]-1-carbapen-2-em-3-carboxylic acid, 9 (5R,6S)-2-[(2S,4S)-2-(1-aminomethyl-2 -carbamoylethyl)pyrrolidin-4-ylthio]-6-[(1R)-1 -hydroxyethyl]-1-carbapen-2-em-3-carboxylic acid, 12 (5R,6S)-2-[(2S,4S)-2-[(1-amino-1,1-dimethyl)methyl] pyrrolidin-4-ylthio]-6-[(1R)-1-hydroxyethyl]-1-carbapen- 2-em-3-carboxylic acid, 14 (1R,5S,6S)-2-[(2S,4S)-2-(1-amino-1-cyanomethyl)pyrrolidin- 4-ylthio]-6-[(1R)-1-hydroxyethyl]-1-methyl-1-carbapen-2-em-3-carboxylic acid, 16 (1R,5S,6S)-2-[(2S,4S)-2-[(2-amino-1-hydroxy)ethyl] pyrrolidin-4-ylthio]-6-[(1R)-1-hydroxyethyl]-1-methyl-1- carbapen-2-em-3-carboxylic acid, 17 (1R,5S,6S)-6-[(1R)-1-hydroxyethyl]-2-[(2S,4S)-2-[(1-hydroxy-2-methylamino)ethyl]pyrrolidin-4-ylthio]-1-methyl-1-carbapen-2-em-3-carboxylic acid, 18 (1R,5S,6S)-2-[(2S,4S)-2-[(2-N-ethylamino-1-hydroxy)ethyl]pyrrolidin-4-ylthio]-6-[(1R)-1-hydroxyethyl]-1-methyl-1-carbapen-2-em-3-carboxylic acid, 19 (1R,5S,6S)-2-[(2S,4S)-2-[(2-N,N-dimethylamino-1 -hydroxy)ethyl]pyrrolidin-4-ylthio]-6-[(1R)-1 -hydroxyethyl]-1-methyl-1-carbapen-2-em-3-carboxylic acid, 20 (1R,5S,6S)-6-[(1R)-1-hydroxyethyl]-2-[(2S,4S)-2-[(1-hydroxy-2-N,N,N-trimethylammonio)ethyl]pyrrolidin-4-ylthio]-1-methyl-1-carbapen-2-em-3-carboxylate, 22 (1R,5S,6S)-2-[(2S,4S)-2-[(1-chloro-2-N-methylamino) ethyl]pyrrolidin-4-ylthio]-6-[(1R)-1-hydroxyethyl]-1 -methyl-1-carbapen-2-em-3-carboxylic acid, 25 (1R,5S,6S)-2-[(2S,4S)-2-(1-acetamido-2-aminoethyl)pyrrolidin- 4-ylthio]-6-[(1R)-1-hydroxyethyl]-1-methyl-1 -carbapen-2-em-3-carboxylic acid, 26 (1R,5S,6S)-6-[(1R)-1-hydroxyethyl]-1-methyl-2 -[(2S,4S)-2-(1-methanesulfonylamido-2-aminoethyl)pyrrolidin- 4-ylthio]-1-carbapen-2-em-3-carboxylic acid, 27 (1R,5S,6S)-6-[(1R)-1-hydroxyethyl]-1-methyl-2 -[(2S,4S)-2-[(2-N-methylamino-1-methanesulfonylamino)ethyl]pyrrolidin-4-ylthio]-1-carbapen-2-em-3-carboxylic acid, 28 (1R,5S,6S)-2-[(2R,4S)-2-(2-amino-2-carbamoylethyl)pyrrolidin- 4-ylthio]-6-[(1R)-1-hydroxyethyl]-1-methyl-1 -carbapen-2-em-3-carboxylic acid, 30 (1R,5S,6S)-2-[(2S,4S)-2-(1-aminomethyl-2 -carbamoylethyl)pyrrolidin-4-ylthio]-6-[(1R)-1 -hydroxyethyl]-1-methyl-1-carbapen-2-em-3-carboxylic acid, 31 (1R,5S,6S)-2-[(2S,4S)-2-[(1-carbamoylmethyl-2-N-methylamino)ethyl]pyrrolidin-4-ylthio]-6-[(1R)-1 -hydroxyethyl]-1-methyl-1-carbapen-2-em-3-carboxylic acid, 32 (1R,5S,6S)-2-[(2S,4S)-2-[[1-(4-ethylpiperazin-1 -yl)carbonylmethyl-2-N-methylamino]ethyl]pyrrolidin-4-ylthio]-6-[(1R)-1-hydroxyethyl]-1-methyl-1-carbapen-2-em- 3-carboxylic acid, 35 (1R,5S,6S)-2-[(2S,4S)-2-[(2-N,N-dimethylamino-1-morpholinocarbonylmethyl)ethyl]pyrrolidin-4-ylthio]-6-[(1R)-1-hydroxyethyl]-1-methyl-1-carbapen-2-em-3- carboxylic acid, 36 (1R,5S,6S)-6-[(1R)-1-hydroxyethyl]-1-methyl-2 -[(2S,4S)-2-[[1-N-methylamino-1-(piperazin-1 -yl)carbonylmethyl]methyl]pyrrolidin-4-ylthio]-1-carbapen- 2-em-3-carboxylic acid, 37 (1R,5S,6S)-6-[(1R)-1-hydroxyethyl]-1-methyl-2 -[(2S, 4S)-2-[(2-N-methylamino-1-sulfamoylamino)ethyl]pyrrolidin-4-ylthio]-1-carbapen-2-em-3-carboxylic acid, 38 (1R,5S,6S)-2-[(2S,4S)-2-[1,2-bis(N-methylamino)ethyl]pyrrolidin-4-ylthio]-6-[(1R)-1 -hydroxyethyl]-1-methyl-1-carbapen-2-em-3-carboxylic acid, 48 (1R,5S,6S)-2-[(2R,4S)-2-[(2-amino-2-methyl)propyl]pyrrolidin-4-ylthio]-6-[(1R)-1-hydroxyethyl]-1-methyl-1- carbapen-2-em-3-carboxylic acid, 56 (1R,5S,6S)-2-[(2S,4S)-2-[(3-amino-1-hydroxy)propyl]pyrrolidin-4-ylthio]-6-[(1R)-1-hydroxyethyl]-1-methyl-1 -carbapen-2-em-3-carboxylic acid, 57 (1R,5S,6S)-6-[(1R)-1-hydroxyethyl]-2-[(2S,4S)-2-[(1-hydroxy-3-N-methylamino)propyl]pyrrolidin-4-ylthio] -1- methyl-1-carbapen-2-em-3-carboxylic acid, 58 (1R,5S,6S)-2-[(2S,4S)-2-[(3-N,N-dimethylamino-1 -hydroxy)propyl]pyrrolidin-4-ylthio]-6-[(1R)-1 -hydroxyethyl]-1-methyl-1-carbapen-2-em-3-carboxylic acid, 59 (1R,5S,6S)-6-[(1R)-1-hydroxyethyl]-2-[(2S,4S)-2-[(1-hydroxy-3-N,N,N-trimethylammonio)propyl]pyrrolidin-4 -ylthio]-1-methyl-1-carbapen-2-em-3-carboxylate, 62 (1R,5S,6S)-2-[(2S,4S)-2-[(3-amino-2-hydroxy)propyl]pyrrolidin-4-ylthio]-6-[(1R)-1-hydroxyethyl]-1-methyl-1- carbapen-2-em-3-carboxylic acid, 63 (1R,5S,6S)-2-[(2S,4S)-2-[(2-hydroxy-3-N-methylamino)propyl]pyrrolidin-4-ylthio]-6-[(1R)-1-hydroxyethyl]-1-methyl-1-carbapen-2-em-3-carboxylic acid, 64 (1R,5S,6S)-2-[(2S,4S)-2-[(3-N,N-dimethylamino-2 -hydroxy)propyl]pyrrolidin-4-ylthio]-6-[(1R)-1 -hydroxyethyl]-1-methyl-1-carbapen-2-em-3-carboxylic acid, 70 (1R,5S,6S)-2-[(2S,4S)-2-[(2-amino-3-hydroxy)propyl]pyrrolidin-4-ylthio]-6-[(1R)-1-hydroxyethyl]-1-methyl-1- carbapen-2-em-3-carboxylic acid, 71 (1R,5S,6S)-2-[(2S,4S)-2-[(3-hydroxy-2-N-methylamino)propyl]pyrrolidin-4-ylthio]-6-[(1R)-1-hydroxyethyl]-1-methyl-1-carbapen-2-em-3-carboxylic acid, 72 (1R,5S,6S)-2-[(2S,4S)-2-[(2-N,N-dimethylamino-3 -hydroxy)propyl]pyrrolidin-4-ylthio]-6-[(1R)-1 -hydroxyethyl]-1-methyl-1-carbapen-2-em-3-carboxylic acid, 73 (1R,5S,6S)-2-[(2S,4S)-2-[(3-hydroxy-2-N,N,N-trimethylammonium)propyl]pyrrolidin-4-ylthio]-6-[(1R)-1-hydroxyethyl]-1-methyl-1-carbapen-2-em-3-carboxylate, 74 (1R,5S,6S)-2-[(2S,4S)-2-[1,3-bis(N-methylamino)propyl]pyrrolidin-4-ylthio]-6-[(1R)-1 -hydroxyethyl]-1-methyl-1-carbapen-2-em-3-carboxylic acid, 78 (1R,5S,6S)-2-[(2S,4S)-2-[[3-amino-1-(4 -ethylpiperazin-1-yl)carbonyl]propyl]pyrrolidin-4-ylthio]-6-[(1R)-1-hydroxyethyl]-1-methyl-1-carbapen-2-em-3 -carboxylic acid, 79 (1R,5S,6S)-6-[(1R)-1-hydroxyethyl]-1-methyl-2 -[(2S, 4S)-2-[(3-N-methylamino-1-morpholinocarbonyl)propyl]pyrrolidin-4-ylthio]-1-carbapen-2-em-3-carboxylic acid, 80 (1R,5S,6S)-2-[(2S,4S)-2-(1,3-diaminopropyl)pyrrolidin-4-ylthio]-6-[(1R)-1-hydroxyethyl]-1-methyl-1 -carbapen-2-em-3-carboxylic acid, 84 (1R,5S,6S)-2-[(2R,4S)-2-[(3-amino-3-methyl)butyl]pyrrolidin-4-ylthio]-6-[(1R)-1-hydroxyethyl]-1-methyl-1-carbapen-2-em-3-carboxylic acid, 88 (1R,5S,6S)-2-[(2R,4S)-2-[(3-amino-2,2-dimethyl)propyl]pyrrolidin-4-ylthio]-6-[(1R)-1-hydroxyethyl]-1 -methyl-1-carbapen-2-em-3-carboxylic acid, 89 (1R,5S,6S)-2-[(2R,4S)-2-[(2,2-dimethyl-3-N-methylamino)propyl]pyrrolidin-4-ylthio]-6-[(1R)-1 -hydroxyethyl]-1-methyl-1-carbapen-2-em-3-carboxylic acid, 92 (1R,5S,6S)-2-[(2R,4S)-2-(3-amino-2-methylpropyl)pyrrolidin- 4-ylthio]-6-[(1R)-1-hydroxyethyl]-1-methyl-1-carbapen-2-em-3-carboxylic acid, 94 (1R,5S,6S)-2-[(2R,4S)-2-(3-N-methylaminobutyl)pyrrolidin- 4-ylthio]-6-[(1R)-1-hydroxyethyl]-1-methyl-1 -carbapen-2-em-3-carboxylic acid, 104 (1R,5S,6S)-2-[(2S,4S)-2-(2-fluoro-3-N-methylaminopropyl)pyrrolidin- 4-ylthio]-6-[(1R)-1 -hydroxyethyl]-1-methyl-1-carbapen-2-em-3-carboxylic acid, 107 (1R,5S,6S)-2-[(2S,4S)-2-[(1-aminomethyl-3 -hydroxy)propyl]pyrrolidin-4-ylthio]-6-[(1R)-1 -hydroxyethyl]-1-methyl-1-carbapen-2-em-3-carboxylic acid, 108 (1R,5S,6S)-6-[(1R)-1-hydroxyethyl]-2-[(2S,4S)-2-[[1-(2-hydroxyethyl)-2-methylamino]ethyl]pyrrolidin-4-ylthio]-1-methyl-1-carbapen-2-em-3-carboxylic acid, 111 (1R,5S,6S)-2-[(2S,4S)-2-[[1-(2-chloroethyl)-2 -methylamino]ethyl]pyrrolidin-4-ylthio]-6-[(1R)-1 -hydroxyethyl]-1-methyl-1-carbapen-2-em-3-carboxylic acid, 114 (1R,5S,6S)-2-[(2S,4S)-2-[(1-aminoethyl-3 -hydroxy)propyl]pyrrolidin-4-ylthio]-6-[(1R)-1 -hydroxyethyl]-1-methyl-1-carbapen-2-em-3-carboxylic acid, 115 (1R,5S,6S)-6-[(1R)-1-hydroxyethyl]-2-[(2S,4S)-2-[[1-(2-hydroxyethyl)-3-N-methylamino]propyl]pyrrolidin-4-ylthio]-1-methyl-1-carbapen-2-em-3-carboxylic acid, 116 (1R,5S,6S)-6-[(1R)-1-hydroxyethyl]-2-[(2S,4S)-2-[[3-N,N-dimethylamino-1-(2-hydroxyethyl)]propyl]pyrrolidin-4 -ylthio]-1-methyl-1-carbapen-2-em-3-carboxylic acid and 117 (1R,5S,6S)-6-[(1R)-1-hydroxyethyl]-2-[(2S,4S)-2-[[1-(2-hydroxyethyl)-3-N,N,N-trimethylammonium]propyl]pyrrolidin-4-ylthio]-1-methyl-1-carbapen-2-em-3 -carboxylate.

Especially preferred is compound No. 57 i.e. (1R,5S,6S)-6-[(1R)-1-hydroxyethyl]-2-[(2S,4S)-2-[(1 -hydroxy-3-methylamino)propyl]pyrrolidin-4-ylthio]-1 -methyl-1-carbapen-2-em-3-carboxylic acid.

Now, the process for producing the compound of the present invention will be described.

An activating reagent is reacted to a compound of the formula:

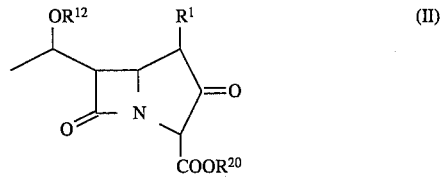

wherein $R^1$ is a hydrogen atom or a methyl group, $R^{12}$ is a hydrogen atom or a hydroxyl-protecting group, and $R^{20}$ is a hydrogen atom or a carboxyl-protecting group, in an inert organic solvent in the presence of a base to form a reactive derivative of the formula (II'):

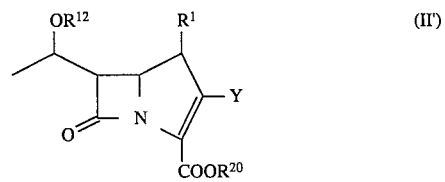

wherein $R^1$, $R^{12}$ and $R^{20}$ are as defined above, and Y is a leaving group.

The inert organic solvent to be used for the reaction may, for example, be diethyl ether, tetrahydrofuran, dioxane, benzene, toluene, chlorobenzene, methylene chloride, chloroform, carbon tetrachloride, dichloroethane, trichloroethylene, acetone, ethyl acetate, acetonitrile, N,N-dimethylformamide, hexamethylphosphoric triamide or a mixture of such solvents. Particularly preferred are acetonitrile and benzene.

The base to be used for the reaction may, for example, be a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) or 1,5-diazabicyclo[4.3.0]non-5-ene (DBN); or an aromatic amine such as pyridine, 4-N,N-dimethylaminopyridine, picoline, lutidine, quinoline or isoquinoline. Particularly preferred are N,N-diisopropylethylamine and triethylamine.

The activating reagent to be used for the reaction may, for example, be an acid anhydride such as trifluoroacetic anhydride, methanesulfonic anhydride, trifluoromethanesulfonic anhydride or p-toluenesulfonic anhydride; or an acid chloride such as methanesulfonyl chloride, p-toluenesulfonyl chloride or diphenyl chlorophosphate. Particularly preferred is diphenyl chlorophosphate.

In the formula (II'), Y is a leaving group such as a trifluoroacetoxy group, a methanesulfonyloxy group, a trifluoromethanesulfonyloxy group, a p-toluenesulfonyloxy group or a diphenoxyphosphoryloxy group. Particularly preferred is a diphenoxyphosphoryloxy group.

For the reaction, from 1 to 3 mols, preferably from 1 to 1.5 mols, of the base and from 1 to 1.2 mols of the activating reagent are used per mol of the compound of the formula (II).

The reaction is conducted usually within a temperature range of from −40° to 50° C., preferably from −20° to 20° C., and usually completed quantitatively in from 0.5 to 3 hours.

After completion of the reaction, the reaction product is treated in accordance with a usual method to obtain the reactive derivative (II') of the compound of the formula (II) quantitatively.

The reaction of the reactive derivative of the formula (II') with a compound of the formula:

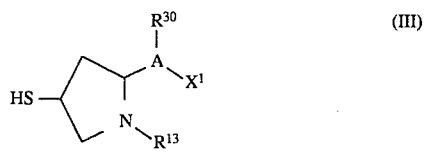

wherein $R^{13}$ is a hydrogen atom or an imino-protecting group, $R^{30}$ is a hydrogen atom, a halogen atom, a hydroxyl group which may be protected, a lower alkoxy group, a lower alkanoyloxy group, an amino or N-lower alkylamino group which may be protected, an N,N-di-lower alkylamino group, a lower alkanoylamino group, an aroylamino group, a (lower alkylsulfonyl)amino group, a sulfamoylamino group which may be protected, a cyano group, a nitro group, a group of —$COOR^{40}$ (wherein $R^{40}$ is a hydrogen atom, a lower alkyl group or a carboxyl-protecting group) or a group of —$CON(R^{50})R^{60}$ (wherein each of $R^{50}$ and $R^{60}$ which may be the same or different, is a hydrogen atom, a lower alkyl group or an amino- or imino-protecting group, or $R^{50}$ and $R^{60}$ form together with the adjacent nitrogen atom a heterocyclic group selected from the group consisting of an aziridinyl group, an azetidinyl group, a pyrrolidinyl group, a piperidyl group, a piperazinyl group which may be protected, a 4-lower alkyl piperazinyl group and a morpholino group, A is a linear or branched lower alkylene group, $X^1$ is a group of the formula —$N(R^{70})R^{80}$ (wherein each of $R^{70}$ and $R^{80}$ which may be the same or different, is a hydrogen atom, a lower alkyl group or an amino- or imino-protecting group) or a group of —$N^+(R^9)(R^{10})R^{11}$ (wherein each of $R^9$, $R^{10}$ and $R^{11}$ which may be the same or different, is a lower alkyl group), provided that when A is a linear lower alkylene group, $R^{30}$ is other than a hydrogen atom, is conducted using the above-mentioned inert organic solvent and base to form a compound of the formula:

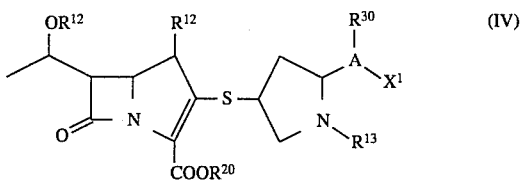

wherein $R^1$, $R^{12}$, $R^{13}$, $R^{20}$, $R^{30}$, A and $X^1$ are as defined above.

The reaction is conducted using from 1 to 2 mols, preferably from 1 to 1.5 mols, of the base and from 1 to 1.2 mols of the compound of the formula (III), per mol of the reactive derivative of the formula (II'). The reaction is conducted usually within a temperature range of from −40° to 50° C., preferably from −20° to 20° C., and the reaction is completed usually in from 0.5 to 3 hours.

Further, the compound of the formula (IV) can be prepared in one step from the compound of the formula (II). Namely, without isolating the reactive derivative of the formula (II') prepared from the compound of the formula (II), the compound of the formula (III) is reacted thereto in the same reaction system to prepare the compound of the formula (IV) efficiently. To conduct the production in one step, from 2 to 4 mols, preferably from 2.5 to 3.5 mols, of the base is employed per mol of the compound of the formula (II).

After completion of the reaction, usual treatment is conducted to obtain a crude product of the formula (IV), which may be subjected to a reaction for removing a protecting group without purification. However, it is preferred to purify the crude product (IV) by crystallization or by column chromatography by means of e.g. silica gel.

From the compound of the formula (IV) thus obtained, a compound of the formula (I) can be obtained, if necessary, by conducting a reaction for removing a protecting group for a hydroxyl group, an amino or imino group and a carboxyl group.

For the removal of the protecting groups, the method varies depending upon the type of the protecting groups. However, the removal can be conducted in accordance with conventional methods, for example, by solvolysis, by chemical reduction or by hydrogenation.

For example, when in the above formula (IV), the protecting group for the hydroxyl group and/or for the amino or imino group is an aralkyloxycarbonyl group such as a benzyloxycarbonyl group or a p-nitrobenzyloxycarbonyl group, and the protecting group for the carboxyl group is an aralkyl group such as a benzyl group, a p-nitrobenzyl group or a benzhydryl group, such protecting groups can be removed by catalytic hydrogenation by means of a platinum catalyst such as platinum oxide, platinum wire or platinum black, or a palladium catalyst such as palladium black, palladium oxide, palladium-carbon or palladium hydroxide-carbon.

As a solvent to be used for such a catalytic hydrogenation reaction, methanol, ethanol, tetrahydrofuran, dioxane, acetic acid or a solvent mixture of such an organic solvent with water or with a buffer solution of e.g. a phosphate, may be used.

The reaction can be completed in from 0.5 to 4 hours at a temperature within a range of from 0° to 50° C. under hydrogen gas stream of from 1 to 4 atm.

When in the above formula (IV), the protecting group for the hydroxyl group and/or the amino or imino group is an allyloxycarbonyl group, and the protecting group for the carboxyl group is an allyl group, such protecting groups can be removed by reacting an organo-soluble palladium complex catalyst in an inert organic solvent containing an allyl group-capturing agent (method by W. McCombie et al., J. Org. Chem., vol. 47, p. 587–590 (1982) and method by F. Guibé, the same literature, vol. 52, p. 4,984–4,993 (1987)).

The solvent useful for the reaction includes, for example, water, acetone, diethyl ether, tetrahydrofuran, dioxane, ethyl acetate, acetonitrile, methylene chloride, chloroform and a solvent mixture thereof.

The palladium compound complex useful for this reaction includes, for example, palladium-carbon, palladium hydroxide-carbon, palladium(II) chloride, palladium(II) acetate, tetrakis(triphenylphosphine)palladium (O), tetrakis(triphenoxyphosphine)palladium (O), tetrakis(triethoxyphosphine)palladium (O), bis[ethylenebis(diphenylphosphine)]palladium (O), tetrakis[tri(2-furyl)phosphine]palladium (O), bis(triphenylphosphine)palladium(II) chloride and bis(triphenylphosphine)palladium(II) acetate.

The allyl group-capturing agent may, for example, be dimedone, formic acid, acetic acid, ammonium formate, sodium formate, sodium 2-ethylhexanoate, potassium 2-ethylhexanoate, pyrrolidine, piperidine and tributyltin hydride.

The reaction is conducted usually within a temperature range of from −10° to 50° C., preferably from 0° to 30° C. using from 0.01 to 0.5 mol of the catalyst and from 1 to 6 mols of the allyl group-capturing agent relative to 1 mol of the compound of the formula (IV), and the reaction is completed usually in from 0.5 to 3 hours.

Further, when in the above formula (IV), the protecting group for the hydroxyl group and/or the amino or imino group is an o-nitrobenzyloxycarbonyl group, and the protecting group for the carboxyl group is an o-nitrobenzyl group, such protecting groups can be removed by a photo reaction (method by Amit et al., J. Org. Chem., vol. 39, p. 192–196 (1974)).

After completion of the reactions for removing the protecting groups, the compound of the formula (I) can be isolated by usual treatment such as column chromatography using silica gel or adsorptive resin, freeze-drying or crystallization.

Further, when the protecting group for the carboxyl group at the 3-position of the compound of the formula (IV) is a lower alkanoyloxyalkyl group such as an acetoxymethyl group or a pivaloyloxymethyl group, a methoxymethyl group, an indanyl group or a phthalidyl group, such an ester will be physiologically hydrolyzed in vivo. Therefore, such a compound can directly be administered to a human being or to an animal without preliminarily removing the protecting group.

The compound of the formula (I) can be converted to a pharmaceutically acceptable salt or ester by a conventional method.

In the reaction of the reactive derivative (II') of the compound of the formula (II) with the compound of the formula (III), the compound of the formula (III) may be used without protecting its functional group such as an imino group on the pyrrolidine ring, or an amino group, a hydroxyl group or a sulfamoyl group as the substituent on the side chain at the 2-position of the pyrrolidine structure. The reaction of the reactive derivative (II') and the compound of the formula (III) can be conducted under the same conditions as described above.

For example, a compound of the formula:

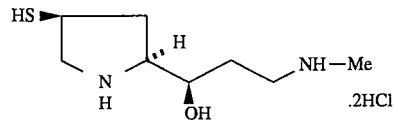

is an important starting material to obtain a compound of the formula:

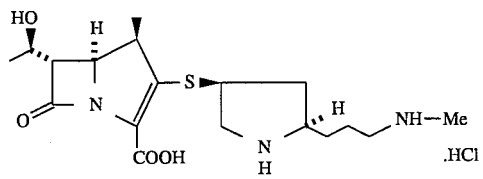

This thiol compound and the reactive derivative (II') are subjected to a coupling reaction, and then a buffer solution such as MOPS buffer is added to the reaction solution. The mixture is then subjected to catalytic hydrogenation under a mild condition to obtain the desired compound.

The protecting groups of the compound of the formula (III) may optionally be selected. In order to increase the yield for the reaction for removing the protecting groups to obtain the desired compound, it is advisable to use the minimum protecting groups.

The starting material of the formula (II) can be prepared, for example, by a method by Salzmann et al. when $R^1$ is a hydrogen atom (J. Am. Chem. Soc., vol. 102, p.6161–6163 (1981)) or by a method by Shih et al. when $R^1$ is a methyl group (Heterocycles, vol. 21, p.29–40 (1984)).

The starting material of the formula (III) can be synthesized by the following method.

The hydroxyl group of the compound 1 is activated by a usual method, and a thioacetate such as potassium thioacetate is reacted thereto to convert it to an acetylthio derivative 3, followed by alkali or acid hydrolysis to obtain a thiol derivative of the formula (III).

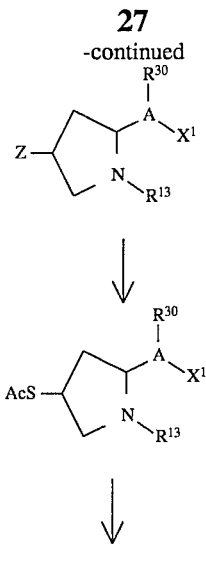

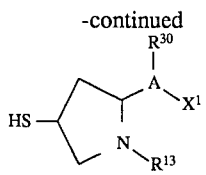

In the above formulas, $R^{14}$ is a hydrogen atom or a hydroxyl-protecting group, Z is a leaving group selected from the group consisting of a chlorine atom, a bromine atom, an iodine atom, a trifluoroacetoxy group, a methanesulfonyloxy group, a trifluoromethanesulfonyloxy group and a p-toluenesulfonyloxy group, Ac is an acetyl group, and $R^{13}$, $R^{30}$, A and $X^1$ are as defined above.

A group of compounds having the formula 1 can be prepared in accordance with the methods described in the Reference Examples.

The compounds of the present invention exhibit strong antibacterial activities against various gram positive bacteria and gram negative bacteria.

To demonstrate the usefulness of the compounds of the present invention, the in vitro antibacterial activities against bacteria were measured by the following agar plate dilution method (standard method by Japan Chemotherapy Society, Chemotherapy, vol. 29, p. 76–79 (1981)). One platinum loopful of each test microorganism incubated overnight in Mueller Hinton broth, was inoculated to Mueller Hinton agar (inoculum size: $10^6$ CFU/ml). Such culture media contained antibacterial agents in various concentrations. After incubation at 37° C. for 16 hours, the minimum inhibitory concentrations (MIC: μg/ml) were measured.

Further, the DHP-I susceptibility was quantitatively analyzed by the method by Kropp et al., Antimicrob. Agents Chemother., vol. 22, p. 62–70 (1982), whereby the smaller the numerical value representing the ratio to imipenem (=1.0), the higher the stability.

The minimum inhibitory concentrations and the DHP-I susceptibility of the compounds of the present invention were compared with imipenem and the compound of

REFERENCE EXAMPLE 13.

The results are shown in Table 1.

TABLE 1

| Test microorganism | Minimum Inhibitory Concentration(MIC μg/ml) and DHP-I Susceptibility | | | | | | |
|---|---|---|---|---|---|---|---|
| | Example 7 | Example 8 | Example 9 | Example 10 | Example 13 | Reference Example 13 | Imipenem |
| P. aeruginosa MB5002 | 0.78 | 0.78 | 0.78 | 0.78 | 1.56 | 6.25 | 1.56 |
| P. aeruginosa MB5178 | 1.56 | 3.13 | 1.56 | 1.56 | 3.13 | 12.5 | 25 |
| DHP-I susceptibility | 0.07 | 0.07 | 0.13 | 0.17 | 0.08 | 0.7 | 1.0 |

The compounds of the present invention have excellent antibacterial activities against various gram positive bacteria and gram negative bacteria and are useful as antibacterial agents for the treatment and prevention of the human infectious diseases caused by such bacteria. Typical pathogens sensitive to the antibacterial agents of the present invention include, for example, species of genus Staphylococcus, genus Enterococcus, genus Escherichia, genus Enterobacter, genus Klebsiella, genus Serratia, genus Proteus and genus Pseudomonas. The compounds of the present invention exhibit excellent antibacterial activities particularly against Methicillin resistant *Staphylococcus aureus* and against thienamycin resistant *Pseudomonas aeruginosa*.

The compounds of the present invention are very stable against DHP-I although the stability varies depending upon the individual compounds, and they are excellent also in the physicochemical stability and in the solubility in water.

Pharmacokinetics in Mice

Materials and Methods

Pharmacokinetics in mice: Groups of three 20 g ddY male mice were given a single dose of 20 mg/kg of the compound of EXAMPLE 19 and imipenem by sc route. One group of three mice was placed in a metabolism cage designed to collect the urine free from fecal contamination. At a specified time after dosing, blood and urine samples were collected from a group for bioassay. The plasma was collected from the pooled blood after centrifugation. Microbiological assays: Bioactivity in the specimens was measured was by the standard disk diffusion procedure using *Bacillus subtilis* ATCC12432 as a test organism.

TABLE 2

Pharmacokinetic parameters of the compound of Example 19 and imipenem in mice following an s.c. injection of 20 mg/kg

| Antibiotic | Pharmacokinetic parameters | | | | Urinary recovery (0–6 h) (%) |
|---|---|---|---|---|---|
| | $C_{max}$ (μg/mg) | $T_{max}$ (hr) | $T_{1/2}$ (hr) | AUC (μg · hr/ml) | |
| Example 19 | 29.0 | 0.18 | 0.13 | 13.8 | 62.5 |
| Imipenem | 21.5 | 0.18 | 0.12 | 9.5 | 21.5 |

The pharmacokinetic parameters and urinary recoveries of the compound of EXAMPLE 19 and imipenem which were determined in mice after subcutaneous administration are summarized in Table 2. The compound of EXAMPLE 19 distinctly showed more favorable pharmacokinetic profile than imipenem (Figure). The plasma half life (0.13 hr) and the area under the curve (AUC; 13.8 μg·hr/ml) of the compound of EXAMPLE 19 were much greater than those of imipenem. Urinary recovery of 62.5% for the compound of EXAMPLE 19 was about 3-fold that of imipenem.

The compounds of the present invention may be used in the form of drug formulations suitable for non-oral administration, oral administration or external administration, by mixing them with carriers of solid or liquid excipients known in this field. The main administration route is non-oral (intravenous or intramuscular injection) administration by injection or local administration. Drug formulations include liquid formulations such as injection solutions, syrups or emulsions, solid formulations such as tablets, capsules or granules, and external application formulations such as ointments or suppositories. These formulations may contain additives such as a base, an assisting agent, a stabilizer, a wetting agent, an emulsifier, an absorption-promoting agent, a surfactant, etc. which are commonly employed, as the case requires.

The additives include, for example, distilled water for injection, Ringer's solution, glucose, sucrose syrup, gelatin, edible oil, cacao butter, ethylene glycol, sucrose, corn starch, magnesium stearate and talc.

The dose varies depending upon the condition of the patient, the weight, the age, the sex, the type of formulation, the number of administration times, etc. Usually, however, a preferred daily dose of the active ingredient to an adult is from about 5 to 50 mg/kg, and a preferred daily dose to a child is within a range of from about 5 to 25 mg/kg, which is preferably administered once a day or in a few times a day.

The compound of the present invention may be administered in combination with a DHP-I inhibiting agent such as cilastatin [sodium (Z)-7-(L-amino-2 -carboxyethylthio)-2-(2,2 -dimethylcyclopropanecarboxamide)-2-heptenoate] (Japanese Unexamined Patent Publication No. 81518/1981; European Patent No. 28,778; J. Med. Chem., vol. 30, p. 1074 (1987)).

EXAMPLES and REFERENCE EXAMPLES

The present invention is now illustrated in greater detail by way of EXAMPLES and REFERENCE EXAMPLES, but it should not be understood that the present invention is deemed to be limited thereto.

Unless otherwise provided, silica gel for column chromatography used herein is Wakogel™ C-300 (Wakojunyaku), and the reverse phase silica gel for column chromatography is LC-SORB™ SP-B-ODS (Chemco). As the high pressure liquid chromatograph, JASCO 800 series (Nippon Bunko) was used. When the NMR spectrum was measured using dimethyl sulfoxide-$d_6$ or chloroform-d solution, tetramethylsilane (TMS) was used as the internal standard, and when measured using a deuterium is oxide solution, 2,2-dimethyl-2-silapentane-5-sulfonate (DSS) was used as the internal standard, and the measurement was conducted by means of XL-200 (200 MHz; Varian) model spectrometer. All δ values are shown by ppm.

The meanings of the abbreviations used for the NMR measurement are as follows:

s: singlet
d: doublet
t: triplet
q: quartet
ABq: AB-type quartet
dd: double doublet
m: multiplet
br: broad
J: coupling constant
Hz: hertz
DMSO-$d_6$: dimethyl sulfoxide-$d_6$
CDCl$_3$: chloroform-d
D$_2$O: deuterium oxide
Abbreviations used herein have the following meanings.
Ac: acetyl group
Boc: tert-butoxycarbonyl group
Bzl: benzyl group
Et: ethyl group
Ms: methanesulfonyl group
Me: methyl group
MOPS: 3-morpholinopropanesulfonate
PNB: p-nitrobenzyl group
PNZ: p-nitrobenzyloxycarbonyl group
PMB: p-methoxybenzyl group
TBS: tert-butyldimethylsilyl group
Tr: triphenylmethyl group
Ts: p-toluenesulfonyl group

EXAMPLE 1

(1R,5S,6S)-2-[(2S,4S)-2-(1-Aminomethyl-2-carbamoyl)ethylpyrrolidin-4-ylthio]-6-[(1R)-1-hydroxyethyl]-1-methyl-1-carbapen-2-em-3-carboxylic Acid

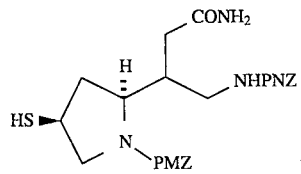

1)

To an ice-cooled solution of the compound prepared in REFERENCE EXAMPLE 1-6 (300 mg, 0.58 mmol) in methanol (50 ml) was added 1N aqueous sodium hydroxide (0.58 ml), and the solution was stirred for 1 h at room temperature. The reaction mixture was again cooled, added 1N aqueous hydrochloric acid (0.64 ml), and concentrated in vacuo. To the residue was added ethyl acetate (50 ml), and the mixture was washed successively with water and saturated aqueous sodium chloride. After drying over anhydrous sodium sulfate, the solvent was removed in vacuo to give crude (2S,4S)-2-[2-carbamoyl-1 -(p-nitrobenzyloxycarbonylaminomethyl)ethyl]-4-mercapto-N-(p-nitrobenzyloxycarbonyl)pyrrolidine (290 mg).

IR(KBr)cm$^{-1}$: 3330,2920,1700,1605,1520,1400,1340

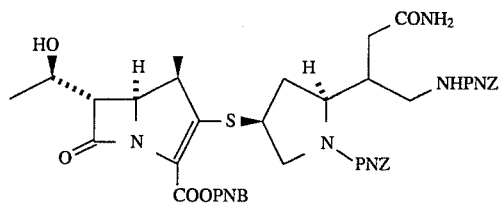

To an ice-cooled solution of p-nitrobenzyl (1R,5S,6S)-2- diphenylphosphoryloxy-6-[(1R)-1-hydroxyethyl]-1-methyl-1-carbapen-2-em-3-carboxylate (344.8 mg, 0.58 mmol) in acetonitrile (12 ml) was added N,N-diisopropylethylamine (0.1 ml, 0.58 mmol) under a nitrogen atmosphere, and then added dropwise the above compound (290 mg) in acetonitrile (5 ml). After stirring overnight at 5° C., ethyl acetate (100 ml) was added to the reaction mixture. The organic layer was washed successively with water and saturated aqueous sodium chloride. After drying over anhydrous sodium sulfate, the solvent was removed in vacuo. The residue was subjected to silica gel column chromatography (chloroform:methanol=80:1) to give p-nitrobenzyl (1R,5S,6S)-6-[(1R)-1-hydroxyethyl]-2-[(2S,4S)-2-[2 -carbamoyl-1-(p-nitrobenzyloxycarbonylaminomethyl)ethyl]-N-(p-nitrobenzyloxycarbonyl)pyrrolidin-4-ylthio]-1 -methyl-1- carbapen-2-em-3-carboxylate (290 mg, yield: 61.2%).

IR(KBr)cm$^{-1}$: 3420,1770,1700,1605,1520,1345 NMR(CDCl$_3$) δ: 1.28 (3H,d,J=8.0Hz), 1.33 (3H,d,J=7.0Hz), 1.60 (2H,br), 1.90–2.60 (5H,m), 3.00–3.60 (4H,m), 4.00–4.30 (3H,m), 5.20 (4H,m), 5.50 (2H,br), 7.53 (4H,d, J=8.0Hz), 7.64 (2H,d,J=8.0Hz), 8.20 (4H,d,J=8.0Hz), 8.22 (2H,d,J=8.0Hz)

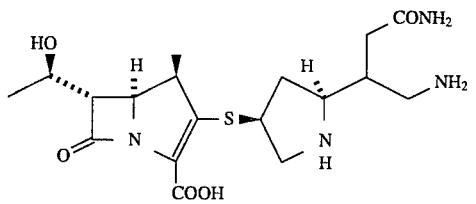

A suspension of 10% palladium-carbon (300 mg) in 0.1M MOPS buffer (pH 7.0, 10 ml) was stirred under a hydrogen atmosphere for 1 h, and the catalyst was collected by filtration, and washed with water. To a solution of the above compound (283 mg, 0.35 mmol) in a mixture of tetrahydrofuran (10 ml) and 0.1M MOPS buffer (pH 7.0, 10 ml) was added the resulting catalyst, and the mixture was stirred for 2 h under an atmospheric pressure of hydrogen at room temperature. The catalyst was filtered off, and tetrahydrofuran was removed in vacuo. The aqueous residue was washed successively with ethyl acetate and chloroform, and a small amount of insoluble material was filtered off. The filtrate was concentrated in vacuo, and purified by reverse phase column chromatography (15% methanol in water), lyophilized to give the title compound (81.96 mg, yield: 57.43%).

IR(KBr)cm$^{-1}$: 3400,1750,1680,1590,1390,1280 NMR(D$_2$O) δ: 1.28 (3H,d,J=8.0Hz), 1.33 (3H,d,J=8.0Hz), 1.60 (2H,m), 2.00–2.40 (3H,m), 2.60–3.50 (4H,m), 3.60–4.30 (6H,m) UV λ$_{max}$ (0.1M MOPS buffer, pH 7.0): 298 nm (ε=8623)

EXAMPLE 2

(5R,6S)-2-[(2S,4S)-2-(1-Aminomethyl-2-carbamoyl)ethylpyrrolidin-4-ylthio]-6-[(1R)-1-hydroxyethyl]-1-carbapen-2-em-3-carboxylic Acid

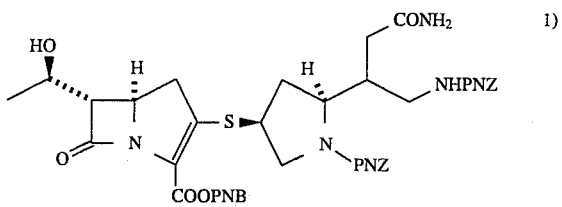

p-Nitrobenzyl (5R,6S)-6-[(1R)-1-hydroxyethyl]-2 -[(2S,4S)-2-[2-carbamoyl-1-(p-nitrobenzyloxycarbonylaminomethyl)ethyl]-N-(p-nitrobenzyloxycarbonyl)pyrrolidin-4-ylthio]-1-carbapen-2-em-3-carboxylate (164 mg, yield: 51.1%) was obtained from the thiol prepared in EXAMPLE 1-1 (190 mg, 0.39 mmol) and p-nitrobenzyl (5R,6S)-2-diphenoxyphosphoryloxy-6-[(1R)-1-hydroxyethyl]-1-carbapen-2-em-3-carboxylate (189.3 mg, 0.39 mmol) in the same manner as in EXAMPLE 1-2.

IR(KBr)cm$^{-1}$: 3400,1770,1700,1520,1340 NMR(CDCl$_3$) δ: 1.38 (3H,d,J=8.0Hz), 1.60 (2H,br), 1.90–2.60 (5H,m), 3.00–3.60 (4H,m), 4.00–4.40 (3H,m), 5.30 (4H,m), 5.55 (2H,br), 7.54 (4H,d,J=8.0Hz), 7.66 (2H,d,J=8.0Hz), 8.24 (4H,d,J=8.0Hz), 8.28 (2H,d,J=8.0Hz)

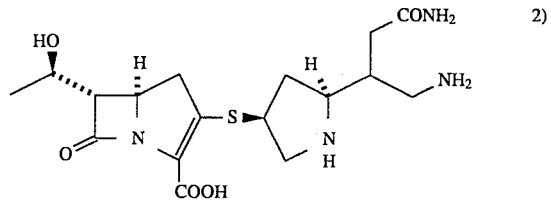

The title compound (46.68 mg, yield: 78.4%) was obtained from the above compound (120 mg) in the same manner as in EXAMPLE 1-3.

IR(KBr)cm$^{-1}$: 3420,1760,1680,1600,1400,1200,1050 NMR (D$_2$O) δ: 1.30 (3H,d,J=8.0Hz), 1.70 (2H,m), 2.00–2.40 (3H,m), 2.50–3.45 (4H,m), 3.60–4.30 (6H,m) UV λ$_{max}$ (0.1M MOPS buffer, pH 7.0): 299 nm (ε=5250)

EXAMPLE 3

(1R,5S,6S)-2-[(2R,4S)-2-(2-Amino-2-carbamoyl)ethylpyrrolidin-4-ylthio]-6-[(1R)-hydroxyethyl]-1-methyl-1-carbapen-2-em-3-carboxylic Acid

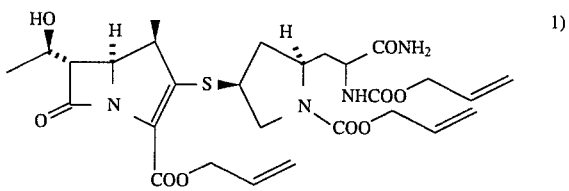

To an ice-cooled solution of (2R,4S)-N-allyloxycarbonyl-2-(2-allyloxycarbonylamino-2-carbamoylethyl)-4 -triphenylmethylthiopyrrolidine prepared in REFERENCE EXAMPLE 2 (120 mg, 0.2 mmol) in methylene chloride (0.5 ml) was added successively trifluoroacetic acid (0.5 ml) and triethylsilane (0.04 ml, 0.25 mmol) under a nitrogen atmosphere, and the solution was stirred for 15 min at the same temperature. After the solvent was removed in vacuo, ethyl acetate (30 ml) was added to the residue. The organic layer was washed successively with 1M phosphate buffer (pH 5.5) and water, and dried over anhydrous sodium sulfate. After the solvent was removed in vacuo, the residue was subjected to silica gel column chromatography (chloroform-methanol) to give the thiol compound. Allyl (1R,5S, 6S)-2-[(2R,4S)-N-allyloxycarbonyl- 2-(2-allyloxycarbonylamino-2-carbamoyl)ethylpyrrolidin- 4-ylthio]-6-[(1R)-1- hydroxyethyl]-1-methyl-1 -carbapen-2-em-3-carboxylate (70 mg, yield: 69%) was obtained from the above thiol compound and allyl (1R,5S,6S)-2-diphenoxyphosphoryloxy-6-[(1R)-1-hydroxyethyl]-1-methyl-1-carbapen-2-em-3-carboxylate (90 mg, 0.18 mmol) in the same manner as in EXAMPLE 1-2.

IR(KBr)cm$^{-1}$: 3420,2970,1775,1790,1540,1445, 1410, 1325, 1275,1205,1135,1045,770 NMR(CDCl$_3$) δ: 1.25 (3H, d,J=7.0Hz), 1.36 (3H,d,J=7.0Hz), 1.55–1.80 (1H,m), 1.80–2.10 (1H,m), 2.15–2.55 (2H,m), 2.55–2.75 (2H,m), 3.10–3.55 (3H,m), 3.55–3.80 (2H,m), 3.90–4.40 (5H,m), 4.40–4.90 (6H,m), 5.00–5.60 (6H,m), 5.60–5.80 (1H,m), 5.80–6.20 (3H,m)

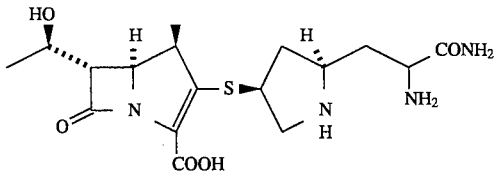
2)

To an ice-cooled solution of the above compound (60 mg, 0.099 mmol) in methylene chloride (1 ml) were added successively water (0.01 ml, 0.553 mmol), bis(triphenylphosphine)palladium dichloride (3 mg, 0.0043 mmol) and tributyltin hydride (0.18 ml, 0.669 mmol) under a nitrogen atmosphere. The mixture was stirred at the same temperature for 5 min and then at room temperature for 30 min. To the mixture was added methylene chloride (10 ml), and the mixture was extracted with water (3×10 ml). The aqueous layer was washed successively with methylene chloride and ethyl acetate, and concentrated in vacuo. The residue was purified by reverse phase column chromatography (0–15% methanol in water), and lyophilized to give the title compound (11 mg, yield: 28%).

IR(KBr)cm$^{-1}$: 3430,1750,1675,1605,1445,1380 NMR(D$_2$O) δ: 1.17 (3H,d,J=8.0Hz), 1.24 (3H,d,J=7.0Hz), 1.50–1.80 (1H,m), 1.80–2.20 (2H,m), 2.55–2.85 (1H,m), 2.85–3.20 (1H,m), 3.20–4.10 (5H,m), 4.10–4.30 (2H,m) UV λ$_{max}$ (0.1M MOPS buffer, pH 7.0): 299 nm (ε=9320)

EXAMPLE 4

(1R,5S,6S)-2-[(2S,4S)-2-(1-Acetamido-2-amino)ethylpyrrolidin-4-ylthio]-6-[(1R)-1-hydroxyethyl]-1-methyl-1 -carbapen-2-em-3-carboxylic Acid

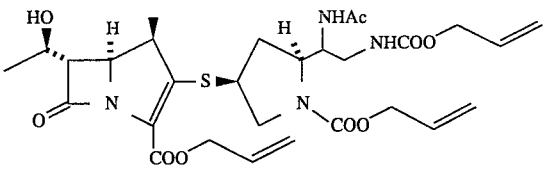

To an ice-cooled solution of (2S,4S)-4-acetylthio-N-allyloxycarbonyl- 2-(1-acetamido-2-allyloxycarbonylamino)ethylpyrrolidine prepared in REFERENCE EXAMPLE 3 (100 mg, 0.26 mmol) in methanol (2 ml) was added 2N aquaeous sodium hydroxide (0.18 ml, 0.36 mmol), and the solution was stirred for 1 h. After adding 6N aqueous hydrochloric acid (0.06 ml, 0.36 mmol), and the mixture was diluted with methylene chloride, and washed with saturated aqueous sodium chloride. The organic layer was dried over anhydrous sodium sulfate, and concentrated in vacuo to give (2S,4S)-2-(1-acetamido-2 -allyloxycarbonylamino)ethyl-N-allyloxycarbonyl-4 -mercaptopyrrolidine. To a solution of the above compound and allyl (1R,5S,6S)-2-diphenoxyphosphoryloxy- 6-[(1R)-1-hydroxyethyl]-1-methyl-1-carbapen-2-em-3 -carboxylate (182 mg, 0.36 mmol) in acetonitrile (2 ml) was added diisopropylethylamine (63 μl, 0.36 mmol) at −10° C., and the mixture was stirred for 6 h at the same temperature. The reaction mixture was diluted with ethyl acetate, and washed with saturated aqueous sodium hydrogencarbonate. After drying over anhydrous magnesium sulfate, the solvent was removed in vacuo. The residue was purified by preparative thin layer chromatography (E. Merck #5717, 2.0 mm, 10×20 cm, developing with ethyl acetate) to give allyl (1R,5S,6S)- 2-[(2S,4S)-2-(1-acetamido-2-allyloxycarbonylamino)ethylpyrrolidin- 4-ylthio]-6-[(1R)-1-hydroxyethyl]-1-methyl-1 -carbapen-2-em-3-carboxylate (105 mg, yield: 65%).

NMR(CDCl$_3$) δ: 1.26 (3H,d,J=8.0Hz), 1.34 (3H,d,J= 8.0Hz), 1.96 (3H,s), 4.60 (6H,m), 5.10–5.60 (6H,m), 5.80–6.10 (3H,m)

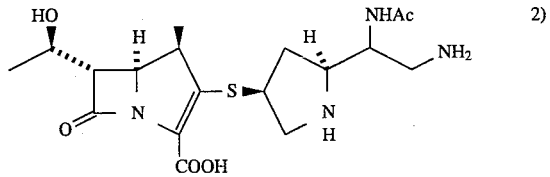
2)

To an ice-cooled mixture of the above compound (105 mg, 0.17 mmol), water (20 ml), and bis(triphenylphosphine) palladium(II) chloride (2.2 mg, 0.003 mmol) was added tributyltin hydride (0.26 ml, 1.02 mmol) under a nitrogen atmosphere. After stirring for 1 h at room temperature, the mixture was diluted with water (10 ml) and chloroform (10 ml), and vigorously stirred. The aqueous layer was separated, and the organic layer was extracted with water (10 ml). The combined aqueous layer was washed with chloroform (10 ml), and concentrated in vacuo. The residue was purified by ODS column chromatography (YMC GEL™, AQ-120-S50, 20 ml, 20 % methanol in water), and lyophilized to give the title compound (19 mg, yield: 27%).

NMR(D$_2$O) δ: 1.12 (3H,d,J=6.0Hz), 1.22 (3H,d,J=6.0Hz), 1.38 (2H,m), 2.06 (3H,s), 2.46 (1H,m), 2.80–3.46 (6H,m), 3.78 (1H,m), 4.22 (3H,m) UV λ$_{max}$ (H$_2$O): 301 nm (ε=8668)

EXAMPLE 5

Sodium (1R,5S,6S)-6-[(1R)-1-hydroxyethyl]-1-methyl-2-[(2S,4S)-2-(1-methanesulfonylamido-2-amino)ethylopyrrolidin-4-ylthio]-1-carbapen-2-em-3-carboxylate

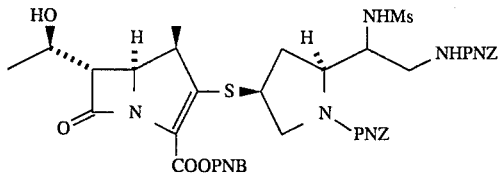
1)

To an ice-cooled solution of (2S,4S)-4-mercapto-N-(p-nitrobenzyloxycarbonyl)- 2-[1-methanesulfonylamido-2-(p-nitrobenzyloxycarbonylamino)ethyl]pyrrolidine prepared in REFERENCE EXAMPLE 4 (253 mg, 0.42 mmol) and p-nitrobenzyl (1R,5S,6S)-2-diphenoxyphosphoryloxy-6- [(1R)-1-hydroxyethyl]-1-methyl-1-carbapen-2-em-3-carboxylate (226 mg, 0.38 mmol) in acetonitrile (5 ml) was added diisopropylethylamine (74 μl, 0.42 mmol), and the mixture was stirred for 1 h. The reaction mixture was diluted with ethyl acetate, and washed with saturated aqueous sodium hydrogencarbonate. After drying over anhydrous magnesium sulfate, the solvent was removed in vacuo. The residue was subjected to silica gel column chromatography (30 ml, 5% methanol in ethyl acetate) to give p-nitrobenzyl (1R,5S,6S)-2-[(2S,4S)-2 -[1-methanesulfonylamido-2-(p-nitrobenzyloxycarbonylamino)ethyl]pyrrolidin-4-ylthio]-6-[(1R)-1-hydroxyethyl]-1-methyl-1-carbapen-2-em-3-carboxylate (240 mg, yield: 61%).

NMR(CDCl$_3$) δ: 1.28 (3H,d,J=6.0Hz), 1.38 (3H,d,J=6.0Hz), 2.86 (3H,s), 5.24 (4H,br s), 5.28 (1H,d,J=12.0Hz), 5.50 (1H,d,J=12.0Hz), 7.56 (4H,m), 7.68 (2H,d,J=10.0Hz), 8.24 (6H,m)

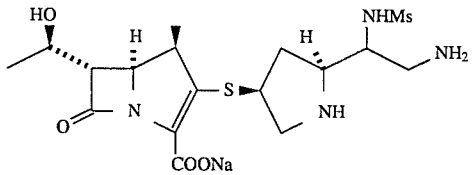
2)

The title compound (46 mg, yield: 39%) was obtained from the above compound (240 mg, 0.26 mmol) in the same manner as in EXAMPLE 1-3.

NMR(D$_2$O) δ: 1.18 (3H,d,J=6.0Hz), 1.28 (3H,d,J=6.0Hz), 3.16 (3H,s) UV λ$_{max}$ (H$_2$O): 300 nm (ε=6164)

EXAMPLE 6

(1R,5S,6S)-2-[(2S,4S)-2-(1-Amino-1-cyano)methylpyrrolidin-4-ylthio]-6-[(1R)-1-hydroxyethyl]-1-methyl-1-carbapen-2-em-3-carboxylic Acid

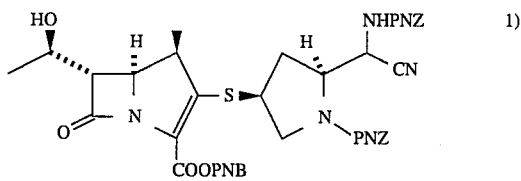
1)

(2S,4R)-2-(1-Cyano-1-p-nitrobenzyloxycarbonylamino)methyl- 4-mercapto-N-(p-nitrobenzyloxycarbonyl)pyrrolidine was obtained as a crude product from (2S,4R)-4-acetylthio-2-(1-cyano-1 -p-nitrobenzyloxycarbonylamino)methyl-N-(p-nitrobenzyloxycarbonyl)pyrrolidine prepared in REFERENCE EXAMPLE 5 (88.1 mg, 0.158 mmol) in the same manner as in EXAMPLE 1-1.

p-Nitrobenzyl (1R,5S,6S)-6-[(1R)-1-hydroxyethyl]-2-[(2S,4R)-N-(p-nitrobenzyloxylcarbonyl)-2-(1-cyano-1-p-nitrobenzyloxycarbonylaminomethyl)pyrrolidin- 4-ylthio]-1-methyl-1-carbapen-2-em-3-carboxylate (103.8 mg, yield: 76.4%) was obtained from the above compound and p-nitrobenzyl (1R,5R,6S)-2-diphenoxyphosphoryloxy-6 -[(1R)-1-hydroxyethyl]-1-methyl-1-carbapen-2-em-3 -carboxylate (93 mg, 0.158 mmol) in the same manner as in EXAMPLE 1-2.

IR(KBr)cm$^{-1}$: 3400,1760,1700 NMR(CDCl$_3$) δ: 1.21 (3H,d,J=7.0Hz), 1.30 (3H,d,J=7.0Hz), 1.90–2.10 (2H,m), 2.80–3.50 (4H,m), 4.20 (2H,m), 2.16 (2H,s), 5.12 & 5.42 (total 2H,each ABq,J=13.0Hz), 5.58 (1H,m), 7.42 (2H,d,J=8.0Hz), 7.58 (2H,d,J=8.0Hz), 8.12 (4H,d,J=8.0Hz)

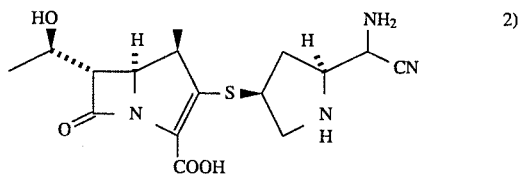
2)

The title compound (18.2 mg, yield: 41.1%) was obtained from the above compound (103.8 mg, 0.121 mmol) in the same manner as in EXAMPLE 1-3.

IR(KBr)cm$^{-1}$: 3400,2250,1760,1600,1400 NMR(CDCl$_3$) δ: 1.21 (3H,d,J=7.0Hz), 1.29 (3H,d,J=7.0Hz), 1.85 (1H,m), 2.65 (1H,m), 3.05 (1H,m), 3.10 (1H,m), 3.40 (3H,m), 4.05

(1H,m), 4.25 (2H,m) UV $\lambda_{max}$ (0.1M MOPS buffer, pH 7.0): 301 nm ($\epsilon$=8400)

EXAMPLE 7

(1R,5S,6S)-2-[(2R,4S)-2-(3-Amino-2-methyl)propylpyrrolidin-4-ylthio]-6-[(1R)-1-hydroxyethyl]-1-methyl-1-carbapen-2-em-3-carboxylic Acid Diastereomer A

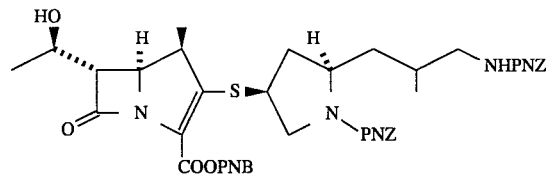
1)

p-Nitrobenzyl (1R,5S,6S)-6-[(1R)-1-hydroxyethyl]-1-methyl-2-[(2R,4S)-2-[2-methyl-3-(p-nitrobenzyloxycarbonylamino)propyl]-N-(p-nitrobenzyloxycarbonyl)pyrrolidin-4-ylthio]-1-carbapen-2-em-3-carboxylate diastereomer A (less polar compound, 120 mg, yield: 13 %) and diastereomer B (polar compound, 130 mg, yield: 14%) were obtained from (2R,4S)-4-acetylthio-2-[(2-methyl-3-p-nitrobenzyloxycarbonylamino)propyl]-N-(p-nitrobenzyloxycarbonyl)pyrrolidine prepared in REFERENCE EXAMPLE 6 (590 mg, 1.03 mmol) and p-nitrobenzyl (1R,5S,6S)-2-diphenoxyphosphoryloxy-6-[(1R)-1-hydroxyethyl]-1-methyl-1-carbapen-2-em-3-carboxylate (610 mg, 1.03 mmol) in the same manner as in EXAMPLES 1-1 and 1-2.

DIASTEREOMER A: IR(KBr)cm$^{-1}$: 3420,1770,1705,1520,1345,1210,1110 NMR(CDCl$_3$) $\delta$: 0.96 (3H,m), 1.28 (3H,d,J=7.0Hz), 1.37 (3H,d,J=7.0Hz), 1.40–2.40 (6H,m), 2.40–2.70 (1H,m), 2.90–3.90 (6H,m), 3.90–4.55 (4H,m), 5.10–5.55 (7H,m), 7.52 (4H,d,J=7.0Hz), 7.66 (2H,d,J=9.0Hz), 8.23 (6H,m)

DIASTEREOMER B: IR(KBr)cm$^{-1}$: 3410,1770,1700,1520,1345,1205,1135 NMR(CDCl$_3$) $\delta$: 0.96 (3H,m), 1.28 (3H,d,J=8.0Hz), 1.37 (3H,d,J=7.0Hz), 1.55–2.20 (6H,m), 2.50–2.80 (1H,m), 2.80–3.80 (5H,m), 3.80–4.40 (4H,m), 4.80–5.60 (7H,m), 7.52 (4H,d,J=8.0Hz), 7.67 (2H,d,J=9.0Hz), 8.26 (6H,m)

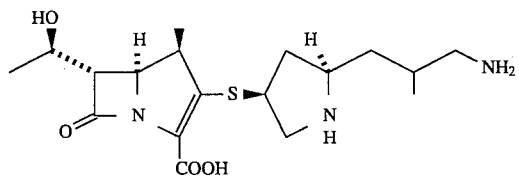
2)

The title compound (8 mg, yield: 15%) was obtained from the above diastereomer A (120 mg, 0.137 mmol) in the same manner as in EXAMPLE 1-3.

IR(KBr)cm$^{-1}$: 3400,2960,1755,1590,1395 NMR(D$_2$O) $\delta$: 0.92 (3H,d,J=7.0Hz), 1.12 (3H,d,J=7.0Hz), 1.20 (3H,d,J=7.0Hz), 1.40–2.00 (5H,m), 2.50–3.00 (3H,m), 3.10–3.40 (3H,m), 3.60–3.80 (2H,m), 4.00–4.20 (2H,m) UV $\lambda_{max}$ (0.1M MOPS buffer, pH 7.0): 298 nm ($\epsilon$=5950)

EXAMPLE 8

(1R,5S,6S)-2-[(2R,4S)-2-[(3-Amino-2-methyl)propyl]pyrrolidin-4-ylthio]-6-[(1R)-1-hydroxyethyl]-1-methyl-1-carbapen-2-em-3-carboxylic Acid Diastereomer B

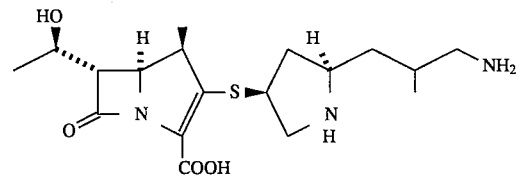

The title compound (21 mg, yield: 37%) was obtained from p-nitrobenzyl (1R,5S,6S)-6-[(1R)-1 -hydroxyethyl]-1-methyl-2-[(2R,4S)-2-[2-methyl-3-(p-nitrobenzyloxycarbonylamino)propyl]-N-(p-nitrobenzyloxycarbonyl)pyrrolidin-4-ylthio]-1-carbapen-2-em-3-carboxylate diastereomer B prepared in EXAMPLE 7-1 (130 mg, 0.148 mmol) in the same manner as in EXAMPLE 1-3.

IR(KBr)cm$^{-1}$: 3400,1755,1585,1390 NMR(D$_2$O) $\delta$: 0.98 (3H,d,J=6.0Hz), 1.15 (3H,d,J=7.0Hz), 1.23 (3H,d,J=7.0Hz), 1.30–2.00 (5H,m), 2.50–3.00 (3H,m), 3.00–3.60 (3H,m), 3.65–3.90 (2H,m), 4.10–4.25 (2H,m) UV $\lambda_{max}$ (0.1M MOPS buffer, pH 7.0): 298 nm ($\epsilon$=7250)

EXAMPLE 9

(1R,5S,6S)-2-[(2S,4S)-2-[(3-Amino-1-hydroxy)propyl]pyrrolidin-4-ylthio]-6-[(1R)-1-hydroxyethyl]-1-methyl-1-carbapen-2-em-3-carboxylic Acid Diastereomer A

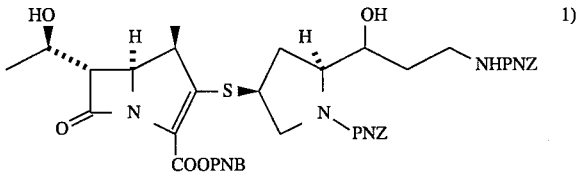
1)

p-Nitrobenzyl (1R,5S,6S)-2-[(2S,4S)-N-p-nitrobenzyloxycarbonyl- 2-[(3-p-nitrobenzyloxycarbonylamino-1-hydroxy)propyl]pyrrolidin-4-ylthio]-6-[(1R)-1-hydroxyethyl]-1-methyl-1-carbapen-2-em-3-carboxylate diastereomer A (271 mg, yield: 68%) was obtained from (2S,4S)-4-acetylthio-N-(p-nitrobenzyloxycarbonyl)-2-[(3 -p-nitrobenzyloxycarbonylamino-1-hydroxy)propyl]pyrrolidine diastereomer B prepared in REFERENCE EXAMPLE 7-6 (259 mg, 0.45 mmol) and p-nitrobenzyl (1R,5S,6S)-2 -diphenoxyphosphoryloxy-6-[(1R)-1-hydroxyethyl]-1-methyl-1-carbapen-2-em-3-carboxylate (267 mg, 0.45 mmol) in the same manner as in EXAMPLES 1-1 and 1-2.

IR(KBr)cm$^{-1}$: 3400,1770,1700,1600,1520,1350 NMR(CDCl$_3$) $\delta$: 1.26 (3H,d,J=4.0Hz), 1.37 (3H,d,J=4.0Hz), 1.44–1.82 (2H,m), 2.20–2.70 (2H,m), 3.00–3.70 (6H,m), 3.84 (1H,m), 3.94–4.35 (4H,m), 5.00–5.30 (5H,m), 5.54 (1H,d,J=7.0Hz), 7.51 (2H,d,J=5.0Hz), 7.52 (2H,d,J=5.0Hz), 7.65 (2H,d,J=5.0Hz), 8.19 (2H,d,J=5.0Hz), 8.20 (2H,d,J=5.0Hz), 8.21 (2H,d,J=5.0Hz)

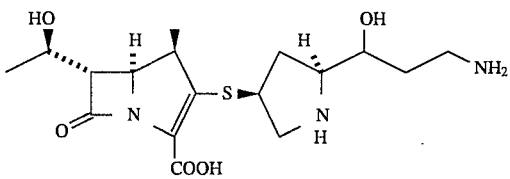 2)

A suspension of 10% palladium-carbon (135 mg) in 0.1M MOPS buffer (pH 7.0, 10 ml) was stirred under a hydrogen atmosphere for 30 min, and then the catalyst was collected by filtration, and washed with water. To a solution of the above compound (270 mg, 0.307 mmol) in tetrahydrofuran (30 ml) and 0.1M MOPS buffer (pH 7.0, 30 ml) was added the above catalyst, and the mixture was stirred for 2 h under an atmospheric pressure of hydrogen at room temperature. The catalyst was filtered off, and the filtrate was concentrated to a volume of ca. 10 ml. After the resulting precipitate was filtered off, the filtrate was further concentrated to a volume of ca. 5 ml. The filtrate was adjusted to pH 8.0 with aqueous sodium hydrogencarbonate, purified by nonionic adsorption resin column chromatography (DIAION™ HP-20SS, 5–10% methanol in water), and lyophilized to give the title compound (35 mg, yield: 30%).

IR(KBr)cm$^{-1}$: 3400,2950,1760,1730,1600,1400 NMR(D$_2$O) δ: 1.16 (3H,d,J=5.0Hz), 1.24 (3H,d,J=5.0Hz), 1.60–1.94 (2H,m), 2.24–2.64 (2H,m), 2.74–3.00 (2H,m), 3.00–3.25 (3H,m), 3.25–3.44 (2H,m), 3.64–3.83 (2H,m), 4.06–4.30 (2H,m) UV λ$_{max}$ (0.1M MOPS buffer, pH 7.0): 297 nm (ε=4870)

EXAMPLE 10

(1R,5S,6S)-2-[(2S,4S)-2-[(3-Amino-1-hydroxy) propyl]pyrrolidin-4-ylthio]-6-[(1R)-1-hydroxyethyl]-1-methyl-1-carbapen-2-em-3-carboxylic Acid Diastereomer B

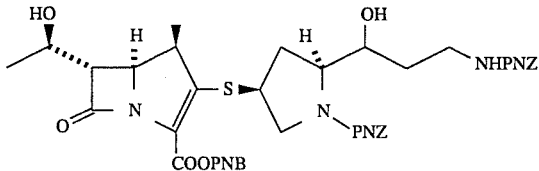 1)

p-Nitrobenzyl (1R,5S,6S)-2-[(2S,4S)-N-p-nitrobenzyloxycarbonyl- 2-[(3-p-nitrobenzyloxycarbonylamino-1 -hydroxy)propyl]pyrrolidin-4-ylthio]-6-[(1R)-1-hydroxyethyl]-1-carbapen-2-em-3-carboxylate diastereomer B (364 mg, yield: 67%) was obtained from (2S,4S)-4 -acetylthio-N-p-nitrobenzyloxycarbonyl-2-[(3-p-nitrobenzyloxycarbonylamino- 1-hydroxy)propyl]pyrrolidine diastereomer A prepared in REFERENCE EXAMPLE 7-6 (357 mg, 0.62 mmol) and p-nitrobenzyl (1R,5S,6S)-2-diphenoxyphosphoryloxy- 6-[(1R)-1-hydroxyethyl]-1-methyl-1 -carbapen-2-em-3-carboxylate (369 mg, 0.62 mmol) in the same manner as in EXAMPLES 1-1 and 1-2.

IR(KBr)cm$^{-1}$: 3400,1770,1700,1600,1520,1340 NMR(CDCl$_3$) δ: 1.26 (3H,d,J=4.0Hz), 1.34 (3H,d,J=4.0Hz), 1.40–1.80 (2H,m), 2.26–2.50 (2H,m), 3.10–3.70 (6H,m), 3.90–4.36 (5H,m), 5.04–5.30 (5H,m), 5.50 (1H,d,J=7.0Hz), 7.48 (2H,d,J=5.0Hz), 7.49 (2H,d,J=5.0Hz), 7.65 (2H,d,J=5.0Hz), 8.18 (2H,d,J=5.0Hz), 8.19 (2H,d,J=5.0Hz), 8.20 (2H,d,J=5.0Hz)

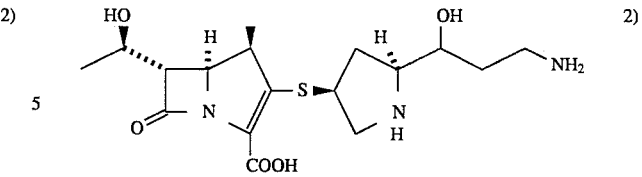 2)

The title compound (50 mg, yield: 31%) was obtained from the above compound (363 mg, 0.413 mmol) in the same manner as in EXAMPLE 9.

IR(KBr)cm$^{-1}$: 3400,2960,1760,1730,1600,1400 NMR(D$_2$O) δ: 1.18 (3H,d,J=5.0Hz), 1.26 (3H,d,J=5.0Hz), 1.40–2.10 (3H,m), 2.44 (1H,m), 2.92 (1H,m), 3.00–3.30 (4H,m), 3.30–3.46 (2H,m), 3.68–3.86 (2H,m), 4.12–4.30 (2H,m) UV λ$_{max}$ (0.1M MOPS buffer, pH 7.0): 298 nm (ε=5730)

EXAMPLE 11

(1R,5S,6S)-2-[(2S,4S)-2-(1,3-Diaminopropyl)pyrrolidin-4-ylthio]-6-[(1R)-1-hydroxyethyl]-1-methyl-1-carbapen-2-em-3-carboxylic Acid Dihydrochloride

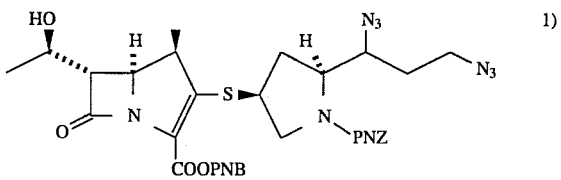 1)

p-Nitrobenzyl (1R,5S,6S)-2-[(2S,4S)-N-p-nitrobenzyloxycarbonyl- 2-(1,3-diazidopropyl)pyrrolidin-4-ylthio]-6-[(1R)-1-hydroxyethyl]-1-methyl-1-carbapen-2-em-3 -carboxylate (889 mg, yield: 95%) was obtained from (2S,4S)-4-acetylthio-N-p-nitrobenzyloxycarbonyl-2-(1,3 -diazidopropyl)pyrrolidine prepared in REFERENCE EXAMPLE 8 (560 mg, 1.25 mmol) and p-nitrobenzyl (1R,5S,6S)-2-diphenoxyphosphoryloxy-6-[(1R)-1-hydroxyethyl]-1-methyl- 1-carbapen-2-em-3-carboxylate (743 mg, 1.25 mmol) in the same manner as in EXAMPLES 1-1 and 1-2.

IR(KBr)cm$^{-1}$: 3450,2100,1770,1700,1600,1520,1340 NMR(CDCl$_3$) δ: 1.25 (3H,d,J=6.0Hz), 1.34 (3H,d,J=6.0Hz), 1.42–1.84 (2H,m), 1.98 (1H,m), 2.34 (1H,m), 2.48–3.10 (2H,m), 3.10–3.72 (5H,m), 3.82–4.52 (4H,m), 5.13 (1H,d, J=12.0Hz), 5.22 (1H,d,J=12.0Hz), 5.36 (1H,d,J=12.0Hz), 5.52 (1H,d,J=12.0Hz)

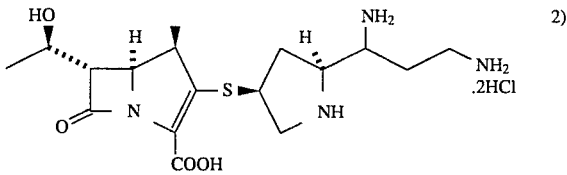 2)

The title compound (16 mg, yield: 8%) was obtained from the above compound (336 mg, 0.448 mmol) by adjusting the solution to pH 6.5 with hydrochloric acid and lyophilization in the same manner as in EXAMPLE 9.

IR(KBr)cm$^{-1}$: 3400,2950,1750,1730,1600,1400 NMR(D$_2$O) δ: 1.11 (3H,d,J=6.0Hz), 1.17 (3H,d,J=6.0Hz), 1.50–2.14 (3H,m), 2.50 (1H,m), 2.80–3.14 (2H,m), 3.20–3.38 (2H,m), 3.40–3.92 (5H,m), 4.04–4.30 (2H,m) UV λ$_{max}$ (0.1M MOPS buffer, pH 7.0): 298 nm (ε=4894)

EXAMPLE 12

(1R,5S,6S)-2-[(2S,4S)-2-[(2-Amino-1-hydroxy)ethyl]pyrrolidin-4-ylthio]-6-[(1R)-1-hydroxyethyl]-1-methyl-1-carbapen-2-em-3-carboxylic Acid Monohydrochloride Diastereomer A

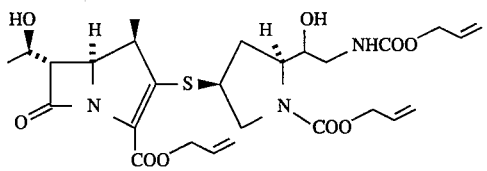 1)

Allyl (1R,5S,6S)-2-[(2S,4S)-N-allyloxycarbonyl-2-(2-allyloxycarbonylamino-1-hydroxy)ethylpyrrolidin-4-ylthio]-6-[(1R)-1-hydroxyethyl]-1-methyl-1-carbapen-2-em- 3-carboxylate Diastereomer B (105 mg, yield: 50%) was obtained from (2S,4S)-4-acetylthio-N-allyloxycarbonyl-2 -(2-allyloxycarbonylamino-1-hydroxy)ethylpyrrolidine diastereomer B prepared in REFERENCE EXAMPLE 9 (165 mg, 0.368 mmol) and allyl (1R,5S,6S)-2-diphenoxyphosphoryloxy- 6-[(1R)-1-hydroxyethyl]-1-methyl-1-carbapen-2-em-3-carboxylate (184 mg, 0.368 mmol) in the same manner as in EXAMPLES 1-1 and 1-2.

IR(KBr)cm$^{-1}$: 3400,2950,1770,1700,1650,1540,1410 NMR(CDCl$_3$) δ: 1.27 (3H,d,J=6.0Hz), 1.35 (3H,d,J=6.0Hz), 2.08 (1H,m), 2.45 (1H,m), 2.71–3.72 (7H,m), 3.83–4.39 (4H,m), 4.45–4.90 (6H,m), 5.09–5.55 (6H,m), 5.80–6.09 (3H,m)

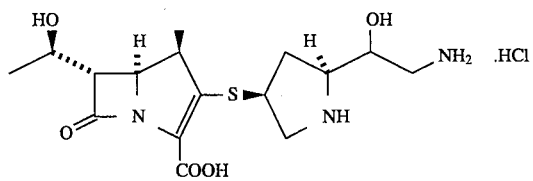 2)

The title compound (11 mg, yield: 15%) was obtained from the above compound (1.5 mg, 0.181 mmol) by adjusting the solution to pH 6.8 with hydrochloric acid and lyophilization in the same manner as in EXAMPLE 3-2.

IR(KBr)cm$^{-1}$: 3400,2950,1750,1730,1600,1390 NMR(D$_2$O) δ: 1.12 (3H,d,J=7.0Hz), 1.18 (3H,d,J=7.0Hz), 1.70 (1H,m), 2.48 (1H,m), 2.90 (1H,m), 3.00–3.68 (6H,m), 3.83 (1H,m), 3.96–4.24 (3H,m) UV λ$_{max}$ (0.1M MOPS buffer, pH 7.0): 300 nm (ε=4760)

EXAMPLE 13

(1R,5S,6S)-2-[(2S,4S)-2-[(2-Amino-1-hydroxy)ethyl]pyrrolidin-4-ylthio]-6-[(1R)-1-hydroxyethyl]-1-methyl-1-carbapen-2-em-3-carboxylic Acid Monohydrochloride Diastereomer B

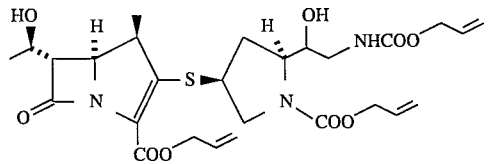 1)

Allyl (1R,5S,6S)-2-[(2S,4S)-N-allyloxycarbonyl-2-(2-allyloxycarbonylamino-1-hydroxy)ethylpyrrolidin-4-ylthio]-6-[(1R)-1-hydroxyethyl]-1-methyl-1-carbapen-2-em- 3-carboxylate diastereomer A (164 mg, yield: 58%) was obtained from (2S,4S)-4-acetylthio-N-allyloxycarbonyl-2 -(2-allyloxycarbonylamino-1-hydroxy)ethylpyrrolidine diastereomer A prepared in REFERENCE EXAMPLE 9 (183 mg, 0.491 mmol) and allyl (1R,5S,6S)-2-diphenoxyphosphoryloxy- 6-[(1R)-1-hydroxyethyl]-1-methyl-1 -carbapen-2-em-3-carboxylate (245 mg, 0.491 mmol) in the same manner as in EXAMPLES 1-1 ad 1-2.

IR(KBr)cm$^{-1}$: 3400,2950,1780,1700,1650,1540,1410 NMR(CDCl$_3$) δ: 1.26 (3H,d,J=7.0Hz), 1.34 (3H,d,J=7.0Hz), 1.82 (1H,m), 2.60 (1H,m), 3.00–3.62 (7H,m), 3.78 (1H,m), 3.94–4.36 (3H,m), 4.46–4.92 (6H,m), 5.16–5.68 (6H,m), 5.76–6.14 (3H,m)

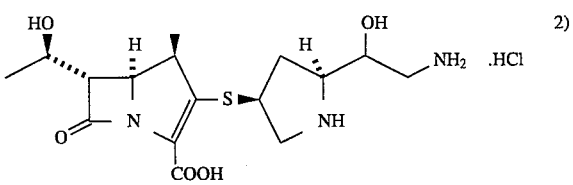 2)

The title compound (10 mg, yield: 8%) was obtained from the above compound (164 mg, 0.283 mmol) by adjusting the solution to pH 6.8 with hydrochloric acid and lyophilization in the same manner as in EXAMPLE 3-2.

IR(KBr)cm$^{-1}$: 3400,2950,1740,1730,1600,1390 NMR(D$_2$O) δ: 1.12 (3H,d,J=7.0Hz), 1.19 (3H,d,J=7.0Hz), 1.60 (1H,m), 2.52 (1H,m), 2.92 (1H,m), 3.08–3.70 (6H,m), 3.80–4.06 (2H,m), 4.08–4.20 (2H,m) UV λ$_{max}$ (0.1M MOPS buffer, pH 7.0): 299 nm (ε=5390)

EXAMPLE 14

(1R,5S,6S)-2-[(2R,4S)-2-[(3-Amino-2,2-dimethyl)propyl]pyrrolidin-4-ylthio]-6-[(1R)-1-hydroxyethyl]-1-methyl-1 -carbapen-2-em-3-carboxylic Acid

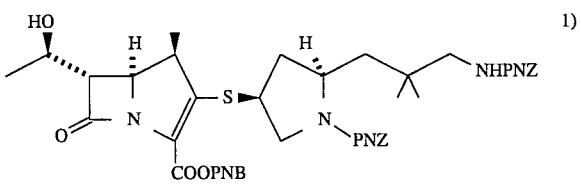 1)

p-Nitrobenzyl (1R,5S,6S)-2-[(2R,4S)-2-[(2,2 -dimethyl-3-p-nitrobenzyloxycarbonylamino)propyl]-N-p-nitrobenzyloxycarbonylpyrrolidin- 4-ylthio]-6-[(1R)-1 -hydroxyethyl]-1-methyl-1-carbapen-2-em-3-carboxylate (350 mg, yield: 80%) was obtained from (2R,4S)-4 -acetylthio-2-[2,2-dimethyl-3-(p-nitrobenzyloxycarbonylamino)propyl]-N-p-nitrobenzyloxycarbonylpyrrolidine prepared in REFERENCE EXAMPLE 10 (290 mg, 0.493 mmol) and p-nitrobenzyl (1R,5S,6S)-2-diphenoxyphosphoryloxy-6 -[(1R)-1-hydroxyethyl]-1-methyl-1-carbapen-2-em-3 -carboxylate (300 mg, 0.505 mmol) in the same manner as in EXAMPLES 1-1 and 1-2.

IR(KBr)cm$^{-1}$: 3420,2960,1775,1700,1605,1520,1400, 1345, 1205,1140,1105,850,735 NMR(CDCl$_3$) δ: 0.90 (6H, s), 1.28 (3H,d,J=7.0Hz), 1.37 (3H,d,J=6.0Hz), 1.50–1.90 (4H,m), 2.70 (1H,m), 3.00 (1H,m), 3.10–3.65 (4H,m), 3.66 (1H,m), 4.27 (2H,m), 3.92 (2H,m), 5.10–5.60 (6H,m), 6.48 (1H,m), 7.52 (4H,m), 7.66 (2H,d,J=8.0Hz), 8.22 (6H,m)

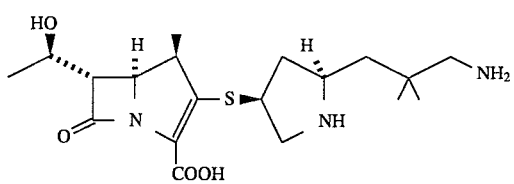
1)

The title compound (53 mg, yield: 37%) was obtained from the above compound (320 mg, 0.359 mmol) in the same manner as in EXAMPLE 1-3.

IR(KBr)cm$^{-1}$: 3420,2960,1750,1590,1380,1255 NMR(D$_2$O) δ: 0.96 & 0.98 (total 6H,each s), 1.16 (3H,d,J=7.0Hz), 1.24 (3H,d,J=7.0Hz), 1.65 (2H,d,J=6.0Hz), 2.56 (1H,m), 2.77 (2H,s), 2.96 (1H,m), 3.10–3.65 (4H,m), 3.65–3.80 (2H,m), 4.10–4.30 (2H,m) UV λ$_{max}$ (0.1M MOPS buffer, pH 7.0): 298 nm (ε=6830)

EXAMPLE 15

(1R,5S,6S)-2-[(2R,4S)-2-[(2,2-Dimethyl-3-N-methylamino)propyl]pyrrolidin-4-ylthio]-6-[(1R)-1-hydroxyethyl]-1-methyl-1-carbapen-2-em-3-carboxylic Acid

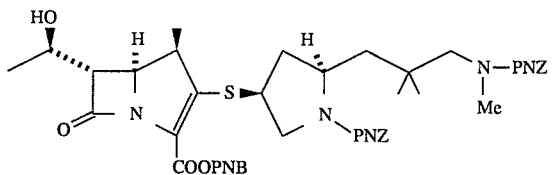
1)

p-Nitrobenzyl (1R,5S,6S)-2-[(2R,4S)-2-[(2,2-dimethyl-3-N-methyl-N-p-nitrobenzyloxycarbonylamino)propyl]-N-p-nitrobenzyloxycarbonylpyrrolidin-4-ylthio]-6-[(1R)-1-hydroxyethyl]-1-methyl-1-carbapen-2-em-3-carboxylate (470 mg, yield: quantitative) was obtained from (2R,4S)-4-acetylthio-2-[(2,2-dimethyl-3-N-methyl-N-p-nitrobenzyloxycarbonylamino)propyl]-N-p-nitrobenzyloxycarbonylpyrrolidine prepared in REFERENCE EXAMPLE 11 (310 mg, 0.514 mmol) and (1R,5S,6S)-2-diphenoxyphosphoryloxy-6-[(1R)-1-hydroxyethyl]-1-methyl-1-carbapen-2-em-3-carboxylate (310 mg, 0.521 mmol) in the same manner as in EXAMPLES 1-1 and 1-2.

IR(KBr)cm$^{-1}$: 3440,2960,1770,1700,1605,1520,1400,1245, 1205,1140,1105,855,735 NMR(CDCl$_3$) δ: 0.92 & 1.02 (total 6H,each br s), 1.27 (3H,d,J=7.0Hz), 1.37 (3H,d,J=7.0Hz), 1.55–1.90 (4H,m), 2.67 (1H,m), 3.02 (3H,br s), 3.05–3.50 (5H,m), 3.56 (1H,m), 4.02 (2H,m), 4.28 (2H,m), 5.00–5.55 (6H,m), 7.52 (4H,d,J=8.0Hz), 7.66 (2H,d,J=8.0Hz), 8.23 (6H,d,J=8.0Hz)

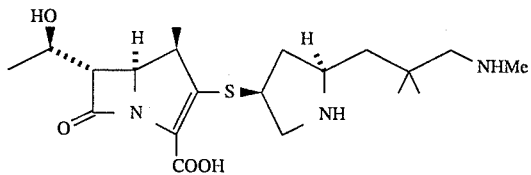
2)

The title compound (108 mg, yield: 52%) was obtained from the above compound (460 mg, 0.508 mmol) in the same manner as in EXAMPLE 1-3.

IR(KBr)cm$^{-1}$: 3420,2960,1750,1595,1390,1250,1095 NMR(D$_2$O) δ: 1.00 & 1.02 (total 6H,each s), 1.17 (3H,d,J=7.0Hz), 1.25 (3H,d,J=6.0Hz), 1.70 (2H,d,J=7.0Hz), 2.45–2.70 (1H,m), 2.63 (3H,s), 2.84 (2H,s), 3.01 (1H,m), 3.20–3.45 (4H,m), 3.65–3.85 (2H,m), 4.10–4.30 (2H,m) UV λ$_{max}$ (0.1M MOPS buffer, pH 7.0): 297 nm (ε=6580)

EXAMPLE 16

(1R,5S,6S)-2-[(2S,4S)-2-(1-Aminomethyl-3-hydroxy)propylpyrrolidin-4-ylthio]-6-[(1R)-1-hydroxyethyl]-1-methyl-1-carbapen-2-em-3-carboxylic Acid Diastereomer B

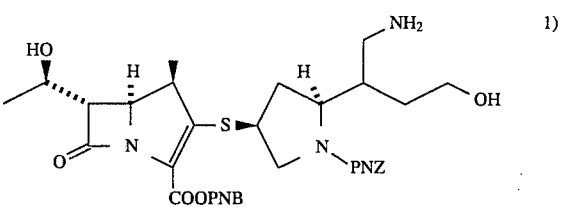
1)

p-Nitrobenzyl (1R,5S,6S)-2-[(2S,4S)-2-[(1-aminomethyl-3-hydroxy)propyl]-N-p-nitrobenzyloxycarbonylpyrrolidin-4-ylthio]-6-[(1R)-1-hydroxyethyl]-1-methyl-1-carbapen-2-em-3-carboxylate diastereomer B (217 mg, yield: 45%) was obtained from (2S,4S)-4-acetylthio-2-(1-aminomethyl-3-hydroxy)propyl-N-p-nitrobenzyloxycarbonylpyrrolidine diasteremer A prepared in REFERENCE EXAMPLE 12 (319 mg, 0.54 mmol) and p-nitrobenzyl (1R,5S,6S)-2-diphenylphosphoryloxy-6-[(1R)-1-hydroxyethyl]-1-methyl-1-carbapen-2-em-3-carboxylate (321 mg, 0.54 mmol) in the same manner as in EXAMPLES 1-1 and 1-2.

IR(KBr)cm$^{-1}$: 3420,1770,1700,1605,1520,1345,1205, 1140,1110,850,735 NMR(CDCl$_3$) δ: 1.27 (3H,d,J=6.0Hz), 1.36 (3H,d,J=7.0Hz), 1.50–1.80 (3H,m), 2.00 (1H,m), 2.32 (1H,m), 2.50 (1H,m), 3.10–3.40 (5H,m), 3.51 (1H,m), 3.76 (2H,m), 4.10–4.30 (4H,m), 5.18 (2H,s), 5.20 (2H,s), 5.29 (1H,d,J=14.0Hz), 5.52 (1H,d,J=14.0Hz), 7.49 (2H,d,J=8.0Hz), 7.50 (2H,d,J=8.0Hz), 7.66 (2H,d,J=9.0Hz), 8.21 (2H,d,J=8.0Hz), 8.22 (2H,d,J=8.0Hz), 8.23 (2H,d,J=9.0Hz)

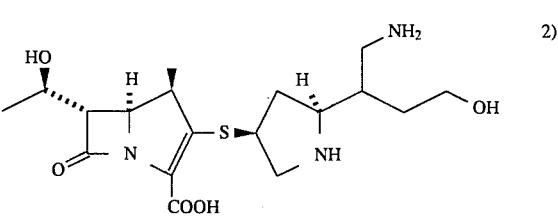
2)

The title compound (54 mg, yield: 56%) was obtained from the above compound (206 mg, 0.24 mmol) in the same manner as in EXAMPLE 1-3.

IR(KBr)cm$^{-1}$: 3400,1750,1600,1390 NMR(D$_2$O) δ: 1.23 (3H,d,J=6.0Hz), 1.31 (3H,d,J=7.0Hz), 1.45–1.80 (2H,br m), 2.14 (1H,m), 2.50 (1H,m), 2.76 (1H,m), 2.95–3.10 (2H,m), 3.10–3.50 (4H,m), 3.72 (2H,m), 3.84 (2H,m), 4.20–4.30 (2H,m)

EXAMPLE 17

(1R,5S,6S)-2-[(2S,4S)-2-[(1R)-1-Methoxy-3-N-methylaminopropyl]pyrrolidin-4-ylthio]-6-[(1R)-1-hydroxyethyl]-1-methyl-1-carbapen-2-em-3-carboxylic Acid Monohydrochloride

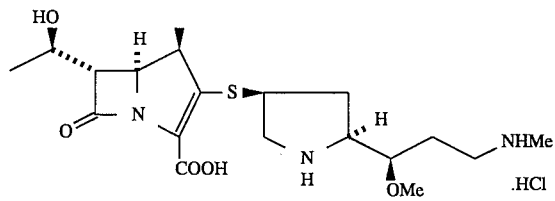

To a solution of the compound prepared in REFERENCE EXAMPLE 14-4 (287 mg, 0.643 mmol) in methanol (1 ml) was added 2N hydrochloric acid-methanol solution (1.3 ml), and the mixture was stirred for 3 days at room temperature. The solvent was removed in vacuo, and the residue was dissolved in a mixed solution of acetonitrile (1.5 ml) and N,N-dimethylformamide (0.5 ml). Under a nitrogen atmosphere at –20° C., to the solution was successively added N,N-diisopropylethylamine (0.22 ml, 1.25 mmol), a solution of p-nitrobenzyl (1R,5S,6S)-2-diphenoxyphosphoryloxy-6-[(1R)-1-hydroxyethyl]-1-methyl-1-carbapen-2-em-3 -carboxylate (344 mg, 0.579 mmol) in acetonitrile (8 ml) and N,N-diisopropylethylamine (0.11 ml, 0.62 mmol), and the mixture was stirred overnight at 5° C. To the reaction mixture was added tetrahydrofuran (15 ml), 0.5 M MOPS buffer (pH 7.0, 0.15 ml), ethanol (4.5 ml) and 10 % palladium-carbon catalyst (0.32 g), and the mixture was stirred for 1 h under a hydrogen atmosphere at room temperature. The catalyst was filtered off, and the filtrate was concentrated to ca. 15 ml in vacuo. The residue was washed with chloroform, and the aqueous layer was concentrated to 2 ml in vacuo. The residue was purified with reverse phase silica gel column chromatography (20% methanol-water), adjusted to pH 5.0 with hydrochloric acid and lyophilized to give the title compound (84 mg, yield: 32%).

IR(KBr)cm$^{-1}$: 3420,2960,1760,1600,1460,1395,1180 NMR(D$_2$O) δ: 1.14 (3H,d,J=7.0Hz), 1.20 (3H,d,J=7.0Hz), 1.70–2.20 (3H,m), 2.60 (1H,m), 2.66 (3H,s), 3.00–3.64 (5H,m), 3.60 (3H,s), 3.78–4.00 (4H,m), 4.08–4.24 (2H,m) UV λ$_{max}$ (0.1M MOPS buffer, pH 7.0): 300 nm (ε=8,810)

EXAMPLE 18

(1R,5S,6S)-2-[(2S,4S)-2-[(1S)-1-Hydroxy-3-N-methylamino]propylpyrrolidin-4-ylthio]-6-[(1R)-1-hydroxyethyl]-1-methyl-1-carbapen-2-em-3-carboxylic Acid Monohydrochloride

1)

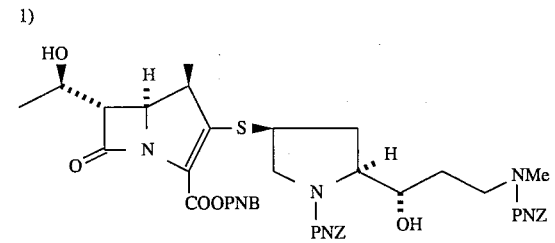

p-Nitrobenzyl (1R,5S,6S)-2-[(2S,4S)-N-p-nitrobenzyloxycarbonyl- 2-[[(1S)-1-hydroxy-3-(N-p-nitrobenzyloxycarbonyl-N-methylamino)] propyl]pyrrolidin-4-ylthio]-6-[(1R)-1-hydroxyethyl]-1-methyl-1-carbapen-2-em-3 -carboxylate (1.26 g, yield: 60%) was obtained from (2S,4S)-4-acetylthio-2-[[(1S)-1-hydroxy-3 -(N-p-nitrobenzyloxycarbonyl-N-methylamino)]propyl]-N-(p-nitrobenzyloxycarbonyl)pyrrolidine prepared in REFERENCE EXAMPLE 15-3 (1.46 g, 2.47 mmol) and p-nitrobenzyl (1R,5S,6S)-2-diphenoxyphosphoryloxy-6-[(1R)-1-hydroxyethyl]-1-methyl-1-carbapen-2-em-3-carboxylate (1.47 g, 2.47 mmol) in the same manner as in EXAMPLES 1-1 and 1 -2.

IR(KBr)cm$^{-1}$: 3430,2950,1780,1700,1610,1520,1400, 1350, 1210,1140,1110 NMR(CDCl$_3$) δ: 1.27 (3H,d,J= 7.3Hz), 1.37 (3H,d,J=6.3Hz), 1.40–2.00 (3H,m), 2.50 (1H, m), 2.94 (3H,m), 3.10–3.80 (6H,m), 4.00–4.35 (5H,m), 5.10–5.30 (5H,m), 5.50 (1H,d,J=13.9Hz), 7.40–7.60 (4H, m), 7.65 (2H,d,J=8.6Hz), 8.18–8.30 (6H,m)

2)

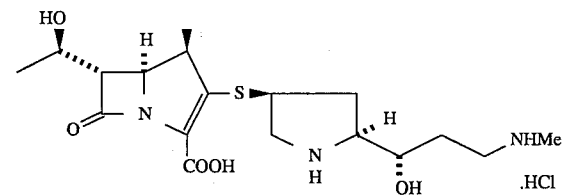

The title compound (122 mg, yield: 20%) was obtained from the above compound (1.26 g, 1.41 mmol) by adjusting the solution to pH 5.0 with hydrochloric acid and lyophilization in the same manner as in EXAMPLE 1-3.

IR(KBr)cm$^{-1}$: 3400,2960,2930,1760,1590,1390 NMR(D$_2$O) δ: 1.37 (3H,d,J=7.3Hz), 1.45 (3H,d,J=6.6Hz), 1.85–2.22 (3H,m), 2.84 (1H,m), 2.90 (3H,s), 3.30–3.68 (5H,m), 3.80–4.00 (2H,m), 4.08–4.30 (2H,m), 4.30–4.45 (2H,m) UV λ$_{max}$ (0.1M MOPS buffer, pH 7.0): 298 nm (ε=9,270)

EXAMPLE 19

(1R,5S,6S)-2-[(2S,4S)-2-[(1R)-1-Hydroxy-3-N-methylamino]propylpyrrolidin-4-ylthio]-6-[(1R)-1-hydroxyethyl]-1-methyl-1-carbapen-2-em-3-carboxylic Acid Monohydrochloride

1)

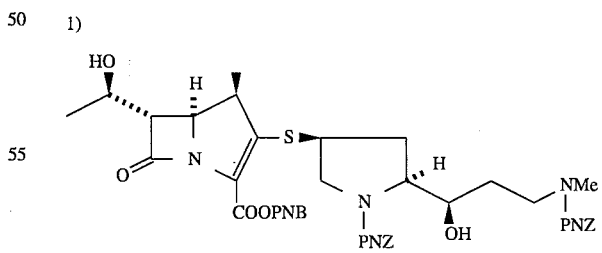

p-Nitrobenzyl (1R,5S,6S)-2-[(2S,4S)-N-p-nitrobenzyloxycarbonyl- 2-[[(1R)-1-hydroxy-3-(N-p-nitrobenzyloxycarbonyl-N-methylamino)]propyl]pyrrolidin-4-ylthio]-6-[(1R)-1-hydroxyethyl]-1-methyl-1-carbapen-2-em-3 -carboxylate (1.58 g, yield: 81%) was obtained from (2S,4S)-4-acetylthio-2-[[(1R)-1-hydroxy-3 -(N-p-nitrobenzyloxycarbonyl-N-methylamino)]propyl]-N-(p- nitrobenzyloxycarbonyl)pyrrolidine prepared in REFERENCE EXAMPLE 15-3 (1.29 g, 2.18 mmol) and p-nitrobenzyl (1R,5S,6S)-2-diphenoxyphosphoryloxy-6-[(1R)-1-hydroxyethyl]-1-methyl-1-carbapen-2-em-3-carboxylate (1.30 g, 2.18 mmol) in the same manner as in EXAMPLES 1-1 and 1-2.

IR(KBr)cm$^{-1}$: 3420,2940,1770,1700,1600,1520,1400, 1340, 1210,1140,1110 NMR(CDCl$_3$) δ: 1.28 (3H,d,J=7.3Hz), 1.37 (3H,d,J=5.9Hz), 1.50–2.40 (4H,m), 2.95 (3H,s), 3.00–3.70 (5H,m), 3.80–4.40 (6H,m), 5.10–5.40 (5H,m), 5.50 (1H,d,J=13.9Hz), 7.40–7.60 (4H,m), 7.65 (2H,d,J=8.9Hz), 8.15–8.30 (6H,m)

2)

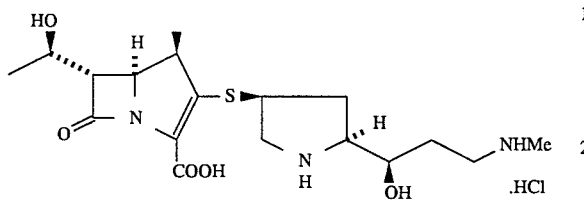

The title compound (269 mg, yield: 35%) was obtained from the above compound (1.58 g, 1.77 mmol) in the same manner as in EXAMPLE 18-2.

IR(KBr)cm$^{-1}$: 3420,2970,1760,1620,1400 NMR(D$_2$O) δ: 1.30 (3H,d,J=6.9Hz), 1.37 (3H,d,J=6.3Hz), 1.80–2.15 (3H,m), 2.70 (1H,m), 2.82 (3H,s), 3.20–3.60 (5H,m), 3.70–3.90 (2H,m), 3.95–4.20 (2H,m), 4.20–4.40 (2H,m) UV λ$_{max}$ (0.1M MOPS buffer, pH 7.0): 299 nm (ε=9,030)

EXAMPLE 20

(1R,5S,6S)-2-[(2S,4S)-2-[(1S)-1-Hydroxy-2-N-methylamino]ethylpyrrolidin-4-ylthio]-6-[(1R)-1-hydroxyethyl]-1-methyl-1-carbapen-2-em-3-carboxylic Acid Monohydrochloride

1)

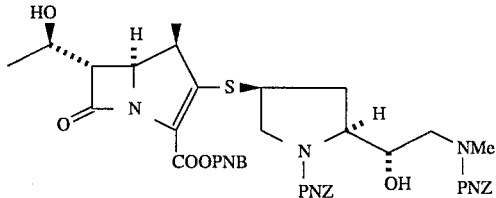

p-Nitrobenzyl (1R,5S,6S)-2-[(2S,4S)-N-p-nitrobenzyloxycarbonyl- 2-[[(1S)-1-hydroxy-2-(N-p-nitrobenzyloxycarbonyl-N-methylamino)]ethylpyrrolidin-4-ylthio]-6-[(1R)-1-hydroxyethyl]-1-methyl-1-carbapen-2-em-3-carboxylate (661 mg, yield: 65%) was obtained from (2S,4S)-4-acetylthio-2-[[(1S)-1-hydroxy-2 -(N-p-nitrobenzyloxycarbonyl-N-methylamino)]ethyl]-N-(p-nitrobenzyloxycarbonyl)pyrrolidine prepared in REFERENCE EXAMPLE 16-3 (670 mg, 1.16 mmol) in the same manner as in EXAMPLES 1-1 and 1-2.

IR(KBr)cm$^{-1}$: 3450,2950,1770,1700,1610,1520,1400, 1340 NMR(CDCl$_3$) δ: 1.27 (3H,d,J=6.9Hz), 1.38 (3H,d,J=6.3Hz), 1.90 (1H,m), 2.60 (1H,m), 3.06 (3H,s), 3.20–3.60 (7H,m), 3.90–4.30 (4H,m), 5.10–5.35 (5H,m), 5.51 (1H,d, J=13.5Hz), 7.50–7.60 (4H,m), 7.65 (2H,d,J=8.9Hz), 8.15–8.30 (6H,m)

2)

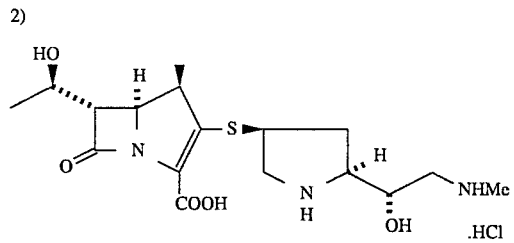

The title compound (53 mg, yield: 17%) was obtained from the above compound (656 mg, 0.746 mmol) in the same manner as in EXAMPLE 18-2.

IR(KBr)cm$^{-1}$: 3420,2960,1770,1600,1390 NMR(D$_2$O) δ: 1.29 (3H,d,J=7.3Hz), 1.36 (3H,d,J=6.6Hz), 1.86 (1H,m), 2.82 (1H,m), 2.86 (3H,s), 3.20 (1H,m), 3.35–3.60 (4H,m), 3.75–3.90 (2H,m), 4.15 (1H,m), 4.25–4.40 (3H,m) UV λ$_{max}$ (0.1M MOPS buffer, pH 7.0): 299 nm (ε=9,810)

EXAMPLE 21

(1R,5S,6S)-2-[(2S,4S)-2-[(1R)-1-Hydroxy-2-N-methylaminoethyl]pyrrolidin-4-ylthio]-6-[(1R)-1-hydroxyethyl]-1-methyl-1-carbapen-2-em-3-carboxylic Acid Monohydrochloride

1)

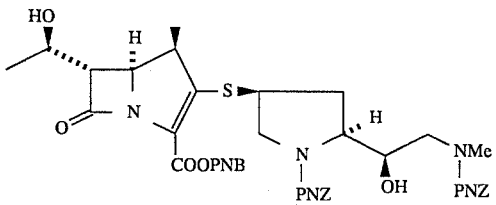

p-Nitrobenzyl (1R,5S,6S)-2-[(2S,4S)-N-p-nitrobenzyloxycarbonyl- 2-[[(1R)-1-hydroxy-2-(N-p-nitrobenzyloxycarbonyl-N-methylamino)]ethyl]pyrrolidin-4-ylthio]-6-[(1R)-1-hydroxyethyl]-1-methyl-1-carbapen-2-em-3 -carboxylate (1.87 g, yield: 55%) was obtained from (2S,4S)-4-acetylthio-2-[[(1R)-1-hydroxy-2 -(N-p-nitrobenzyloxycarbonyl-N-methylamino)]ethyl]-N-(p-nitrobenzyloxycarbonyl)pyrrolidine prepared in REFERENCE EXAMPLE 17-3 (2.00 g, 3.85 mmol) and p-nitrobenzyl (1R,5S,6S)-2-diphenoxyphosphoryloxy-6-[(1R)-1-hydroxyethyl]-1-methyl-1-carbapen-2-em-3-carboxylate (2.29 g, 3.85 mmol) in the same manner as in EXAMPLES 1-1 and 1-2.

IR(KBr)cm$^{-1}$: 3440,2970,2940,1770,1700,1610,1520, 1400, 1340,1210,1140,1110 NMR(CDCl$_3$) δ: 1.25 (3H,d,J=7.3Hz), 1.37 (3H,d,J=6.3Hz), 2.00–2.50 (2H,m), 3.04 (3H,s), 3.00–3.80 (8H,m), 3.95–4.40 (3H,m), 5.10–5.35 (5H,m), 5.51 (1H,d,J=13.5Hz), 7.40–7.60 (4H,m), 7.65 (2H,d,J=8.6Hz), 8.15–8.30 (6H,m)

2)

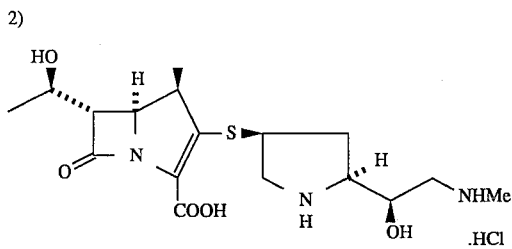

The title compound (256 mg, yield: 29%) was obtained from the above compound (1.87 g, 2.13 mmol) in the same manner as in EXAMPLE 18-2.

IR(KBr)cm$^{-1}$: 3420,2970,1760,1600,1400 NMR(D$_2$O) δ: 1.19 (3H,d,J=7.6Hz), 1.25 (3H,d,J=6.6Hz), 1.92 (1H,m), 2.62 (1H,m), 2.75 (3H,s), 3.05 (1H,m), 3.15–3.60 (4H,m), 3.70 (1H,m), 3.82 (1H,m), 4.02 (1H,m), 4.15–4.25 (2H,m), 4.35 (1H,m) UV λ$_{max}$ (0.1M MOPS buffer, pH 7.0): 300 nm (ε=9,440)

EXAMPLE 22

(1R,5S,6S)-6-[(1R)-1-Hydroxyethyl]-1-methyl-2-[[(2R,4S)-2-[2-(N-methylamino)]propyl]pyrrolidin-4-ylthio]-1-carbapen-2-em-3-carboxylic Acid Monohydrochloride Diastereomer A

1)

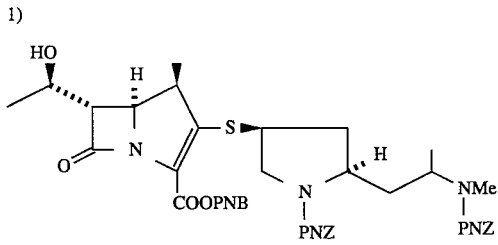

p-Nitrobenzyl (1R,5S,6S)-6-[(1R)-1-hydroxyethyl]-1-methyl-2-[(2R,4S)-2-[2-(N-methyl-N-p-nitrobenzyloxycarbonylamino)propyl]-N-p-nitrobenzyloxycarbonylpyrrolidin-4-ylthio]-1-carbapen-2-em-3-carboxylate diastereomer A (480 mg, yield: 81%) was obtained from (2R,4S)-4-acetylthio-2-[2-(N-methyl-N-p-nitrobenzyloxycarbonylamino)propyl]-N-p-nitrobenzyloxycarbonylpyrrolidine diastereomer A prepared in REFERENCE EXAMPLE 18 (390 mg, 0.679 mmol) and p-nitrobenzyl (1R,5S,6S)-2-diphenoxyphosphoryloxy-6-[(1R)-1-hydroxyethyl]-1-methyl-1-carbapen-2-em-3-carboxylate (400 mg, 0.673 mmol) in the same manner as in EXAMPLES 1-1 and 1-2.

IR(KBr)cm$^{-1}$: 3420,2960,1770,1700,1605,1520,1445, 1400, 1345,1205,1135,850,735 NMR(CDCl$_3$) δ: 1.05–1.30 (3H,m), 1.25 (3H,d,J=7.0Hz), 1.36 (3H,d,J=6.0Hz), 1.60–2.40 (4H,m), 2.48 (1H,m), 2.78 (3H,s), 3.20–3.40 (3H,m), 3.54 (1H,m), 3.85–4.20 (2H,m), 4.20–4.50 (3H,m), 5.10–5.60 (6H,m), 7.51 (4H,d,J=8.0Hz), 7.65 (2H,d,J=9.0Hz), 8.21 (6H,d,J=9.0Hz)

2)

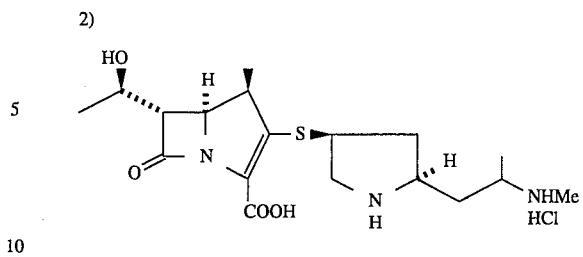

The title compound (114 mg, yield: 50%) was obtained from the above compound (480 mg, 0.547 mmol) in the same manner as in EXAMPLE 1-3 excepting that the column eluate was adjusted to pH 6.0 with 0.1N HCl, concentrated, and lyophilized.

IR(KBr)cm$^{-1}$: 3410,2960,1760,1590,1455,1390,1280, 1255, 1145 NMR(D$_2$O) δ: 1.28 (3H,d,J=7.0Hz), 1.34 (3H, d,J=6.0Hz), 1.42 (3H,d,J=7.0Hz), 1.80 (1H,m), 2.15–2.40 (2H,m), 2.79 (3H,s), 2.85 (1H,m), 3.35–3.60 (4H,m), 3.76 (1H,m), 3.90 (1H,m), 4.10 (1H,m), 4.25–4.35 (2H,m) UV λ$_{max}$ (0.1M MOPS buffer, pH 7.0): 299 nm (ε=9,200)

EXAMPLE 23

(1R,5S,6S)-6-[(1R)-1-Hydroxyethyl]-1-methyl-2-[(2R,4S)-2-[2-(N-methylamino)propyl]pyrrolidin-4-ylthio]-1-carbapen-2-em-3-carboxylic Acid Monohydrochloride Diastereomer B

1)

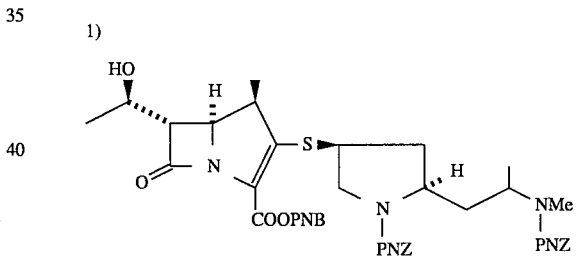

p-Nitrobenzyl (1R,5S,6S)-6-[(1R)-1-hydroxyethyl]-1-methyl-2-[(2R,4S)-2-[2-(N-methyl-N-p-nitrobenzyloxycarbonylamino)propyl]-N-p-nitrobenzyloxycarbonylpyrrolidin-4-ylthio]-1-carbapen-2-em-3-carboxylate diastereomer B (70 mg, yield: 57%) was obtained from (2R,4S)-4-acetylthio-2-[2-(N-methyl-N-p-nitrobenzyloxycarbonylamino)propyl]-N-p-nitrobenzyloxycarbonylpyrrolidine diastereomer B prepared in REFERENCE EXAMPLE 19 (80 mg, 0.139 mmol) and p-nitrobenzyl (1R,5S,6S)-2-diphenoxyphosphoryloxy-6-[(1R)-1-hydroxyethyl]-1-methyl-1-carbapen-2-em-3-carboxylate (90 mg, 0.151 mmol) in the same manner as in EXAMPLES 1-1 and 1-2.

IR(KBr)cm$^{-1}$: 3440,2960,1770,1700,1605,1520,1445, 1400, 1345,1205,1135,1105,850,735 NMR(CDCl$_3$) δ: 1.14 (3H,d,J=6.0Hz), 1.26 (3H,d,J=7.0Hz), 1.37 (3H,d,J=6.0Hz), 1.60–2.80 (4H,m), 2.90 (3H,s), 3.20–3.40 (3H,m), 3.56 (1H,m), 3.71 (1H,m), 3.98 (1H,m), 4.20–4.40 (3H,m), 5.10–5.60 (6H,m), 7.51 (4H,d,J=9.0Hz), 7.65 (2H,d,J=9.0Hz), 8.22 (6H,d,J=9.0Hz)

2)

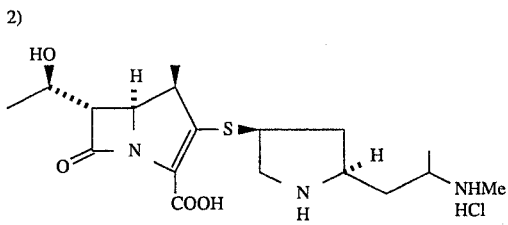

The title compound (17 mg, yield: 51%) was obtained from the above compound (70 mg, 0.080 mmol) in the same manner as in EXAMPLE 22-2.

IR(KBr)cm$^{-1}$: 3420,2970,1760,1600,1455,1390,1260, 1150, 1040 NMR(D$_2$O) δ: 1.24 (3H,d,J=7.0Hz), 1.31 (3H, d,J=6.0Hz), 1.41 (3H,d,J=7.0Hz), 1.74 (1H,m), 2.12 (1H,m), 2.75 (3H,s), 2.83 (1H,m), 3.20–3.50 (3H,m), 3.50 (1H,m), 3.63 (1H,m), 3.82 (1H,m), 3.90–4.10 (1H,m), 4.20–4.35 (2H,m) UV λ$_{max}$ (0.1M MOPS buffer, pH 7.0): 299 nm (ε=8,600)

EXAMPLE 24

(1R,5S,6S)-2-[(2R,4S)-2-[3-Hydroxy-2-(N-methylamino)propyl]pyrrolidin-4-ylthio]-6-[(1R)-1-hydroxyethyl]-1-methyl-1-carbapen-2-em-3-carboxylic Acid Monohydrochloride Diastereomer A

1)

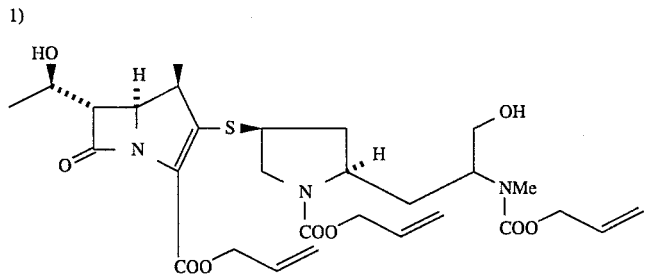

Allyl (1R,5S,6S)-2-[(2R,4S)-N-allyloxycarbonyl-2-[2-(N-allyloxycarbonyl-N-methylamino)-3-hydroxy]propyl pyrrolidin-4-ylthio]-6-[(1R)-1-hydroxyethyl]-1-methyl-1-carbapen-2-em-3-carboxylate diastereomer A (70 mg, yield: 38%) was obtained from (2R,4S)-N-allyloxycarbonyl-2-[2-(N-allyloxycarbonyl-N-methylamino)-3-hydroxy]propyl-4-triphenylmethythiopyrrolidine diastereomer A prepared in REFERENCE EXAMPLE 20 (180 mg, 0.30 mmol) and allyl (1R,5S,6S)-2-diphenoxyphosphoryloxy-6-[(1R)-1-hydroxyethyl]-1-methyl-1-carbapen-2-em-3-carboxylate (160 mg, 0.32 mmol) in the same manner as in EXAMPLE 3-1.

IR(KBr)cm$^{-1}$: 3430,1775,1695,1450,1405,1325,1280, 1200, 1140,1040,980,930,765 NMR(CDCl$_3$) δ: 1.26 (3H,d, J=7.0Hz), 1.35 (3H,d,J=6.0Hz), 1.20–2.40 (5H,m), 2.57 (1H,m), 2.84 (3H,s), 3.20–3.45 (3H,m), 3.45–3.80 (3H,m), 3.90–4.15 (2H,m), 4.15–4.40 (3H,m), 4.50–4.90 (6H,m), 5.20–5.50 (6H,m), 5.85–6.05 (3H,m)

2)

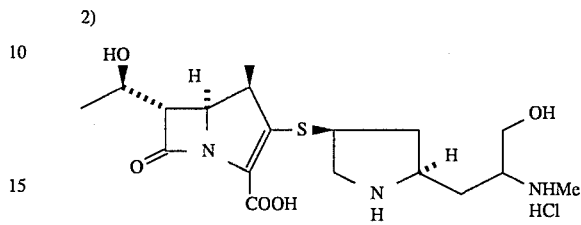

The title compound (7 mg, yield: 16%) was obtained from the above compound (60 mg, 0.099 mmol) in the same manner as in EXAMPLE 18-2.

IR(KBr)cm$^{-1}$: 3400,1755,1590,1455,1390,1260,1150, 1040 NMR(D$_2$O) δ: 1.25 (3H,d,J=7.0Hz), 1.32 (3H,d,J= 7.0Hz), 1.78 (1H,m), 2.15–2.45 (2H,m), 2.80 (3H,s), 2.83 (1H,m), 3.25–3.55 (4H,m), 3.60–3.90 (3H,m), 3.90–4.10 (2H,m), 4.20–4.35 (2H,m) UV λ$_{max}$ (0.1M MOPS buffer, pH 7.0): 298 nm (ε=7,400)

EXAMPLE 25

(1R,5S,6S)-2-[(2R,4S)-2-[3-Hydroxy-2-(N-methylamino)propyl]pyrrolidin-4-ylthio]-6-[(1R)-1-hydroxyethyl]-1-methyl-1-carbapen-2-em-3-carboxylic Acid Monohydrochloride Diastereomer B

1)

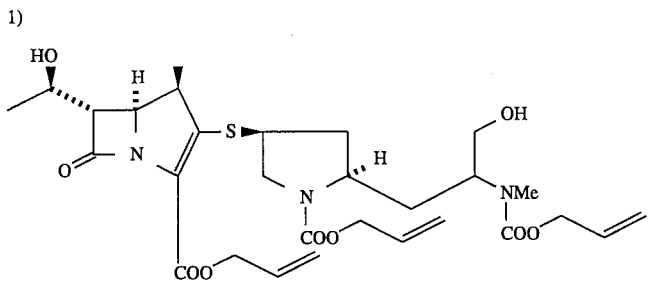

Allyl (1R,5S,6S)-2-[(2R,4S)-N-allyloxycarbonyl-2-[2-(N-allyloxycarbonyl-N-methylamino)-3-hydroxy]propylpyrrolidin- 4-ylthio]-6-[(1R)-1-hydroxyethyl]-1-methyl-1-carbapen-2-em-3-carboxylate diastereomer B (90 mg, yield: 49%) was obtained from (2R,4S)-N-allyloxycarbonyl- 2-[2-(N-allyloxycarbonyl-N-methylamino)-3 -hydroxy]propyl-4-(triphenylmethylthio)pyrrolidine diastereomer B prepared in REFERENCE EXAMPLE 20 (180 mg, 0.30 mmol) and ally (1R,5S,6S)-2-diphenoxyphosphoryloxyoxy- 6-[(1R)-1-hydroxyethyl]-1-methyl-1 -carbapen-2-em-3-carboxylate (160 mg, 0.32 mmol) in the same manner as in EXAMPLE 3-1.

IR(KBr)cm$^{-1}$: 3440,1770,1695,1450,1405,1325,1280, 1205, 1140,970,765 NMR(CDCl$_3$) δ: 1.26 (3H,d,J=7.0Hz), 1.35 (3H,d,J=6.0Hz), 1.60–2.80 (6H,m), 2.83 & 2.91 (total 3H,each s), 3.20–3.45 (3H,m), 3.45–3.70 (3H,m), 3.81 (1H, m), 3.90–4.40 (4H,m), 4.50–4.90 (6H,m), 5.20–5.50 (6H, m), 5.80–6.10 (3H,m)

2)

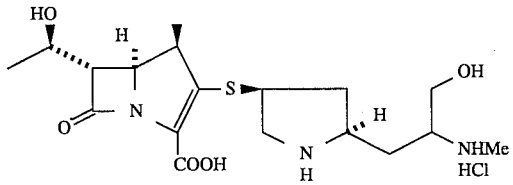

The title compound (17 mg, yield: 26%) was obtained from the above compound (90 mg, 0.148 mmol) in the same manner as in EXAMPLE 3-2.

IR(KBr)cm$^{-1}$: 3400,1760,1585,1450,1390,1260,1150, 1040 NMR(D$_2$O) δ: 1.24 (3H,d,J=7.0Hz), 1.31 (3H,d,J= 7.0Hz), 1.79 (1H,m), 2.15–2.40 (2H,m), 2.79 (3H,s), 2.86 (1H,s), 3.30–3.55 (4H,m), 3.60–4.10 (5H,m), 4.20–4.35 (2H,m) UV λ$_{max}$ (0.1M MOPS buffer, pH 7.0): 299 nm (ε=7,700)

EXAMPLE 26

(1R,5S,6S)-2-[(2R,4S)-2-(2-Amino-2-methyl)propylpyrrolidin-4-ylthio]-6-[(1R)-1-hydroxyethyl]-1-methyl-1-carbapen-2-em-3-carboxylic Acid Monohydrochloride

1)

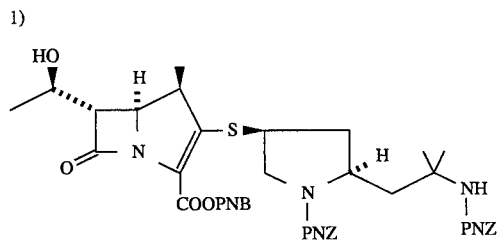

p-Nitrobenzyl (1R,5S,6S)-6-[(1R)-1-hydroxyethyl]-1-methyl-2-[(2R,4S)-2-[2-methyl-2-(p-nitrobenzyloxycarbonylamino)propyl]-N-p-nitrobenzyloxycarbonylpyrrolidin-4-ylthio]-1-carbapen-2-em-3-carboxylate (280 mg, yield: 83%) was obtained from (2S,4S)-4 -acetylthio-2-[2-methyl-2-(p-nitrobenzyloxycarbonylamino)propyl]-N-p-nitrobenzyloxycarbonylpyrrolidine prepared in REFERENCE EXAMPLE 21 (220 mg, 0.383 mmol) and p-nitrobenzyl (1R,5S,6S)-2-diphenoxyphosphoryloxy-6 -[(1R)-1-hydroxyethyl]-1-methyl-1-carbapen-2-em-3 -carboxylate (230 mg, 0.387 mmol) in the same manner as in EXAMPLES 1-1 and 1-2.

IR(KBr)cm$^{-1}$: 3420,2970,1770,1705,1610,1520,1345, 1210, 1105,850,740 NMR(CDCl$_3$) δ: 1.27 (3H,d,J=7.0Hz), 1.37 (9H,d,J=6.0Hz), 1.50–2.30 (4H,m), 2.68 (1H,m), 3.30 (3H,m), 3.45–3.75 (1H,m), 3.90–4.20 (2H,m), 4.27 (2H,m), 5.00–5.60 (6H,m), 6.26 (1H,br s), 7.50 (4H,d,J=8.0Hz), 7.65 (2H,d,J=9.0Hz), 8.15–8.30 (6H,m)

2)

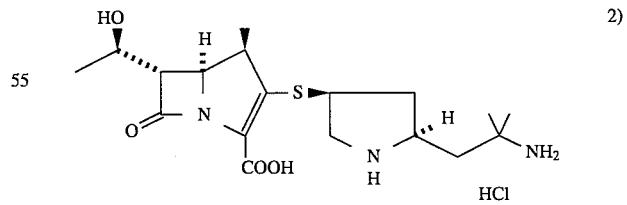

The title compound (52 mg, yield: 42%) was obtained from the above compound (260 mg, 0.297 mmol) in the same manner as in EXAMPLE 22-2.

IR(KBr)cm$^{-1}$: 3420,2970,1760,1585,1395,1290,1265, 1180, 1150 NMR(D$_2$O) δ: 1.24 (3H,d,J=7.0Hz), 1.31 (3H, d,J=6.0Hz), 1.42 (3H,s), 1.44 (3H,s), 1.63 (1H,m), 2.05–2.25 (2H,m), 2.81 (1H,m), 3.24 (1H,m), 3.39 (1H,m), 3.51 (1H,m), 3.70 (1H,m), 3.92 (1H,m), 4.25 (2H,m) UV $\lambda_{max}$ (0.1M MOPS buffer, pH 7.0): 299 nm ($\epsilon$ =9,000)

EXAMPLE 27

(1R,5S,6S)-6-[(1R)-1-Hydroxyethyl]-1-methyl-2-[(2R,4S)-2-[2-methyl-2-(N-methylamino)propyl]pyrrolidin-4-ylthio]-1-carbapen-2-em-3-carboxylic Acid Monohydrochloride

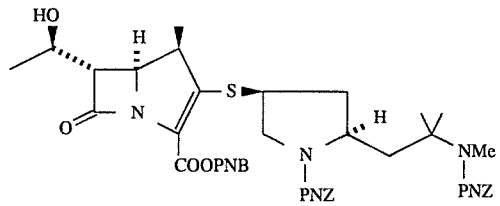
1)

p-Nitrobenzyl (1R,5S,6S)-6-[(1R)-1-hydroxyethyl]-1-methyl-2-[(2R,4S)-2-[2-methyl-2-(N-methyl-N-p-nitrobenzyloxycarbonylamino)propyl]-N-p-nitrobenzyloxycarbonylpyrrolidin- 4-ylthio]-1-carbapen-2-em-3 -carboxylate (270 mg, yield: 66%) was obtained from (2R,4S)-4-acetylthio-2-[2-methyl-2-(N-methyl-N-p-nitrobenzyloxycarbonylamino)propyl]-N-p-nitrobenzyloxycarbonylpyrrolidine prepared in REFERENCE EXAMPLE 22 (270 mg, 0.459 mmol) and p-nitrobenzyl (1R,5S,6S)-2 -diphenoxyphosphoryloxy-6-[(1R)-1-hydroxyethyl]-1-methyl- 1-carbapen-2-em-3-carboxylate (300 mg, 0.505 mmol) in the same manner as in EXAMPLES 1-1 and 1-2.

IR(KBr)cm$^{-1}$: 3450,2960,1770,1700,1605,1520,1340, 1205, 1120,850,735 NMR(CDCl$_3$) δ: 1.25 (3H,d,J=7.0Hz), 1.37 (3H,d,J=6.0Hz), 1.44 (6H,br s), 1.60–2.00 (3H,m), 2.32 (1H,m), 2.47 (1H,m), 2.97 (3H,s), 3.17 (1H,m), 3.25–3.45 (2H,m), 3.51 (1H,m), 3.90–4.20 (2H,m), 4.25 (2H,m), 5.10–5.60 (6H,m), 7.51 (4H,d,J=9.0Hz), 7.66 (2H,d,J= 9.0Hz), 8.22 (6H,d,J=9.0Hz)

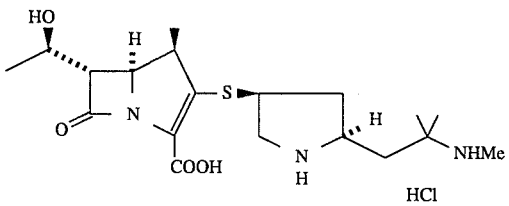
2)

The title compound (70 mg, yield: 53%) was obtained from the above compound (270 mg, 0.303 mmol) in the same manner as in EXAMPLE 22-2.

IR(KBr)cm$^{-1}$: 3420,2970,1760,1590,1390,1260,1145 NMR(D$_2$O) δ: 1.26 (3H,d,J=7.0Hz), 1.33 (3H,d,J=6.0Hz), 1.43 (3H,s), 1.47 (3H,s), 1.81 (1H,m), 2.24 (1H,dd,J=8.0, 14.0Hz), 2.36 (1H,dd,J=5.0,14.0Hz), 2.71 (3H,s), 2.94 (1H, m), 3.30–3.50 (2H,m), 3.52 (1H,dd,J=3.0,6.0Hz), 3.68 (1H, dd,J=7.0,12.0Hz), 3.87 (1H,m), 4.06 (1H,m), 4.29 (2H,m) UV $\lambda_{max}$ (0.1M MOPS buffer, pH 7.0): 299 nm ($\epsilon$ =9,500)

EXAMPLE 28

(1R,5S,6S)-2-[(2R,4S)-2-(3-Amino-3-methyl)butylpyrrolidin-4-ylthio]-6-[(1R)-1-hydroxyethyl]-1-methyl-1 -carbapen-2-em-3-carboxylic Acid Monohydrochloride

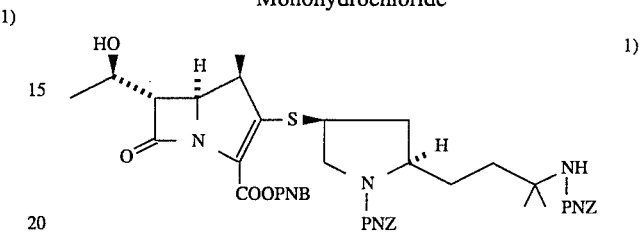
1)

p-Nitrobenzyl (1R,5S,6S)-6-[(1R)-1-hydroxyethyl]-1-methyl-2-[(2R,4S)-2-[3-methyl-3-(p-nitrobenzyloxycarbonylamino)butyl]-N-p-nitrobenzyloxycarbonylpyrrolidin-4-ylthio]-1-carbapen-2-em-3-carboxylate (300 mg, yield: 86%) was obtained from (2S,4S)- 4-acetylthio-2-[3-methyl-3-(p-nitrobenzyloxycarbonylamino)butyl]-N-p-nitrobenzyloxycarbonylpyrrolidine prepared in REFERENCE EXAMPLE 23 (230 mg, 0.391 mmol) and p-nitrobenzyl (1R,5S,6S)-2-diphenoxyphosphoryloxy-6 -[(1R)-1-hydroxyethyl]-1-methyl-1-carbapen-2-em-3 -carboxylate (260 mg, 0.437 mmol) in the same manner as in EXAMPLES 1-1 and 1-2.

IR(KBr)cm$^{-1}$: 3420,2970,1770,1705,1605,1520,1400, 1345, 1260,1210,1140,1105,850,735 NMR(CDCl$_3$) δ: 1.27 (9H,d,J=7.0Hz), 1.36 (3H,d,J=6.0Hz), 1.40–2.20 (6H,m), 2.52 (1H,m), 3.20–3.50 (3H,m), 3.57 (1H,m), 3.80–4.20 (2H,m), 4.26 (2H,m), 4.69 & 4.80 (total 1H,each br s), 5.05–5.60 (6H,m), 7.50 (4H,d,J=8.0Hz), 7.64 (2H,d,J= 9.0Hz), 8.15–8.30 (6H,m)

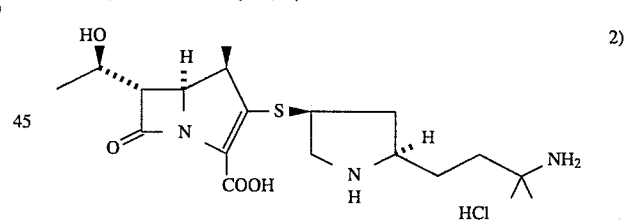
2)

The title compound (45 mg, yield: 31%) was obtained from the above compound (300 mg, 0.337 mmol) in the same manner as in EXAMPLE 22-2.

IR(KBr)cm$^{-1}$: 3420,2970,1755,1580,1450,1390,1285, 1260, 1145 NMR(D$_2$O) δ: 1.26 (3H,d,J=7.0Hz), 1.33 (3H, d,J=7.0Hz), 1.41 (6H,s), 1.70–1.90 (3H,m), 1.90–2.10 (2H, m), 2.84 (1H,m), 3.30–3.55 (3H,m), 3.65–3.85 (2H,m), 4.07

(1H,m), 4.29 (2H,m) UV $\lambda_{max}$ (0.1M MOPS buffer, pH 7.0): 298 nm ($\epsilon$=10,400)

EXAMPLE 29

(1R,5S,6S)-2-[(2S,4S)-2-[(1-Aminomethyl-3-hydroxy)propyl]pyrrolidin-4-ylthio]-6-[(1R)-1-hydroxyethyl]-1-methyl-1-carbapen-2-em-3-carboxylic Acid Diastereomer A

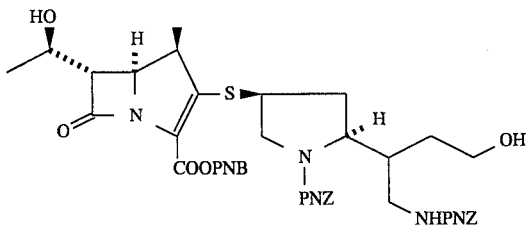
1)

p-Nitrobenzyl (1R,5S,6S)-6-[(1R)-1-hydroxyethyl]-2-[(2S,4S)-2-[3-hydroxy-1-(p-nitrobenzyloxycarbonylaminomethyl)propyl]-N-p-nitrobenzyloxycarbonylpyrrolidin-4-ylthio]-1-methyl-1 -carbapen-2-em-3-carboxylate diastereomer B (366 mg, yield: 65%) was obtained from (2S,4S)-4-acetylthio-2-[3 -hydroxy-1-(p-nitrobenzyloxycarbonylaminomethyl)propyl]-N-p-nitrobenzyloxycarbonylpyrrolidine diastereomer B prepared in REFERENCE EXAMPLE 24-5 (374 mg, 0.63 mmol) and p-nitrobenzyl (1R,5S,6S)-2-diphenoxyphosphoryloxy-6-[(1R)-1-hydroxyethyl]-1-methyl-1-carbapen-2-em-3 -carboxylate (339 mg, 0.57 mmol) in the same manner as in EXAMPLES 1-1 and 1-2.

IR(KBr)cm$^{-1}$: 3400,2920,1770,1700,1600,1520,1340, 1200, 1130,1100,845,730 NMR(CDCl$_3$) δ: 1.26 (3H,d,J=7.3Hz), 1.36 (3H,d,J=6.3Hz), 1.46 (1H,m), 1.72 (2H,m), 2.10 (1H,m), 2.53 (1H,m), 3.05 (1H,m), 3.15 (1H,m), 3.29 (2H,m), 3.51 (2H,m), 3.75 (2H,m), 4.00–4.30 (4H,m), 5.20 (5H,m), 5.49 (1H,d,J=13.5Hz), 6.04 (1H,br s), 7.51 (4H,d, J=8.6Hz), 7.65 (2H,d,J=8.9Hz), 8.21 (6H,m)

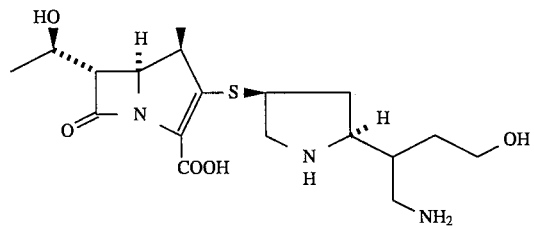
2)

The title compound (79.6 mg, yield: 48%) was obtained from the above compound (366 mg, 0.41 mmol) in the same manner as in EXAMPLE 1-3.

IR(KBr)cm$^{-1}$: 3400,2960,1750,1600,1390,1050 NMR(D$_2$O) δ: 1.22 (3H,d,J=6.9Hz), 1.30 (3H,d,J=6.6Hz), 1.48 (1H,m), 1.65 (1H,m), 1.77 (1H,m), 1.94 (1H,m), 2.57 (1H,ddd, J=8.3,8.3,13.5Hz), 2.90 (1H,dd,J=4.6,11.9Hz), 3.12 (2H,d,J=5.9Hz), 3.20–3.40 (4H,m), 3.71 (3H,m), 4.23

(2H,m) UV $\lambda_{max}$ (0.1M MOPS buffer, pH 7.0): 300 nm ($\epsilon$=9140)

EXAMPLE 30

(1R,5S,6S)-2-[(2S,4S)-2-[1-(2-Aminoethyl)-3-hydroxypropyl]pyrrolidin-4-ylthio]-6-[(1R)-1-hydroxyethyl]-1methyl-1carbapen-2-em-3-carboxylic Acid Monohydrochloride Diastereomer A

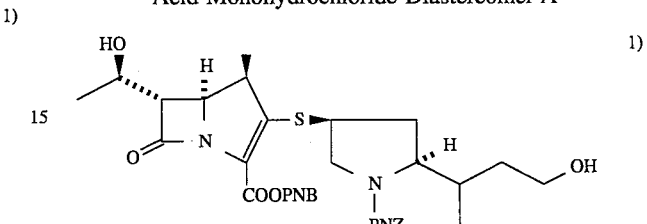
1)

p-Nitrobenzyl (1R,5S,6S)-6-[(1R)-1-hydroxyethyl]-2-[(2S,4S)-2-[3-hydroxy-1-(2-p-nitrobenzyloxycarbonylaminoethyl)propyl]-N-p-nitrobenzyloxycarbonylpyrrolidin-4-ylthio]-1-methyl-1 -carbapen-2-em-3-carboxylate diastereomer A (1.29 g, yield: 75%) was obtained from (2S,4S)-4-acetylthio-2-[3 -hydroxy-1-(2-p-nitrobenzyloxycarbonylaminoethyl)propyl]-N-p-nitrobenzyloxycarbonylpyrrolidine diastereomer A prepared in REFERENCE EXAMPLE 25-6 (1.13 g, 1.87 mmol) and p-nitrobenzyl (1R,5S,6S)-2-diphenoxyphosphoryloxy-6-[(1R)-1-hydroxyethyl]-1-methyl-1-carbapen-2-em-3 -carboxylate (1.11 g, 1.87 mmol) in the same manner as in EXAMPLES 1-1 and 1-2.

IR(KBr)cm$^{-1}$: 3400,2940,1770,1700,1605,1520,1345, 1205, 1140,1110,850,740 NMR(CDCl$_3$) δ: 1.27 (3H,d,J=7.3Hz), 1.37 (3H,d,J=6.2Hz), 1.40–1.70 (4H,m), 1.81 (1H, d,J=4.6Hz), 2.40 (2H,m), 3.1–3.30 (4H,m), 3.37 (1H,m), 3.50 (1H,m), 3.71 (2H,m), 4.13 (2H,m), 4.25 (2H,m), 5.01 (1H,br m), 5.20 (5H,m), 5.51 (1H,d,J=13.9Hz), 7.50 (4H,m), 7.81 (2H,d,J=8.6Hz), 8.20 (6H,m)

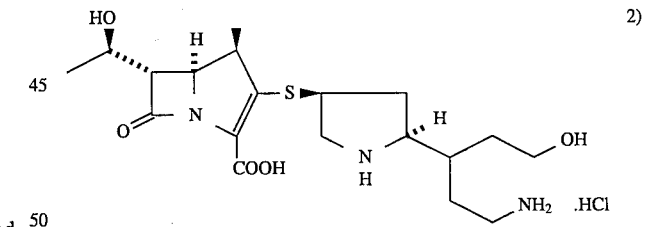
2)

The title compound (373 mg, yield: 58%) was obtained from the above compound (1.29 g, 1.42 mmol) in the same manner as in EXAMPLE 22-2.

IR(KBr)cm$^{-1}$: 3400,2950,1760,1580,1390 NMR(D$_2$O) δ: 1.23 (3H,d,J=7.3Hz), 1.30 (3H,d,J=6.6Hz), 1.70–2.00 (5H,m), 2.09 (1H,m), 2.79 (1H,m), 3.09 (2H,m), 3.37 (2H, m), 3.48 (1H,dd,J=2.6,6.3Hz), 3.60–3.80 (4H,m), 4.04 (1H, m), 4.24 (2H,m) UV $\lambda_{max}$ (0.1M MOPS buffer, pH 7.0): 298 nm

EXAMPLE 31

(1R,5S,6S)-2-[(2S,4S)-2-[1-(2-Aminoethyl)-3-hydroxypropyl]pyrrolidin-4-ylthio]-6-[(1R)-1-hydroxyethyl]-1-methyl-1-carbapen-2-em-3-carboxylic Acid Monohydrochloride Diastereomer B

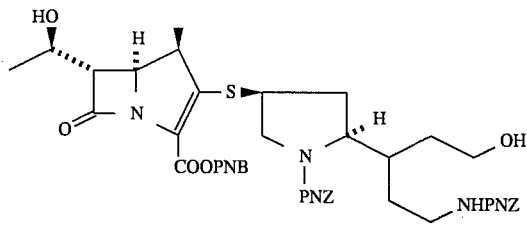
1)

p-Nitrobenzyl (1R,5S,6S)-6-[(1R)-1-hydroxyethyl]-2-[(2S,4S)-2-[3-hydroxy-1-(2-p-nitrobenzyloxycarbonylaminoethyl)propyl] -N-p-nitrobenzyloxycarbonylpyrrolidin-4-ylthio]-1-methyl-1 -carbapen-2-em-3-carboxylate diastereomer B (442 mg, yield: 49%) was obtained from (2S,4S)-4-acetylthio-2-[3 -hydroxy-1-(2-p-nitrobenzyloxycarbonylaminoethyl)propyl]-N-p-nitrobenzyloxycarbonylpyrrolidine diastereomer B prepared in REFERENCE EXAMPLE 25-6 (423 mg, 0.70 mmol) and p-nitrobenzyl (1R,5S,6S)-2-diphenoxyphosphoryloxy-6-[(1R)-1-hydroxyethyl]-1-methyl-1-carbapen-2-em-3 -carboxylate (416 mg, 0.70 mmol) in the same manner as in EXAMPLES 1-1 and 1-2.

IR(KBr)cm$^{-1}$: 3420,2940,1770,1700,1610,1520,1400, 1350, 1210,1140,1110,1050,850,740 NMR(CDCl$_3$) δ: 1.25 (3H,d,J=7.6Hz), 1.36 (3H,d,J=6.3Hz), 1.40–1.70 (4H,m), 1.89 (1H,m), 2.41 (2H,m), 3.10–3.40 (5H,m), 3.56 (1H,m), 3.62 (2H,m), 4.11 (2H,m), 4.25 (2H,m), 5.23 (5H,m), 5.50 (1H,d,J=13.5Hz), 7.53 (4H,m), 7.65 (2H,d,J=8.9Hz), 8.21 (6H,m)

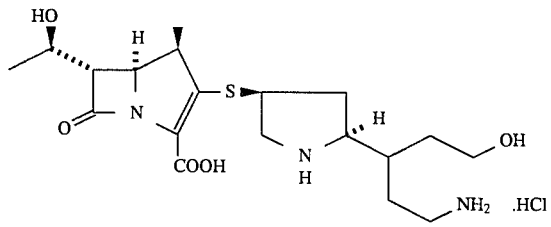
2)

The title compound (102 mg, yield: 47%) was obtained from the above compound (442 mg, 0.487 mmol) in the same manner as in EXAMPLE 22-2.

IR(KBr)cm$^{-1}$: 3400,2950,1760,1590,1390,1040 NMR(D$_2$O) δ: 1.23 (3H,d,J=7.3Hz), 1.29 (3H,d,J=6.3Hz), 1.70–1.90 (5H,m), 2.08 (1H,m), 2.77 (1H,m), 3.0–3.4 (4H, m), 3.48 (1H,dd,J=2.6,5.9Hz), 3.6–3.8 (4H,m), 4.04 (1H,m), 4.23 (2H,m) UV $\lambda_{max}$ (0.1M MOPS buffer, pH 7.0): 299 nm (ε=8380)

EXAMPLE 32

(1R,5S,6S)-6-[(1R)-1-Hydroxyethyl]-2-[(2S,4S)-2-[3-hydroxy-1-(N-methylaminomethyl)propyl]pyrrolidin-4-ylthio]-1-methyl-1-carbapen-2-em-3-carboxylic Acid Diastereomer B

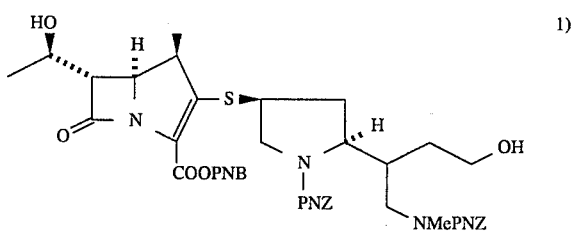
1)

p-Nitrobenzyl (1R,5S,6S)-6-[(1R)-1-hydroxyethyl]-2-[(2S,4S)-2-[3-hydroxy-1 -(N-methyl-N-p-nitrobenzyloxycarbonylaminomethyl)propyl-N-p-nitrobenzyloxycarbonylpyrrolidin- 4-ylthio]-1-methyl-1-carbapen- 2-em-3-carboxylate diastereomer B (165 mg, yield: 64%) was obtained from (2S,4S)-4-acetylthio-2-[3 -hydroxy-1-(N-methyl-N-p-nitrobenzyloxycarbonylaminomethyl)propyl]-N-p-nitrobenzyloxycarbonylpyrrolidine diastereomer B prepared in REFERENCE EXAMPLE 26-6 (172 mg, 0.28 mmol) and p-nitrobenzyl (1R,5S,6S)-2-diphenoxyphosphoryloxy-6-[(1R)- 1-hydroxyethyl]-1-methyl-1-carbapen-2-em-3-carboxylate (152 mg, 0.26 mmol) in the same manner as in EXAMPLES 1-1 and 1-2.

IR(KBr)cm$^{-1}$: 3450,2930,2880,1770,1700,1605,1520, 1345, 1200,1140,1105,1050,850,740 NMR(CDCl$_3$) δ: 1.27 (3H,d,J=4.7Hz), 1.37 (3H,d,J=6.3Hz), 1.50–1.80 (4H,m), 2.60–3.70 (7H,m), 3.01 (3H,br s), 3.27 (2H,dd,J=2.6,6.9Hz), 4.05 (2H,m), 4.11 (2H,m), 5.21 (4H,s), 5.24 (1H,d,J= 13.9Hz), 5.50 (1H,d,J=13.6Hz), 7.51 (4H,d,J=8.3Hz), 7.65 (2H,d,J=8.9Hz), 8.22 (6H,m)

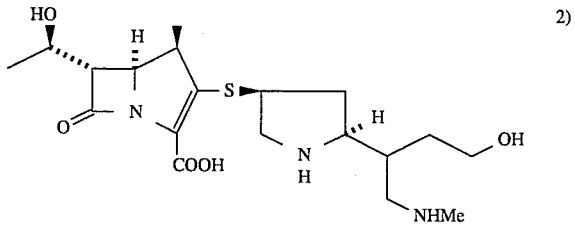
2)

The title compound (37 mg, yield: 49%) was obtained from the above compound (165 mg, 0.18 mmol) in the same manner as in EXAMPLE 1-3.

IR(KBr)cm$^{-1}$: 3396,2968,1749,1589,1462,1392,1290, 1265, 1184,1149,1074,1045,941,814,771 NMR(D$_2$O) δ: 1.23 (3H,d,J=7.4Hz), 1.31 (3H,d,J=6.4Hz), 1.50 (2H,m), 1.75 (1H,m), 1.96 (1H,m), 2.56 (1H,m), 2.72 (3H,s), 2.82 (1H,dd,J=5.1,11.8Hz), 3.12 (2H,m), 3.31 (2H,m), 3.45 (2H, m), 3.68 (3H,m), 4.25 (2H,m) UV $\lambda_{max}$ (0.1M MOPS buffer, pH 7.0): 300 nm (ε=9140)

EXAMPLE 33

(1R,5S,6S)-2-[(2R,4S)-2-(3-Amino-2-hydroxypropyl)pyrrolidin-4-ylthio]-6-[(1R)-1-hydroxyethyl]-1-methyl-1-carbapen-2-em-3-carboxylic Acid Monohydrochloride Diastereomer A

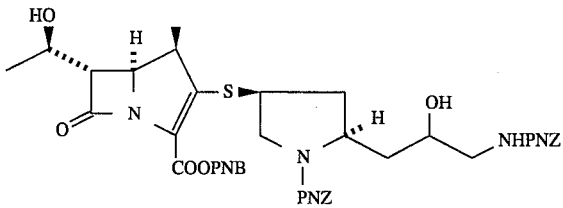
1)

(2R,4S)-2-(2-Acetoxy-3-p-nitrobenzyloxycarbonylaminopropyl)- 4-acetylthio-N-p-nitrobenzyloxycarbonylpyrrolidine diastereomer A (806 mg, 1.3 mmol) was dissolved in dioxane (2.4 ml), and 5.5N hydrochloric acid-methanol (2.4 ml) was added thereto. The mixture was stirred under a nitrogen atmosphere at room temperature for 3 h. The reaction solution was concentrated in vacuo and again dissolved by an addition of dioxane (2 ml) and ethanol (2 ml). The solution was again concentrated in vacuo to remove excess hydrochloric acid. The same operation was repeated to completely remove hydrochloric acid and to obtain a crude thiol.

Using this crude thiol and p-nitrobenzyl (1R,5S,6S)-2-diphenoxyphosphoryloxy-6-[(1R)-1-hydroxyethyl]-1-methyl-1-carbapen-2-em-3-carboxylate (773 mg, 1.3 mmol), the same reaction as in EXAMPLE 1-2 was conducted to obtain p-nitrobenzyl (1R,5S,6S)-6-[(1R)-1-hydroxyethyl]-2-[(2R,4S)-2-(2-hydroxy-3 -p-nitrobenzyloxycarbonylaminopropyl)-N-p-nitrobenzyloxycarbonylpyrrolidin- 4-ylthio]-1-methyl-1-carbapen-2-em-3-carboxylate diastereomer A (638 mg, yield: 56%) as the main product and p-nitrobenzyl (1R,5S, 6S)-2-[(2R,4S)-2-(2-acetoxy-3 -p-nitrobenzyloxycarbonylaminopropyl)-N-p-nitrobenzyloxycarbonylpyrrolidin-4-ylthio]-6-[(1R)-1 -hydroxyethyl]-1-methyl-1-carbapen-2-em-3-carboxylate diastereomer A (137 mg, yield: 15%) as a byproduct.

MAIN PRODUCT: IR(KBr)cm$^{-1}$: 3437,2939,1768,1705, 1606,1520,1433,1404, 1346,1275,1209,1140,1109,852,739 NMR(CDCl$_3$) δ: 1.28 (3H,d,J=7.5Hz), 1.38 (3H,d,J=6.4Hz), 2.11 (1H,m), 2.63 (1H,m), 3.15 (1H,m), 3.29 (4H,m), 3.64 (1H,m), 3.78 (1H,m), 4.00–4.20 (2H,m), 4.28 (2H,m), 5.20 (2H,s), 5.21 (2H,s), 5.23 (1H,d,J=11.1Hz), 5.35 (1H,br m), 5.50 (1H,d,J=12.9Hz), 7.50 (4H,d,J=8.8Hz), 7.65 (2H,d,J= 8.6Hz), 8.20 (6H,m)

BYPRODUCT: IR(KBr)cm$^{-1}$: 3421,1770,1731, 1709,1606,1522,1429,1348, 1236,1141,1109,1014,852,739 NMR(CDCl$_3$) δ: 1.27 (3H,d,J=7.2Hz), 1.36 (3H,d,J=6.4Hz), 1.76 (4H,m), 2.03 (3H,s), 2.63 (1H,m), 3.32 (5H,m), 3.62 (5H,m), 3.62 (1H,m), 4.02 (2H,m), 4.27 (2H,m), 5.01 (1H,br m), 5.20 (4H,s), 5.24 (1H,d,J=13.9Hz), 5.50 (1H,d,J= 13.9Hz), 7.49 (4H,m), 7.64 (2H,d,J=8.8Hz), 8.19 (6H,m)

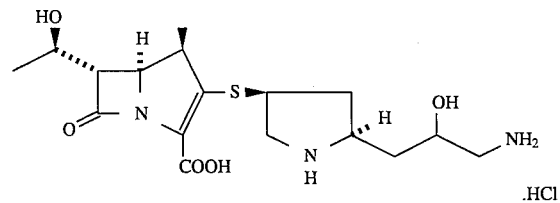
2)

The title compound (200 mg, yield: 65%) was obtained from the above main product (638 mg, 0.725 mmol) in the same manner as in EXAMPLE 22-2.

IR(KBr)cm$^{-1}$: 3420,2968,1749,1589,1396,1288,1182, 1045 NMR(D$_2$O) δ: 1.22 (3H,d,J=7.3Hz), 1.29 (3H,d,J= 6.4Hz), 1.75 (1H, m), 2.03 (2H,m), 2.83 (1H,m), 3.02 (1H,dd,J=4.5,8.6Hz), 3.19 (1H,dd,J=3.2,13.3Hz), 3.40 (3H, m), 3.70 (1H,m), 3.90 (1H,m), 4.03 (2H,m), 4.22 (2H,m) UV λ$_{max}$ (0.1M MOPS buffer, pH 7.0): 298 nm (ε=7400)

EXAMPLE 34

(1R,5S,6S)-2-[(2R,4S)-2-(3-Amino-2-hydroxypropyl)pyrrolidin-4-ylthio]-6-[(1R)-1-hydroxyethyl]-1-methyl-1-carbapen-2-em-3-carboxylic Acid Monohydrochloride Diastereomer B

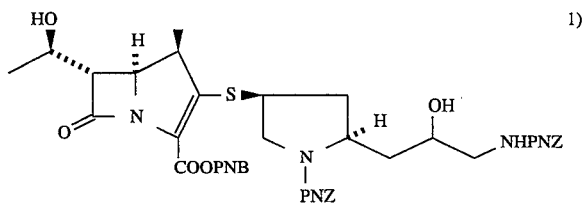
1)

p-Nitrobenzyl (1R,5S,6S)-6-[(1R)-1-hydroxyethyl]-2-[(2R,4S)-2-(2-hydroxy-3 -p-nitrobenzyloxycarbonylaminopropyl)-N-p-nitrobenzyloxycarbonylpyrrolidin- 4-ylthio]-1-methyl-1 -carbapen-2-em-3-carboxylate diastereomer B (154 mg, yield: 52%) was obtained from (2R,4S)-2-(2-acetoxy-3 -p-nitrobenzyloxycarbonylaminopropyl)-4-acetylthio-N-p-nitrobenzyloxycarbonylpyrrolidine diastereomer B (207 mg, 0.335 mmol) and p-nitrobenzyl (1R,5S, 6S)-2 -diphenoxyphosphoryloxy-6-[(1R)-1-hydroxyethyl]-1-methyl- 1-carbapen-2-em-3-carboxylate (199 mg, 0.335 mmol) in the same manner as in EXAMPLE 33-1.

IR(KBr)cm$^{-1}$: 3438,1770,1705,1606,1520,1346,1211, 1140, 1109,852,739 NMR(CDCl$_3$) δ: 1.27 (3H,d,J=7.3Hz), 1.37 (3H,d,J=6.3Hz), 1.60–1.90 (3H,m), 2.72 (1H,m), 2.98 (1H,m), 3.20–3.50 (4H,m), 3.69 (2H,m), 4.11 (1H,dd,J=7.0, 11.7Hz), 4.29 (3H,m), 5.20 (2H,s), 5.22 (2H,s), 5.23 (1H, d,J=13.8Hz), 5.39 (1H,br m), 5.50 (1H,d,J=13.8Hz), 7.51 (4H,d,J=7.7Hz), 7.65 (2H,d,J=8.9Hz), 8.21 (6H,m)

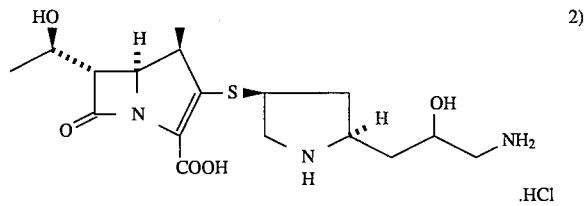
2)

The title compound (40 mg, yield: 54%) was obtained from the above compound (154 mg, 0.175 mmol) in the same manner as in EXAMPLE 22-2.

IR(KBr)cm$^{-1}$: 3385,1757,1633,1574,1392,1261,1153,1068, 781 NMR(D$_2$O) δ: 1.27 (3H,d,J=7.3Hz), 1.34 (3H,d,J=6.4Hz), 1.84 (1H,m), 2.06 (1H,m), 2.19 (1H,m), 2.87 (1H,m), 3.04 (1H,dd,J=9.4,13.1Hz), 3.23 (1H,dd,J=3.1,13.1Hz), 3.44 (2H,m), 3.52 (1H,dd,J=2.7,16.1Hz), 3.71 (1H,dd,J=7.0, 12.5Hz), 3.97 (1H,m), 4.10 (2H,m), 4.29 (2H,m) UV λ$_{max}$ (0.1M MOPS buffer, pH 7.0): 298 nm (ε=8930)

EXAMPLE 35

(1R,5S,6S)-2-[(2R,4S)-2-(2-Acetoxy-3-aminopropyl)pyrrolidin-4-ylthio]-6-[(1R)-1-hydroxyethyl]-1-methyl-1-carbapen-2-em-3-carboxylic Acid Diastereomer A

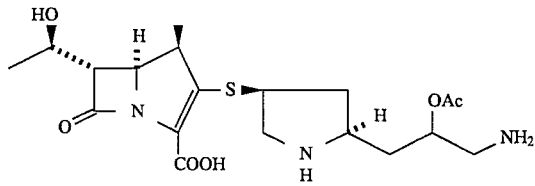

The title compound (33 mg, yield: 41%) was obtained from p-nitrobenzyl (1R,5S,6S)-2-[(2R,4S)-2-(2-acetoxy-3-p-nitrobenzyloxycarbonylaminopropyl)-N-p-nitrobenzyloxycarbonylpyrrolidin- 4-ylthio]-6-[(1R)-1-hydroxyethyl]-1-methyl-1-carbapen-2-em-3-carboxylate diastereomer A as the byproduct prepared in EXAMPLE 33-1 (137 mg, 0.188 mmol) in the same manner as in EXAMPLE 1 -3.

IR(KBr)cm$^{-1}$: 3385,2970,1755,1633,1589,1392,1290, 1182, 1147,1109 NMR(D$_2$O) δ: 1.21 (3H,d,J=7.3Hz), 1.28 (3H,d,J=6.1Hz), 1.70 (1H,m), 1.96 (2H,m), 2.01 (3H,s), 2.78 (1H,m), 3.20–3.40 (4H,m), 3.15 (1H,m), 3.71 (2H,m), 3.98 (1H,m), 4.23 (2H,m) UV λ$_{max}$ (0.1M MOPS buffer, pH 7.0): 298 nm (ε=8820)

EXAMPLE 36

(1R,5S,6S)-2-[(2S,4S)-2-[(1R)-1-Hydroxy-3-N-methylaminopropyl]pyrrolidin-4-ylthio]-6-[(1R)-1-hydroxyethyl]-1-methyl-1-carbapen-2-em-3-carboxylic Acid Monohydrochloride

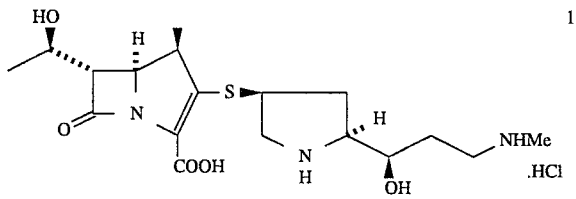

The compound prepared in REFERENCE EXAMPLE 27-3 (664 mg, 2.52 mmol) and p-nitrobenzyl (1R,5S,6S)-2-diphenoxyphosphoryloxy-6-[(1R)-1-hydroxyethyl]-1-methyl- 1-carbapen-2-em-3-carboxylate (1.35 g, 2.27 mmol) were suspended in N,N-dimethylformamide (15 ml), and N,N-diisopropylethylamine (0.88 ml, 5.04 mmol) was added thereto under cooling with ice under a nitrogen atmosphere. The mixture was stirred at 5° C. for 3 h. To the reaction solution were added 0.25M MOPS buffer solution (pH 7.0, 50 ml), tetrahydrofuran (50 ml), ethanol (12 ml) and 10% palladium-carbon catalyst (300 mg), and the mixture was stirred under atmospheric pressure under a hydrogen atmosphere at room temperature for 2 h. The catalyst was filtered off, and the filtrate was washed with methylene chloride-methanol. A small amount of insoluble material was filtered off, and the residue was concentrated in vacuo. The residue was purified by nonionic absorption resin column chromatography (HP-20®, manufactured by Mitsubishi Kasei Corporation, eluted with 30% aqueous methanol) to obtain a desired fraction, which was concentrated and adjusted to pH 5.0 by hydrochloric acid and lyophilized to give the title compound (660 mg, yield: 66%). The physicochemical data agreed with those obtained in EXAMPLE 19.

EXAMPLE 37

(1R,5S,6S)-2-[(2R,4S)-2-(2-Aminopropyl)pyrrolidin-4-ylthio]-6-[(1R)-1-hydroxyethyl]-1-methyl-1-carbapen-2-em- 3-carboxylic Acid Monohydrochloride Diastereomer A

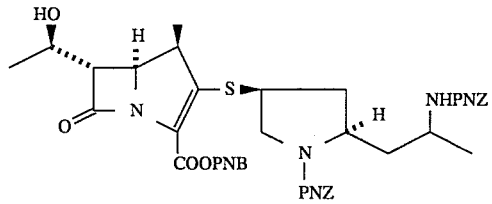

p-Nitrobenzyl (1R,5S,6S)-6-[(1R)-1-hydroxyethyl]-1-methyl-2-[(2R,4S)-2-[2-(p-nitrobenzyloxycarbonylamino) propyl]-N-(p-nitrobenzyloxycarbonyl)pyrrolidin-4-ylthio]-1-carbapen-2-em-3-carboxylate diastereomer A (2.04 g, yield: 99.8%) was obtained from (2S,4S)-4-acetylthio-2 -[2-(p-nitrobenzyloxycarbonylamino)propyl]-N-(p-nitrobenzyloxycarbonyl)pyrrolidine diastereomer A prepared in REFERENCE EXAMPLE 28 (1.33 g, 2.37 mmol) and p-nitrobenzyl (1R,5S,6S)-2-diphenoxyphosphoryloxy-6-[(1R)-1-hydroxyethyl]-1-methyl-1-carbapen-2-em-3 -carboxylate (1.41 g, 2.37 mmol) in the same manner as in EXAMPLES 1-1 and 1-2.

IR(KBr)cm$^{-1}$: 3400,1770,1700,1610,1520,1200,1100, 850, 740 NMR(CDCl$_3$) δ: 1.26 (6H,d,J=6.9Hz), 1.37 (3H, d,J=6.3Hz), 1.73 (2H,m), 2.14 (1H,br m), 2.56 (1H,m), 3.28 (3H,m), 3.54 (1H,m), 3.73 (1H,m), 4.00 (2H,m), 4.25 (2H, m), 5.15 (2H,s), 5.20 (2H,s), 5.23 (1H,d,J=13.8Hz), 5.50 (1H,d,J=13.8Hz), 7.49 (4H,d,J=8.6Hz), 7.65 (2H,d,J= 8.9Hz), 8.21 (6H,d,J=8.6Hz)

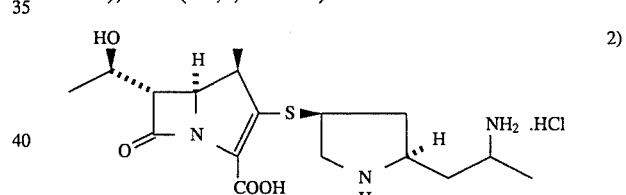

The title compound (456 mg, yield: 47%) was obtained from the above compound (2.04 g, 2.36 mmol) in the same manner as in EXAMPLE 22-2.

IR(KBr)cm$^{-1}$: 3400,2950,1760,1580,1390 NMR(D$_2$O) δ: 1.18 (3H,d,J=7.3Hz), 1.25 (3H,d,J=6.27Hz), 1.33 (3H,d,J= 7.4Hz), 1.71 (1H,m), 2.17 (2H,m), 2.78 (1H,m), 3.18–3.51 (3H,m), 3.67 (1H,m), 3.81 (1H,m), 4.01 (1H,m), 4.21 (2H, m) UV λ$_{max}$ (0.1M MOPS buffer, pH 7.0): 298 nm (ε=8890)

EXAMPLE 38

(1R,5S,6S)-2-[(2R,4S)-2-(2-Aminopropyl)pyrrolidin-4-ylthio]-6-[(1R)-1-hydroxyethyl]-1-methyl-1-carbapen-2-em- 3-carboxylic Acid Monohydrochloride Diastereomer B

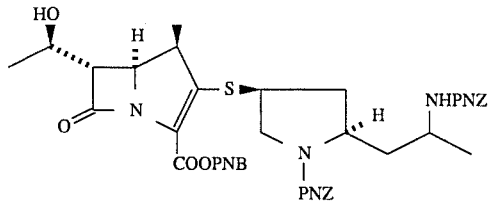

p-Nitrobenzyl (1R,5S,6S)-6-[(1R)-1-hydroxyethyl]-1-methyl-2-[(2R,4S)-N-(p-nitrobenzyloxycarbonyl)-2-[2 -(p-nitrobenzyloxycarbonylamino)propyl]pyrrolidin-4-ylthio]-1-carbapen-2-em-3-carboxylate diastereomer B (239 mg, yield: 62%) was obtained from (2S,4S)-4-acetylthio-N-(p-nitrobenzyloxycarbonyl)- 2-[2 -(p-nitrobenzyloxycarbonylamino)propyl]pyrrolidine diastereomer B prepared in REFERENCE EXAMPLE 29 (250 mg, 0.44 mmol) and p-nitrobenzyl (1R,5S,6S)-2 -diphenoxyphosphoryloxy-6-[(1R)-1-hydroxyethyl]-1-methyl- 1-carbapen-2-em-3-carboxylate (265 mg, 0.44 mmol) in the same manner as in EXAMPLES 1-1 and 1-2.

IR(KBr)cm$^{-1}$: 3410,1770,1700,1610,1520,1350,1200, 1100,850, 740 NMR(CDCl$_3$) δ: 1.19 (3H,d,J=6.3Hz), 1.27 (3H,d,J=7.3Hz), 1.37 (3H,d,J=6.3Hz), 1.70–2.20 (3H,m), 2.71 (1H,m), 3.28 (3H,m), 3.61 (2H,m), 3.94 (2H,m), 4.24 (2H,m), 5.17 (2H,s), 5.22 (2H,s), 5.23 (1H,d,J=13.5Hz), 5.51 (1H,d,J=13.5Hz), 7.51 (4H,d,J=8.9Hz), 7.65 (2H,d,J=8.6Hz), 8.21 (6H,m)

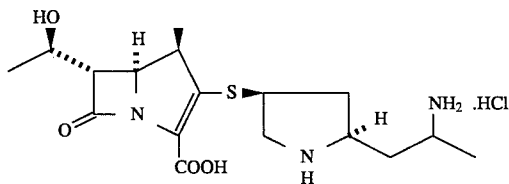
2)

The title compound (65 mg, yield: 58%) was obtained from the above compound (239 mg, 0.277 mmol) in the same manner as in EXAMPLE 22-2.

IR(KBr)cm$^{-1}$: 3400,1760,1580,1400,1180,1040 NMR(D$_2$O) δ: 1.26 (3H,d,J=6.9Hz), 1.33 (3H,d,J=6.3Hz), 1.43 (3H,d,J=6.6Hz), 1.82 (1H,m), 2.10–2.40 (3H,m), 2.90 (2H,m), 3.05 (2H,m), 3.30–3.60 (3H,m), 3.72 (1H,m), 3.90 (1H,m), 4.10 (1H,m), 4.28 (2H,m) UV λ$_{max}$ (0.1M MOPS buffer, pH 7.0): 299 nm (ε=6940)

EXAMPLE 39

(1R,5S,6S)-2-[(2R,4S)-2-(3-N-Methylaminobutyl)pyrrolidin-4-ylthio]-6-[(1R)-1-hydroxyethyl]-1-methyl-1-carbapen-2- em-3-carboxylic Acid Monohydrochloride

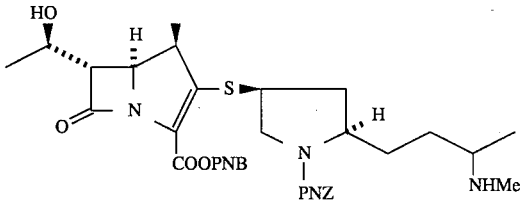
1)

p-Nitrobenzyl (1R,5S,6S)-2-[(2R,4S)-2-[3 -(N-methyl-N-p-nitrobenzyloxycarbonylamino)butyl]-N-p-nitrobenzyloxycarbonylpyrrolidin- 4-ylthio]-6-[(1R)-1 -hydroxyethyl]-1-methyl-1-carbapen-2-em-3-carboxylate (1.45 g, yield: 70%) was obtained from the compound prepared in REFERENCE EXAMPLE 30 (1.2 g, 2.33 mmol) in the same manner as in EXAMPLES 1-1 and 1-2.

IR(KBr)cm$^{-1}$: 3400,2960,1770,1700,1605 NMR(CDCl$_3$) δ: 1.10 (3H,br d), 1.25 (3H,d,J=7.0Hz), 1.35 (3H,d,J=6.0Hz), 1.60–1.80 (2H,m), 2.50 (1H,m), 2.75 (3H,s), 3.20–3.40 (2H,m), 3.55 (1H,m), 3.95 (1H,m), 4.25 (2H,m), 5.20–5.50 (6H,m), 7.50 (4H,d,J=8.0Hz), 7.62 (2H,d,J=8.0Hz), 8.20 (6H,d,J=8.0Hz)

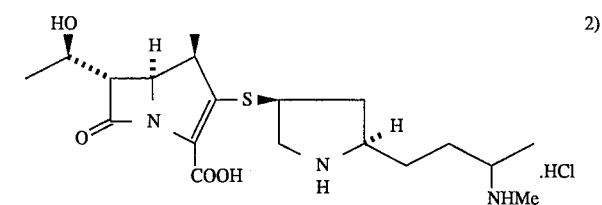
2)

The title compound (200 mg, yield: 28.3%) was obtained from the above compound (1.45 g, 1.63 mmol) in the same manner as in EXAMPLE 1-3.

IR(KBr)cm$^{-1}$: 3440,2960,1760,1700 NMR(D$_2$O) δ: 1.20 (3H,d,J=7.0Hz), 1.25 (3H,d,J=7.0Hz), 1.70 (3H,d,J=7.0Hz), 1.60–1.80 (2H,m), 1.80–2.00 (3H,m), 2.65 (3H,s), 2.68 (1H,m), 3.30–3.45 (3H,m), 3.70 (1H,m), 4.00 (1H,m), 4.20 (1H,m) UV λ$_{max}$ (0.1M MOPS buffer, pH 7.0): 298 nm (ε=8230)

EXAMPLE 40

(1R,5S,6S)-2-[(2R,4S)-2-[(2-Fluoro-3-N-methylamino)propyl]pyrrolidin-4-ylthio]-6-[(1R)-1-hydroxyethyl]-1-methyl-1-carbapen-2-em-3-carboxylic Acid Monohydrochloride

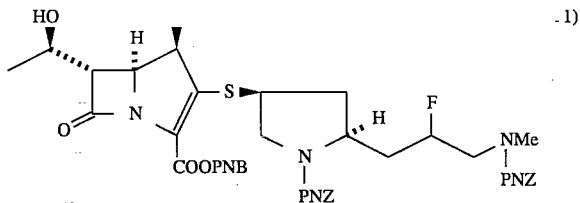
1)

p-Nitrobenzyl (1R,5S,6S)-2-[(2R,4S)-2-[2-fluoro-3 -(N-methyl-N-p-nitrobenzyloxycarbonylamino)propyl]-N-p-nitrobenzyloxycarbonylpyrrolidin- 4-ylthio]-6-[(1R)-1 -hydroxyethyl]-1-methyl-1-carbapen-2-em-3-carboxylate (192 mg, yield: quantitative) was obtained from the compound prepared in REFERENCE EXAMPLE 31 (133 mg, 0.22 mmol) in the same manner as in EXAMPLES 1-1 and 1-2.

IR(KBr)cm$^{-1}$: 3440,2960,1770,1700 NMR(CDCl$_3$) δ: 1.22 (3H,d,J=7.0Hz), 1.35 (3H,d,J=7.0Hz), 1.60–1.80 (3H, m), 2.60 (1H,m), 2.90–3.00 (1H,m), 3.05 (3H,s), 3.25–3.65 (3H,m), 4.25 (2H,m), 4.60–5.00 (1H,m), 5.20–5.50 (6H,m), 7.50 (2H,d,J=8.0Hz), 7.68 (2H,d,J=8.0Hz), 8.25 (6H,d,J=8.0Hz)

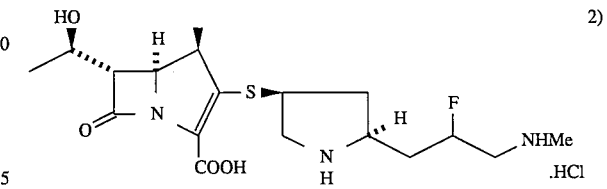
2)

The title compound (27 mg, yield: 28.4%) was obtained from the above compound (190 mg, 0.22 mmol) in the same manner as in EXAMPLE 1-3.

IR(KBr)cm$^{-1}$: 3400,2960,1750,1600 NMR(D$_2$O) δ: 1.15 (3H,d,J=7.0Hz), 1.25 (3H,d,J=7.0Hz), 1.70 (1H,m), 2.10–2.30 (2H,m), 2.70 (3H,s), 2.80–3.00 (1H,m), 3.20–3.50 (4H,m), 3.60 (1H,m), 3.95 (1H,m), 4.20 (1H,m), 4.90–5.20 (1H,m) UV λ$_{max}$ (0.1M MOPS buffer, pH 7.0): 298 nm (ε=8500)

The compounds of EXAMPLES 41 to 43 were obtained in the same manner as in EXAMPLE 18.

EXAMPLE 41

(1R,5S,6S)-2-[(2R,4S)-2-[(1-Methyl-3-N-methylamino)propyl]pyrrolidin-4-ylthio]-6-[(1R)-1-hydroxyethyl]-1-methyl-1-carbapen-2-em-3-carboxylic Acid Monohydrochloride

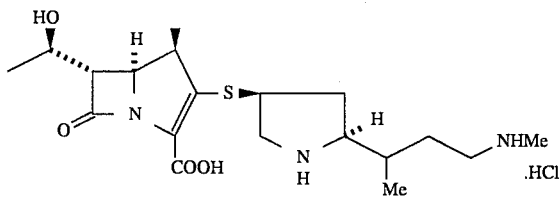

IR(KBr)cm$^{-1}$: 3420,2970,1750,1595,1395 NMR(D$_2$O) δ: 1.08 (3H,d,J=7.0Hz), 1.17 (3H,d,J=7.0Hz), 1.24 (3H,d,J=7.0Hz), 1.60–1.75 (1H,m), 2.20–2.35 (1H,m), 2.60–2.80 (4H,m), 2.80–3.60 (7H,m), 3.85–4.00 (1H,m), 4.15–4.25 (2H,m) UV λ$_{max}$ (0.1M MOPS buffer, pH 7.0): 299 nm (ε=10590)

EXAMPLE 42

(1R,5S,6S)-2-[(2R,4S)-2-(1-Aminomethyl)ethylpyrrolidin-4-ylthio]-6-[(1R)-1-hydroxyethyl]-1-methyl-1-carbapen-2-em-3-carboxylic Acid Monohydrochloride Diastereomer A

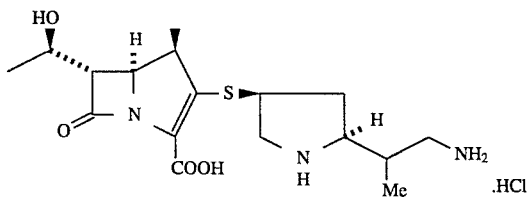

IR(KBr)cm$^{-1}$: 3420,2970,1760,1590,1390 NMR(D$_2$O) δ: 1.15–1.20 (6H,m), 1.25 (3H,d,J=7.0Hz), 1.65–1.80 (1H,m), 2.10–2.30 (2H,m), 2.70–3.00 (3H,m), 3.10–3.70 (4H,m), 3.90–4.10 (1H,m), 4.15–4.25 (2H,m) UV λ$_{max}$ (0.1M MOPS buffer, pH 7.0): 298 nm (ε=6600)

EXAMPLE 43

(1R,5S,6S)-2-[(2R,4S)-2-(1-Aminomethyl)ethylpyrrolidin-4-ylthio]-6-[(1R)-1-hydroxyethyl]-1-methyl-1-carbapen-2-em-3-carboxylic Acid Monohydrochloride Diastereomer B

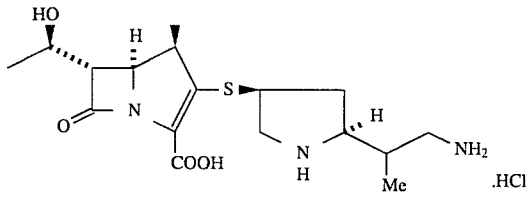

IR(KBr)cm$^{-1}$: 3420,2970,1760,1585,1390 NMR(D$_2$O) δ: 1.10 (3H,d,J=7.0Hz), 1.18 (3H,d,J=7.0Hz), 1.25 (3H,d,J=7.0Hz), 1.65–1.80 (1H,m), 2.20–2.30 (1H,m), 2.60–2.80 (1H,m), 2.80–3.00 (1H,m), 3.18 (1H,dd,J=4.0, 13.0Hz), 3.25–3.60 (5H,m), 3.85–4.00 (1H,m), 4.15–4.25 (2H,m) UV λ$_{max}$ (0.1M MOPS buffer, pH 7.0): 299 nm (ε=8840)

EXAMPLE 44

(1R,5S,6S)-2-[(2S,4S)-2-[(1R)-3-N,N-Dimethylamino-1-hydroxypropyl]pyrrolidin-4-ylthio]-6-[(1R)-1-hydroxyethyl]-1-methyl-1-carbapen-2-em-3-carboxylic Acid Monohydrochloride 1)
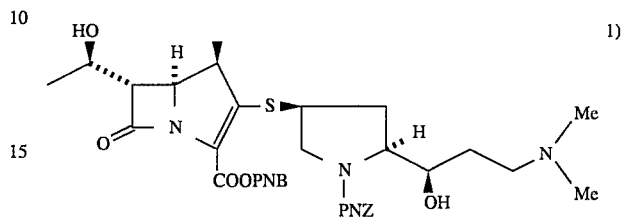

p-Nitrobenzyl (1R,5S,6S)-2-[(2S,4S)-2-[(1R)-3-N,N-dimethylamino-1-hydroxypropyl]-N-p-nitrobenzyloxycarbonylpyrrolidin-4-ylthio]-6-[(1R)-1-hydroxyethyl]-1-methyl-1-carbapen-2-em-3-carboxylate (3.3 g, yield: 96%) was obtained from the compound prepared in REFERENCE EXAMPLE 34-5 (3.7 g, 5.7 mmol) in the same manner as in REFERENCE EXAMPLE 3-1.

IR(KBr)cm$^{-1}$: 3370,1770,1702,1590,1455,1345 NMR(CDCl$_3$) δ: 1.10–1.40 (6H,m), 1.50–2.40 (5H,m), 2.55 (6H,s), 2.80–3.70 (3H,m), 3.80–4.10 (2H,m), 4.25 (1H,m), 5.10–5.50 (4H,m), 6.90–7.70 (12H,m), 8.10–8.30 (2H,m)

2)
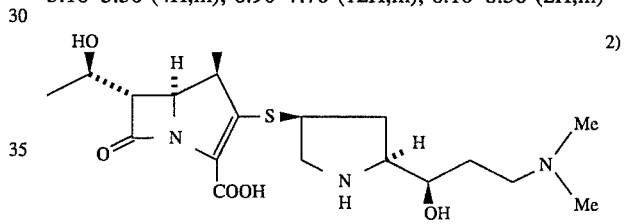

The title compound (154 mg, yield: 27%) was obtained from the above compound (1 g, 1.4 mmol) in the same manner as in EXAMPLE 18-2.

IR(KBr)cm$^{-1}$: 1785,1590,1490,1250,1090 NMR(D$_2$O) δ: 1.34 (3H,d,J=7.4Hz), 1.41 (3H,d,J=6.4Hz), 1.80–2.20 (3H, m), 2.60–2.80 (1H,m), 3.02 (6H,s), 3.20–3.90 (8H,m), 4.00–4.20 (2H,m), 4.30–4.40 (2H,m) UV λ$_{max}$ (0.1M MOPS buffer, pH 7.0): 298 nm (ε=5340)

REFERENCE EXAMPLE 1

(2S,4S)-4-Acetylthio-2-[2-carbamoyl-N-(p-nitrobenzyloxycarbonylaminomethyl)ethyl]-N-(p-nitrobenzyloxycarbonyl)pyrrolidine 1)
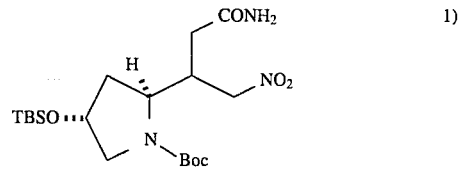

An ice-cooled solution of (2S,4R)-4-tert-butyldimethylsiloxy-N-tert-butoxycarbonyl- 2-[(2-ethoxycarbonyl- 1-nitromethyl)ethyl]pyrrolidine (5 g, 11.99 mmol) in methanol (100 ml) was saturated with ammonia. After putting a stopper on the flask, the solution was left for 1 week at room temperature. After methanol was removed in vacuo, ethyl acetate (150 ml) was added to the residue. The organic layer was washed successively with water and saturated aqueous sodium chloride, and dried over anhydrous magnesium sulfate. The solvent was removed in vacuo, and the residue was subjected to silica gel column chromatography (chloroform:methanol=100:1) to give (2S,4R)-4-tert-butyldimethylsiloxy-N-tert-butoxycarbonyl-2-[(2-carbamoyl-1-nitromethyl)ethyl]pyrrolidine (3.44 g, yield: 72.6%).

IR(KBr)cm$^{-1}$: 3300,1750,1700,1560,1380 NMR(CDCl$_3$) δ: 0.06 (6H,s), 0.86 (9H,s), 1.48 (9H,s), 1.60–1.90 (4H,m), 1.95–2.50 (2H,m), 3.10 (2H,m), 3.50 (1H,br), 4.10–4.60 (3H,m), 5.50–6.00 (2H,br)

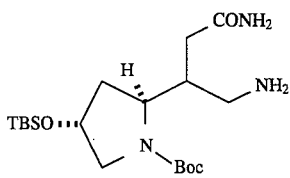
2)

To a solution of the above compound (3.1 g, 7.1 mmol) in methanol (100 ml) was added Raney Ni (W-2, 3.1 g), and the mixture was stirred overnight under a hydrogen atmosphere (3 kg/cm$^2$). The catalyst was filtered off, and the filtrate was concentrated in vacuo to give (2S,4R)-2-(1-aminomethyl-2-carbamoyl)ethyl-N-tert-butoxycarbonyl-4-tert-butyldimethylsiloxypyrrolidine as a crude oil (2.43 g, yield: 81.6%).

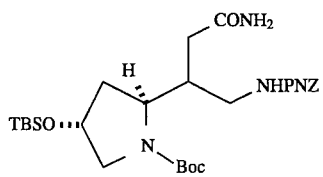
3)

To a solution of the above compound (2.42 g, 6.04 mmol) in a mixture of dioxane (30 ml) and water (30 ml) was added 4,6-dimethyl-2-(p-nitrobenzyloxycarbonylthio)pyrimidine (2.11 g, 6.64 mmol) keeping pH 8 with triethylamine, and the mixture was stirred overnight at room temperature. To the reaction mixture was added ethyl acetate (150 ml), and the organic layer was washed successively with water, 1N aqueous hydrochloric acid, saturated aqueous sodium hydrogencarbonate and saturated aqueous sodium chloride. After drying over anhydrous magnesium sulfate, the solvent was removed in vacuo. The residue was subjected to silica gel column chromatography (chloroform:methanol=100:1) to give (2S,4R)-N-tert-butoxycarbonyl-4-tert-butyldimethylsiloxy- 2-[2-carbamoyl-1-(p-nitrobenzyloxycarbonylaminomethyl)ethyl]pyrrolidine (2.05 g, yield: 63.3%).

IR(KBr)cm$^{-1}$: 3400,2950,1700,1520,1390 NMR(CDCl$_3$) δ: 0.06 (6H,s), 0.86 (9H,s), 1.48 (9H,s), 1.60–2.40 (6H,m), 2.90–3.80 (4H,m), 3.30–4.40 (2H,m), 5.20 (2H,br), 5.50 (2H,br), 5.80 (2H,br), 7.50 (2H,d,J=9.0Hz), 8.20 (2H,d,J=9.0Hz)

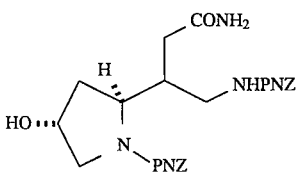
4)

To an ice-cooled solution of the above compound (2.1 g, 3.91 mmol) in methanol (50 ml) was added 2.5N hydrochloric acid methanol solution (5.1 ml), and the solution was stirred for 3 h at room temperature. The solvent was removed to give the crude powder, which was dissolved in dioxane (50 ml) and water (50 ml). To the solution was added 4,6-dimethyl-2-(p-nitrobenzyloxycarbonylthio)pyrimidine (1.25 g, 4 mmol) keeping pH 8 with triethylamine, and the solution was stirred for 6 h at room temperature. To the reaction mixture was added ethyl acetate (100 ml), and the organic layer was washed with water (50 ml). After drying over anhydrous magnesium sulfate, the solvent was removed in vacuo. The residue was subjected to silica gel column chromatography (chloroform:methanol=20:1) to give (2S,4R)-2-[2-carbamoyl-1-(p-nitrobenzyloxycarbonylaminomethyl)ethyl]-4-hydroxy-N-(p-nitrobenzyloxycarbonyl)pyrrolidine (1.53 g, yield: 85.65%).

IR(KBr)cm$^{-1}$: 3400,1690,1520,1345,1110,860 NMR(CDCl$_3$) δ: 1.70–2.80 (6H,m), 3.20–3.60 (2H,m), 3.80 (1H,m), 4.00–4.50 (2H,m), 5.20 (4H,m), 6.10 (2H,br), 7.50 (4H,d,J=9.0Hz), 8.20 (4H,d,J=9.0Hz)

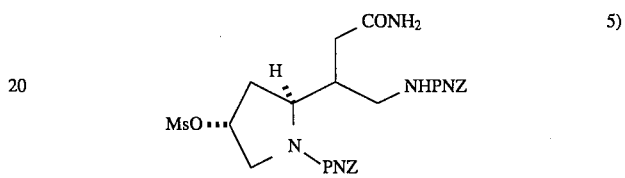
5)

To an ice-cooled solution of the above compound (1.5 g, 2.77 mmol) in tetrahydrofuran (50 ml) were added triethylamine (0.77 ml, 5.54 mmol) and methanesulfonyl chloride (0.43 ml, 5.54 mmol) under a nitrogen atmosphere, and the mixture was stirred overnight at room temperature. After the reaction mixture was concentrated in vacuo, ethyl acetate (100 ml) was added. The organic layer was washed successively with 1N aqueous hydrochloric acid, saturated aqueous sodium hydrogencarbonate and saturated aqueous sodium chloride, and dried over anhydrous magnesium sulfate. After filtration, the filtrate was concentrated to give (2S,4R)-2-[2-carbamoyl-1-(p-nitrobenzyloxycarbonylaminomethyl)ethyl]-4-methanesulfonyloxy-N-(p-nitrobenzyloxycarbonyl)pyrrolidine (1.72 g, yield: 97.9%).

IR(KBr)cm$^{-1}$: 3400,1700,1605,1520,1350,1170,905 NMR(CDCl$_3$) δ: 1.90–2.60 (6H,m), 3.10 (3H,s), 3.30–3.70 (2H,m), 3.90–4.40 (3H,m), 5.30 (4H,m), 6.10 (2H,br), 7.50 (4H,d,J=9.0Hz), 8.20 (4H,d,J=9.0Hz)

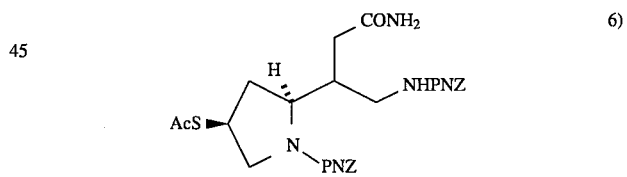
6)

To a solution of the above compound (1.7 g, 2.75 mmol) in N,N-dimethylformamide (20 ml) were added potassium thioacetate (627 mg, 5.5 mmol) and sodium iodide (412 mg, 2.75 mmol), and the mixture was stirred for 4 h at 60°–70° C. To the reaction mixture was added ethyl acetate (200 ml), and the organic layer was washed successively with 1N aqueous hydrochloric acid, saturated aqueous sodium hydrogencarbonate and saturated aqueous sodium chloride. The organic layer was dried over anhydrous magnesium sulfate, and concentrated in vacuo. The resulting residue was subjected to silica gel column chromatography (chloroform:methanol=80:1) to give the title compound (1.04 g, yield: 63.6%).

IR(KBr)cm$^{-1}$: 3400,1700,1605,1520,1400,1345 NMR(CDCl$_3$) δ: 1.80–2.30 (6H,m), 2.30 (3H,s), 3.20–3.60 (2H,m), 3.70–4.50 (3H,m), 5.20 (4H,br), 6.30 (2H,br), 7.50 (4H,d,J=9.0Hz), 8.15 (4H,d,J=9.0Hz)

REFERENCE EXAMPLE 2

(2S,4S)-N-Allyloxycarbonyl-2-(2-allyloxycarbonylamino-2-carbamoyl)ethyl-4-triphenylmethylthiopyrrolidine

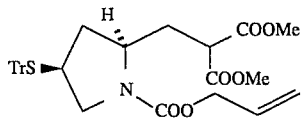  1)

To an ice-cooled suspension of sodium hydride (60%, in oil suspension, 300 mg, 7.5 mmol) in N,N-dimethylformamide (15 ml) was added dropwise dimethyl malonate (0.92 ml, 8.05 mmol) under a nitrogen atmosphere, and the mixture was stirred for 3.0 min at the same temperature. To the mixture was added a solution of (2S,4S)-N-allyloxycarbonyl-2-iodomethyl-4-triphenylmethylthiopyrrolidine (2.85 g, 5 mmol) in N,N-dimethylformamide (10 ml), and the mixture was stirred for 30 min under ice-cooling, for 1 h at room temperature, and then for 6 h at 60° C. The reaction mixture was poured into a mixture of water (30 ml) and 1 N aqueous potassium hydrogensulfate (30 ml), and extracted with ethyl acetate (1×100 ml, 2×50 ml). The combined organic layer was washed successively with water and saturated aqueous sodium chloride, and dried over anhydrous magnesium sulfate. The solvent was removed in vacuo, and the residue was subjected to silica gel column chromatography (hexane-ethyl acetate) to give (2S,4S)-N-allyloxycarbonyl-2-[2,2-bis(methoxycarbonyl)ethyl]-4-triphenylmethylthiopyrrolidine (2.59 g, yield: 90%).

IR(KBr)cm$^{-1}$: 3450,2960,1760,1740,1705,1495,1450, 1410, 1200,750,705 NMR(CDCl$_3$) δ: 1.30–1.50 (1H,m), 1.90–2.50 (3H,m), 2.50–3.00 (3H,m), 3.25–3.60 (2H,m), 3.71 (3H,s), 3.72 (3H,s), 4.30–4.55 (2H,m), 5.15–5.31 (2H, m), 5.75–6.00 (1H,m), 7.10–7.60 (15H,m)

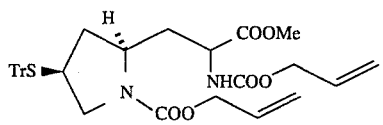  2)

To an ice-cooled solution of the above compound (1.15 g, 2.12 mmol) in tetrahydrofuran (10 ml) was added dropwise 1N aqueous sodium hydroxide (2.2 ml, 2.2 mmol), and the solution was stirred for 30 min at the same temperature, and then for 4 h at room temperature. After the solvent was removed, to the residue was added water (20 ml), and the aqueous layer was washed with ether. To the aqueous layer was added 1N aqueous hydrochloric acid (2.2 ml, 2.2 mmol) under ice-cooling, and the aqueous layer was extracted with ethyl acetate (1×30 ml, 2×20 ml). The combined organic layer was washed successively with water and saturated aqueous sodium chloride, and dried over anhydrous magnesium sulfate. The solvent was removed in vacuo to give the crude carboxylic acid. To a solution of the crude carboxylic acid in benzene (5 ml) were added triethylamine (0.25 ml, 1.79 mmol) and diphenylphosphoric azide (0.39 ml, 1.81 mmol). After the mixture was refluxed for 1 h under a nitrogen atmosphere, to the mixture was added allyl alcohol (0.13 ml, 1.91 mmol), and the mixture was additionally refluxed for 2 h. After the solvent was removed in vacuo, to the residue was added ethyl acetate (150 ml), and the organic layer was washed successively with 1N aqueous potassium hydrogensulfate, water, saturated aqueous sodium hydrogencarbonate, water and saturated aqueous sodium chloride, and dried over anhydrous magnesium sulfate. After the solvent was removed in vacuo, the residue was subjected to silica gel column chromatography (heptane-ethyl acetate) to give (2R,4 S)-N-allyloxycarbonyl-2-(2-allyloxycarbonylamino-2-methoxycarbonylethyl)-4-triphenylmethylthiopyrrolidine (260 mg, yield: 29%).

IR(KBr)cm$^{-1}$: 3420,1750,1700,1530,1445,1410,1200,745, 700 NMR (CDCl$_3$) δ: 1.35–1.70 (1H,m), 1.70–2.00 (1H,m), 2.00–2.45 (2H,m), 2.50–3.10 (3H,m), 3.10–3.50 (1H,m), 3.70 (3H,s), 4.30–4.65 (4H,m), 4.10–4.30 (1H,m), 5.10–5.40 (4H,m), 5.70–6.10 (3H,m), 7.15–7.60 (15H,m)

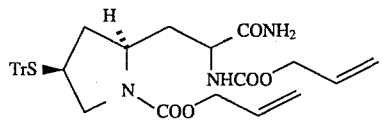  3)

To a solution of the above compound (230 mg, 0.374 mmol) in methanol (2 ml) was added 1N aqueous sodium hydroxide (0.45 ml, 0.45 mmol) under a hydrogen atmosphere, and the mixture was stirred overnight at room temperature. After the solvent was removed in vacuo, to the residue was added water (10 ml), and the aqueous layer was washed with ether. To the aqueous layer was added 1N aqueous hydrochloric acid (0.45 ml, 0.45 mmol), and extracted with ethyl acetate (1×20 ml, 2×10 ml). The combined organic layer was washed successively with water and saturated aqueous sodium chloride, and dried over anhydrous magnesium sulfate. The solvent was removed in vacuo to give the crude carboxylic acid. To a solution of the crude carboxyl acid in tetrahydrofuran (1.5 ml) were added triethylamine (0.05 ml, 0.359 mmol) and ethyl chlorocarbonate (0.035 ml, 0.366 mmol) at −30° C. under a nitrogen atmosphere, and the mixture was stirred for 1 h at the same temperature. To the mixture was added 28% ammonia water (0.4 ml), and the mixture was stirred for 1 h at −20° C., and then for 1 h at room temperature. After the solvent was removed in vacuo, water (5 ml) was added to the residue, and the aqueous layer was extracted with chloroform (3×10 ml). The combined organic layer was dried over anhydrous magnesium sulfate, and the solvent was removed in vacuo. The residue was subjected to silica gel column chromatography (methanol-chloroform) to give the title compound (130 mg, yield: 72%).

IR(KBr)cm$^{-1}$: 3400,3320,1680,1530,1450,1410,1340, 1255, 1200,745,705 NMR(CDCl$_3$) δ: 1.35–1.70 (1H,m), 1.70–2.00 (1H,m), 2.00–2.45 (2H,m), 2.50–3.10 (3H,m), 3.10–3.50 (1H,m), 3.70 (3H,s), 4.10–4.30 (1H,m), 4.30–4.65 (4H,m), 5.10–5.40 (4H,m), 5.70–6.10 (3H,m), 7.15–7.60 (15H,m)

REFERENCE EXAMPLE 3

(2S,4S)-4-Acetylthio-N-allyloxycarbonyl-2-(1-acetamido-2-allyloxycarbonylamino)ethylpyrrolidine

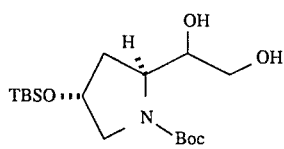  1)

To a solution of (2S,4R)-N-butoxycarbonyl-2-vinyl-4-tert-butyldimethylsiloxypyrrolidine (14.3 g, 47.5 mmol) and 4-methylmorpholine N-oxide (8.8 g, 75 mmol) in acetone (140 ml) and water (140 ml) was added 4% aqueous osmium tetroxide (9.6 ml), and the mixture was stirred overnight at the same temperature. The reaction mixture was adjusted to pH 2.0 with 6N aqueous hydrochloric acid, and extracted with ethyl acetate. The organic layer was dried over anhydrous magnesium sulfate, and concentrated in vacuo to give (2S,4R)-N-tert-butoxycarbonyl- 4-tert-butyldimethylsiloxy-2-(1,2 -dihydroxyethyl)pyrrolidine (16.7 g, yield: 105%).

NMR(CDCl$_3$) δ: 0.08 (6H,s), 0.88 (9H,s), 1.48 (9H,s), 2.06 (2H,m), 3.40 (2H,m), 3.58 (3H,m), 4.05 (1H,m), 4.38 (1H,m)

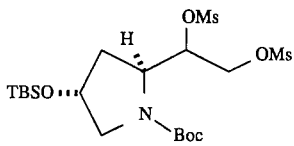

2)

To an ice-cooled solution of the above crude compound (8.7 g, 26 mmol as a pure material) in methylene chloride (174 ml) were successively added methanesulfonyl chloride (6.0 ml, 78 mmol) and triethylamine (16.2 ml, 117 mmol), and the mixture was stirred for 1 h at the same temperature. The mixture was washed with saturated aqueous sodium hydrogencarbonate, and dried over anhydrous magnesium sulfate. The solvent was removed in vacuo, and the residue was subjected to silica gel column chromatography (600 ml, ethyl acetate:hexane=1:1) to give (2S,4R)-N-tert-butoxycarbonyl- 4-tert-butyl-dimethylsiloxy-2-(1,2 -dimethanesulfonyloxyethyl)pyrrolidine (9.5 g, yield: 74%).

NMR(CDCl$_3$) δ: 0.05 (6H,s), 0.86 (9H,s), 1.46 (9H,s), 2.00 (2H,m), 3.06 (3H,s), 3.08 (3H,s), 3.34 (2H,m), 4.12 (1H,m), 4.40 (3H,m), 5.42 (1H,m)

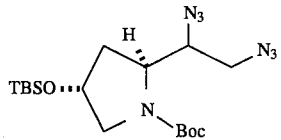

3)

A mixture of the above compound (9.5 g, 19.3 mmol) and sodium azide (8.72 g, 134 mmol) in dimethylsulfoxide (95 ml) was stirred at 100° C. for 1.5 h. After cooling, the reaction mixture was diluted with ethyl acetate (300 ml), and the organic layer was washed successively with water (100 ml) and saturated aqueous sodium chloride (50 ml). The organic layer was dried over anhydrous magnesium sulfate, and concentrated in vacuo. The residue was subjected to silica gel column chromatography (400 ml, ethyl acetate:hexane=1:5) to give (2S,4R)-N-tert-butoxycarbonyl-4-tert-butyl-dimethylsiloxy- 2-(1,2-diazidoethyl)pyrrolidine (4.54 g, yield: 61%).

NMR(CDCl$_3$) δ: 0.08 (6H,s), 0.86 (9H,s), 1.48 (9H,s), 3.10–3.90 (5H,m), 4.22 (1H,m), 4.38 (1H,m)

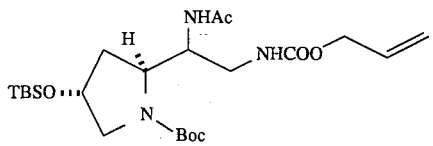

4)

To a solution of the above compound (434 mg, 1.13 mmol) in methanol (9 ml) was added 10% palladium-carbon catalyst (90 mg), and the mixture was stirred 1 h under a hydrogen atmosphere at room temperature. The catalyst was filtered off, the filtrate was concentrated in vacuo. To an ice-cooled solution of the resulting residue in methylene chloride (20 ml) was added 2 -allyloxycarbonylthio-4,6- dimethylpyrimidine (252 mg, 1.12 mmol), and the mixture was stirred for 30 min at room temperature. The mixture was diluted with methylene chloride (50 ml), and the organic layer was washed successively with 2N aqueous sodium hydroxide (0.56 ml) and water (10 ml). The organic layer was dried over anhydrous magnesium sulfate, and concentrated. To an ice-cooled solution of the resulting residue in methylene chloride (20 ml) were added acetyl chloride (96 μl, 1.35 mmol) and triethylamine (0.19 ml, 1.35 mmol), and the mixture was stirred for 30 min. The mixture was washed with saturated aqueous sodium hydrogencarbonate, and dried over anhydrous magnesium sulfate. The solvent was removed to give (2S,4R)-2-(1-acetamido-2 -allyloxycarbonylamino)ethyl-N-tert-butoxycarbonyl-4 -tert-butyldimethylsiloxypyrrolidine (210 mg, yield: 41%).

NMR(CDCl$_3$) δ: 0.06 (6H,s), 0.86 (9H,s), 1.48 (9H,s), 1.70–2.20 (2H,m), 1.96 (3H,s), 3.18–3.40 (3H,m), 3.50 (1H,m), 3.78 (1H,m), 4.10 (1H,m), 4.32 (1H,m), 4.56 (2H, d,J=6.0Hz), 5.18–5.20 (2H,m), 5.90 (1H,m)

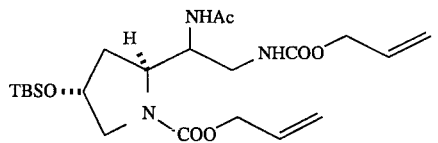

5)

The above compound (250 mg, 0.55 mmol) was dissolved in a mixture of methylene chloride and trifluoroacetic acid (1:1, 5 ml), and the solution was left for 10 min at room temperature. After the solvent was removed in vacuo to an ice-cooled solution of the residue in methylene chloride (5 ml) was added a solution of triethylamine (0.38 ml, 2.75 mmol) and allyl chlorocarbonate (0.17 ml, 1.65 mmol) in methylene chloride (0.8 ml), and the mixture was stirred for 30 min. The mixture was washed with saturated aqueous sodium hydrogencarbonate, and dried over anhydrous magnesium sulfate. The solvent was removed to give (2S,4R)-2-(1-acetamido-2-allyloxycarbonylamino)ethyl-N-allyloxycarbonyl- 4-tert-butyldimethylsiloxypyrrolidine (326 mg).

NMR(CDCl$_3$) δ: 0.06 (6H,s), 0.84 (9H,s), 1.94 (3H,s), 1.80–2.20 (2H,m), 3.32 (2H,m), 3.62 (1H,m), 3.84 (1H,m), 4.10 (2H,m), 4.40 (1H,m), 4.58 (4H,m), 5.10–5.40 (4H,m), 5.96 (2H,m)

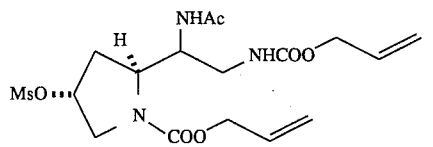

6)

To a solution of the above compound (326 mg) in tetrahydrofuran (6.0 ml) was added a solution of 1N tetra-n-butylammonium fluoride in tetrahydrofuran (0.82 ml, 0.82 mmol), and the mixture was stirred for 3 h at room temperature. The reaction mixture was diluted with ethyl acetate, and the organic layer was washed with saturated aqueous sodium chloride, and dried over anhydrous magnesium sulfate. After the solvent was removed, to an ice-cooled solution of the resulting residue in methylene chloride (6.0 ml) were added methanesuflonyl chloride (63 μl, 0.82 mmol) and triethylamine (0.15 ml, 1.1 mmol), and the mixture was stirred for 15 min. The reaction mixture was washed with saturated aqueous sodium hydrogencarbonate, and dried over anhydrous magnesium sulfate. After the solvent was removed, the resulting residue was subjected to silica gel column chromatography (40 ml, 5% methanol in ethyl acetate) to give (2S,4R)-2-(1-acetamido-2 -allyloxycarbonylamino)ethyl-N-allyloxycarbonyl-4 -methanesulfonyloxypyrrolidine (201 mg, yield: 67%).

NMR(CDCl₃) δ: 1.98 (3H,s), 1.95–2.30 (2H,m), 3.04 (3H,s), 3.10–3.60 (3H,m), 3.70–4.40 (4H,m), 4.58 (2H,m), 4.66 (2H,m), 5.10–5.40 (5H,m), 5.94 (2H,m)

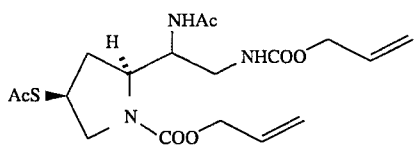
7)

A mixture of the above compound (200 mg, 0.46 mmol) and potassium thioacetate (159 mg, 1.39 mmol) in N,N-dimethylformamide (4 ml) was stirred at 70° C. for 1 h. The reaction mixture was diluted with ethyl acetate, and washed with saturated aqueous sodium hydrogencarbonate. After drying over anhydrous magnesium sulfate, the solvent was removed in vacuo. The resulting residue was subjected to silica gel column chromatography (40 ml, ethyl acetate) to give the title compound (100 mg, yield: 52%).

NMR(CDCl₃) δ: 1.70–2.10 (2H,m), 1.96 (3H,s), 2.36 (3H,m), 3.12 (1H,m), 3.38 (2H,m), 3.82 (1H,m), 4.00–4.30 (3H,m), 4.62 (4H,m), 5.20–5.50 (4H,m), 5.80–6.10 (2H,m)

REFERENCE EXAMPLE 4

(2S,4S)-4-Mercapto-2-[1-methanesulfonylamido-2-(4-nitrobenzyloxycarbonylamino)]ethyl-N-(p-nitrobenzyloxycarbonyl)pyrrolidine

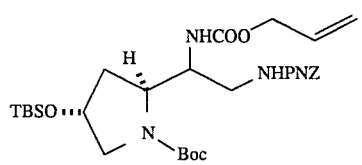
1)

To a solution of (2S,4R)-N-tert-butoxycarbonyl-4-tert-butyldimethylsiloxy-2-(1,2-diazido)ethylpyrrolidine prepared in REFERENCE EXAMPLE 3-3 (1.6 g, 3.89 mmol) in methanol (32 ml) was added 10% palladium-carbon catalyst (320 mg), and the mixture was stirred under a hydrogen atmosphere at room temperature for 1 h. The catalyst was filtered off, and the filtrate was concentrated in vacuo. To an ice-cooled solution of the resulting residue in methylene chloride (32 ml) was added 4,6-dimethyl-2-(p-nitrobenzyloxycarbonylthio)pyrimidine (1.1 g, 3.45 mmol), and the mixture was stirred for 1 h. The reaction mixture was washed with 1 N aqueous sodium hydroxide (3.5 ml), dried over anhydrous magnesium sulfate, and concentrated. To an ice-cooled solution of the resulting residue in methylene chloride (30 ml) were added triethylamine (0.81 ml, 5.35 mmol) and allylchloroformate (0.49 ml, 4.27 mmol), and the mixture was stirred for 30 min. The reaction mixture was washed with saturated aqueous sodium hydrogencarbonate, dried over anhydrous magnesium sulfate, and concentrated to give (2S,4R)-2-[1-allyloxycarbonylamino- 2-(p-nitrobenzyloxycarbonylamino)ethyl]-N-tert-butoxycarbonyl- 4-tert-butyldimethylsiloxypyrrolidine (2.28 g, yield: 94%).

NMR(CDCl₃) δ: 0.06 (6H,s), 0.86 (9H,s), 1.50 (9H,s), 2.00 (2H,m), 3.00–4.00 (5H,m), 4.18 (1H,m), 4.38 (1H,m), 4.60 (2H,m), 5.10–5.50 (4H,m), 6.00 (1H,m), 7.56 (2H,d, J=8.0Hz), 8.28 (2H,d,J=8.0Hz)

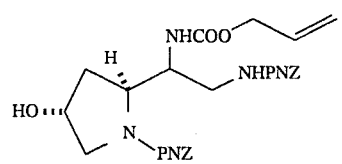
2)

To an ice-cooled solution of the above compound (2.28 g, 3.66 mmol) in methylene chloride (10 ml) was added trifluoroacetic acid (10 ml), and the mixture was stirred for 30 min at room temperature. The mixture was concentrated to give the oily residue, which was dissolved in methylene chloride (20 ml). To the solution were added p-nitrobenzyloxycarbonyl chloride (1 g, 4.65 mmol) and triethylamine (1.62 ml, 10.7 mmol), and the mixture was stirred for 30 min. The mixture was washed with saturated aqueous sodium hydrogencarbonate, dried over anhydrous magnesium sulfate, and concentrated. To a solution of the resulting residue in tetrahydrofuran (40 ml) was added 1N tetra-n-butylammonium fluoride solution (7.3 ml, 7.3 mmol), and the mixture was stirred for 4 h at room temperature. The reaction mixture was washed with saturated aqueous sodium chloride, and dried over anhydrous magnesium sulfate. The solvent was removed, and the residue was subjected to silica gel column chromatography (100 ml, ethyl acetate) to give (2S,4R)-2-[1-allyloxycarbonylamino- 2-(p-nitrobenzyloxycarbonylamino)ethyl]-4 -hydroxy-N-(p-nitrobenzyloxycarbonyl)pyrrolidine (1.74 g, yield: 81%).

NMR(CDCl₃) δ: 1.90 (2H,m), 3.30 (2H,m), 3.62 (2H,m), 4.18 (2H,m), 4.36 (1H,m), 4.54 (2H,m), 5.10–5.40 (6H,m), 5.84 (1H,m), 7.52 (4H,m), 8.22 (4H,m)

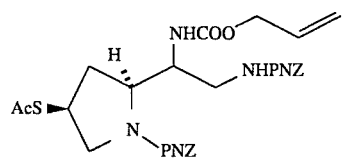
3)

To an ice-cooled solution of the above compound (1.74 g, 2.96 mmol) in methylene chloride (34 ml) were added triethylamine (0.62 ml, 4.44 mmol) and methanesulfonyl chloride (0.34 ml, 4.44 mmol), and the mixture was stirred for 30 min. The reaction mixture was washed with saturated aqueous sodium hydrogencarbonate, dried over anhydrous magnesium sulfate, and concentrated to give 1.8 g of the residue. To a solution of the residue in N,N-dimethylformamide (36 ml) was added potassium thioacetate (1.0 g, 8.77 mmol), and the mixture was stirred for 22 h at 70° C. The reaction mixture was diluted with ethyl acetate, washed with saturated aqueous sodium chloride, dried over anhydrous magnesium sulfate, and concentrated. The resulting residue was subjected to silica gel column chromatography (100 ml, ethyl acetate:hexane=1:1) to give (2S,4S)-4-acetylthio-2-[1-allyloxycarbonylamino- 2-(p-nitrobenzyloxycarbonylamino)ethyl]-N-(p-nitrobenzyloxycarbonyl)pyrrolidine (1.38 g, yield: 72%).

NMR(CDCl₃) δ: 1.80 (2H,m), 2.38 (3H,s), 2.60 (1H,m), 3.12 (2H,m), 3.28 (2H,m), 3.82 (1H,m), 4.10 (1H,m), 4.56 (2H,m), 5.10–5.40 (6H,m), 5.90 (1H,m), 7.54 (4H,m), 8.24 (4H,m)

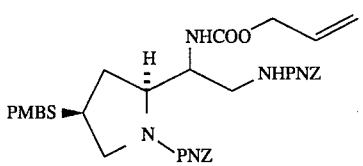

4)

To an ice-cooled solution of the compound (1.3 g, 2.01 mmol) in methanol (26 ml) was added 2N sodium hydroxide (1.2 ml, 2.4 mmol), and the mixture was stirred for 1 h. To the reaction mixture were added p-methoxybenzyl chloride (0.55 ml, 4.0 mmol) and 2N aqueous sodium hydroxide (1.2 ml, 2.4 mmol), and the mixture was stirred for 1 hr at room temperature. The reaction mixture was diluted with methylene chloride, washed with saturated aqueous sodium chloride, dried over anhydrous magnesium sulfate, and concentrated. The resulting residue was subjected to silica gel column chromatography (100 ml, ethyl acetate:hexane=2:1) to give (2S,4S)-2-[1-allyloxycarbonylamino-2 -(p-nitrobenzyloxycarbonylamino)ethyl]-4-(4-methoxybenzylthio)-N-(p-nitrobenzyloxycarbonyl)pyrrolidine (1.10 g, yield: 75%).

NMR(CDCl$_3$) δ: 1.76 (2H,m), 2.48 (1H,m), 3.00 (2H,m), 3.32 (2H,m), 3.80 (3H,s), 3.80–4.20 (2H,m), 4.56 (2H,m), 5.00–5.40 (6H,m), 5.90 (1H,m), 6.84 (2H,d,J=8.0Hz), 7.24 (2H,d,J=8.0Hz), 7.52 (4H,m), 8.24 (4H,m)

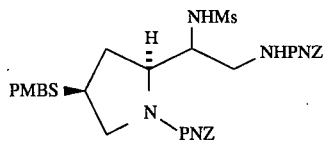

5)

To a solution of the above compound (1.1 g, 1.52 mmol) in methylene chloride (22 ml) were added water (0.22 ml), bistriphenylphosphine palladium(II) chloride (21 mg, 0.03 mmol), and tributyltin hydride (0.9 ml, 3.34 mmol), and the mixture was stirred for 3 hr at room temperature. After the solvent was removed in vacuo, to an ice-cooled solution of the resulting residue in methylene chloride (20 ml) were added triethylamine (0.32 ml, 2.28 mmol) and methanesulfonyl chloride (0.14 ml, 1.82 mmol), and the mixture was stirred 1 h. The reaction mixture was washed with saturated aqueous sodium hydrogencarbonate, dried over anhydrous magnesium sulfate, and concentrated. The resulting residue was subjected to silica gel column chromatography (100 ml, ethyl acetate:hexane=3:1) to give (2S,4S)-2-[1 -methanesulfonylamido-2-(p-nitrobenzyloxycarbonylamino)ethyl]-4-(p-methoxybenzylthio)-N-(p-nitrobenzyloxycarbonyl)pyrrolidine (720 mg, yield: 66%).

NMR(CDCl$_3$) δ: 1.90 (2H,m), 2.50 (1H,m), 2.86 (3H,s), 2.90–3.40 (4H,m), 3.80 (3H,s), 3.60–4.20 (2H,m), 5.24 (4H,m), 6.86 (2H,d,J=8.0Hz), 7.22 (2H,d,J=8.0Hz), 7.52 (4H,m), 8.26 (4H,m)

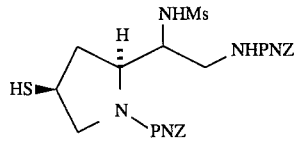

6)

A mixture of the above compound (400 mg, 0.56 mmol), trifluoroacetic acid (4 ml) and anisole (90 μl, 0.84 mmol) was stirred under refluxing for 30 min. After cooling, the reaction mixture was concentrated. The resulting residue was subjected to silica gel column chromatography (30 ml, ethyl acetate:hexane=3:1) to give the title compound (253 mg, yield: 76%).

NMR(CDCl$_3$) δ: 1.80 (2H,m), 2.70 (1H,m), 2.90 (3H,s), 3.10–3.50 (4H,m), 3.76 (1H,m), 4.10 (1H,m), 5.24 (4H,m), 7.56 (4H,m), 8.24 (4H,m)

REFERENCE EXAMPLE 5

(2S,4S)-4-Acetylthio-2-(1-cyano-1-p-nitrobenzyloxycarbonylamino)methyl-N-p-nitrobenzyloxycarbonylpyrrolidine

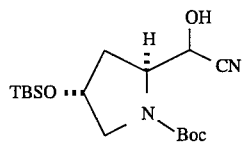

1)

To a solution of N,N-dimethylformamide (2.54 ml, 35.8 mmol) and methylene chloride (34.5 ml) was added oxalyl chloride (1.53 ml, 17.5 mmol) at −78° C., and the mixture was stirred for 15 min at the same temperature. To the mixture was added dropwise a solution of (2S,4R)-N-tert-butoxycarbonyl- 4-tert-butyldimethylsiloxy-2 -hydroxymetylpyrrolidine (3.92 g, 11.8 mmol) in methylene chloride (34.5 ml) over a 10 min period. After stirring for 30 min, triethylamine (8.27 ml, 59.3 mmol) was added to the mixture, and the mixture was allowed to warm to room temperature. After stirring for 15 min, the reaction mixture was washed with water, dried over anhydrous magnesium sulfate, and concentrated in vacuo to give an oily residue, which was dissolved in benzene (20 ml). To the solution was added trimethylsilylcyanide (1.75 ml, 13.1 mmol), and the mixture was stirred for 12 h at room temperature. To the mixture was added methanol (15 ml), and further stirred. The solvent was removed in vacuo. The resulting residue was subjected to silica gel column chromatography (hexane:ethyl acetate=5:1) to give (2S,4R)-N-tert-butoxycarbonyl- 4-tert-butyldimethylsiloxy-2-(1-cyano-1 -hydroxymethyl)pyrrolidine (3.8 g, yield: 88.1%).

IR(KBr)cm$^{-1}$: 3400,2900,2260,1700,1670 NMR(CDCl$_3$) δ: 0.10 (6H,s), 0.90 (9H,s), 1.50 & 1.54 (total 9H,each s), 1.85 (1H,m), 2.18 (1H,m), 3.40–3.60 (2H,m), 4.50 (2H,m), 5.80 (1H,m)

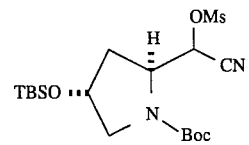

2)

To an ice-cooled solution of the above compound (2.33 g, 6.37 mmol) in tetrahydrofuran (40 ml) were added triethylamine (1.28 ml, 9.12 mmol) and methanesulfonyl chloride (0.73 ml, 9.43 mmol), and the mixture was stirred for 1 h at the same temperature. The reaction mixture was diluted with ethyl acetate (40 ml), washed successively with water and saturated aqueous sodium chloride, dried over anhydrous magnesium sulfate, and concentrated. The residue was subjected to silica gel column chromatography (hexane:ethyl acetate=4:1) to give (2S,4R)-N-tert-butoxycarbonyl-4 -tert-butyldimethylsiloxy-2-(1-cyano-1-methanesulfonyloxy)methylpyrrolidine (2.1 g, yield: 80.5%).

NMR(CDCl$_3$) δ: 0.40 (6H,s), 0.82 (9H,s), 1.60 (9H,s), 2.12 (2H,m), 3.08 & 3.17 (total 3H,each s), 3.40 (2H,m), 4.40 (2H,m), 5.95 (1H,m)

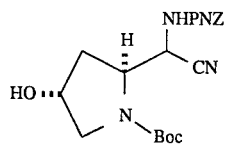
3)

To a solution of the above compound (819 mg, 2 mmol) in N,N-dimethylformamide (16 ml) was added sodium azide (390 mg, 6 mmol), and the mixture was stirred for 3 h at 50° C. The reaction mixture was diluted with ethyl acetate (40 ml), washed successively with water (2×30 ml) and saturated aqueous sodium chloride, dried over anhydrous magnesium sulfate, and concentrated in vacuo to give the residue, which was dissolved in methanol (20 ml). To the solution was added 10% palladium-carbon catalyst (300 mg), and the mixture was stirred under a hydrogen atmosphere for 1 h. The catalyst was filtered off, the filtrate was concentrated in vacuo. To a solution of the resulting residue in chloroform (20 ml) was added 4,6-dimethyl-2-(p-nitrobenzyloxythio)pyrimidine (640 mg, 2 mmol), and the mixture was stirred for 2 h. The reaction mixture was washed successively with saturated aqueous sodium hydrogencarbonate and saturated aqueous sodium chloride, and concentrated in vacuo. The residue was subjected to silica gel column chromatography (hexane:ethyl acetate=1:1) to give (2S,4R)-N-tert-butoxycarbonyl-4-tert-butyldimethylsiloxy- 2-[1-cyano-1-(p-nitrobenzyloxyamino)methyl]pyrrolidine (520 mg, yield: 48.7%). The above compound was dissolved in a methanol saturated with hydrogen chloride, the solution was left for 5 h. After the solvent was removed in vacuo, the residue was dissolved in ethyl acetate (20 ml), and the mixture was was washed successively with saturated aqueous sodium hydrogencarbonate and saturated aqueous sodium chloride. After drying over anhydrous magnesium sulfate, the solvent was removed. To a solution of the resulting residue in chloroform (10 ml) was added 4,6-dimethyl-2 -(p-nitrobenzyloxycarbonylthio)pyrimidine (319 mg, 1 mmol), and the the mixture was stirred for 2 h. The reaction mixture was worked up and purified by the same manner aforementioned to give (2S,4R)-2-(1-cyano-1 -p-nitrobenzyloxycarbonylmethyl)-4-hydroxy-N-p-nitrobenzyloxycarbonyl-pyrrolidine (260 mg, yield: 53.4%).

IR(KBr)cm$^{-1}$: 3400,2950,2250,1700 NMR(CDCl$_3$) δ: 2.20 (2H,m), 3.56–3.84 (2H,m), 4.40 (1H,m), 4.60 (1H,br s), 5.10 (1H,m), 5.26 (2H,s), 5.30 (2H,s), 6.20 (1H,m), 7.52 (4H,d,J=7.0Hz), 8.12 (4H,d,J=7.0Hz)

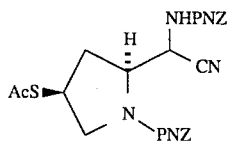
4)

The title compound (88.1 mg, yield: 32.2%) was obtained from the above compound (260 mg, 0.52 mmol) in the same manner as in REFERENCE EXAMPLES 1-5 and 1-6.

NMR(CDCl$_3$) δ: 2.10 (3H,s), 2.20 (2H,m), 3.40–3.70 (2H,m), 4.20 (1H,m), 4.60 (1H,m), 5.10 (1H,m), 5.30 (2H, s), 5.35 (2H,s), 6.20 (1H,m), 7.50 (4H,d,J=7.0Hz), 8.10 (4H,d,J=7.0Hz)

REFERENCE EXAMPLE 6

(2S,4S)-4-Acetylthio-2-(2-methyl-3-p-nitrobenzyloxycarbonylamino)propyl-N-p-nitrobenzyloxycarbonylpyrrolidine

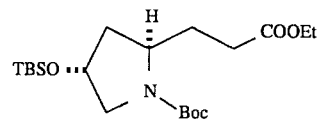
1)

To a solution of (2S,4R)-N-tert-butoxycarbonyl-4 -tert-butyldimethylsiloxy-2-[(E)-2-ethoxycarbonylvinyl]pyrrolidine (29 g, 50 mmol) in ethanol (500 ml) was added 10% palladium-carbon catalyst (5 g), and the mixture was stirred under a hydrogen atmosphere at room temperature for 2 h. To the mixture was added an additional 10% palladium-carbon catalyst (2 g), and the mixture was stirred for 1.5 h under the same condition. The catalyst was filtered off, and the filtrate was concentrated in vacuo. The residue was subjected to silica gel column chromatography (heptane-ethyl acetate) to give (2S,4R)-N-tert-butoxycarbonyl-4-tert-butyldimethylsiloxy- 2-(2-ethoxycarbonyl)ethylpyrrolidine (15.62 g, yield: 78%).

IR(KBr)cm$^{-1}$: 2930,1735,1695,1390,1365,1250,1170, 1110, 835,775 NMR(CDCl$_3$) δ: 0.06 (6H,s), 0.86 (9H,s), 1.26 (3H,t,J=7.0Hz), 1.46 (9H,s), 1.60–1.85 (2H,m), 1.85–2.20 (2H,m), 2.20–2.40 (2H,m), 3.25–3.55 (2H,m), 3.95 (1H,m), 4.14 (2H,q,J=7.0Hz), 4.35 (1H,m)

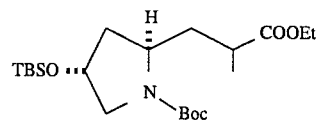
2)

To a mixture of 2.1M lithium diisopropylamide tetrahydrofuran solution (3 ml, 6.3 mmol) and tetrahydrofuran (12 ml) was added dropwise a solution of the above compound (2.01 g, 5 mmol) in tetrahydrofuran (3 ml) at −78° C. under a nitrogen atmosphere, and the mixture was stirred for 1 h at the same temperature. To the mixture was added methyl iodide (1 ml, 11.9 mmol), and the mixture was stirred at −78° C. for 10 min, and then room temperature overnight. The reaction mixture was poured into a mixture of water (200 ml) and 1N aqueaous potassium hydrogensulfate (20 ml), and extracted with ethyl acetate (3×50 ml). The combined organic layer was washed successively with 10% aqueous sodium sulfite, water, 1N aqueaous potassium hydrogen-sulfate, water and saturated aqueous sodium chloride. After drying over anhydrous magnesium sulfate, the solvent was removed in vacuo. The residue was subjected to silica gel column chromatography (heptane-ethyl acetate) to give (2S,4R)-N-tert-butoxycarbonyl-4-tert-butyldimethylsiloxy- 2-(2-ethoxycarbonyl-2-methyl)ethylpyrrolidine (1.93 g, yield: 93%).

IR(KBr)cm$^{-1}$: 2940,1740,1700,1465,1395,1370,1260, 1160, 1120,840,780 NMR(CDCl$_3$) δ: 0.06 (6H,s), 0.86 (9H, s), 1.20 (3H,d,J=7.0Hz), 1.27 (3H,t,J=7.0Hz), 1.46 (9H,s), 1.50–1.80 (2H,m), 1.80–2.10 (1H,m), 2.10–2.30 (1H,m), 2.30–2.60 (1H,m), 3.20–3.55 (2H,m), 3.80–4.00 (1H,m), 4.14 (2H,q,J=7.0Hz), 4.25–4.40 (1H,m)

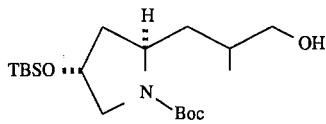
3)

To an ice-cooled suspension of lithium aluminium hydride (80 mg, 2.11 mmol) in diethyl ether (8 ml) was added a solution of the above compound (830 mg, 2.0 mmol) in ether (2 ml) under a nitrogen atmosphere, and the mixture was stirred for 1 h at the same temperature. To the resulting reaction mixture was added successively water (0.08 ml), 20% aqueous sodium hydroxide (0.06 ml) and water (0.28 ml) under ice-cooling and vigorously stirring. After stirring for a while, diethyl ether (20 ml) was added to the mixture. The resulting precipitate was filtered off, and the precipitate was washed with diethyl ether (2×20 ml). The combined ether layer was washed successively with water and saturated aqueous sodium chloride. After drying over anhydrous magnesium sulfate, the solvent was removed in vacuo. The residue was subjected to silica gel column chromatography (heptane-ethyl acetate) to give (2R,4R)-N-tert-butoxycarbonyl- 4-tert-butyldimethylsiloxy-2-(3-hydroxy-2 -methyl)propylpyrrolidine (750 mg, yield: quantitative yield).

IR(KBr)cm$^{-1}$: 3460,3420,2930,1695,1675,1400,1365, 1255, 1165,840,775 NMR(CDCl$_3$) δ: 0.06 (6H,s), 0.87 (6H,s), 0.96 (3H,d,J=7.0Hz), 1.45 (9H,s), 1.55–2.30 (6H,m), 3.20–3.80 (4H,m), 3.90–4.10 (1H,m), 4.25–4.45 (1H,m)

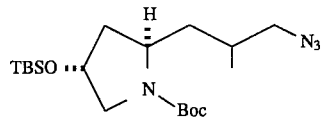
4)

To an ice-cooled solution of the above compound (700 mg, 1.87 mmol) in tetrahydrofuran (10 ml) was added triethylamine (0.4 ml, 2.87 mmol) and methanesulfonyl chloride (0.22 ml, 2.84 mmol) under a nitrogen atmosphere, and the mixture was stirred for 1 h at the same temperature. The reaction mixture was diluted with ethyl acetate (150 ml), and the organic layer was washed successively with water, 1N aqueous potassium hydrogensulfate, water, saturated aqueous sodium carbonate, water and saturated aqueous sodium chloride. After drying over anhydrous magnesium sulfate, the solvent was removed in vacuo to give the crude mesyl compound. To a solution of the above crude mesyl compound in N,N-dimethylformamide (6 ml) was added sodium azide (410 mg, 6.31 mmol), and the mixture was stirred for 2 h at 70° C. under a nitrogen atmosphere. The reaction mixture was poured into water (200 ml), and extracted with ethyl acetate (3×50 ml). The combined organic layer was washed successively with water and saturated aqueous sodium chloride. After drying over anhydrous magnesium sulfate, the solvent was removed in vacuo. The residue was subjected to silica gel column chromatography (heptane-ethyl acetate) to give (2R,4R)- 2-(3-azido-2-methyl)propyl-N-tert-butoxycarbonyl-4 -tert-butyldimethylsiloxypyrrolidine (610 mg, yield: 82%).

IR(KBr)cm$^{-1}$: 2930,2100,1695,1390,1365,1255,1160, 840, 775 NMR(CDCl$_3$) δ: 0.06 (6H,s), 0.86 (9H,s), 1.01 (3H,d,J=7.0Hz), 1.45 (9H,s), 1.55–2.10 (5H,m), 3.05–3.50 (4H,m), 3.85–4.10 (1H,m), 4.30–4.40 (1H,m)

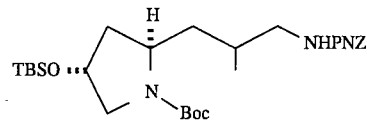
5)

To a solution of the above compound (600 mg, 1.51 mmol) in methanol (15 ml) was added 10% palladium-carbon catalyst (120 mg), and the mixture was stirred under a hydrogen atmosphere for 1 h at room temperature. The catalyst was filtered off, and the solvent was removed in vacuo to give the crude amine compound. To a solution of the amine compound in dioxane (5 ml) was added 4,6-dimethyl-2-(p-nitrobenzyloxycarbonylthio)pyrimidine (490 mg, 1.53 mmol), and the mixture was stirred for 4 h at room temperature. The reaction mixture was diluted with ethyl acetate (150 ml), and successively washed with 1N aqueous potassium hydrogensulfate, water, and saturated aqueous sodium chloride. After drying over anhydrous magnesium sulfate, the solvent was removed in vacuo. The residue was subjected to silica gel column chromatography (heptane-ethyl acetate) to give (2R,4R)-N-tert-butoxycarbonyl-4-tert-butyldimethylsiloxy-2-[(2-methyl-3 -p-nitrobenzyloxycarbonylamino)propyl]pyrrolidine (750 mg, yield: 90%).

IR(KBr)cm$^{-1}$: 2930,1725,1695,1680,1525,1400,1345, 1250 NMR(CDCl$_3$) δ: 0.06 (6H,s), 0.86 (9H,s), 0.94 (3H, d,J=7.0Hz), 1.45 & 1.46 (total 9H,each s), 1.50–2.10 (5H, m), 3.00–4.50 (4H,m), 3.80–4.10 (1H,m), 4.33 (1H,m), 5.22 (2H,s), 5.50–6.30 (1H,m), 7.53 (2H,m), 8.23 (2H,d,J= 8.0Hz)

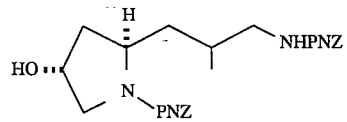
6)

A solution of the above compound (740 mg, 1.34 mmol) trifluoroacetic acid (5 ml) was stirred overnight at room temperature. After the solvent was removed, the residue was distilled with benzene for several times to give the crude amine compound. To a solution of the amine compound in dioxane (3 ml) and water (1 ml) were added sodium hydrogencarbonate (1.13 g, 13.45 mmol) and 4,6-dimethyl-2-(p-nitrobenzyloxycarbonylthio)pyrimidine (430 mg, 1.35 mmol), and the mixture was stirred overnight at room temperature. The reaction mixture was diluted with ethyl acetate (150 ml), and washed successively with water, 1N aqueous potassium hydrogensulfate, water and saturated aqueous sodium chloride. After drying over anhydrous magnesium sulfate, the solvent was removed in vacuo. The residue was subjected to silica gel column chromatography (methylene chloride—ethyl acetate) to give (2S,4R)-4 -hydroxy-2-(2-methyl-3 -p-nitrobenzyloxycarbonylamino)propyl-N-p-nitrobenzyloxycarbonylpyrrolidine (640 mg, yield: 92%).

IR(KBr)cm$^{-1}$: 3400,2940,1700,1605,1520,1430,1400, 1345, 1240,1105,850,735 NMR(CDCl$_3$) δ: 0.96 (3H,d,J= 6.0Hz), 1.00–1.40 (1H,m), 1.50–2.30 (5H,m), 2.80–3.80 (4H,m), 3.95–4.20 (1H,m), 4.30–4.50 (1H,m), 4.70–5.70 (1H,m), 5.21 & 5.24 (total 4H,each s), 7.52 (4H,d,J=8.0Hz), 8.22 (4H,d,J=8.0Hz)

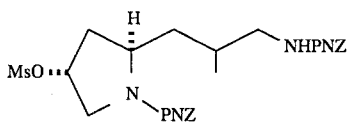

To an ice-cooled solution of the above compound (630 mg, 1.22 mmol) in tetrahydrofuran (5 ml) were added dropwise triethylamine (0.26 ml, 1.87 mmol) under a nitrogen atmosphere, and then methanesulfonyl chloride (0.14 ml, 1.81 mmol), and the mixture was stirred for 30 min at the same temperature. The reaction mixture was diluted with ethyl acetate (150 ml), and the organic layer was successively washed with water, 1N aqueous potassium hydrogensulfate, water, saturated aqueous sodium hydrogencarbonate, water and saturated aqueous sodium chloride. After drying over anhydrous magnesium sulfate, the solvent was removed in vacuo. The residue was subjected to silica gel column chromatography (methylene chloride—ethyl acetate) to give (2R,4R)-4-methanesulfonyloxy-2-(2-methyl-3-p-nitrobenzyloxycarbonylamino)propyl-N-p-nitrobenzyloxycarbonylpyrrolidine (710 mg, yield: 98%).

IR(KBr)cm$^{-1}$: 3450,2930,1720,1700,1690,1600,1520, 1340, 1240,1165,1105,900,735 NMR(CDCl$_3$) δ: 0.97 (3H, d,J=7.0Hz), 1.10–1.15 (1H,m), 1.50–2.10 (5H,m), 2.40–2.60 (1H,m), 2.90–3.40 (1H,m), 3.05 (3H,s), 3.50–3.70 (1H,m), 3.90–4.20 (2H,m), 4.80–5.50 (1H,m), 5.22 & 5.25 (total 4H,each s), 7.53 (4H,d,J=8.0Hz), 8.24 (4H,m)

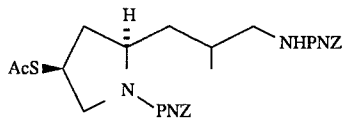

To a solution of the above compound (700 mg, 1.18 mmol) in N,N-dimethylformamide (6 ml) were added potassium thioacetate (270 mg, 2.36 mmol) and sodium iodide (270 mg, 1.80 mmol), and the mixture was stirred for 4 h at 70° C. under a nitrogen atmosphere. The reaction mixture was poured into water (300 ml), and extracted with ethyl acetate (1×100 ml, 2×50 ml). The combined organic layer was washed successively with 10% aqueous sodium sulfite and saturated aqueous sodium chloride. After drying over anhydrous magnesium sulfate, the solvent was removed in vacuo. The residue was subjected to silica gel column chromatography (heptane-ethyl acetate) to give the title compound (620 mg, yield: 92%).

IR(KBr)cm$^{-1}$: 3400,2950,1700,1605,1520,1400,1345, 1240, 1110,1010,855,740 NMR(CDCl$_3$) δ: 0.95 (3H,d,J= 6.0Hz), 1.20–1.40 (1H,m), 1.40–1.80 (3H,m), 2.34 & 2.35 (total 3H,each s), 2.40–2.70 (1H,m), 3.00–3.35 (3H,m), 3.80–4.20 (3H,m), 5.21 & 5.23 (total 4H,each s), 5.25–5.60 (1H,m), 7.52 (4H,d,J=8.0Hz), 8.23 (4H,m)

REFERENCE EXAMPLE 7

(2S,4S)-4-Acetylthio-N-p-nitrobenzyloxycarbonyl-2-[[3-(p-nitrobenzyloxycarbonylamino)-1-hydroxy] propyl]pyrrolidine Diastereomer A and B

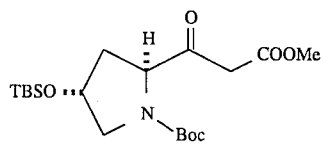

To a solution of (2S,4R)-N-tert-butoxycarbonyl-4-tert-butyldimethylsiloxyproline methyl ester (9.06 g, 25.2 mmol) in methanol (75 ml) was added 1N aqueous sodium hydroxide (27 ml, 27 mmol), and the mixture was stirred for 5 h at room temperature. The reaction mixture was concentrated in vacuo, the residue was dissolved in water (50 ml). The resulting solution was washed with diethyl ether (50 ml), and 1N aqueous hydrochloric acid (27 ml, 27 mmol) was added, and then extracted with ethyl acetate. The organic layer was washed successively with water and saturated aqueous sodium chloride. After drying over anhydrous magnesium sulfate, the solvent was removed in vacuo to give the crude carboxylic acid. To a solution of the above carboxylic acid in tetrahydrofuran (25 ml) was slowly added carbodiimidazole (4.08 g, 25.2 mmol), and the mixture was stirred for 1 h at room temperature. To a solution of malonic acid monomethyl ester (13.84 g, 126 mmol) in tetrahydrofuran (125 ml) were added magnesium chloride (7.19 g, 75.5 mmol) and triethylamine (19.3 ml, 75.5 mmol), and the mixture was stirred for 1 h at room temperature. To the resulting mixture was added the above imidazolide solution, and the mixture was stirred overnight. To the reaction mixture was added 10% aqueous citric acid (150 ml), and extracted with ethyl acetate (2×150 ml). The organic layer was washed successively with saturated aqueous sodium hydrogencarbonate, water and saturated aqueous sodium chloride. After drying over anhydrous magnesium sulfate, the solvent was removed in vacuo. The residue was subjected to silica gel column chromatography (heptane—ethyl acetate) to give (2S,4R)-N-tert-butoxycarbonyl-4-tert-butyldimethylsiloxy-2-(2-carboxymethyl-1-oxo)ethylpyrrolidine (6.0 g, yield: 59%).

IR(KBr)cm$^{-1}$: 3450,2950,1750,1700,1690,1390,1250 NMR(CDCl$_3$) δ: 0.06 (6H,s), 0.86 (9H,s), 1.38 & 1.40 (total 9H), 1.80–2.20 (2H,m), 3.35–3.65 (4H,m), 3.73 & 3.75 (total 3H), 4.33–4.57 (2H,m)

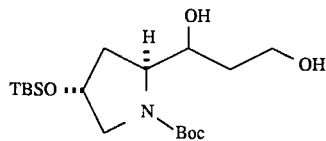

To a suspension of the above compound (4.02 g, 10 mmol) and sodium borohydride (0.95 g, 25.0 mmol) in tetrahydrofuran (20 ml) was added dropwise methanol (8 ml) under refluxing over a 30 min period. After cooling to room temperature, to the reaction mixture was successively added water (5 ml) and 10% aqueous citric acid (20 ml), and extracted with ethyl acetate (3×50 ml). The organic layer was washed successively with water and saturated aqueous sodium chloride. After drying over anhydrous magnesium sulfate, the solvent was removed in vacuo to give the crude (2S,4R)-N-tert-butoxycarbonyl- 4-tert-butyldimethylsiloxy-2-[(1R,S)-1,3-dihydroxypropyl]pyrrolidine (3,75 g, quantitative yield).

IR(KBr)cm$^{-1}$: 3400,2930,1670,1400 NMR(CDCl$_3$) δ: 0.06 (6H,s), 0.86 (9H,s), 1.43 (9H,s), 1.25–1.65 (2H,m), 1.65–2.00 (2H,m), 3.25 (1H,dd,J=2.0,6.0Hz), 3.51 (1H,m), 3.86 (2H,t,J=3.0Hz), 3.93–4.22 (2H,m), 4.32 (1H,m)

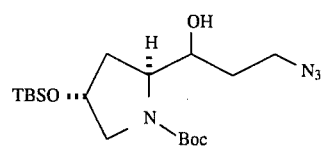

To an ice-cooled solution of the above compound (1.05 g, 2.8 mmol) in pyridine (5.6 ml) was added p-toluenesulfonyl chloride (640 mg, 3.36 mmol), and the mixture was stirred overnight at 0°–5° C. To the reaction mixture were added ethyl acetate (6 ml) and saturated aqueous sodium hydrogencarbonate (6 ml), and the mixture was stirred for 15 min at room temperature. The mixture was poured into saturated aqueous sodium hydrogencarbonate (30 ml), and extracted with chloroform (3×20 ml). After drying over anhydrous magnesium sulfate, the solvent was removed in vacuo to give the crude monotosylate. To a solution of the above monotosylate in N,N-dimethylformamide (2.8 ml) was added sodium azide (546 mg, 8.4 mmol), and the mixture was stirred for 2 h at 70° C. The reaction mixture was poured into water (50 ml), and extracted with ethyl acetate (3×25 ml). The organic layer was washed successively with water and saturated aqueous sodium chloride. After drying over anhydrous magnesium sulfate, the solvent was removed in vacuo. The residue was subjected to silica gel column chromatography (heptane-ethyl acetate) to give (2S,4R)-2-(3-azido-1 -hydroxy)propyl-N-tertbutoxycarbonyl-4-tert-butyldimethylsiloxypyrrolidine diastereomer A (310 mg, yield: 28%, polar diastereomer) and diastereomer B (280 mg, yield: 25%, less polar diastereomer).

DIASTEREOMER A: IR(KBr)cm$^{-1}$: 3430,2950,2100,1690,1670,1400,1250 NMR(CDCl$_3$) δ: 0.06 (6H,s), 0.84 & 0.86 (total 9H), 1.47 (9H,s), 1.40–2.05 (4H,m), 3.23 (1H,dd,J=2.0,6.0Hz), 3.35–3.65 (4H,m), 3.85 (1H,m), 4.29 (1H,m)

DIASTEREOMER B: IR(KBr)cm$^{-1}$: 3400,2930,2100,1700,1660,1400,1250 NMR(CDCl$_3$) δ: 0.06 (6H,s), 0.86 (9H,s), 1.43 (9H,s), 1.40–2.05 (4H,m), 3.25 (1H,dd,J=2.0,6.0Hz), 3.44–3.72 (4H,m), 4.00 (1H,m), 4.27 (1H,m)

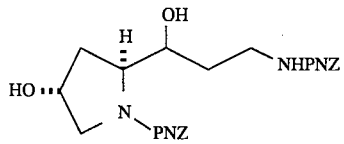
4)

To a solution of the above diastereomer A (448 mg, 1.12 mmol) in methanol (11 ml) was added 10% palladium-carbon catalyst (45 mg), and the mixture was stirred for 1 h under an atmospheric pressure of hydrogen at room temperature. The catalyst was filtered off, and the solvent was removed in vacuo. To a solution of the residue in methanol (8 ml) was added 3M hydrochloric acid—dioxane solution (16 ml), and the mixture was stirred overnight at room temperature. The solvent was removed in vacuo, and to the residue were added methanol (11 ml) and triethylamine (1.56 ml, 11.2 mmol). To the mixture was added a solution of 4,6-dimethyl-2 -(p-nitrobenzyloxycarbonythio)pyrimidine (715 mg, 2.24 mmol) in methylene chloride (4 ml), and the mixture was stirred for 5 h at room temperature. The reaction mixture was concentrated in vacuo, and the residue was dissolved with ethyl acetate (50 ml), washed successively with 1N aqueous hydrochloric acid, water and saturated aqueous sodium chloride. After drying over anhydrous magnesium sulfate, the solvent was removed in vacuo. The residue was subjected to silica gel column chromatography (heptane-ethyl acetate) to give (2S,4R)-4-hydroxy-2-(1-hydroxy-3 -N-p-nitrobenzyloxycarboanylamino)pyropyl-N-p-nitrobenzyloxycarbonylpyrrolidine diastereomer A (484 mg, yield: 83%).

(2S,4R)-4-Hydroxy-2-(1-hydroxy-3 -N-p-nitrobenzyloxycarbonylamino)propyl-N-p-nitrobenzyloxycarbonylpyrrolidine diastereomer B (363 mg, yield: 63%) was obtained from the above diastereomer B (484 mg, 1.12 mmol) in the same manner.

DIASTEREOMER A: IR(KBr)cm$^{-1}$: 3400,1700,1620,1520,1340 NMR(CDCl$_3$) δ: 1.29–2.05 (4H,m), 3.31 (1H,m), 3.37–3.62 (2H,m), 3.70 (1H,m), 4.00–4.22 (2H,m), 4.49 (1H,m), 5.10–5.35 (4H,m), 7.48 (2H,d,J=7.0Hz), 7.53 (2H,d,J=7.0Hz), 8.22 (2H,d,J=7.0Hz), 8.23 (2H,d,J=7.0Hz)

DIASTEREOMER B: IR(KBr)cm$^{-1}$: 3400,1700,1600,1520,1350 NMR(CDCl$_3$) δ: 1.40–2.15 (4H,m), 3.15–3.41 (3H,m), 3.41–3.85 (2H,m), 4.12 (1H,m), 4.25 (1H,m), 5.08–5.29 (4H,m), 7.29 (2H,d,J=7.0Hz), 7.30 (2H,d,J=7.0Hz), 8.22 (2H,d,J=7.0Hz), 8.23 (2H,d,J=7.0Hz)

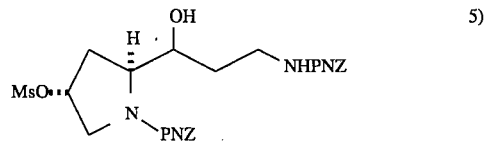
5)

To an ice-cooled solution of the above diastereomer A (478 mg, 0.922 mmol) in a mixture of methylene chloride (9 ml) and N,N-dimethylformamide (1 ml) was added dropwise triethylamine (0.17 ml, 1.2 mmol) under a nitrogen atmosphere, and then methanesulfonyl chloride (0.08 ml, 1.01 mmol), and the mixture was stirred for 30 min under ice-cooling. The reaction mixture was diluted with methylene chloride (30 ml), and washed successively with 10% aqueous citric acid, water and saturated aqueous sodium chloride. After drying over anhydrous magnesium sulfate, the solvent was removed in vacuo. The residue was subjected to silica gel column chromatography (heptane-ethyl acetate) to give (2S,4R)- 2-(1-hydroxy-3-N-p-nitrobenzyloxycarbonylamino)propyl-4 -methanesulfonyloxy-N-p-nitrobenzyloxycarbonylpyrrolidine diastereomer A (550 mg, yield: quantitative).

(2S,4R)-2-(1-Hydroxy-3-N-p-nitrobenzyloxycarbonylamino)propyl- 4-methanesulfonyloxy-N-p-nitrobenzyloxycarbonylpyrrolidine diastereomer B (317 mg, yield: 78%) was obtained from the above diastereomer B (355 mg, 0.685 mmol) in the same manner.

DIASTEREOMER A: IR(KBr)cm$^{-1}$: 3400,2950,1700,1600,1520,1350,1170 NMR(CDCl$_3$) δ: 1.30–1.70 (2H,m), 2.17–2.46 (2H,m), 3.05 (3H,s), 3.15–3.79 (4H,m), 3.93–4.25 (3H,m), 5.09–5.37 (4H,m), 7.48 (2H,d,J=6.0Hz), 7.53 (2H,d,J=6.0Hz), 8.82 (2H,d,J=6.0Hz), 8.83 (2H,d,J=6.0Hz)

DIASTEREOMER B: IR(KBr)cm$^{-1}$: 3400,2940,1700,1620,1520,1350,1170 NMR(CDCl$_3$) δ: 1.44–1.79 (2H,m), 2.08 (1H,m), 2.39 (1H,m), 3.04 (3H,s), 3.15–3.77 (5H,m), 4.02–4.24 (2H,m), 5.10–5.36 (4H,m), 7.34 (2H,d,J=6.0Hz), 7.35 (2H,d,J=6.0Hz), 8.23 (2H,d,J=6.0Hz), 8.24 (2H,d,J=6.0Hz)

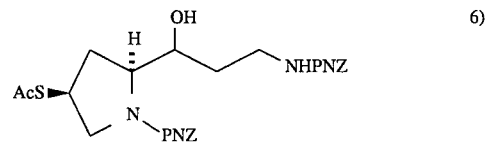
6)

To a solution of the above diastereomer A (550 mg, 0.922 mmol) in N,N-dimethylformamide (9.2 ml) were added potassium thioacetic acid (210 mg, 1.84 mmol) and sodium iodide (167 mg, 1.11 mmol), and the mixture was stirred for 4 h at 70° C. under a nitrogen atmosphere. The reaction mixture was poured into water (75 ml), and extracted with ethyl acetate (3×25 ml). The organic layer was washed successively with water and saturated aqueous sodium chloride. After drying over anhydrous magnesium sulfate, the solvent was removed in vacuo. The residue was subjected to silica gel column chromatography (heptane-ethyl acetate) to give the title compound diastereomer A (357 mg, yield: 67%).

The title compound diastereomer B (316 mg, yield: 85%) was obtained from the above diastereomer B (259 mg, 0.53 mmol) in the same manner.

DIASTEREOMER A: IR(KBr)cm⁻¹: 3400,1700,1600,1520,1340 NMR(CDCl₃) δ: 1.32–2.10 (4H,m), 2.34 (3H,s), 3.06–3.58 (3H,m), 3.66–4.28 (4H,m), 5.06–5.31 (4H,m), 7.49 (2H,d,J=6.0Hz), 7.53 (2H,d,J=6.0Hz), 8.19 (2H,d,J=6.0Hz), 8.20 (2H,d,J=6.0Hz)

DIASTEREOMER B: IR(KBr)cm⁻¹: 3400,1700,1610,1520,1340 NMR(CDCl₃) δ: 1.42–1.86 (4H,m), 2.36 (3H,s), 3.16 (1H,m), 3.32 (1H,m), 3.48 (1H,m), 3.68–3.88 (2H,m), 4.00 (1H,m), 4.22 (1H,m), 5.10–5.30 (4H,m), 7.53 (2H,d,J=6.0Hz), 7.54 (2H,d,J=6.0Hz), 8.23 (2H,d,J=6.0Hz), 8.24 (2H,d,J=6.0Hz)

REFERENCE EXAMPLE 8

(2S,4S)-4-Acetylthio-N-p-nitrobenzyloxycarbonyl-2-(1,3-diazido)propylpyrrolidine

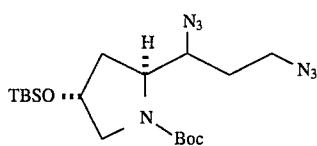
1)

(2S,4R)-N-tert-butoxycarbonyl-4-tert-butyldimethylsiloxy- 2-(1,3-diazido)propylpyrrolidine (1.01 g, yield: 22%) was obtained from (2S,4R)-N-tert-butoxycarbonyl-4-tert-butyldimethylsiloxy-2-[(1R,S)-1,3-dihydroxypropyl]pyrrolidine prepared in REFERENCE EXAMPLE 7-2 (3.98 g, 10.6 mmol) in the same manner as in REFERENCE EXAMPLES 3-2 and 3-3.

IR(KBr)cm⁻¹: 3450,2950,2100,1690,1500,1400,1360 NMR(CDCl₃) δ: 0.06 (6H,s), 0.87 (9H,s), 1.48 (9H,s), 1.32–2.10 (4H,m), 3.18–3.71 (4H,m), 3.82 (1H,m), 4.16–4.28 (2H,m)

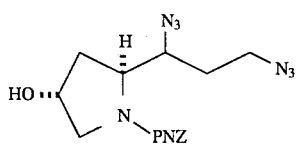
2)

(2S,4R)-4-Hydroxy-2-(1,3-diazido)propyl-N-p-nitrobenzyloxycarbonylpyrrolidine (946 mg, yield: quantitative) was obtained from the above compound (1.01 g, 2.37 mmol) in the same manner as in REFERENCE EXAMPLE 1-4.

IR(KBr)cm⁻¹: 3450,2950,2100,1700,1610,1520,1430, 1400, 1350 NMR(CDCl₃) δ: 1.32–1.86 (2H,m), 1.86–2.24 (2H,m), 3.28–3.64 (3H,m), 3.70–3.94 (2H,m), 4.19 (1H,m), 4.42 (1H,m), 5.28 (2H,m), 7.51 (2H,m), 8.24 (2H,m)

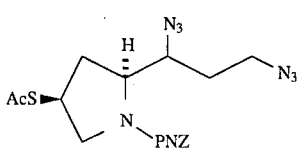
3)

The title compound (560 mg, yield: 53%) was obtained from the above compound (946 mg, 2.42 mmol) in the same manner as in REFERENCE EXAMPLES 7-5 and 7-6.

IR(KBr)cm⁻¹: 3400,2950,2100,1700,1600,1520,1400, 1340 NMR(CDCl₃) δ: 1.36–2.06 (4H,m), 2.38 (3H,s), 3.16 (1H,m), 3.32–3.66 (2H,m), 3.72–4.12 (2H,m), 4.12–4.52 (2H,m), 5.28 (2H,m), 7.56 (2H,m), 8.24 (2H,m)

REFERENCE EXAMPLE 9

(2S,4S)-4-Acetylthio-N-allyloxycarbonyl-2-(2-allyloxylcarbonylamino-1-hydroxyethyl)pyrrolidine Diastereomer A and B

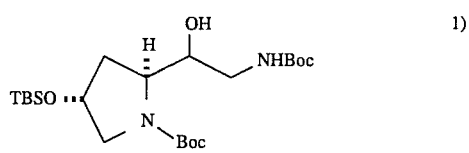
1)

To an ice-cooled suspension of lithium aluminum hydride (226 mg, 5.95 mmol) in anhydrous ether (12 ml) was added dropwise a solution of (2S,4R)-N-tert-butoxycarbonyl-4-tert-butyldimethylsiloxy-2-(1-cyano-1-hydroxy)methylpyrrolidine prepared in REFERENCE EXAMPLE 5-1 (2.12 g, 5.95 mmol) in diethyl ether (4 ml) under a nitrogen atmosphere, and the mixture was stirred for 4 h at room temperature. To the mixture were added successively water (0.24 ml), 20% aqueous sodium hydroxide (0.18 ml) and water (0.84 ml) under ice-cooling while vigorously stirring. After stirring for a while, the mixture was diluted with diethyl ether. An insoluble matter was filtered off, and washed with diethyl ether. The combined ether layer was washed successively with water and saturated aqueous sodium chloride. After drying over anhydrous magnesium sulfate, the solvent was removed in vacuo to give the crude amine compound. To a solution of the above amine compound in ethyl acetate (4 ml) was added a solution of di-tert-butyl dicarbonate (1.24 g, 5.69 mmol) in ethyl acetate (2 ml), and the mixture was stirred for 3 days at room temperature. The reaction mixture was diluted with ethyl acetate (50 ml), and washed successively with 10% aqueous citric acid, water and saturated aqueous sodium chloride. After drying over anhydrous magnesium sulfate, the solvent was removed in vacuo. The residue was subjected to silica gel column chromatography (heptane-ethyl acetate) to give (2S,4R)-N-tert-butoxycarbonyl- 4-tert-butyldimethylsiloxy-2-(2-butoxycarbonylamino- 1-hydroxyethyl)pyrrolidine diastereomer A (745 mg, yield: 27%, polar diastereomer) and the diastereomer B (743 mg, yield 27%, less polar diastereomer).

DIASTEREOMER A: IR(KBr)cm⁻¹: 3400,2950,1690,1500,1400,1360 NMR(CDCl₃) δ: 0.05 (6H,s), 0.86 (9H,s), 1.42 (9H,s), 1.44 (9H,s), 1.80–2.08 (2H,m), 2.90 (1H,m), 3.16–3.72 (4H,m), 4.16 (1H,m), 4.30 (1H,m)

DIASTEREOMER B: IR(KBr)cm⁻¹: 3400,2950,1690,1500,1400,1360 NMR(CDCl₃) δ: 0.04 (6H,s), 0.85 (9H,s), 1.44 (9H,s), 1.47 (9H,s), 1.65 (1H,m), 2.05 (1H,m), 3.14–3.32 (2H,m), 3.48–3.65 (2H,m), 4.03 (1H,m), 4.27 (1H,m), 5.21 (1H,m)

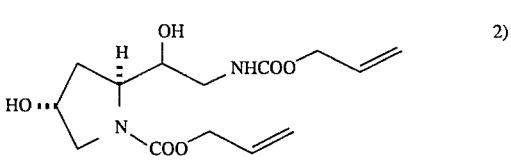
2)

To a solution of the above diastereomer A (543 mg, 1.18 mmol) in methanol (5 ml) was added 3M hydrochloric acid-dioxane solution, and the mixture was stirred overnight at room temperature. The solvent was removed in vacuo, and the residue was dissolved in methanol (10 ml). To the resulting solution were added triethylamine (0.82 ml, 5.9 mmol) and allyl chlorocarbonate (0.31 ml, 3.0 mmol) under ice-cooling, and the mixture was stirred for 30 min at the same temperature. The reaction mixture was diluted with ethyl acetate (100 ml), and washed successively with 1N hydrochloric acid, water and saturated aqueous sodium chloride. After drying over anhydrous magnesium sulfate, the solvent was removed in vacuo. The residue was subjected to silica gel column chromatography (heptane-ethyl acetate) to give (2S,4R)-N-allyloxycarbonyl-2-(2-allyloxycarbonylamino- 1-hydroxy)ethyl-4-hydroxypyrrolidine diastereomer A (298 mg, yield: 80%).

(2S,4R)-N-Allyloxycarbonyl-2-(2-allyloxycarbonylamino- 1-hydroxy)ethyl-4-hydroxypyrrolidine diastereomer B (280 mg, yield: 76%) was obtained from the above diastereomer B (543 mg, 1.18 mmol) in the same manner.

DIASTEREOMER A: IR(KBr)cm$^{-1}$: 3400,2940,1680,1530,1430,1410 NMR(CDCl$_3$) δ: 1.68–2.32 (2H,m), 3.02 (1H,m), 3.18–3.94 (4H,m), 4.18 (1H,m), 4.44 (1H,m), 4.50–4.68 (4H,m), 5.16–5.41 (4H,m), 5.70–6.07 (2H,m)

DIASTEREOMER B: IR(KBr)cm$^{-1}$: 3400,2940,1690,1520,1410 NMR(CDCl$_3$) δ: 1.94 (1H,m), 2.11 (1H,m), 3.08–3.36 (2H,m), 3.43 (1H,m), 3.56–3.82 (2H,m), 4.14 (1H,m), 4.44 (1H,m), 4.52–4.66 (4H,m), 5.18–5.44 (4H,m), 5.80–6.08 (2H,m)

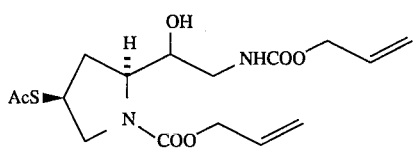

3)

Diastereomer A of the title compound (165 mg, yield: 47%) was obtained from the above diastereomer A (298 mg, 0.949 mmol) in the same manner as in REFERENCE EXAMPLES 7-5 and 7-6.

Diastereomer B of the title compound (183 mg, yield: 55%) was obtained from the above diastereomer B (280 mg, 0.892 mmol) in the same manner.

DIASTEREOMER A: IR(KBr)cm$^{-1}$: 3320,2920,1690,1540,1410 NMR(CDCl$_3$) δ: 2.00 (1H,m), 2.34 (3H,s), 2.45 (1H,m), 2.84–3.20 (2H,m), 3.50 (1H,m), 3.68–4.38 (4H,m), 4.50–4.66 (4H,m), 5.18–5.41 (4H,m), 5.72–6.12 (2H,m)

DIASTEREOMER B: IR(KBr)cm$^{-1}$: 3400,2940,1690,1520,1410 NMR(CDCl$_3$) δ: 1.74 (1H,m), 2.37 (3H,s), 2.53 (1H,m), 3.11 (1H,m), 3.27 (2H,m), 3.47–3.87 (2H,m), 4.03 (1H,m), 4.20 (1H,m), 4.45–4.71 (4H,m), 5.16–5.42 (4H,m), 5.81–6.08 (2H,m)

REFERENCE EXAMPLE 10

(2R,4S)-4-Acetylthio-2-[2,2-dimethyl-3-(p-nitrobenzyloxycarbonylamino) propyl]-N-p-nitrobenzyloxycarbonylpyrrolidine

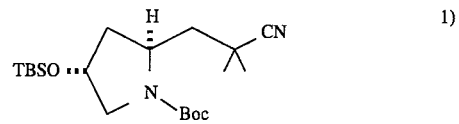

1)

To a solution of 2.1M lithium diisopropylamide tetrahydrofuran solution (3.1 ml, 6.51 mmol) was added dropwise a solution of isobutylonitrile (420 mg, 6.08 mmol) in tetrahydrofuran (2 ml) under a nitrogen atmosphere, and the solution was stirred for 1 h at the same temperature. To the reaction mixture was added dropwise a solution of (2S,4R)-N-tert-butoxycarbonyl-4 -tert-butyldimethylsiloxy-2-iodomethylpyrrolidine (2.21 g, 5.01 mmol) in tetrahydrofuran (3 ml), and the mixture was stirred for 30 min at −78° C., and then overnight at room temperature. The reaction mixture was diluted with water (100 ml) and 1N aqueous potassium hydrogensulfate (20 ml), and extracted with ethyl acetate (3×50 ml). The combined organic layer was washed successively with water and saturated aqueous sodium chloride. After drying over anhydrous sodium sulfate, the solvent was removed in vacuo. The residue was subjected to silica gel column chromatography (heptane-ethyl acetate) to give (2R, 4R)-N-tert-butoxycarbonyl-4-tert-butyldimethylsiloxy-2-(2-cyano-2,2-dimethylethyl)pyrrolidine (1.12 g, yield: 58%).

IR(KBr)cm$^{-1}$: 2930,2230,1695,1475,1390,1365,1255, 1170, 1140,1105,1025,840,775 NMR(CDCl$_3$) δ: 0.07 & 0.08 (total 6H,each s), 0.86 (9H,s), 1.35–1.55 (6H), 1.46 (9H,s), 1.62 (1H,dd,J=14.0,4.0Hz), 1.98 (1H,m), 2.22 (2H,m), 3.29 (1H,dd,J=12.0,5.0Hz), 3.65 (1H,m), 4.08 (1H,m), 4.34 (1H,m)

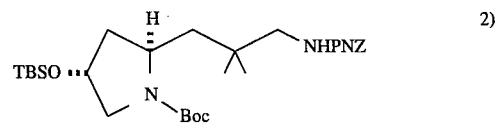

2)

To an ice-cooled suspension of lithium aluminum hydride (170 mg, 4.48 mmol) in ether (8 ml) was added dropwise a solution of the above compound (830 mg, 2.17 mmol) in ether (2 ml) under a nitrogen atmosphere, and the mixture was stirred for 30 min at the same temperature, and then for 1 h at room temperature. To the mixture was added successively water (0.17 ml), 20% aqueous sodium hydroxide (0.13 ml) and water (0.6 ml) under ice-cooling with vigorously stirring. After stirring for a while, the reaction mixture was diluted with diethyl ether (20 ml), and an insoluble matter was filtered off. The insoluble matter was washed with diethyl ether (2×20 ml). The combined ether layer was washed successively with water and saturated aqueous sodium chloride. After drying over anhydrous sodium sulfate, the solvent was removed in vacuo to give the crude amine compound. To a solution of the above amine compound in dioxane (7 ml) was added 4,6-dimethyl-2 -(p-nitrobenzyloxycarbonylthio)pyrimidine (700 mg, 2.19 mmol), and the mixture was stirred for 1 h at room temperature. The reaction mixture was diluted with ethyl acetate (70 ml), and washed successively with 1N aqueous potassium hydrogensulfate, water and saturated aqueous sodium chloride. After drying over anhydrous sodium sulfate, the solvent was removed in vacuo. The residue was subjected to silica gel column chromatography (heptane-ethyl acetate) to give (2R,4 R)-N-tert-butoxycarbonyl-4-tert-butyldimethylsiloxy-2-[2,2 -dimethyl-3-(p-nitrobenzyloxycarbonylamino)propyl]pyrrolidine (730 mg, yield: 59%).

IR(KBr)cm⁻¹: 3300,2950,1725,1675,1520,1405,1345, 1245, 1150,1105,840,775 NMR(CDCl$_3$) δ: 0.06 (6H,s), 0.80–0.90 (6H), 0.87 (9H,s), 1.48 (6H,s), 1.55–1.80 (2H,m), 1.85–2.15 (2H,m), 3.02 (1H,dd,J=14.0,3.0Hz), 3.15–3.45 (3H,m), 3.84 (1H,m), 4.34 (1H,m), 5.23 (2H,s), 7.43 (1H,br d,J=10.0Hz), 7.55 (2H,d,J=9.0Hz), 8.20 (2H,d,J=9.0Hz)

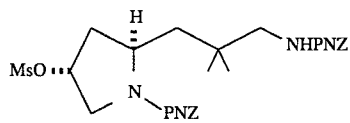
3)

(2R,4R)-2-[2,2-Dimethyl-3-(p-nitrobenzyloxycarbonylamino)propyl]-4-methanesulfonyloxy-N-p-nitrobenzyloxycarbonylpyrrolidine (790 mg, yield: 94%) was obtained from the above compound (780 mg, 1.38 mmol) in the same manner as in REFERENCE EXAMPLES 6-6 and 6-7.

IR(KBr)cm⁻¹: 3400,2950,1700,1605,1520,1400,1345, 1240, 1175,1105,900 NMR(CDCl$_3$) δ: 0.91 (6H,s), 1.19 (1H,m), 1.63 (2H,s), 1.85–2.25 (2H,m), 2.59 (1H,m), 3.05 (3H,s), 3.32 (1H,m), 3.62 (1H,dd,J=14.0,4.0Hz), 3.99 (2H,m), 5.24 & 5.28 (total 4H,each s), 6.51 (1H,br d,J=9.0Hz), 7.54 (4H,m), 8.22 (4H,d,J=9.0Hz)

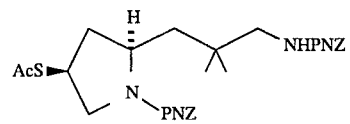
4)

The title compound (590 mg, yield: 80%) was obtained from the above compound (760 mg, 1.25 mmol) in the same manner as in REFERENCE EXAMPLE 6-8.

IR(KBr)cm⁻¹: 3340,2950,1725,1695,1605,1520,1400, 1345, 1240,1105,1015,855,740 NMR(CDCl$_3$) δ: 0.89 (6H, s), 1.30 (1H,m), 1.64 (2H,s), 2.05 (1H,d,J=14.0Hz), 2.34 (3H,s), 2.65 (1H,m), 3.01 (1H,m), 3.26 (2H,m), 3.70–4.10 (2H,m), 5.23 (4H,s), 6.61 (1H,br d,J=7.0Hz), 7.52 (4H,m), 8.21 (4H,d,J=9.0Hz)

REFERENCE EXAMPLE 11

(2R,4S)-4-Acetylthio-2-[2,2-dimethyl-3-(N-methyl-N-p-nitrobenzyloxycarbonylamino)propyl]-N-p-nitrobenzyloxycarbonylpyrrolidine

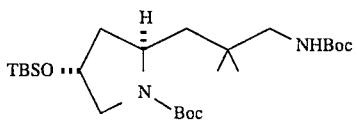
1)

The crude amine compound was obtained from (2R,4 R)-N-tert-butoxycarbonyl-4-tert-butyldimethylsiloxy-2-(2 -cyano-2,2-dimethyl)ethylpyrrolidine prepared in REFERENCE EXAMPLE 10-1 (1.44 g, 3.76 mmol) in the same manner as in REFERENCE EXAMPLE 10-2. To a solution of the above amine compound in dioxane (10 ml) was added 2 -(tert-butoxycarbonylthio)-4,6-dimethylpyrimidine (900 mg, 3.74 mmol), and the mixture was stirred for 2 h at room temperature. The reaction mixture was diluted with ethyl acetate (150 ml), and washed successively with 1N aqueous potassium hydrogensulfate, water and saturated aqueous sodium chloride. After drying over anhydrous sodium sulfate, the solvent was removed in vacuo. The residue was subjected to silica gel column chromatography (heptane-ethyl acetate) to give (2R,4R)-N-tert-butoxycarbonyl-2 -[3-(tert-butoxycarbonylamino)-2,2-dimethyl]propyl-4 -tert-butyldimethylsiloxypyrrolidine (1.35 g, yield: 74%).

IR(KBr)cm⁻¹: 2900,1715,1680,1530,1470,1400,1360, 1245, 1170,1105,835,770 NMR(CDCl$_3$) δ: 0.06 (6H,s), 0.80–0.95 (6H), 0.87 (9H,s), 1.44 (9H,s), 1.46 (9H,s), 1.65–2.15 (4H,m), 2.92 (1H,dd,J=13.0,4.0Hz), 3.10–3.45 (3H,m), 3.87 (1H,m), 4.34 (1H,m), 6.57 (1H,br s)

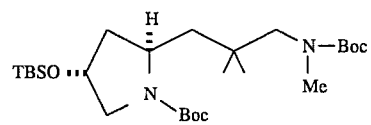
2)

To an ice-cooled solution of the above compound (1.05 g, 2.16 mmol) in N,N-dimethylformamide (7 ml) was added 60% sodium hydride in oil (170 mg, 4.25 mmol) under a nitrogen atmosphere, and stirred for 1 h at room temperature. To the reaction mixture was dropwise added iodomethyl (1.8 ml, 21.4 mmol) under ice-cooling, and stirred 30 min at the same temperature, and then for 1 h at room temperature. The reaction mixture was diluted with ice water (200 ml) and 1N aqueous potassium hydrogensulfate (20 ml), and extracted with ethyl acetate (3×50 ml). The combined organic layer was washed successively with 10% sodium sulfite solution, water and saturated aqueous sodium chloride. After drying over anhydrous sodium sulfate, the solvent was removed in vacuo. The residue was subjected to silica gel column chromatography (heptane-ethyl acetate) to give (2R,4R)-N-tert-butoxycarbonyl-2-[3-(N-tert-butoxycarbonyl-N-methylamino)- 2,2-dimethyl]propyl-4-tert-butyldimethylsiloxypyrrolidine (630 mg, yield: 58%).

IR(KBr)cm⁻¹: 2920,1695,1470,1390,1360,1250,1165, 1100, 835,770 NMR(CDCl$_3$) δ: 0.06 (6H,s), 0.86 (9H,s), 0.93 & 1.00 (total 6H,each s), 1.45 (9H,s), 1.46 (9H,s), 1.60–2.15 (4H,m), 2.94 (3H,s), 3.05 & 3.15 (total 2H,each ABq,J=14.0Hz), 3.52 (2H,s), 3.98 (1H,m), 4.32 (1H,m)

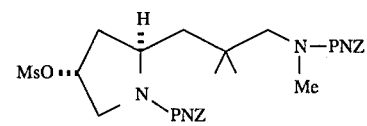
3)

(2R,4R)-2-[2,2-Dimethyl-3 -(N-methyl-N-p-nitrobenzyloxycarbonylamino)propyl]-4-methanesulfonyloxy-N-p-nitrobenzyloxycarbonylpyrrolidine (700 mg, yield: 89%) was obtained from the above compound (630 mg, 1.26 mmol) in the same manner as in REFERENCE EXAMPLES 6-6 and 6-7.

IR(KBr)cm⁻¹: 2950,2940,1700,1605,1520,1400,1345, 1170, 1105,960,900,850 NMR(CDCl$_3$) δ: 0.70–1.10 (6H, m), 1.26 (1H,m), 1.64 (1H,m), 1.80–2.20 (2H,m), 2.55 (1H,m), 2.85–3.10 (1H,m), 3.04 (3H,s), 3.22 (1H,m), 3.53 (1H,m), 3.90–4.20 (2H,m), 5.10–5.60 (4H,m), 7.52 (4H,d, J=8.0Hz), 8.22 (4H,d,J=8.0Hz)

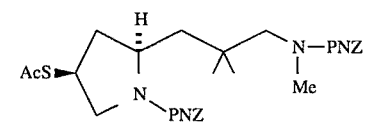
4)

The title compound (550 mg, yield: 84%) was obtained from the above compound (680 mg, 1.09 mmol) in the same manner as in REFERENCE EXAMPLE 6-8.

IR(KBr)cm⁻¹: 2950,1700,1600,1520,1400,1340,1200, 1110,850 NMR(CDCl$_3$) δ: 0.94 & 1.02 (total 6H,each br s), 1.40 (1H,m), 1.64 (2H,s), 2.05 (1H,m), 2.34 (3H,s), 2.64 (1H,m), 3.03 (3H,br s), 3.05–3.35 (2H,m), 3.75–4.20 (3H, m), 5.22 (4H,s), 7.53 (4H,d,J=9.0Hz), 8.23 (4H,d,J=9.0Hz)

REFERENCE EXAMPLE 12

(2S,4S)-4-Acetylthio-2-[3-hydroxy-1-(p-nitrobenzyloxycarbonylaminomethyl)propyl]-N-p-nitrobenzyloxycarbonylpyrrolidine Diastereomer A

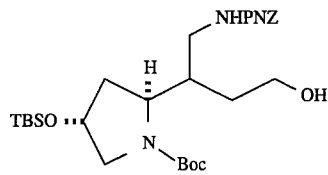
1)

To an ice-cooled suspension of lithium aluminum hydride (2.5 g, 66 mmol) in diethyl ether (100 ml) was added a solution of methyl 3-[(2S, 4R)-N-tert-butoxycarbonyl-4-tert-butyldimethylsiloxypyrrolidin-2-yl]-4 -nitrobutylate diastereomer A (less polar diastereomer, 9.8 g, 22 mmol) in diethylether (10 ml) under a nitrogen atmosphere, and the mixture was stirred for 30 min at the same temperature. The reaction mixture was diluted with methanol (50 ml) and 1N aqueous sodium hydroxide (20 ml), and an insoluble matter was filtered off. The solvent was removed in vacuo, and the residue was dissolved in dioxane (100 ml) and water (100 ml). To the solution was added 4,6-dimethyl-2-(p-nitrobenzyloxycarbonylthio)pyrimidine (7.03 g, 22 mmol), and the mixture was stirred for 2 h at room temperature. The reaction mixture was concentrated in vacuo, and extracted with ethyl acetate (100 ml). The organic layer was washed successively with water and saturated aqueous sodium chloride. After drying over anhydrous sodium sulfate, the solvent was removed in vacuo. The residue was subjected to silica gel column chromatography (hexane-ethyl acetate) to give (2S, 4R)-N-tert-butoxycarbonyl- 4-tert-butyldimethylsiloxy-2-(3-hydroxy-1-p-nitrobenzyloxycarbonylaminomethyl)propylpyrrolidine diastereomer A (2.55 g, yield: 20.4%).

IR(KBr)cm$^{-1}$: 3400,2950,1690,1670,1520,1400,1255, 1160, 835,775 NMR(CDCl$_3$) δ: 0.05 (6H,s), 0.86 (9H,s), 1.48 (9H,s), 1.60–2.20 (4H,m), 3.10–3.30 (3H,m), 3.50–3.80 (4H,m), 4.10–4.30 (3H,m), 5.22 (2H,d,J=3.0Hz), 6.15 (1H,br m), 7.54 (2H,d,J=9.0Hz), 8.24 (2H,d,J=9.0Hz)

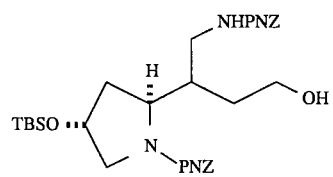
2)

To an ice-cooled solution of the above compound (2.55 g, 4.49 mmol) in methylene chloride (9.0 ml) was added dropwise trifluoroacetic acid (4.5 ml) under a nitrogen atmosphere, and the mixture was stirred for 40 min at the same temperature. The reaction mixture was added dropwise to a mixture of dioxane (58 ml) and 1N aqueous sodium hydroxide at the same temperature. To the solution was added 4,6-dimethyl-2-(p-nitrobenzyloxycarbonylthio)pyrimidine (1.43 g, 4.49 mmol), and the mixture was stirred for 2 h at room temperature keeping at pH 10 with 1N aqueous sodium hydroxide. The reaction mixture was concentrated in vacuo, and extracted with ethyl acetate (100 ml). The organic layer was washed successively with 10% aqueous citric acid, saturated aqueous sodium hydrogencarbonate and saturated aqueous sodium chloride. After drying over anhydrous sodium sulfate, the solvent was removed in vacuo. The residue was subjected to silica gel column chromatography (4% methanol-chloroform) to give (2S, 4R)-4-tert-butyldimethylsiloxy-2-(3-hydroxy-1 -p-nitrobenzyloxycarbonylaminomethyl)propyl-N-p-nitrobenzyloxycarbonylpyrrolidine diastereomer A (1.15 g, yield: 37.9%).

IR(KBr)cm$^{-1}$: 3400,2900,1700,1605,1520,1400,1350, 1250, 1105,840,770 NMR(CDCl$_3$) δ: 0.05 (6H,s), 0.84 (9H,s), 1.52 (2H,m), 1.80–2.00 (2H,m), 2.10–2.40 (2H,m), 3.10–3.30 (3H,m), 3.60–3.80 (3H,m), 4.34 (2H,m), 5.20 (4H,s), 5.92 (1H,m), 7.51 (4H,d,J=8.0Hz), 8.22 (4H,d,J=8.0Hz)

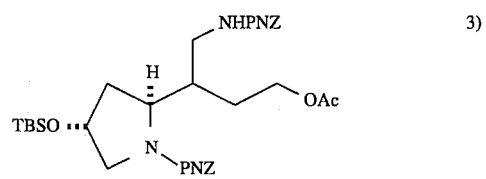
3)

To an ice-cooled solution of the above compound (1.15 g, 1.78 mmol) in pyridine (10 ml) was added acetic anhydride (2 ml), and the mixture was stirred for 2 h at the same temperature. The reaction mixture was diluted with ice water, and extracted with ethyl acetate (50 ml). The organic layer was washed successively with water, 10% aqueous citric acid, saturated aqueous sodium hydrogencarbonate and saturated aqueous sodium chloride. After drying over anhydrous sodium sulfate, the solvent was removed in vacuo. The residue was subjected to silica gel column chromatography (2% methanol-chloroform) to give (2S, 4R)-2-(3-acetoxy-1 -p-nitrobenzyloxycarbonylaminomethyl)propyl-4 -tert-butyldimethylsiloxy-N-p-nitrobenzyloxycarbonylpyrrolidine diastereomer A (698 mg, yield: 57%).

IR(KBr)cm$^{-1}$: 3400,2940,1700,1520,1430,1400,1340, 1250, 1100,850,735 NMR(CDCl$_3$) δ: 0.05 (3H,s), 0.08 (3H,s), 0.85 (9H,s), 1.40–1.60 (2H,m), 1.70–1.90 (1H,m), 2.05 (3H,s), 2.10 (1H,m), 3.00–3.40 (3H,m), 3.70 (1H,s), 3.76 (1H,s), 4.16 (2H,m), 4.35 (2H,m), 5.19 (4H,s), 5.85 (1H,m), 7.51 (4H,d,J=9.0Hz), 8.22 (4H,d,J=9.0Hz)

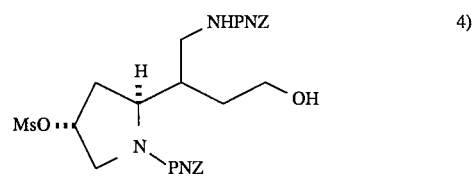
4)

To a solution of the above compound (698 mg, 1.01 mmol) in tetrahydrofuran (15 ml) was added 1N tetrabutylammonium fluoride solution (1.05 ml, 1.05 mmol), and the mixture was stirred for 1 h at room temperature. The reaction mixture was concentrated in vacuo, and extracted with ethyl acetate (50 ml). The organic layer was washed successively with water and saturated aqueous sodium chloride. After drying over anhydrous sodium sulfate, the solvent was removed in vacuo to give the crude alcohol compound. To a solution of the above alcohol compound in methylene chloride (15 ml) were added triethylamine (0.07 ml, 1.0 mmol) and methanesulfonyl chloride (0.08 ml, 1.0 mmol), and the mixture was stirred for 30 min at room temperature. The reaction mixture was washed successively with water and saturated aqueous sodium chloride. After drying over anhydrous sodium sulfate, the solvent was removed in vacuo to give the crude mesyl compound. To a mixture of the above mesyl compound in tetrahydrofuran (10 ml) and methanol (10 ml) was added sodium methoxide (77 mg, 1.4 mmol), and the mixture was stirred for 20 min at room temperature. The reaction mixture was concentrated in vacuo, and extracted with ethyl acetate (50 ml). The organic layer was washed successively with water and saturated aqueous sodium chloride. After drying over anhydrous sodium sulfate, the solvent was removed in vacuo. The residue was subjected to silica gel column chromatography (4% methanol-chloroform) to give (2S,4R)-2-(3-hydroxy-1-p-nitrobenzyloxycarbonylaminomethyl)propyl- 4-methanesulfonyloxy-N-p-nitrobenzyloxycarbonylpyrrolidine diastereomer A (413 mg, yield: 67.6%).

IR(KBr)cm$^{-1}$: 1700,1520,1340,1170,900,735 NMR(CDCl$_3$) δ: 1.51 (2H,m), 1.70 (1H,m), 2.00–2.50 (4H, br m), 3.02 (3H,s), 3.15 (1H,m), 3.35 (1H,m), 3.52 (1H,dd, J=14.0,4.0Hz), 3.78 (2H,m), 4.23 (1H,d,J=14.0Hz), 4.36 (1H,m), 5.24 (4H,m), 5.81 (1H,br s), 7.49 (2H,d,J=8.0Hz), 7.52 (2H,d,J=8.0Hz), 8.21 (2H,d,J=8.0Hz), 8.27 (2H,d,J= 8.0Hz)

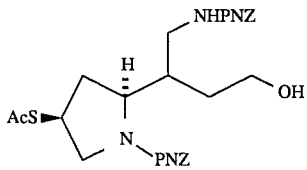

5)

The title compound (319 mg, yield: 80.5%) was obtained from the above compound (413 mg, 0.67 mmol) in the same manner as in REFERENCE EXAMPLE 1-6.

IR(KBr)cm$^{-1}$: 3400,1695,1520,1400,1345,1250,1110,850, 735, 630 NMR(CDCl$_3$) δ: 1.50–1.70 (4H,m), 2.35 (3H,s), 2.30–2.50 (2H,m), 3.00–3.40 (3H,m), 3.78 (3H,m), 4.19 (1H,s), 4.28 (1H,dd,J=15.0,8.0Hz), 5.19 (2H,s), 5.22 (2H,s), 5.84 (1H,br s), 7.49 (2H,d,J=8.0Hz), 7.52 (2H,d,J=8.0Hz), 8.22 (2H,d, J=8.0Hz), 8.24 (2H,d,J=8.0Hz)

REFERENCE EXAMPLE 13

(1R,5S,6S)-2-[(2S,4S)-2-(Acetylaminomethyl)pyrrolidin-4-ylthio]-6-[(1R)-1-hydroxyethyl]-1-methyl-1-carbapen-2-em-3-carboxylic Acid

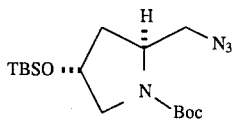

1)

To an ice-cooled solution of (2S,4R)-N-tert-butoxycarbonyl- 4-tert-butyldimethylsiloxy-2-hydroxymethylpyrrolidine (1.66 g, 5 mmol) in tetrahydrofuran (10 ml) was added triethylamine (1.4 ml, 10 mmol), and then methanesulfonylchloride (0.76 ml, 9.82 mmol) under a nitrogen atmosphere. After stirring for 30 min at the same temperature, the mixture was diluted with ice in water (100 ml), and extracted with ethyl acetate (3× 50 ml). The combined organic layer was washed is successively with 1N aqueous potassium hydrogensulfate, water, saturated aqueous sodium hydrogencarbonate, water and saturated aqueous sodium chloride. After drying over anhydrous sodium sulfate, the solvent was removed in vacuo to give the crude mesylate. To a solution of the above mesylate in dimethylsulfoxide (15 ml) was added sodium azide (1.10 g, 15.94 mmol), and the mixture was stirred for 2 h 70° C. The reaction mixture was diluted with water (100 ml), and extracted with ethyl acetate (3×50 ml). The combined organic layer was washed with successively with water and saturated aqueous sodium chloride. After drying over anhydrous sodium sulfate, the solvent was removed in vacuo. The residue was subjected to silica gel column chromatography (heptane-ethyl acetate) to give (2S, 4R)- 2-azidomethyl-N-tert-butoxycarbonyl-4-tert-butyldimethylsiloxypyrrolidine (1.19 g, yield: 67%).

IR(KBr)cm$^{-1}$: 2940,2110,1700,1395,1365,1255,1165, 1120, 840,775 NMR(CDCl$_3$) δ:

0.07 (6H,s), 0.86 (9H,s), 1.47 (9H,s), 1.96 (2H,m), 3.20–3.60 (4H,m), 4.10 (1H,m), 4.38 (1H,m)

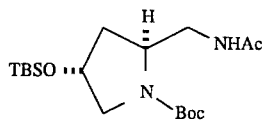

2)

To a solution of the above compound (1.19 g, 3.34 mmol) in methanol (33 ml) was added 10% palladium-carbon catalyst (240 mg), and the mixture was stirred for 1 h under an atmospheric pressure of hydrogen. The catalyst was filtered off, and the solvent was removed in vacuo to give the crude amine. To an ice-cooled solution of the above amine in methylene chloride (10 ml) was added triethylamine (0.94 ml, 6.74 mmol), and then acetic anhydride (0.64 ml, 6.78 mmol) under a nitrogen atmosphere. After stirring for 1 h at the same temperature, the reaction mixture was diluted with water (100 ml), and extracted with ethyl acetate (1×100 ml, 2×30 ml). The combined organic layer was washed with successively 1N aqueous potassium hydrogensulfate, water, saturated aqueous sodium hydrogencarbonate, water and saturated aqueous sodium chloride. After drying over anhydrous sodium sulfate, the solvent was removed in vacuo. The residue was subjected to silica gel column chromatography (heptane-ethyl acetate) to give (2S,4R)-2-acetylaminomethyl-N-tert-butoxycarbonyl-4 -tert-butyldimethylsiloxypyrrolidine (1.18 g, yield: 95 %).

IR(KBr)cm$^{-1}$: 2920,1695,1655,1550,1395,1360,1250, 1160, 1115,835,770 NMR(CDCl$_3$) δ: 0.05 (6H,s), 0.86 (9H, s), 1.47 (9H,s), 1.60–1.90 (2H,m), 1.98 (3H,s), 3.12 (1H,m), 3.25–3.55 (3H,m), 4.11 (1H,m), 4.33 (1H,m), 7.52 (1H,br s)

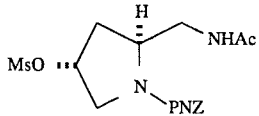

3)

The above compound (1.15 g, 3.09 mmol) was dissolved in trifluoroacetic acid (10 ml), and the mixture was stirred overnight at room temperature. The solvent was removed in vacuo, and the residue was distilled with benzene several times to give the crude amino alcohol. To a solution of the above amino alcohol in a mixture of dioxane (7.5 ml) and water (2.5 ml) was added sodium hydrogencarbonate (2.6 g, 30.9 mmol), and then 4,6 -dimethyl-2-(p-nitrobenzyloxycarbonylthio)pyrimidine (990 mg, 3.10 mmol). After stirring for 3 h at room temperature, the reaction mixture was diluted with ethyl acetate (150 ml), and washed with successively water, 1N aqueous potassium hydrogensulfate, water, saturated aqueous sodium hydrogencarbonate, water and saturated aqueous sodium chloride. After drying over anhydrous sodium sulfate, the solvent was removed in vacuo to give the crude alcohol. To an ice-cooled solution of the above alcohol in tetrahydrofuran (10 ml) was added dropwise triethylamine (0.86 ml, 6.17 mmol), and then methanesulfonyl chloride (0.48 ml, 6.20 mmol) under a nitrogen atmosphere. After stirring for 30 min at the same temperature, the reaction mixture was diluted with ethyl acetate (150 ml), and washed with successively water, 1N aqueous potassium hydrogensulfate, water, saturated aqueous sodium hydrogencarbonate, water and saturated aqueous sodium chloride. After drying over anhydrous sodium sulfate, the solvent was removed in vacuo. The residue was subjected to silica gel column chromatography (chloroform-methanol) to give (2S, 4R)-2 -acetylaminomethyl-4-methanesulfonyloxy-N-p-nitrobenzyloxycarbobonylpyrrolidine (740 mg, yield: 58%).

IR(KBr)cm$^{-1}$: 3400,1700,1660,1520,1430,1400,1340, 1170, 1110,955,900 NMR(CDCl$_3$) δ: 1.80 (1H,s), 1.95–2.20 (1H,m), 1.98 (3H,s), 2.47 (1H,dd,J=8.0,14.0Hz), 3.05 (3H, s), 3.20–3.45 (1H,m), 3.45–3.80 (2H,m), 4.00–4.25 (2H,m), 5.15–5.35 (2H,m), 6.82 (1H,br s), 7.54 (2H,d,J=9.0Hz), 8.25 (2H,d,J=9.0Hz)

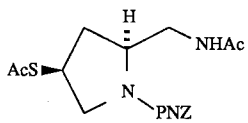
4)

To the above compound (690 mg, 1.66 mmol) in N,N-dimethylformamide solution (7 ml) were added potassium thioacetate (380 mg, 3.33 mmol) and sodium iodide (370 mg, 2.47 mmol), and the mixture was stirred for 70° C. under a nitrogen atmosphere. The reaction mixture was diluted with ice in water (150 ml), and extracted with ethyl acetate (1×100 ml, 2×50 ml). The combined organic layer was washed successively with 10% aqueous sodium sulfite and saturated aqueous sodium chloride. After drying over anhydrous sodium sulfate, the solvent was removed in vacuo. The residue was subjected to silica gel column chromatography (heptane-ethyl acetate) to give (2S,4S)-2-acetylaminomethyl-4-acetylthio-N-p-nitrobenzyloxycarbonylpyrrolidine (560 mg, yield: 85%).

IR(KBr)cm$^{-1}$: 3330,1700,1680,1640,1520,1425,1345, 1200, 1125,1105,630 NMR(CDCl$_3$) δ: 1.55–1.90 (1H,m), 1.96 (3H,s), 2.34 (3H,s), 2.58 (1H,m), 3.10–3.45 (2H,m), 3.63 (1H,m), 3.88 (1H,m), 3.95–4.25 (2H,m), 5.25 (2H,s), 6.99 (1H,br s), 7.54 (2H,d,J=9.0Hz), 8.25 (2H,d,J=9.0Hz)

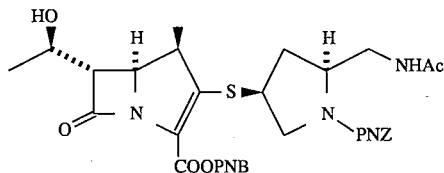
5)

p-Nitrobenzyl (1R,5S,6S)-2-[(2S,4S)-2 -acetylaminomethyl-N-p-nitrobenzyloxycarbonylpyrrolidine-4-ylthio]-6-[(1R)-1-hydroxyethyl]-1-methyl-1-carbapen-2-em-3-carboxylate (420 mg, yield: 88%) was obtained from the above compound (270 mg, 0.683 mmol) and p-nitrobenzyl (1R, 5S,6S)-2-diphenoxyphosphoryloxy-6-[(1R)- 1-hydroxyethyl]-1-methyl-1-carbapen-2-em-3-carboxylate (430 mg, 0.723 mmol) in the same manner as in EXAMPLES 1-1) and 1-2).

IR(KBr)cm$^{-1}$: 3400,1770,1700,1660,1520,1345,1200, 1105 NMR(CDCl$_3$) δ: 1.28 (3H,d,J=7.0Hz), 1.36 (3H,d,J= 6.0Hz), 1.60–2.15 (2H,m), 1.96 (3H,s), 2.59 (1H,m), 3.20–3.45 (4H,m), 3.45–3.85 (2H,m), 3.90–4.20 (2H,m), 4.20–4.30 (2H,m), 5.10–5.55 (4H,m), 6.87 (1H,br s), 7.45–7.75 (4H,m), 8.15–8.30 (4H,m)

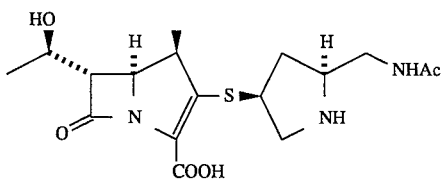
6)

The title compound (130 mg, yield: 64%) was obtained from the above compound (370 mg, 0.53 mmol) in the same manner as in EXAMPLE 1-3.

IR(KBr)cm$^{-1}$: 3400,1755,1660,1600,1550,1390,1285 NMR(D$_2$O) δ: 1.14 (3H,d,J=7.0Hz), 1.21 (3H,d,J=6.0Hz), 1.66 (1H,m), 1.96 (3H,m), 2.65 (1H,m), 3.10–3.45 (3H,m), 3.45–3.70 (3H,m), 3.70–4.05 (2H,m), 4.05–4.30 (2H,m) UV λ$_{max}$ (0.1M MOPS buffer, pH 7.0): 298 nm (ε =8,800)

REFERENCE EXAMPLE 14

(2S,4S)-4-Acetylthio-N-tert-butoxycarbonyl-2-[(1R)-3 -(N-tert-butoxycarbonyl-N-methylamino)- 1-methoxy]propylpyrrolidine

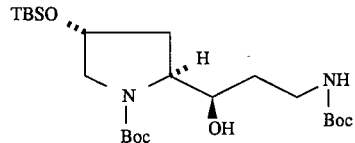
1)

To a solution of (2S,4R)-2-[(1R)-3-azido-1 -hydroxy]propyl-N-tert-butoxycarbonyl-4-tert-butyldimethysiloxypyrrolidine diastereomer A prepared in REFERENCE EXAMPLE 7-3 (1.39 g, 3.47 mmol) in methanol (14 ml) was added 10% palladium-carbon catalyst (140 mg), and the mixture was stirred for 2 h at room temperature under a hydrogen atmosphere. The catalyst was filtered off, and the filtrate was concentrated in vacuo. To the resulting methanol solution (14 ml) was added di-tert-butyl dicarbonate (0.98 g, 4.51 mmol), and the mixture was stirred for 1 h adjusting at pH 8 with triethylamine. The mixture was concentrate in vacuo, and the residue was subjected to silica gel column chromatography (heptane-ethyl acetate) to give (2S,4 R)-N-tert-butoxycarbonyl-4-tert-butyldimethylsiloxy-2 -[(1R)-3-tert-butoxycarbonylamino-1-hydroxy]propylpyrrolidine (1.05 g, yield: 64%).

IR(KBr)cm$^{-1}$: 3440,3320,2970,2930,2850,1680,1550, 1470, 1410,1280,1250,1180 NMR(CDCl$_3$) δ: 0.04 (6H,s), 0.85 (9H,s), 1.44 (9H,s), 1.46 (9H,s), 1.22–1.98 (4H,m), 3.05–3.65 (4H,m), 3.77–4.40 (3H,m)

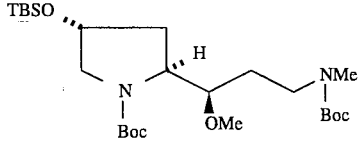
2)

To a solution of the above compound (1.05 g, 2.21 mmol) in N,N-dimethylformamide (6.6 ml) was added sodium hydride (60%, in oil suspension, 177 mg, 4.43 mmol) at 0° C. under a nitrogen atmosphere, and the mixture was stirred for 30 min at the same temperature. To the mixture was added iodomethyl (0.15 ml, 2.43 mmol) under ice-cooling, and stirred for 2 h at room temperature. The reaction mixture was added ethyl acetate (100 ml), and washed successively with water (2×50 ml) and saturated aqueous sodium chloride. After drying over anhydrous magnesium sulfate, the solvent was removed in vacuo, and the residue was subjected to silica gel column chromatography (heptane-ethyl acetate) to give (2S,4R)-N-tert-butoxycarbonyl-4-tert-butyldimethylsiloxy- 2-[(1R)-3-(N-tert-butoxycarbonyl-N-methylamino)- 1-methoxy]propylpyrrolidine (177 mg, yield: 16%).

IR(KBr)cm$^{-1}$: 2930,2850,1700,1460,1400,1360,1250, 1170, 1110 NMR(CDCl$_3$) δ: 0.04 (6H,s), 0.80 (9H,s), 1.42 (18H,s), 1.10–1.60 (2H,m), 1.70 (1H,m), 2.00 (1H,m), 2.79 (3H,s), 3.25 (3H,s), 3.00–3.50 (4H,m), 3.60–3.90 (2H,m), 4.30 (1H,m)

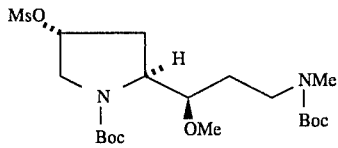

To a solution of the above compound (562 mg, 1.12 mmol) in tetrahydrofuran (2 ml) was added 1M tetrabutylammoniun fluoride (1.23 ml, 1.23 mmol), and the mixture was stirred for 1 h at room temperature. The reaction mixture was diluted with ethyl acetate (100 ml), and washed successively with water and saturated aqueous sodium chloride. After drying over anhydrous magnesium sulfate, the solvent was removed in vacuo to give the crude alcohol derivative. (2S,4R)-N-tert-butoxycarbonyl- 4-methanesulfonyloxy-2-[(1R)-3 -(N-tert-butoxycarbonyl-N-methylamino)-1-methoxy]propylpyrrolidine (510 mg, yield: 98%) was obtained from the above alcohol derivative in the same manner as in REFERENCE EXAMPLE 1-5).

IR(KBr)cm$^{-1}$: 2970,2930,1695,1480,1460,1400,1365, 1170 NMR(CDCl$_3$) δ: 1.46 (9H,s), 1.48 (9H,s), 1.20–1.50 (2H,m), 2.10–2.44 (2H,m), 2.86 (3H,s), 3.04 (3H,s), 3.40 (3H,s), 3.20–3.60 (4H,m), 3.64–4.06 (3H,m)

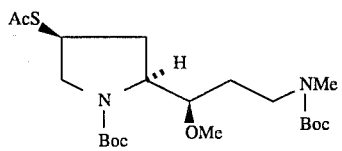

The title compound (287 mg, yield: 59%) was obtained from the above compound (510 mg, 1.09 mmol) in the same manner as in REFERENCE EXAMPLE 1-6.

IR(KBr)cm$^{-1}$: 2980,2930,1695,1480,1460,1400,1365, .1160 NMR(CDCl$_3$) δ: 1.48 (18H,s), 1.28–1.64 (2H,m), 2.00 (1H,m), 2.30 (1H,m), 2.35 (3H,s), 2.86 (3H,s), 2.90–3.54 (4H,m), 3.40 (3H,s), 3.60–3.92 (2H,m), 4.08 (1H,m)

REFERENCE EXAMPLE 15

(2S,4S)-4-Acetylthio-2-[(1S)-1-hydroxy-3 -(N-p-nitrobenzyloxycarbonyl-N-methylamino)propyl]-N-(p-nitrobenzyloxycarbonyl)pyrrolidine and (2S,4S)-4-acetylthio-2-[(1R)-1-hydroxy-3-(N-p-nitrobenzyloxycarbonyl-N-methylamino)propyl]-N-(p-nitrobenzyloxycarbonyl)pyrrolidine

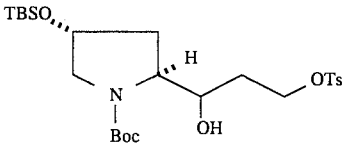

To an ice-cooled solution of (2S,4R)-N-tert-butoxycarbonyl- 4-tert-butyldimethylsiloxy-2-[(1R,S)-1,3 -dihydroxy] propylpyrrolidine prepared in REFERENCE EXAMPLE 7-2 (13.79 g, 36.71 mmol) in methylene chloride (370 ml) were added triethylamine (15.35 ml, 110.1 mmol), dimethylaminopyridine (448 mg, 3.67 mmol) and p-toluenesulfonyl chloride (10.5 g, 55.07 mmol) under ice-cooling and a nitrogen atmosphere, and the mixture was stirred overnight at room temperature. To the reaction mixture was added saturated aqueous sodium hydrogencarbonate (100 ml), and the mixture was stirred for 30 min at room temperature. The methylene chloride layer was separated, and washed successively 10% aqueous citric acid, water and saturated aqueous sodium chloride. After drying over anhydrous magnesium sulfate, the solvent was removed in vacuo. The residue was subjected to silica gel column chromatography (heptane-ethyl acetate) to give (2S,4R)-N-tert-butoxycarbonyl- 4-tert-butyldimethylsiloxy-2-[[(1S)-1-hydroxy- 3-p-toluenesulfonyloxy]propyl]pyrrolidine (2.56 g, yield: 13%, less polar isomer), (2S,4R)-N-tert-butoxycarbonyl- 4-tert-butyldimethylsiloxy-2-[[(1R)-1 -hydroxy-3-p-toluenesulfonyloxy]propyl]pyrrolidine (4.8 g, yield: 25%, polar isomer), the mixture (4.1 g, yield: 21%) and the starting material (3.28 g, recovery: 24%).

(1S)-DERIVATIVE (Less Polar Isomer) IR(KBr)cm$^{-1}$: 3400,2950,2930,2850,1690,1660,1600,1460, 1400,1360,1250,1180 NMR(CDCl$_3$) δ: 0.05 (6H,s), 0.85 (9H,s), 1.44 (9H,s), 1.50–1.70 (2H,m), 1.75–2.00 (2H,m), 2.43 (3H,s), 3.20 (1H,dd,J=3.5,11.7Hz), 3.40–3.70 (2H,m), 3.92 (1H,dd,J=8.1,16.0Hz), 4.10–4.40 (3H,m), 7.33 (2H,d, J=8.3Hz), 7.78 (2H,d,J=8.3Hz)

(1R)-DERIVATIVE (Polar Isomer) IR(KBr)cm$^{-1}$: 3400, 2950,2930,2850,1690,1670,1600,1460, 1400,1360,1250,1180 NMR(CDCl$_3$) δ: 0.04 (6H,s), 0.84 (9H,s), 1.43 (9H,s), 1.40–2.00 (4H,m), 2.43 (3H,s), 3.20 (1H,dd,J=3.6,11.5Hz), 3.48 (1H,m), 3.74 (1H,m), 4.18–4.23 (4H,m), 7.32 (2H,d,J=7.3Hz), 7.77 (2H,d,J=7.3Hz)

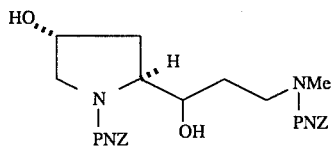

To a solution of 40% methylamine methanol solution (37 ml) was added a solution of the above compound (1S)-derivative (2.56 g, 4.83 mmol) in methanol (10 ml) at room temperature, and the mixture was heated in a sealed tube at 120° C. (outside temperature) in a sealed tube for 30 min. The reaction mixture was cooled to room temperature, and concentrated in vacuo. The residue was dissolved in methanol (40 ml), and added a solution of 4,6-dimethyl-2-(p-nitrobenzyloxycarbonylthio)pyrimidine (1.54 g, 4.83 mmol) in chloroform (10 ml). The mixture was stirred for 3 h at room temperature adjusting to pH 8 with triethylamine. The reaction mixture was concentrated in vacuo, and the residue was dissolved in ethyl acetate (100 ml). The solution was washed successively with 10% aqueous citric acid, water and saturated aqueous sodium chloride. After drying over anhydrous magnesium sulfate, the solvent was removed in vacuo, and the residue was dissolved in methanol (5 ml). To the solution was added a solution of 2.6N methanolic hydrochloride, and the mixture was stirred overnight at room temperature. The reaction mixture was concentrated in vacuo, and the residue was dissolved in methanol (40 ml), and adjusted to pH 8 with triethylamine. To the ice-cooled solution was added a solution of 4,6 -dimethyl-2-(p-nitrobenzyloxycarbonylthio)pyrimidine (1.54 g, 4.83 mmol) in chloroform (10 ml), and the mixture was stirred for 3 h at room temperature. The mixture was concentrated in vacuo, and the residue was dissolved in ethyl acetate (100 ml). The solution was washed successively with 10% aqueous citric acid, water and saturated aqueous sodium chloride. After drying over anhydrous magnesium sulfate, the solvent was removed in vacuo. The residue was subjected to silica gel column chromatography (ethyl acetate) to give (2S,4R)-4-hydroxy-2-[[(1S)-1-hydroxy-3 -(N-p-nitrobenzyloxycarbonyl-N-methylamino)]propyl]-N-(p-nitrobenzyloxycarbonyl)pyrrolidine (1.92 g, yield: 75%).

(2S,4R)-4-Hydroxy-2-[[(1R)-1-hydroxy-3 -(N-p-nitrobenzyloxycarbonyl-N-methylamino)]propyl]-N-(p-nitrobenzyloxycarbonyl)pyrrolidine (1.75 g, yield: 78%) was obtained from the above (1R)-derivative (2.23 g, 4.20 mmol) in the same manner.

(1S)-DERIVATIVE IR(KBr)cm$^{-1}$: 3390,2940,1680,1600, 1520,1400,1340,1310, 1150 NMR(CDCl$_3$) δ: 1.50–2.20 (4H,m), 2.95 (3H,s), 3.30–3.90 (5H,m), 4.00–4.30 (2H,m), 5.17–5.32 (4H,m), 7.50–7.65 (4H,m), 8.20–8.25 (4H,m)

(1R)-DERIVATIVE IR(KBr)cm$^{-1}$: 3400,2950,1670, 1610,1520,1440,1400,1340, 1320,1150 NMR(CDCl$_3$) δ: 1.40 (1H,m), 1.55 (1H,m), 1.72 (1H,m), 2.05 (1H,m), 3.20–3.60 (4H,m), 3.32 (3H,s), 3.70–4.05 (2H,m), 4.15 (1H,m), 5.10–5.35 (4H,m), 7.50–7.70 (4H,m), 8.10–8.30 (4H,m)

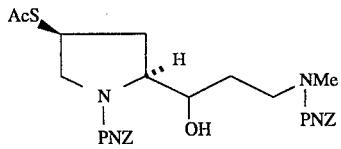
3)

The title compound (1S)-derivative (1.46 g, yield: 83%) was obtained from the above (1S)-derivative (1.92 g, 3.61 mmol) in the same manner as in REFERENCE EXAMPLE 4-3.

The title compound (1R)-derivative (1.29 g, yield: 82%) was obtained from the above (1R)-derivative (1.75 g, 3.29 mmol) in the same manner.

(1S)-DERIVATIVE IR(KBr)cm$^{-1}$: 3440,2950,1700,1610, 1520,1430,1400,1340, 1210,1110 NMR(CDCl$_3$) δ: 1.40–1.80 (3H,m), 2.34 (3H,s), 2.50 (1H,m), 2.96 (3H,s), 3.10–4.30 (7H,m), 5.10–5.30 (4H,m), 7.43–7.60 (4H,m), 8.18–8.30 (4H,m)

(1R)-DERIVATIVE IR(KBr)cm$^{-1}$: 3450,2950, 1700,1610,1520,1430,1400,1350 NMR(CDCl$_3$) δ: 1.30–2.10 (4H,m), 2.34 (3H,s), 2.96 (3H,s), 3.00–3.60 (3H, m), 3.60–4.30 (4H,m), 5.10–5.36 (4H,m), 7.40–7.60 (4H, m), 8.18–8.30 (4H,m)

REFERENCE EXAMPLE 16

(2S,4S)-4-Acetylthio-2-[[(1S)-1-hydroxy-2-(N-p-nitrobenzyloxycarbonyl-N-methylamino)]ethyl]-N-p-nitrobenzyloxycarbonyl)pyrrolidine

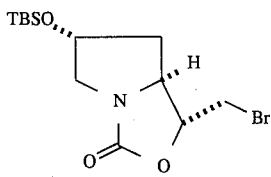
1)

To an ice-cooled solution of (2S,4R)-N-tert-butoxycarbonyl- 2-vinyl-4-tert-butyldimethylsiloxypyrrolidine (1.44 g, 4.40 mmol) in 2:1 dioxane-water (21 ml) was added N-bromosuccinimide (1.57 g, 8.79 mmol), and the mixture was stirred for 1 h at room temperature. The reaction mixture was diluted with ethyl acetate (100 ml), and washed successively with saturated aqueous potassium hydrogensulfate, water and saturated aqueous sodium chloride. After drying over anhydrous magnesium sulfate, the solvent was removed in vacuo. The residue was subjected to silica gel column chromatography (heptane-ethyl acetate) to give (4R,5S,7R)-4-bromomethyl-7-tert-butyldimetylsiloxy-1 -aza-3-oxobicyclo[3,3,0]octan-2-one (1.20 g, yield: 78%).

IR(KBr)cm$^{-1}$: 2950,2920,2880,2850,1750,1460,1390, 1360, 1240,1210,1170 NMR(CDCl$_3$) δ: 0.07 (6H,s), 0.88 (9H,s), 1.60 (1H,m), 2.03 (1H,m), 3.05 (1H,dd,J=1.6, 12.0Hz), 3.48 (1H,dd,J=8.6,10.3Hz), 3.61 (1H,dd,J=4.5, 10.3Hz), 3.82 (1H,dd,J=5.5,12.0Hz), 4.06 (1H,m), 4.47 (1H, m), 4.56 (1H,m)

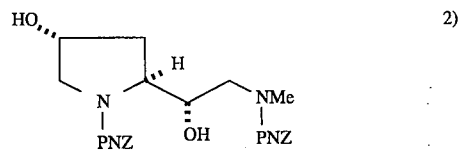
2)

To 40% methylamine methanol solution (58 ml) was added a solution of the above compound (2.69 g, 7.67 mmol) in methanol (12 ml) at room temperature, and the mixture was heated in a sealed tube at 120° C. (outside temperature) for 30 min. The reaction mixture was cooled to room temperature, and concentrated in vacuo. To the residue was added methanol (30 ml) and 20% aqueous potassium hydroxide (15 ml), and the mixture was stirred overnight under refluxing. The mixture was adjusted to pH 9 with conc. hydrochloric acid, and a solution of 4,6-dimethyl-2-(p-nitrobenzyloxycarbonylthio)pyrimidine (4.89 g, 15.3 mmol) in chloroform (10 ml). The reaction mixture was stirred for 3 h adjusting at pH 9 with 1N aqueous sodium hydroxide. The solution was concentrated to ca. 20 ml in vacuo, and diluted with ethyl acetate (200 ml). The solution was washed successively with 2N hydrochloric acid, water and saturated aqueous sodium chloride. After drying over anhydrous magnesium sulfate, the solvent was removed in vacuo. The residue was subjected to silica gel column chromatography (heptane-ethyl acetate) to give (2S,4R)-4-hydroxy-2-[[(1S)-1-hydroxy-2 -(N-p-nitrobenzyloxycarbonyl-N-methylamino)]ethyl]-N-(p-nitrobenzyloxycarbonyl)pyrrolidine (699 mg, yield: 17%).

IR(KBr)cm$^{-1}$: 3430,2950,1700,1610,1520,1430,1410, 1350 NMR(CDCl$_3$) δ: 1.90–2.20 (2H,m), 3.10 (3H,s), 3.30–3.60 (3H,m), 3.70–3.90 (2H,m), 4.10 (1H,m), 4.45 (1H,m), 5.15–5.30 (4H,m), 7.45–7.60 (4H,m), 8.15–8.30 (4H,m)

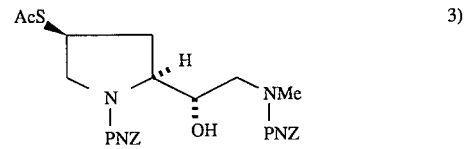
3)

The title compound (675 mg, yield: 87%) was obtained from the above compound (699 mg, 1.35 mmol) in the same manner as in REFERENCE EXAMPLE 4-3.

IR(KBr)cm$^{-1}$: 3440,2940,1700,1610,1520,1400,1350 NMR(CDCl$_3$) δ: 1.90–2.20 (2H,m), 2.33 (3H,s), 3.08 (3H, s), 3.20–4.30 (7H,m), 5.15–5.30 (4H,m), 7.40–7.60 (4H,m), 8.10–8.30 (4H,m)

REFERENCE EXAMPLE 17

(2S,4S)-4-Acetylthio-2-[[(1R)-1-hydroxy-2-(N-p-nitrobenzyloxycarbonyl-N-methylamino)]ethyl]-N-(p-nitrobenzyloxycarbonyl)pyrrolidine

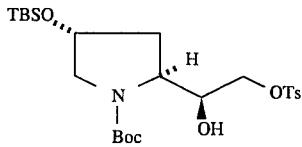
1)

(2S,4R)-tert-Butoxycarbonyl-4-tert-butyldimethylsiloxy-2-[[(1R)-1-hydroxy-2-p-toluenesulfonyloxy]ethyl]pyrrolidine (3.14 g, yield: 65%) was obtained from (2S,4R)-N-tert-butoxycarbonyl-2-(1,2-dihydroxyethyl)-4-tert-butyldimethylsiloxypyrrolidine prepared in REFERENCE EXAMPLE 3-1 (3.40 g, 9.40 mmol) in the same manner as in REFERENCE EXAMPLE 15-1.

IR(KBr)cm$^{-1}$: 3430,2960,2940,2860,1700,1670,1600, 1410, 1370,1260,1190,1180,1100 NMR(CDCl$_3$) δ: 0.05 (6H,s), 0.85 (9H,s), 1.42 (9H,s), 1.90–2.05 (2H,m), 2.44 (3H,s), 3.27 (1H,m), 3.46 (1H,m), 3.90–4.05 (3H,m), 4.13 (1H,m), 4.30 (1H,m), 7.34 (2H,d,J=8.3Hz), 7.78 (2H,d,J=8.3Hz)

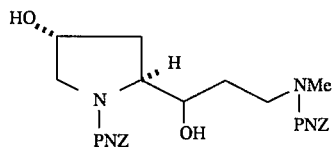
2)

(2S,4R)-4-Hydroxy-2-[[(1R)-1-hydroxy-2-(N-p-nitrobenzyloxycarbonyl-N-methylamino)]ethyl]-N-(p-nitrobenzyloxycarbonyl)pyrrolidine (2.80 g, yield: 89%) was obtained from the above compound (3.14 g, 6.09 mmol) in the same manner as in REFERENCE EXAMPLE 15-2.

IR(KBr)cm$^{-1}$: 3430,2950,1700,1610,1520,1430,1400, 1350 NMR(CDCl$_3$) δ: 1.90–2.40 (2H,m), 3.07 (3H,s), 3.18 (1H,m), 3.30–3.55 (2H,m), 3.75 (1H,m), 4.00–4.30 (2H,m), 4.50 (1H,m), 5.20–5.35 (4H,m), 7.40–7.60 (4H,m), 8.15–8.30 (4H,m)

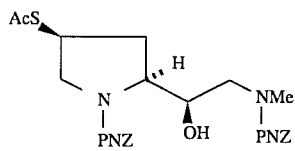
3)

The title compound (2.00 g, yield: 64%) was obtained from the above compound (2.80 g, 5.40 mmol) in the same manner as in REFERENCE EXAMPLE 4-3.

IR(KBr)cm$^{-1}$: 3420,2940,1700,1610,1520,1430,1400, 1350, 1110 NMR(CDCl$_3$) δ: 2.10 (1H,m), 2.34 (3H,s), 2.35 (1H,m), 3.05 (3H,s), 3.00–3.30 (2H,m), 3.40–4.40 (5H,m), 5.10–5.30 (4H,m), 7.45–7.60 (4H,m), 8.15–8.30 (4H,m)

REFERENCE EXAMPLE 18

(2R,4S)-4-Acetylthio-2-[2-(N-methyl-N-p-nitrobenzyloxycarbonylamino)propyl]-N-p-nitrobenzyloxycarbonylpyrrolidine diastereomer A

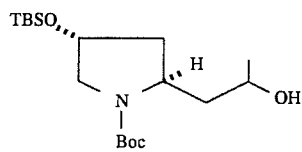
1)

To a solution of 1.6M methyllithium-ether solution (5.5 ml, 8.8 mmol) in tetrahydrofuran (20 ml) was added (2S,4R)-N-tert-butoxycarbonyl-4-tert-butyldimethylsiloxy-2-(formylmethyl)pyrrolidine (1.67 g, 4.86 mmol) under a nitrogen atmosphere at −70° C., and the mixture was stirred for 2 h at the same temperature. To the mixture was added saturated aqueous ammonium chloride (3 ml) below −70° C., and then the mixture was warmed at room temperature. The reaction mixture was poured into a mixture of water (200 ml) and 1N aqueous potassium hydrogensulfate (20 ml), and extracted with ethyl acetate (3×50 ml). The combined organic layer was washed successively with water and saturated aqueous sodium chloride, and dried over anhydrous sodium sulfate. The solvent was removed in vacuo, and the residue was subjected to silica gel column chromatography (heptane-ethyl acetate) to give (2R,4R)-N-tert-butoxycarbonyl-4-tert-butyldimethylsiloxy-2-(2-hydroxypropyl)pyrrolidine diastereomer A (890 mg, yield: 51%) and diastereomer B (350 mg, yield: 20%).

DIASTEREOMER A: IR(KBr)cm$^{-1}$: 3420,2930,1695,1675,1400,1365,1250,1165, 1115,835,775 NMR(CDCl$_3$) δ: 0.06 (6H,s), 0.87 (9H,s), 1.19 (3H,d,J=6.0Hz), 1.30–1.60 (2H,m), 1.46 (9H,s), 1.75 (1H,m), 2.00–2.40 (2H,m), 3.37 (2H,m), 3.88 (1H,m), 4.07 (1H,m), 4.33 (1H,m)

DIASTEREOMER B: IR(KBr)cm$^{-1}$: 3440,2930,1695,1675,1395,1365,1250,1160, 1120,835,775 NMR(CDCl$_3$) δ: 0.06 (6H,s), 0.87 (9H,s), 1.17 (3H,d,J=6.0Hz), 1.30–1.60 (2H,m), 1.45 & 1.46 (total 9H,each s), 1.71 (1H,m), 2.00–2.20 (2H,m), 3.34 (2H,m), 3.73 (1H,m), 4.20–4.40 (2H,m)

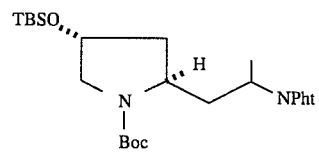
2)

To an ice-cooled solution of the above compound, diastereomer A (890 mg, 2.48 mmol) in tetrahydrofuran (6 ml), were added triphenylphosphine (980 mg, 3.74 mmol) and phthalimide (550 mg, 3.74 mmol), and then diethyl azodicarboxylate (0.6 ml, 3.81 mmol) under a nitrogen atmosphere. The mixture was stirred for 15 min at the same temperature, and then overnight at room temperature. The reaction mixture was concentrated in vacuo, and the residue was subjected to silica gel column chromatography (heptane-ethyl acetate) to give (2R,4R)-N-tert-butoxycarbonyl-4-tert-butyldimethylsiloxy-2-(2-phthalimido)propylpyrrolidine diastereomer A (1.00 g, yield: 83%).

IR(KBr)cm$^{-1}$: 2930,1775,1710,1695,1470,1390,1365, 1250, 1165,1030,835,775,720 NMR(CDCl$_3$) δ: 0.00 (6H,s), 0.81 (9H,s), 1.39 (3H,m), 1.47 & 1.50 (total 9H,each s), 1.60–2.60 (4H,m), 3.20–3.45 (2H,m), 3.80–4.10 (1H,m), 4.20–4.50 (2H,m), 7.70 (2H,m), 7.80 (2H,m)

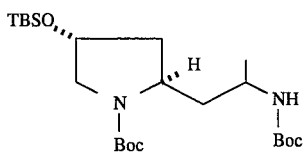
3)

To a solution of the above compound (1.00 g, 2.05 mmol) in ethanol (20 ml) was added hydrazine monohydrate (0.8 ml, 16.49 mmol), and the mixture was stirred for 1.5 h at room temperature. The solvent was removed in vacuo to give the crude amine. To a solution of the above amine in a mixture of dioxane (6 ml) and water (3 ml) was added triethylamine (1.15 ml, 8.25 mmol), and then 2-tert-butoxycarbonylthio-4,6-dimethylpyrrolidine (990 mg, 4.12 mmol). After stirring overnight at room temperature, to the reaction mixture was added ethyl acetate (150 ml), and washed successively with 1N aqueous potassium hydrogensulfate, water, saturated aqueous sodium hydrogencarbonate, water and saturated aqueous sodium chloride. After drying over anhydrous sodium sulfate, the solvent was removed in vacuo, and the residue was subjected to silica gel column chromatography (heptane-ethyl acetate) to give (2R,4 R)-N-tert-butoxycarbonyl-2-[2-(tert-butoxycarbonylamino)propyl]-4-tert-butyldimethylsiloxypyrrolidine diastereomer A (590 mg, yield: 63%).

IR(KBr)cm$^{-1}$: 3340,2920,1690,1510,1455,1390,1360, 1250, 1170,1130,1070,835,775 NMR(CDCl$_3$) δ: 0.05 (6H, s), 0.86 (9H,s), 1.17 (3H,d,J=6.0Hz), 1.43 (9H,s), 1.46 (9H,s), 1.60–2.10 (4H,m), 3.30 (2H,m), 3.59 (1H,m), 3.70–4.10 (1H,m), 4.30 (1H,m), 4.68 (1H,m)

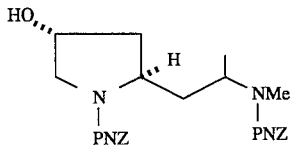
4)

(2R,4R)-4-Hydroxy-2-[2 -(N-methyl-N-p-nitrobenzyloxycarbonylamino)propyl]-N-p-nitrobenzyloxycarbonylpyrrolidine diastereomer A (490 mg, yield: 67%) was obtained from the above compound (650 mg, 1.42 mmol) in the same manner as in REFERENCE EXAMPLES 11-2 and 6-6.

IR(KBr)cm$^{-1}$: 3450,2940,1700,1610,1520,1405,1350, 1110, 1015,850,740 NMR(CDCl$_3$) δ: 1.05–1.30 (3H,m), 1.40–2.40 (5H,m), 2.70–2.90 (3H,m), 3.40–3.75 (2H,m), 4.04 (1H,m), 4.30 (1H,m), 4.42 (1H,m), 5.21 (4H,s), 7.50 (4H,d,J=8.0Hz), 8.21 (4H,d,J=9.0Hz)

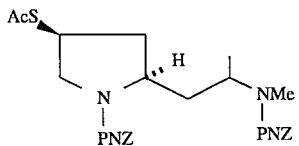
5)

The title compound (480 mg, yield: 88%) was obtained from the above compound (490 mg, 0.949 mmol) in the same manner as in REFERENCE EXAMPLES 6-7 and 6-8.

IR(KBr)cm$^{-1}$: 3420,2930,1700,1605,1520,1400,1345, 1120, 850,735 NMR(CDCl$_3$) δ: 1.00–1.30 (3H,m), 1.40–2.60 (4H,m), 2.33 (3H,s), 2.78 (3H,s), 3.14 (1H,dd,J= 8.0,11.0Hz), 3.83 (2H,m), 4.07 (1H,m), 4.30 (1H,m), 5.10–5.30 (4H,m), 7.51 (4H,d,J=8.0Hz), 8.22 (4H,d,J= 9.0Hz)

REFERENCE EXAMPLE 19

(2R,4S)-4-Acetylthio-2-[2-N-methyl-N-p-nitrobenzyloxycarbonylamino)propyl]-N-p-nitrobenzyloxycarbonylpyrrolidine diastereomer B

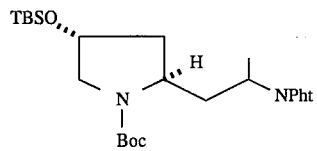
1)

(2R,4R)-N-tert-Butoxycarbonyl-4-tert-butyldimethylsiloxy- 2-(2-phthalimidopropyl)pyrrolidine diastereomer B (320 mg, yield: 51%) was obtained from (2R,4R)-N-tert-butoxycarbonyl- 4-tert-butyldimethylsiloxy-2-(2 -hydroxy)propylpyrrolidine diastereomer B prepared in REFERENCE EXAMPLE 18-1 (460 mg, 1.28 mmol) in the same manner as in REFERENCE EXAMPLE 18-2.

IR(KBr)cm$^{-1}$: 2930,1775,1710,1695,1465,1395,1365, 1255, 1165,1100,1080,835,775,720 NMR(CDCl$_3$) δ: 0.03 (6H,s), 0.81 (9H,s), 1.40 (9H,s), 1.51 (3H,d,J=7.0Hz), 1.55–1.85 (2H,m), 2.06 (1H,m), 2.66 (1H,m), 3.30–3.50 (2H,m), 3.74 (1H,m), 4.25–4.50 (2H,m), 7.70 (2H,m), 7.81 (2H,m)

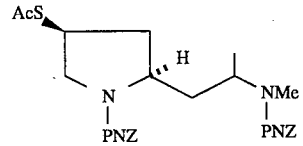
2)

The title compound (80 mg, yield: 22%) was obtained from the above compound (310 mg, 0.634 mmol) in the same manner as in REFERENCE EXAMPLES 18-3, 18-4, and 18-5.

IR(KBr)cm$^{-1}$: 2940,1695,1605,1520,1400,1345,1325, 1120, 850,735 NMR(CDCl$_3$) δ: 1.14 (3H,d,J=7.0Hz), 1.32 (1H,m), 1.68 (1H,m), 2.30–2.70 (2H,m), 2.34 (3H,s), 2.89 (3H,s), 3.20 (1H,m), 3.60–3.90 (2H,m), 4.09 (1H,m), 4.20–4.45 (1H,m), 5.10–5.30 (4H,m), 7.51 (4H,d,J=8.0Hz), 8.22 (4H,d,J=9.0Hz)

REFERENCE EXAMPLE 20

(2R,4S)-N-Allyloxycarbonyl-2-[2-(N-allyloxycarbonyl-N-methylamino)-3-hydroxypropyl]-4-(triphenylmethylthio)pyrrolidine Diastereomer A and Diastereomer B

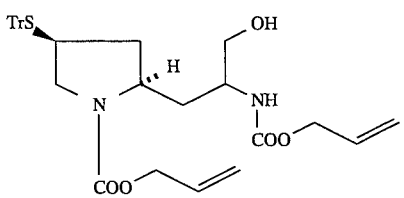
1)

To a solution of (2R,4S)-N-allyloxycarbonyl-2-(2 -allyloxycarbonylamino-2-methoxycarbonylethyl)-4 -(triphenylmethylthio)pyrrolidine prepared in REFERENCE EXAMPLE 2-2 (810 mg, 1.32 mmol) in tetrahydrofuran (5 ml) was added lithium chloride (100 mg, 2.58 mmol), sodium borohydride (110 mg, 2.59 mmol) and ethanol (5 ml) under a nitrogen atmosphere, and the mixture was stirred overnight at room temperature. The reaction mixture was acidified with 10% aqueous citric acid under ice-cooling, and then the organic solvent was removed in vacuo. The residual aqueous solution was extracted with methylene chloride (1×40 ml, 2×20 ml), and the combined organic layer was washed successively with water and saturated aqueous sodium chloride. After drying over anhydrous sodium sulfate, the solvent was removed in vacuo, and the residue was subjected to silica gel column chromatography (heptane-ethyl acetate) to give (2R,4S)-N-allyloxycarbonyl-2-(2 -allyloxycarbonylamino-3-hydroxypropyl)-4-(triphenylmethylthio)pyrrolidine (440 mg, yield: 57%).

IR(KBr)cm$^{-1}$: 3420,1700,1530,1445,1410,1330,1255, 1200, 1060,990,925,740,700 NMR(CDCl$_3$) δ: 1.40–2.40 (5H,m), 2.60–3.00 (3H,m), 3.40–3.80 (4H,m), 4.40–4.65 (4H,m), 5.10–5.40 (4H,m), 5.56 (1H,m), 5.86 (2H,m), 7.10–7.60 (15H,m)

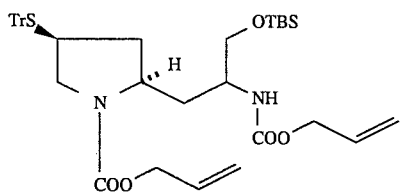
2)

To a solution of the above compound (440 mg, 0.750 mmol) in N,N-dimethylformamide (1.5 ml) was added imidazole (110 mg, 1.62 mmol), and then tert-butyldimethylchlorosilane (170 mg, 1.13 mmol) under a nitrogen atmosphere, and the mixture was stirred overnight at room temperature. The reaction mixture was poured into water (200 ml), and extracted with ethyl acetate (1×40 ml, 2×20 ml). The combined organic layer was washed successively with 1N aqueous potassium hydrogensulfate, water and saturated aqueous sodium chloride. After drying over anhydrous sodium sulfate, the solvent was removed in vacuo, and the residue was subjected to silica gel column chromatography (heptane-ethyl acetate) to give (2R,4S)-N-allyloxycarbonyl-2-[2 -allyloxycarbonylamino-3-(tert-butyldimethysiloxy)propyl]-4-(triphenylmethylthio)pyrrolidine (480 mg, yield: 91%).

IR(KBr)cm$^{-1}$: 3440,3320,2950,2930,1720,1700,1500, 1440,1400,1325,1250,1095,990,920,835,700 NMR(CDCl$_3$) δ: 0.03 (6H,s), 0.87 (9H,s), 1.40–1.70 (2H,m), 2.00–2.50 (2H,m), 2.60–3.00 (2H,m), 3.45–3.80 (4H,m), 4.40–4.65 (4H,m), 4.77 (1H,m), 5.15–5.40 (4H,m), 5.88 (1H,m), 7.20–7.60 (15H,m)

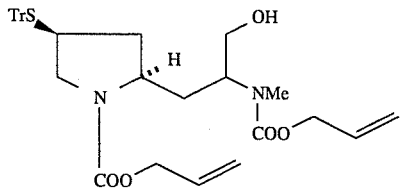
3)

A crude methyl derivative was obtained from the above compound (470 mg, 0.670 mmol) in the same manner as in REFERENCE EXAMPLE 11-2. To a solution of the methyl derivative in tetrahydrofuran (2.5 ml) was added 1M tetrabutylammonium fluoride tetrahydrofuran solution (0.8 ml, 0.8 mmol), and the mixture was stirred for 1 h at room temperature. The reaction mixture was concentrated in vacuo, and the residual aqueous solution was extracted with ethyl acetate (80 ml). The organic layer was washed successively with 1N potassium hydrogensulfate, water and saturated aqueous sodium chloride. After drying over anhydrous sodium sulfate, the solvent was removed in vacuo, and the residue was subjected to silica gel column chromatography (heptane-ethyl acetate) to give the diastereomer A of the title compound (190 mg, yield: 47%) and the diastereomer B (190 mg, yield: 47%).

DIASTEREOMER A: IR(KBr)cm$^{-1}$: 3440,2940,1695,1485,1445,1405,1330,1200, 1140,990,920, 740,700 NMR(CDCl$_3$) δ: 1.20–2.50 (5H,m), 2.60–3.00 (3H, m), 2.81 (3H,s), 3.40–3.75 (3H,m), 4.11 (1H,m), 4.40–4.70 (4H,m), 5.15–5.40 (4H,m), 5.91 (2H,m), 7.20–7.55 (15H,m)

DIASTEREOMER B: IR(KBr)cm$^{-1}$: 3450,2940,1695,1485,1445,1400,1330,1200, 1160,990,920, 740,700 NMR(CDCl$_3$) δ: 1.20–2.50 (5H,m), 2.60–2.90 (3H, m), 2.86 (3H,s), 3.45–3.70 (3H,m), 4.25 (1H,m), 4.35–4.70 (4H,m), 5.15–5.45 (4H,m), 5.88 (2H,m), 7.20–7.60 (15H,m)

REFERENCE EXAMPLE 21

(2R,4S)-4-Acetylthio-2-[2-methyl-2 -(p-nitrobenzyloxycarbonylamino) propyl]-N-p-nitrobenzyloxycarbonylpyrrolidine

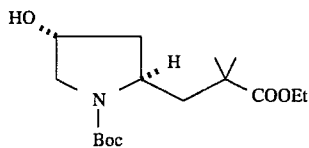
1)

A crude dimethyl derivative was obtained from (2R,4R)-N-tert-butoxycarbonyl-4-tert-butyldimethylsiloxy- 2-(2-ethoxycarbonyl-2-methyl)ethylpyrrolidine prepared in REFERENCE EXAMPLE 6-2 (15.84 g, 38.1 mmol) in the same manner as in REFERENCE EXAMPLE 6-2. To a solution of the dimethyl derivative in tetrahydrofuran (150 ml) was added 75% aqueous tetrabutylammonium fluoride solution (15.94 g, 45.7 mmol), and the mixture was stirred for 1.5 h at room temperature. The reaction mixture was concentrated in vacuo, and extracted with ethyl acetate (700 ml). The organic layer was washed successively with water, 1N aqueous potassium hydrogensulfate, water and saturated aqueous sodium chloride. After drying over anhydrous sodium sulfate, the solvent was removed in vacuo, and residue was subjected to silica gel column chromatography (heptane-ethyl acetate) to give (2R,4R)-N-tert-butoxycarbonyl-2 -(2-ethoxycarbonyl-2-methyl)propyl-4-hydroxypyrrolidine (11.33 g, yield: 94%).

IR(KBr)cm$^{-1}$: 3420,2980,1725,1695,1670,1475,1395, 1365, 1250,1170,1140,1025,860,770 NMR(CDCl$_3$) δ: 1.23 (6H,s), 1.27 (3H,t,J=7.0Hz), 1.47 (9H,s), 1.60–1.80 (2H,m), 1.80–2.25 (3H,m), 3.35 (1H,dd,J=4.0,8.0Hz), 3.52 (1H,m), 4.051 (1H,m), 4.13 (2H,q,J=7.0Hz), 4.38 (1H,m)

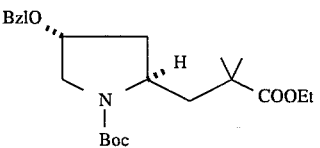
2)

To a solution of the above compound (13.09 g, 41.5 mmol) in N,N-dimethylformamide (100 ml) was added sodium hydride (60%, in oil suspension, 2.0 g, 50 mmol) under a nitrogen atmosphere, and the mixture was stirred for 1 h at room temperature. To the mixture were added tetrabutylammonium iodide (1.53 g, 4.14 mmol) and benzyl bromide (9.9 ml, 83.23 mmol), and the mixture was stirred 1 h at room temperature, and overnight at 70° C. The reaction mixture was poured into ice in water (500 ml) and 1N aqueous potassium hydrogensulfate (100 ml), and extracted with ethyl acetate (3×200 ml). The combined organic layer was washed successively with 10% aqueous sodium sulfite, water and saturated aqueous sodium chloride, and dried over anhydrous sodium sulfate. The solvent was removed in vacuo, and the residue was subjected to silica gel column chromatography (heptane-ethyl acetate) to give (2R, 4R)- 4-benzyloxy-N-tert-butoxycarbonyl-2-(2-ethoxycarbonyl-2-methyl)propylpyrrolidine (10.44 g, yield: 62%).

IR(KBr)cm⁻¹: 3430,2970,1725,1695,1480,1455,1395, 1365, 1170,1140,1110,865,740 NMR(CDCl₃) δ: 1.22 (6H, s), 1.25 (3H,t,J=7.0Hz), 1.47 (9H,s), 1.60–1.80 (2H,m), 1.90–2.40 (2H,m), 3.30 (1H,m), 3.45–3.95 (1H,m), 3.95–4.20 (4H,m), 4.47 (2H,m), 7.25–7.50 (5H,m)

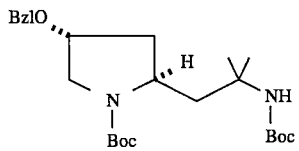

3)

To a solution of the above compound (10.44 g, 25.74 mmol) in ethanol (100 ml) was added 1N aqueous sodium hydroxide (52 ml, 52 mmol), and the mixture was refluxed for 3 h. The ethanol was removed in vacuo, and the residue was washed with diethyl ether. To the aqueous layer was added 1N aqueous hydrochloric acid (52 ml, 52 mmol) under ice-cooling and stirring, the mixture was extracted with ethyl acetate (3×200 ml). The combined organic layer was washed successively with water and saturated aqueous sodium chloride, and dried over anhydrous sodium sulfate. The solvent was removed in vacuo to give the crude carboxylic acid. To a solution of the carboxylic acid in tert-buthanol (80 ml) was added triethylamine (4 ml, 28.70 mmol), and then diphenylphosphoric azide (6.2 ml), and the mixture was refluxed overnight. To the reaction mixture was added tert-buthanol (50 ml), and the mixture was refluxed for 3 days. The solvent was removed in vacuo, and to the residue was added ethyl acetate (600 ml), and the organic layer was washed successively with 1N aqueous potassium hydrogensulfate, water, saturated aqueous sodium hydrogencarbonate, water and saturated aqueous sodium chloride. After drying over anhydrous sodium sulfate, the solvent was removed in vacuo, and the residue was subjected to silica gel column chromatography (methylene chloride-ethyl acetate) to give (2R,4R)-4-benzyloxy-N-tert-butoxycarbonyl-2-(2-tert-butoxycarbonylamino-2-methyl)propylpyrrolidine (6.49 g, yield: 56%).

IR(KBr)cm⁻¹: 3340,2970,1710,1690,1500,1390,1360, 1245, 1160,1070,865,770,735,695 NMR(CDCl₃) δ: 1.30 (3H,s), 1.34 (3H,s), 1.43 (9H,s), 1.48 (9H,s), 1.68 (1H,m), 1.86 (1H,m), 2.04 (1H,m), 2.23 (1H,m), 3.35 (1H,m), 3.40–3.95 (1H,m), 3.95–4.20 (2H,m), 4.40–4.70 (2H,m), 5.30–5.60 (1H,m), 7.20–7.50 (5H,m)

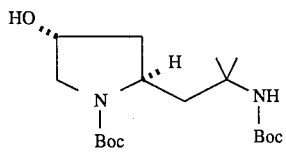

4)

To a solution of the above compound (4.61 g, 10.3 mmol) in methanol (90 ml) was added 10% palladium-carbon catalyst (4.6 g) and ammonium formate (3.25 g, 51.5 mmol), and the mixture was refluxed. Every 1 h, ammonium formate (3.25 g, 51.5 mmol) was additionally added, and the mixture was refluxed 8 h in total. The catalyst was filtered off, and the filtrate was concentrated in vacuo. To the residue was added ethyl acetate (400 ml), and the organic layer was washed successively with water and saturated aqueous sodium chloride. After drying over anhydrous sodium sulfate, the solvent was removed in vacuo, and the residue was subjected to silica gel column chromatography (heptane-ethyl acetate) to give (2R,4R)-N-tert-butoxycarbonyl-2-(2-tert-butoxycabonylamino-2-methyl)propyl-4-hydroxypyrrolidine (1.74 g, yield: 47%).

IR(KBr)cm⁻¹: 3430,2980,1715,1695,1680,1505,1455, 1405, 1365,1255,1170,1070,775 NMR(CDCl₃) δ: 1.25–1.40 (6H,m), 1.43 (9H,s), 1.48 (9H,s), 1.60–1.95 (3H,m), 1.95–2.30 (2H,m), 3.30–3.70 (2H,m), 4.03 (1H,m), 4.40 (1H,m), 4.57 & 5.50 (total 1H,each br s)

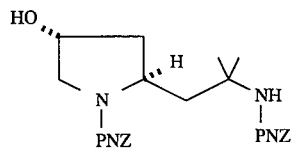

5)

To a solution of the above compound (140 mg, 0.391 mmol) in methylene chloride (1 ml) was added trifluoroacetic acid (1 ml), and the mixture was stirred for 30 min at room temperature. The solvent was removed in vacuo, and the mixture was distilled with benzene several times to give the crude amine. To a solution of the amine in a mixture of dioxane (0.9 ml) and water (0.3 ml) was added sodium hydrogencarbonate (330 mg, 3.93 mmol), and then 4,6-dimethyl-2-(p-nitrobenzyloxycarbonylthio)pyrimidine (250 mg, 0.783 mmol). The mixture was stirred for 2 h at room temperature, and then at 50° C. overnight. To a reaction mixture was added ethyl acetate (30 ml), and the organic layer was washed successively with water, 1N potassium hydrogensulfate, water and saturated aqueous sodium chloride. After drying over anhydrous sodium sulfate, the solvent was removed in vacuo, and the residue was subjected to silica gel column chromatography (heptane-ethyl acetate) to give (2R,4R)-4-hydroxy-2-[2-methyl-2 -(p-nitrobenzyloxycarbonylamino)propyl]-N-p-nitrobenzyloxycarbonylpyrrolidine (160 mg, yield: 79%).

IR(KBr)cm⁻¹: 3420,2940,1690,1605,1520,1430,1405, 1345, 1260,1210,1090,850,740 NMR(CDCl₃) δ: 1.36 (3H, s), 1.39 (3H,s), 1.60–2.00 (3H,m), 2.10–2.30 (2H,m), 3.30–3.70 (2H,m), 4.12 (1H,m), 4.47 (1H,m), 5.00–5.40 (4H,m), 6.45 (1H,s), 7.50 (4H,m), 8.20 (4H,m)

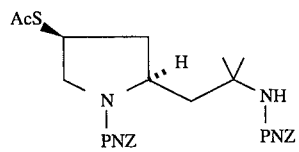

6)

The title compound (230 mg, yield: 80%) was obtained from the above compound (260 mg, 0.503 mmol) in the same manner as in REFERENCE EXAMPLES 6-7 and 6-8.

IR(KBr)cm⁻¹: 3340,2970,1725,1695,1605,1520,1430, 1400, 1345,1265,1210,1105,1095,855,740 NMR(CDCl₃) δ: 1.36 (3H,s), 1.37 (3H,s), 1.60– 1.90 (2H,m), 2.17 (1H,m), 2.35 (3H,s), 2.62 (1H,m), 3.28 (1H,m), 3.80–4.20 (3H,m), 5.05–5.35 (4H,m), 6.36 (1H,s), 7.49 (4H,m), 8.21 (4H,m)

REFERENCE EXAMPLE 22

(2R,4S)-4-Acetylthio-2-[2-methyl-2-(N-methyl-N-p-nitrobenzyloxycarbonylamino)propyl]-N-p-nitrobenzyloxycarbonylpyrrolidine

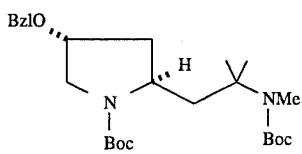
1)

(2R,4R)-4-Benzyloxy-N-tert-butoxycarbonyl-2-[2 -(N-tert-butoxycarbonyl-N-methylamino)-2-methyl]propylpyrrolidine (880 mg, yield: 95%) was obtained from (2R,4R)-4-benzyloxy-N-tert-butoxycarbonyl-2-(2 -tert-butoxycarbonylamino-2-methyl)propylpyrrolidine prepared in REFERENCE EXAMPLE 21-3 (900 mg, 2.01 mmol) in the same manner as in REFERENCE EXAMPLE 11-2.

IR(KBr)cm$^{-1}$: 3440,2970,1695,1455,1390,1365,1250, 1160, 1120 NMR(CDCl$_3$) δ: 1.40 (6H,s), 1.46 (9H,s), 1.47 (9H,s), 1.80–1.95 (2H,m), 2.05–2.60 (2H,m), 2.84 (3H,s), 3.32 (1H,m), 3.40–3.90 (1H,m), 3.90–4.20 (2H,m), 4.40–4.60 (2H,m), 7.25–7.40 (5H,m)

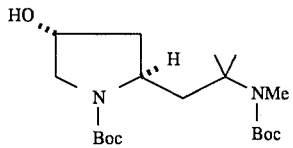
2)

(2R,4R)-N-tert-Butoxycarbonyl-2-[2 -(N-tert-butoxycarbonyl-N-methylamino)-2-methyl]propyl-4-hydroxypyrrolidine (610 mg, yield: 86%) was obtained from the above compound (880 mg, 2.36 mmol) in the same manner as in REFERENCE EXAMPLE 21-4.

IR(KBr)cm$^{-1}$: 3450,2980,1695,1480,1455,1390,1365, 1250, 1170,1120,865,770 NMR(CDCl$_3$) δ: 1.41 (3H,s), 1.42 (3H,s), 1.46 (9H,s), 1.47 (9H,s), 1.65–2.20 (4H,m), 2.35 (1H,m), 2.85 (3H,s), 3.35 (1H,m), 3.48 (1H,m), 4.04 (1H, m), 4.37 (1H,m)

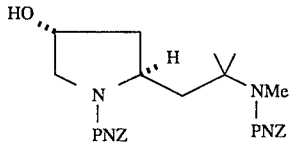
3)

(2R,4R)-4-Hydroxy-2-[2-(N-methyl-N-p-nitrobenzyloxycarbonylamino)propyl]-N-p-nitrobenzyloxycarbonylpyrrolidine (420 mg, yield: 48%) was obtained from the above compound (610 mg, 1.64 mmol) in the same manner as in REFERENCE EXAMPLE 21-5.

IR(KBr)cm$^{-1}$: 3440,2940,1695,1605,1520,1400,1340, 1190, 1110,855,735 NMR(CDCl$_3$) δ: 1.25–1.60 (6H,m), 1.60–2.40 (5H,m), 2.92 & 2.98 (total 3H,each s), 3.40 (1H,m), 3.57 (1H,m), 4.11 (1H,m), 4.34 (1H,m), 5.10–5.30 (4H,m), 7.51 (4H,d,J=8.0Hz), 8.21 (4H,d,J=8.0Hz)

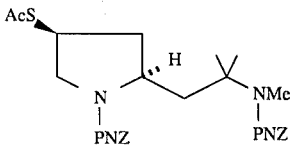
4)

The title compound (390 mg, yield: 78%) was obtained from the above compound (450 mg, 0.848 mmol) in the same manner as in REFERENCE EXAMPLE 21-6.

IR(KBr)cm$^{-1}$: 3400,2950,1695,1605,1520,1400,1345, 1205, 1120,850,735 NMR(CDCl$_3$) δ: 1.20–1.70 (2H,m), 1.44 (6H,s), 2.00–2.50 (2H,m), 2.32 (3H,s), 2.97 (3H,s), 3.07 (1H,m), 3.77 (1H,m), 3.85–4.20 (2H,m), 5.10–5.30 (4H,m), 7.45–7.60 (4H,m), 8.20–8.30 (4H,m)

REFERENCE EXAMPLE 23

(2R,4S)-4-Acetylthio-2-[3-methyl-3-(p-nitrobenzyloxycarbonylamino)butyl]-N-p-nitrobenzyloxycarbonylpyrrolidine

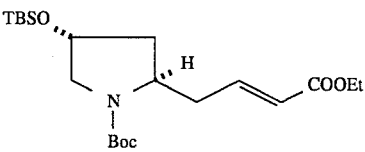
1)

To an ice-cooled solution of ethyl diethylphosphonoacetate (1.1 ml, 5.54 mmol) in tetrahydrofuran (10 ml) was added sodium hydride (60%, in oil suspension, 220 mg, 5.5 mmol) under a nitrogen atmosphere, and the mixture was stirred for 30 min at the same temperature. To the ice-cooled reaction mixture was added a solution of (2S,4R)-N-tert-butoxycarbonyl- 4-tert-butyldimethylsiloxy-2-(formylmethyl)pyrrolidine (1.72 g, 5.01 mmol) in tetrahydrofuran (3 ml), and the mixture was stirred for 1 h. The reaction mixture was poured into a mixture of ice water (200 ml) and 1N aqueous potassium hydrogensulfate (20 ml), and extracted with ethyl acetate (3×50 ml). The combined organic layer was washed successively with water and saturated aqueous sodium chloride, and dried over anhydrous sodium sulfate. The solvent was removed in vacuo, and the residue was subjected to silica gel column chromatography (heptane-ethyl acetate) to give (2R,4R)-N-tert-butoxycarbonyl-4-tert-butyldimethylsiloxy- 2-[(E)-3-ethoxycarbonylallyl]pyrrolidine (1.98 mg, yield: 96%).

IR(KBr)cm$^{-1}$: 3430,2930,1725,1700,1660,1475,1465, 1395, 1365,1320,1260,1160,1115,840,775 NMR(CDCl$_3$) δ: 0.05 (6H,s), 0.86 (9H,s), 1.29 (3H,t,J=7.0Hz), 1.46 (9H,s), 1.72 (1H,m), 1.96 (1H,m), 2.40 (1H,m), 2.50–2.80 (1H,m), 3.30–3.60 (2H,m), 4.03 (1H,m), 4.19 (2H,q,J=7.0Hz), 4.29 (1H,m), 5.85 (1H,d,J=16.0Hz), 6.86 (1H,m)

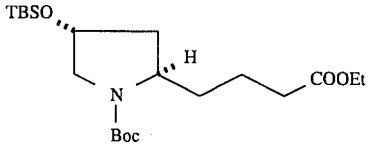
2)

(2R,4R)-N-tert-Butoxycarbonyl-4-tert-butyldimethylsiloxy- 2-(3-ethoxycarbonylpropyl)pyrrolidine (1.83 g, yield: 97%) was obtained from the above compound (1.88 g, 4.55 mmol) in the same manner as in REFERENCE EXAMPLE 6-1.

IR(KBr)cm$^{-1}$: 3450,2930,1735,1695,1470,1460,1390, 1365, 1250,1170,1110,1060,1030,835,775 NMR(CDCl$_3$) δ: 0.05 (6H,s), 0.86 (9H,s), 1.25 (3H,t,J=7.0Hz), 1.30–1.90 (5H,m), 1.45 (9H,s), 1.98 (1H,m), 2.31 (2H,m), 3.30–3.60 (2H,m), 3.87 (1H,m), 4.12 (2H,q,J=7.0Hz), 4.31 (1H,m)

3)

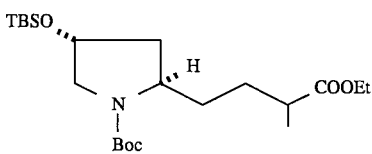

(2R,4R)-N-tert-Butoxycarbonyl-4-tert-butyldimethylsiloxy- 2-(3-ethoxycarbonyl)butylpyrrolidine (1.56 g, yield: 83%) was obtained from the above compound (1.81 g, 4.35 mmol) in the same manner as in REFERENCE EXAMPLE 6-2.

IR(KBr)cm$^{-1}$: 3440,2930,1735,1695,1460,1390,1365, 1255, 1160,1130,1110,1025,900,835,775 NMR(CDCl$_3$) δ: 0.05 (6H,s), 0.86 (9H,s), 1.15 (3H,d,J=7.0Hz), 1.25 (3H,t, J=7.0Hz), 1.35–1.50 (1H,m), 1.45 (9H,s), 1.55–1.90 (4H,m), 1.96 (1H,m), 2.40 (1H,m), 3.30–3.55 (2H,m), 3.83 (1H,m), 4.12 (2H, q, J=7.0Hz), 4.30 (1H,m)

4)

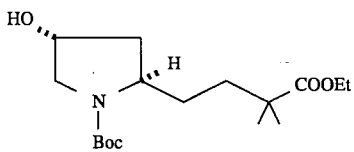

(2R,4R)-N-tert-butoxycarbonyl-2-(3-ethoxycarbonyl-3 -methyl)butyl-4-hydroxypyrrolidine (1.12 g, yield: 95%) was obtained from the above compound (1.54 g, 3.58 mmol) in the same manner as in REFERENCE EXAMPLE 21-1.

IR(KBr)cm$^{-1}$: 3430,2970,1730,1695,1670,1480,1455, 1395, 1365,1250,1165,860,770 NMR(CDCl$_3$) δ: 1.16 (6H, s), 1.24 (3H,t,J=7.0Hz), 1.30–1.60 (2H,m), 1.46 (9H,s), 1.65–2.00 (4H,m), 2.00–2.20 (1H,m), 3.37 (1H,m), 3.54 (1H,m), 3.87 (1H,m), 4.11 (2H,q,J=7.0Hz), 4.38 (1H,m)

5)

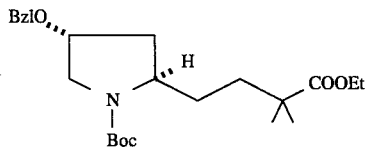

(2R,4R)-4-Benzyloxy-N-tert-butoxycarbonyl-2-(3 -ethoxycarbonyl-3-methylbutyl)pyrrolidine (870 mg, yield: 63%) was obtained from the above compound (1.09 g, 3.31 mmol) in the same manner as in REFERENCE EXAMPLE 21-2.

IR(KBr)cm$^{-1}$: 3430,2980,1730,1695,1475,1455,1395, 1365, 1250,1170,740,700 NMR(CDCl$_3$) δ: 1.16 (6H,s), 1.23 (3H,t,J=7.0Hz), 1.30–2.90 (5H,m), 1.46 (9H,s), 2.15 (1H, m), 3.34 (1H,m), 3.50–3.95 (2H,m), 4.00–4.20 (1H,m), 4.10 (2H,q,J=7.0Hz), 4.40–4.60 (2H,m), 7.25–7.45 (5H,m)

6)

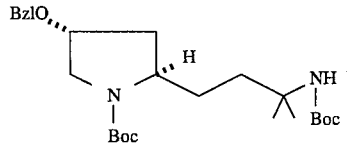

(2R,4R)-4-Benzyloxy-N-tert-butoxycarbonyl-2-(3 -tert-butoxycarbonylamino-3-methyl)butylpyrrolidine (730 mg, yield: 78%) was obtained from the above compound (850 mg, 2.03 mmol) in the same manner as in REFERENCE EXAMPLE 21-3.

IR(KBr)cm$^{-1}$: 3350,2970,1715,1695,1500,1455,1390, 1365, 1250,1170,1110,1070,740,700 NMR(CDCl$_3$) δ: 1.23 (3H,s), 1.25 (3H,s), 1.42 (9H,s), 1.46 (9H,s), 1.40–1.70 (3H,m), 1.70–1.95 (2H,m), 2.15 (1H,m), 3.35 (1H,m), 3.45–4.00 (2H,m), 4.07 (1H,m), 4.38 (1H,br s), 4.40–4.60 (2H,m), 7.25–7.45 (5H,m)

7)

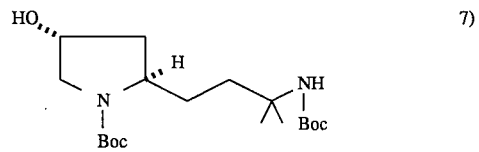

(2R,4R)-N-tert-Butoxycarbonyl-2-(3-tert-butoxycarbonylamino- 3-methyl)butyl-4-hydroxypyrrolidine (210 mg, yield: 37%) was obtained from the above compound (700 mg, 1.51 mmol) in the same manner as in REFERENCE EXAMPLE 21-4. The starting material was recovered (270 mg, 39%).

IR(KBr)cm$^{-1}$: 3450,3350,2970,1695,1680,1500,1455, 1400,1365,1250,1170,1070,920,875,775,735 NMR(CDCl$_3$) δ: 1.24 (3H,s), 1.25 (3H,s), 1.42 (9H,s), 1.47 (9H,s), 1.50–1.70 (2H,m), 1.70–2.00 (4H,m), 2.05 (1H,m), 3.38 (1H,m), 3.54 (1H,m), 3.91 (1H,m), 4.35–4.60 (2H,m)

8)

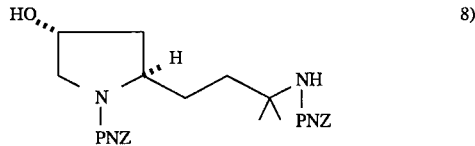

(2R,4R)-4-Hydroxy-2-[3-methyl-3 -(p-nitrobenzyloxycarbonylamino)butyl]-N-p-nitrobenzyloxycarbonylpyrrolidine (290 mg, yield: 73%) was obtained from the above compound (280 mg, 0.752 mmol) in the same manner as in REFERENCE EXAMPLE 21-5.

IR(KBr)cm$^{-1}$: 3420,2940,1700,1605,1520,1430,1405, 1345, 1260,1210,1105,850,735 NMR(CDCl$_3$) δ: 1.29 (6H, s), 1.30–2.20 (7H,m), 3.45 (1H,m), 3.66 (1H,m), 4.01 (1H, m), 4.40 (1H,m), 4.66 & 4.85 (total 1H,each br s), 5.00–5.40 (4H,m), 7.50 (4H,d,J=9.0Hz), 8.20 (4H,d,J=9.0Hz)

9)

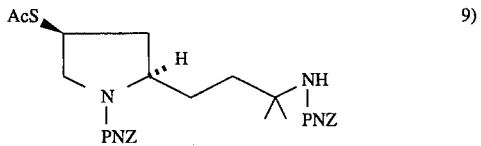

The title compound (240 mg, yield: 80%) was obtained from the above compound (270 mg, 0.509 mmol) in the same manner as in REFERENCE EXAMPLE 21-6.

IR(KBr)cm$^{-1}$: 3350,2970,1700,1605,1520,1400,1345, 1260, 1210,1105,850,735 NMR(CDCl$_3$) δ: 1.29 (6H,s), 1.30–2.30 (5H,m), 2.32 (3H,s), 2.49 (1H,m), 3.16 (1H,m), 3.84 (2H,m), 4.11 (1H,m), 4.66 & 4.79 (total 1H,each br s), 5.05–5.35 (4H,m), 7.51 (4H,d,J=9.0Hz), 8.21 (4H,d,J= 9.0Hz)

REFERENCE EXAMPLE 24

(2S,4S)-4-Acetylthio-2-[3-hydroxy-1-(p-nitrobenzyloxycarbonylaminomethyl)propyl]-N-p-nitrobenzyloxycarbonylpyrrolidine Diastereomer B

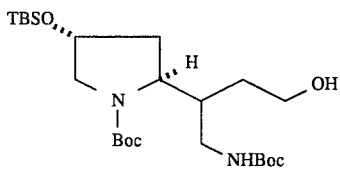 1)

(2S,4R)-N-tert-Butoxycarbonyl-2-[(1 -N-tert-butoxycarbonylaminomethyl-3-hydroxy)propyl]-4 -tert-butyldimethylsiloxypyrrolidine diastereomer B (14.05 g, yield: 60%) was obtained from (2S,4R)-N-tert-butoxycarbonyl- 2-(N-tert-butoxycarbonyl-2-pyrrolidon-4 -yl)-4-tert-butyldimethylsiloxypyrrolidine diastereomer B (23.22 g, 47.9 mmol) in the same manner as in REFERENCE EXAMPLE 20-1.

IR(KBr)cm$^{-1}$: 3400,2930,2850,1690,1510,1390,1360, 1250, 1170,1100,1060,1000,920,830,770 NMR(CDCl$_3$) δ: 0.06 (6H,s), 0.88 (9H,s), 1.55 (18H,s), 1.75 (2H,s), 1.97 (1H,m), 2.15 (2H,m), 2.96 (1H,m), 3.16 (1H,dd,J=3.7, 13.6Hz), 3.40–3.80 (4H,m), 3.95 (1H,m), 4.30 (1H,m), 5.80 (1H,br s)

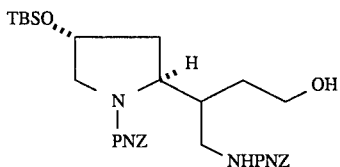 2)

To a solution of the above compound (1.95 g, 4 mmol) in methylene chloride (8.0 ml) was dropwise added trifluoroacetic acid (40 ml) under a nitrogen atmosphere under cooling with ice. The mixture was stirred at the same temperature for 1 h. This reaction solution was dropwise added at the same temperature to a mixture of dioxane (52 ml) and 1N aqueous sodium hydroxide. To this solution was added 4,6-dimethyl-2-(p-nitrobenzyloxycarbonylthio)pyrimidine (2.55 g, 8 mmol), and the reaction solution was stirred at room temperature for 1 h while maintaining the pH at a level of from 8 to 9 with 1N aqueous sodium hydroxide. The reaction solution was extracted with methylene chloride (50 ml). The organic layer was washed successively with 10% aqueous citric acid, saturated aqueous sodium hydrogen carbonate and saturated aqueous sodium chloride, and dried over anhydrous sodium sulfate. The solvent was removed in vacuo, and the residue was subjected to silica gel column chromatography (3% methanol-chloroform) to give (2S,4R)-4-tert-butyldimethylsiloxy-2-[3-hydroxy-1 -(p-nitrobenzyloxycarbonylaminomethyl)propyl]-N-p-nitrobenzyloxycarbonylpyrrolidine diastereomer B (1.56 g, yield: 60%).

IR(KBr)cm$^{-1}$: 3400,2930,2860,1700,1610,1525,1405, 1350, 1250,1165,1110,1010,840,775 NMR(CDCl$_3$) δ: 0.06 (6H,s), 0.88 (6H,s), 1.82 (3H,m), 2.04 (2H,m), 3.02 (1H,m), 3.21 (1H,m), 3.67 (4H,m), 4.01 (1H,m), 4.35 (1H,m), 5.20 (4H,s), 6.32 & 6.59 (total 1H,each br s), 7.51 (4H,m), 8.22 (4H,d,J=8.2Hz)

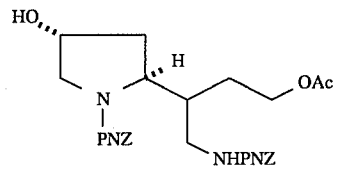 3)

To a solution of the above compound (1.56 g, 2.41 mmol) in pyridine (15 ml) was dropwise added acetic anhydride (3 ml), and the mixture was stirred at room temperature for 2 h. The reaction solution was poured into ice water and extracted with ethyl acetate (100 ml). The organic layer was washed successively with dilute hydrochloric acid, water and saturated aqueous sodium chloride, and dried over anhydrous sodium sulfate. The solvent was removed in vacuo to obtain an oily residue (1.64 g).

To a solution of this oily residue in tetrahydrofuran (15 ml) was added 1N tetrabutylammonium fluoride in tetrahydrofuran (2.5 ml, 2.5 mmol) under cooling with ice. The mixture was stirred at room temperature for 30 minutes. The reaction solution was concentrated in vacuo, and the residue was extracted with ethyl acetate (50 ml). The organic layer was washed successively with water and saturated aqueous sodium chloride, and dried over anhydrous sodium sulfate. The solvent was removed in vacuo, and the residue was subjected to silica gel column chromatography (methanol-chloroform) to give (2S,4R)-2-[3-acetoxy-1 -(p-nitrobenzyloxycarbonylaminomethyl)propyl]-4-hydroxy-N-p-nitrobenzyloxycarbonylpyrrolidine diastereomer B (1.26 g, yield: 92%).

IR(KBr)cm$^{-1}$: 3420,2940,1720,1610,1520,1405,1350, 1250, 1165,1110,1035,860,775,740 NMR(CDCl$_3$) δ: 1.85 (3H,m), 2.03 (3H,s), 2.07 (1H,m), 3.05 (1H,m), 3.34 (3H, m), 3.72 (1H,m), 4.12 (3H,m), 4.39 (1H,m), 5.18 (4H,m), 5.98 & 6.21 (total 1H, each br s), 7.51 (4H,d,J=8.3Hz), 8.21 (4H,d,J=8.7Hz)

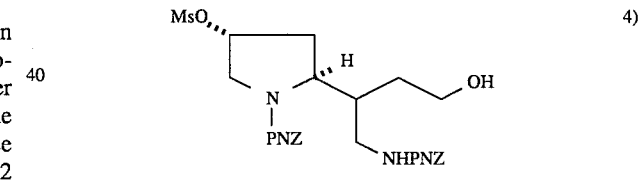 4)

Crude mesyl product was obtained from the above compound (1.26 g, 2.19 mmol) in the same manner as REFERENCE EXAMPLE 1-5.

This crude mesyl product was dissolved using methanol (15 ml) and tetrahydrofuran (5 ml). To this solution was added sodium methoxide (58 mg, 0.5 mmol). The mixture was stirred under a nitrogen atmosphere at room temperature for 2 h. To the reaction solution was added 1N aqueous hydrochloric acid (0.5 ml). The solvent was removed in vacuo. The residue was extracted with ethyl acetate (100 ml), and the organic layer was washed successively with water and saturated aqueous sodium chloride, and dried over anhydrous sodium sulfate. Then, the solvent was removed in vacuo. The residue was subjected to silica gel column chromatography (heptane-ethyl acetate) to give (2S,4R)-2-[3-hydroxy-1 -(p-nitrobenzyloxycarbonylaminomethyl)propyl]-4 -methanesulfonyloxy-N-p-nitrobenzyloxycarbonylpyrrolidine diastereomer B (692 mg, yield: 55%).

IR(KBr)cm$^{-1}$: 3400,2940,1700,1610,1520,1400,1350, 1250, 1170,1110,1050,1010,960,900,840,740,525 NMR(CDCl$_3$) δ: 2.02 (2H,m), 2.44 (2H,m), 3.01 (3H,s), 3.06 (1H,m), 3.40–3.90 (5H,m), 4.10–4.30 (3H,m), 5.20

(4H,m),6.14 (1H,br s), 7.51 (4H,m), 8.20 (2H,d,J=8.6Hz), 8.22 (2H,d,J=8.6Hz)

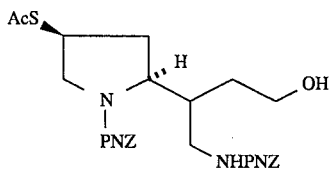

5)

The title compound (374 mg, yield: 56%) was obtained from the above compound (692 mg, 1.13 mmol) in the same manner as in REFERENCE EXAMPLE 1-6.

IR(KBr)cm$^{-1}$: 3400,2920,1690,1600,1520,1400,1340,1250, 1105,850,735, 625 NMR(CDCl$_3$) δ: 1.61 (2H,m), 2.03 (1H,m), 2.34 (3H,s), 2.52 (1H,m), 3.03 (2H,m), 3.61 (1H,m), 3.80 (3H,m), 4.00 (1H,m), 4.31 (1H,m), 5.19 (2H,s), 5.24 (2H,s), 7.52 (4H,d, J=8.2Hz), 8.23 (4H,m)

REFERENCE EXAMPLE 25

(2S,4S)-4-Acetylthio-2-[3-hydroxy-1-(2-p-nitrobenzyloxycarbonylaminoethyl)propyl]-N-p-nitrobenzyloxycarbonylpyrrolidine Diastereomer A and Diastereomer B

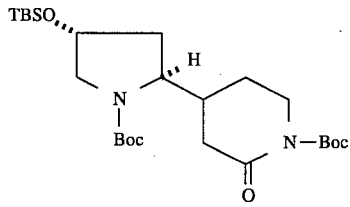

1)

To a solution of (2S,4R)-N-tert-butoxycarbonyl-4 -tert-butyldimethylsiloxy-2-(2-piperidon-4-yl)pyrrolidine (7.96 g, 20 mmol) in methylene chloride (120 ml) were added di-tert-butyl dicarbonate (6.55 g, 30 mmol) and 4 -dimethylaminopyridine (1.22 g, 10 mmol), and the mixture was stirred overnight at room temperature. Then, 4 -dimethylaminopyridine (1.22 g, 10 mmol) and di-tert-butyl dicarbonate (6.55 g, 30 mmol) were additionally added and further stirred overnight. The reaction solution was washed successively with 10% aqueous citric acid, water and saturated aqueous sodium chloride, and dried over anhydrous sodium sulfate. The solvent was removed in vacuo. The residue thereby obtained was subjected to silica gel column chromatography (hexane-ethyl acetate) to give (2S,4R)-N-tert-butoxycarbonyl-2-(N-tert-butoxycarbonyl- 2-piperidon-4-yl)-4-tert-butyldimethylsiloxypyrrolidine (10.0 g, yield: quantitative).

IR(KBr)cm$^{-1}$: 3400,2930,2850,1770,1710,1690,1470, 1390, 1365,1290,1250,1160,1110,1070,1010,935,905, 835, 775 NMR(CDCl$_3$) δ: 0.08 (6H,s), 0.87 (9H,s), 1.48 (9H,s), 1.50 (2H,m), 1.52 (9H,s), 1.73 (1H,m), 1.88 (2H,m), 2.19 (1H,m), 2.52 (1H,m), 3.20 (1H,m), 3.46 (2H,m), 3.86 (2H, m), 4.31 (1H,m)

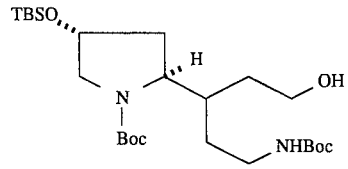

2)

(2S,4R)-N-tert-Butoxycarbonyl-2-[1-(2 -tert-butoxycarbonylamino)ethyl-3-hydroxypropyl]-4-tert-butyldimethylsiloxypyrrolidine diastereomer A (2.97 g, yield: 29%) and diastereomer B (2.70 g, yield: 27%) were obtained from the above compound (10.0 g, 20 mmol) in the same manner as in REFERENCE EXAMPLE 20-1.

DIASTEREOMER A: IR(KBr)cm$^{-1}$: 3350,2930,2855,1695,1680,1515,1400,1365, 1250,1165,1115,1070,935,910,835,775 NMR(CDCl$_3$) δ: 0.06 (6H,s), 0.87 (9H,s), 1.20–1.90 (6H,m), 1.46 (18H,s), 2.28 (1H,m), 3.17 (3H,m), 3.51 (1H,m), 3.37 (2H,m), 4.10 (1H,m), 4.29 (1H,m), 4.60 & 4.75 (total 1H, each br s)

DIASTEREOMER B: IR(KBr)cm$^{-1}$: 3370,2930,2855,1695,1515,1390,1365,1250, 1165,1115,1065,1005,935,910,840,775 NMR(CDCl$_3$) δ: 0.06 (6H,s), 0.86 (9H,s), 1.20–1.80 (5H,m), 1.86 (1H,m), 2.29 (1H,m), 3.20 (3H,m), 3.66 (3H,m), 4.04 (1H,m), 4.29 (1H,m), 4.81 (1H,br s)

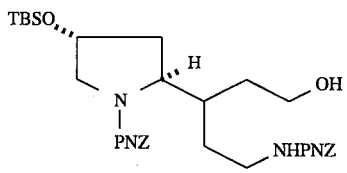

3)

(2S,4R)-4-tert-Butyldimethylsiloxy-2-[3-hydroxy-1-(2-p-nitrobenzyloxycarbonylaminoethyl)propyl]-N-p-nitrobenzyloxycarbonylpyrrolidine diastereomer A (2.08 g, yield: 64%) was obtained from the above diastereomer A (2.47 g, 4.9 mmol) in the same manner as in REFERENCE EXAMPLE 12-2.

Likewise, (2S,4R)-4-tert-butyldimethylsiloxy-2-[3 -hydroxy-1-(2-p-nitrobenzyloxycarbonylaminoethyl)propyl]-N-p-nitrobenzyloxycarbonylpyrrolidine diastereomer B (1.14 g, yield: 51%) was obtained from the above diastereomer B (1.70 g, 3.38 mmol).

DIASTEREOMER A: IR(KBr)cm$^{-1}$: 3420,2930,2850,1700,1605,1520,1400,1340, 1250,1105,1010,925,835,775,735 NMR(CDCl$_3$) δ: 0.03 (3H,s), 0.06 (3H,s), 0.84 (9H,s), 1.20–1.90 (5H,m), 2.16 (1H,m), 2.42 (1H,m), 3.10–3.40 (3H,m), 3.60–3.80 (3H,m), 4.17 (1H,m), 4.33 (1H,m), 5.15 (5H,m), 7.47 (4H,m), 8.19 (4H,m)

DIASTEREOMER B: IR(KBr)cm$^{-1}$: 3430,2940,2850,1700,1605,1520,1400,1345, 1250,1110,1010,840,775,735 NMR(CDCl$_3$) δ: 0.04 (3H,s), 0.06 (3H,s), 0.84 (9H,s), 1.30–1.80 (5H,m), 1.88 (1H,m), 3.20–3.40 (3H,m), 3.64 (3H,m), 4.14 (1H,m), 4.34 (1H,m), 5.10–5.30 (5H,m), 7.50 (4H,d,J=7.6Hz), 8.21 (4H,d,J= 8.6Hz)

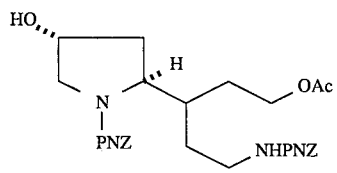

4)

(2S,4R)-2-[3-Acetoxy-1-(2-p-nitrobenzyloxycarbonylaminoethyl)propyl]-4-hydroxy-N-p-nitrobenzyloxycarbonylpyrrolidine diastereomer A (1.37 g, yield: 74%) was obtained from the above diastereomer A (2.08 g, 3.14 mmol) in the same manner as in REFERENCE EXAMPLE 24-3.

Likewise, (2S,4R)-2-[3-acetoxy-1-(2 -p-nitrobenzyloxycarbonylaminoethyl)propyl]-4-hydroxy-N-p-nitrobenzyloxycarbonylpyrrolidine diastereomer B (0.68 g, yield:

67%) was obtained from the above diastereomer B (1.14 g, 1.73 mmol).

DIASTEREOMER A: IR(KBr)cm⁻¹: 3410,2950,1730,1710,1690,1605,1520,1435, 1400,1340,1240,1105,1030,850,735 NMR(CDCl₃) δ: 1.20–1.90 (5H,m), 2.02 (1H,m), 2.04 (3H,s), 2.44 (1H,m), 3.10–3.30 (2H,m), 3.43 (1H,m), 3.77 (1H,m), 4.10–4.30 (3H,m), 4.43 (1H,m), 4.81 & 5.07 (total 1H, each br s), 5.16 (2H,s), 5.26 (2H,s), 7.48 (4H,d,J=8.6Hz), 8.19 (4H,d,J=8.6Hz)

DIASTEREOMER B: IR(KBr)cm⁻¹: 3410,2950,1730,1700,1605,1520,1430,1400, 1345,1240,1105,1030,850,740 NMR(CDCl₃) δ: 1.30–1.90 (5H,m), 1.99 (3H,s), 2.03 (1H,m), 2.41 (1H,m), 3.20–3.50 (3H,m), 3.80 (1H,m), 4.03 (2H,m), 4.20 (1H,m), 4.45 (1H, m), 5.23 (5H,m), 7.51 (4H,d,J=8.9Hz), 8.21 (2H,d,J=8.9Hz), 8.22 (2H,d,J=8.9Hz)

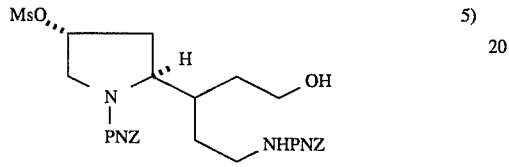
5)

(2S,4R)-2-[3-Hydroxy-1-(2 -p-nitrobenzyloxycarbonylaminoethyl)propyl]-4-methanesulfonyloxy-N-p-nitrobenzyloxycarbonylpyrrolidine diastereomer A (1.33 g, yield: 91%) was obtained from the above diastereomer A (1.37 g, 2.33 mmol) in the same manner as in REFERENCE EXAMPLE 24-4.

Likewise, (2S,4R)-2-[3-hydroxy-1-(2 -p-nitrobenzyloxycarbonylaminoethyl)propyl]-4 -methanesulfonyloxy-N-p-nitrobenzyloxycarbonylpyrrolidine diastereomer B (0.50 g, yield: 69%) was obtained from the above diastereomer B (0.68 g, 1.16 mmol).

DIASTEREOMER A: IR(KBr)cm⁻¹: 3400,2940,1700,1605,1520,1430,1405,1350, 1250,1170,1110,1050,1010,955,900,850,740,530 NMR(CDCl₃) δ: 1.10–1.70 (4H,m), 2.04 (1H,m), 2.30–2.50 (2H,m), 3.03 (3H,s), 3.20 (2H,m), 3.55 (1H,m), 3.73 (2H, m), 4.14 (1H,m), 4.24 (1H,m), 5.16 (6H,s), 7.48 (4H,d,J=8.3Hz), 8.20 (4H,d,J=8.6Hz)

DIASTEREOMER B: IR(KBr)cm⁻¹: 3400,2950,1700,1605,1520,1430,1405,1350, 1250,1170,1050,1015,1010,960,900,850,740,525 NMR(CDCl₃) δ: 1.30–1.90 (4H,m), 2.01 (1H,m), 2.30–2.50 (2H,m), 3.04 (3H,s), 3.34 (2H,m), 3.50–3.70 (3H,m), 4.10–4.30 (2H,m), 5.10–5.40 (6H,m), 7.51 (4H,d,J=7.9Hz), 8.19 (2H,d,J=8.9Hz), 8.22 (2H,d,J=8.9Hz)

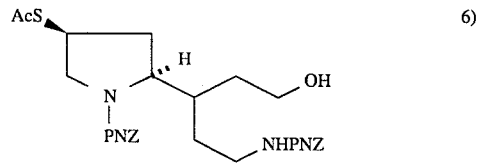
6)

The title compound diastereomer A (1.13 g, yield: 88 %) was obtained from the above diastereomer A (1.33 g, 2.13 mmol) in the same manner as in REFERENCE EXAMPLE 24 -5.

Likewise, the title compound diastereomer B (423 mg, yield: 87%) was obtained from the above diastereomer B (0.50 g, 0.80 mmol).

DIASTEREOMER A: IR(KBr)cm⁻¹: 3400,2840,1700,1605,1520,1400,1345,1250, 1110,850,735, 625 NMR(CDCl₃) δ: 1.30–1.70 (5H,m), 2.34 (3H,s), 2.40 (2H,m), 3.06 (1H,m), 3.22 (2H,m), 3.71 (3H,m), 4.11 (1H, m), 4.23 (1H,m), 5.10 (1H,br s), 5.18 (4H,s), 7.48 (4H,d,J=8.3Hz), 8.20 (2H,d,J=8.6Hz), 8.21 (2H,d,J=8.9Hz)

DIASTEREOMER B: IR(KBr)cm⁻¹: 3400,2940,1700,1605,1520,1430,1400,1345, 1250,1110,850,740,630 NMR(CDCl₃) δ: 1.30–1.80 (5H,m), 2.34 (3H,s), 2.37 (2H,m), 3.05 (1H,m), 3.28 (2H,m), 3.62 (2H,m), 3.72 (1H,m), 4.04 (1H,m), 4.23 (1H,m), 5.18 (3H, s), 5.20 (2H,s), 7.52 (4H,d,J=8.6Hz), 8.21 (2H,d,J=8.6Hz), 8.22 (2H,d,J=8.6Hz)

REFERENCE EXAMPLE 26

(2S,4S)-4-Acetylthio-2-[3-hydroxy-1-(N-methyl-N-p-nitrobenzyloxycarbonylaminomethyl) propyl]-N-p-nitrobenzyloxycarbonylpyrrolidine Diastereomer B

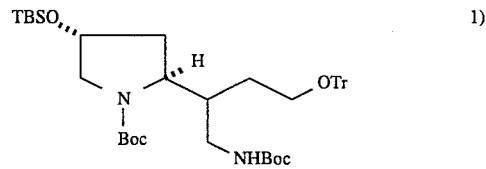
1)

To a solution of (2S,4R)-N-tert-butoxycarbonyl-2-(1 -tert-butoxycarbonylaminomethyl-3-hydroxypropyl)-4-tert-butyldimethylsiloxypyrrolidine diastereomer B prepared in REFERENCE EXAMPLE 24-1 (1.01 g, 2 mmol) in methylene chloride (20 ml) were added triethylamine (0.307 ml, 2.2 mmol) and triphenylmethyl chloride (584 mg, 2.1 mmol). The mixture was stirred for 3 h at room temperature under a nitrogen atmosphere. The reaction solution was washed successively with water and saturated aqueous sodium chloride, and dried over anhydrous sodium sulfate. The solvent was removed in vacuo. The residue was subjected to silica gel column chromatography (hexane-ethyl acetate) to give (2S,4S)-N-tert-butoxycarbonyl-2-(1 -tert-butoxycarbonylaminomethyl- 3-triphenylmethoxypropyl)-4-tert-butyldimethylsiloxypyrrolidine diastereomer B (1.48 g, yield: quantitative).

IR(KBr)cm⁻¹: 3400,2930,1710,1695,1445,1390,1365, 1250, 1160,1065,830,770,760,700,630 NMR(CDCl₃) δ: 0.06 (6H,s), 0.86 (9H,s), 1.39 (18H,s), 1.20–1.50 (2H,m), 1.72 (1H,m), 1.89 (1H,m), 2.09 (1H,m), 2.85 (1H,m), 3.15 (4H,m), 3.50 (1H,m), 3.99 (1H,m), 4.22 (1H,m), 4.86 & 5.33 (total 1H, each br s), 7.2–7.5 (15H,m)

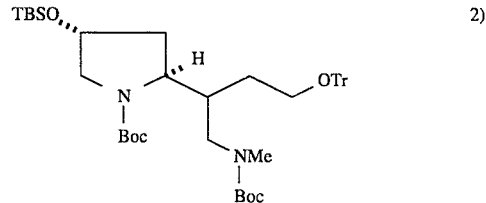
2)

To a solution of the above compound (731 mg, 1.0 mmol) in N,N-dimethylformamide (7 ml) were added 60% sodium hydride (80 mg, 2 mmol) in oil and methyl iodide (0.06 ml, 10 mmol). The mixture was stirred at 40° C. for 2 days. The reaction solution was extracted with ethyl acetate (50 ml) and washed successively with water and saturated aqueous sodium chloride, and dried over anhydrous sodium sulfate. The solvent was removed in vacuo. The residue was subjected to silica gel column chromatography (hexane-ethyl acetate) to give (2S,4R)-N-tert-butoxycarbonyl- 2-[1-(N-tert-butoxycarbonyl-N-methylaminomethyl)- 3-triphenylmethoxypropyl]-4-tert-butyldimethylsiloxypyrrolidine diastereomer B (743 mg, yield: quantitative).

IR(KBr)cm⁻¹: 2930,1690,1450,1400,1365,1250,1160, 1120, 1070,1025,835,775,705,635 NMR(CDCl₃) δ: 0.05 (6H,s), 0.85 (9H,s), 1.20–1.60 (3H,m), 1.41 (9H,s), 1.46 (9H,s), 1.72 (1H,m), 1.97 (1H,m), 2.52 (1H,m), 2.77 (3H,s), 3.11 (3H,m), 3.42 (1H,m), 3.62 (1H,m), 3.96 (1H,m), 4.22 (1H,m), 7.2–7.5 (15H,m)

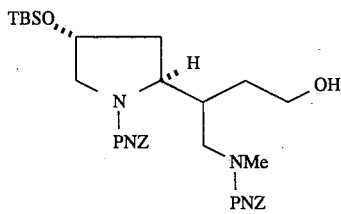
3)

To a solution of the above compound (743 mg, 1 mmol) in methylene chloride (1.5 ml) were added trifluoroacetic acid (1.5 ml, 10 mmol) and triethylsilane (0.16 ml, 1.2 mmol). The mixture was stirred for 2 h at room temperature under a nitrogen atmosphere. This reaction solution was dropwise added to a mixture of dioxane (10 ml) and 1N aqueous sodium hydroxide to be neutralized. To this solution was added 4,6-dimethyl-2-(p-nitrobenzyloxycarbonylthio)pyrimidine (0.67 g, 2.1 mmol). The mixture was stirred for 1 h at room temperature while maintaining the pH at a level of from 9 to 10 with 1N aqueous sodium hydroxide. The reaction solution was extracted with methylene chloride (70 ml). The organic layer was washed successively with 10% aqueous citric acid, water and saturated aqueous sodium chloride, and dried over anhydrous sodium sulfate. The solvent was removed in vacuo, and the residue was subjected to silica gel column chromatography (chloroform-methanol) to give (2S,4R)-4-tert-butyldimethylsiloxy-2-[3-hydroxy-1 -(N-methyl-N-p-nitrobenzyloxycarbonylaminomethyl)propyl]-N-p-nitrobenzyloxycarbonylpyrrolidine diastereomer B (332 mg, yield: 51%).

IR(KBr)cm⁻¹: 3460,2930,1700,1605,1520,1400,1345, 1150, 1110,840,775 NMR(CDCl₃) δ: 0.06 (6H,s), 0.83 (9H, s), 1.33 (1H,m), 1.53 (1H,m), 1.81 (2H,m), 2.07 (1H,m), 2.84 (1H,m), 3.05 (3H,s), 3.26 (1H,m), 3.36 (1H,m), 3.65 (3H,m), 4.10 (1H,m), 4.34 (1H,m), 5.20 (4H,s), 7.56 (4H, d,J=8.1Hz), 8.22 (4H,d,J=8.2Hz)

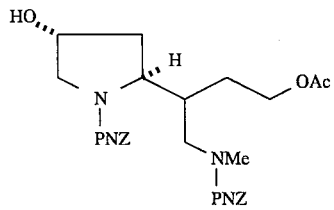
4)

(2S,4R)-2-[3-Acetoxy-1-(N-methyl-N-p-nitrobenzyloxycarbonylaminomethyl)propyl]-4-hydroxy-N-p-nitrobenzyloxycarbonylpyrrolidine diastereomer B (266 mg, yield: 90%) was obtained from the above compound (332 mg, 0.5 mmol) in the same manner as in REFERENCE EXAMPLE 24-3.

IR(KBr)cm⁻¹: 3450,2940,1730,1700,1605,1520,1400, 1340, 1240,1150,1110,1050,855,760,735 NMR(CDCl₃) δ: 1.37 (1H,m), 1.56 (1H,m), 1.85 (1H,m), 2.00 (3H,s), 2.10 (1H,m), 2.85 (2H,m), 3.04 (3H,s), 3.44 (2H,m), 3.74 (1H, m), 4.16 (3H,m), 4.41 (1H,m), 5.21 (4H,s), 7.54 (4H,d,J= 8.1Hz), 8.23 (2H,d,J=8.1Hz), 8.24 (2H,d,J=8.1Hz)

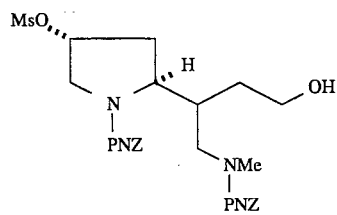
5)

(2S,4R)-2-[3-Hydroxy-1-(N-methyl-N-p-nitrobenzyloxycarbonylaminomethyl)propyl]-4-methanesulfonyloxy-N-p-nitrobenzyloxycarbonylpyrrolidine diastereomer B (200 mg, yield: 64%) was obtained from the above compound (266 mg, 0.45 mmol) in the same manner as in REFERENCE EXAMPLE 24-4.

IR(KBr)cm⁻¹: 3450,2930,1700,1610,1520,1400,1350, 1170, 1110,1050,960,900,850,765,735,525 NMR(CDCl₃) δ: 1.31 (2H,m), 1.50 (1H,m), 2.03 (1H,m), 2.51 (1H,m), 2.82 (3H,br s), 3.01 (1H,m), 3.02 (3H,s), 3.17 (1H,m), 3.3–3.7 (4H,m), 4.18 (2H,m), 5.22 (4H,s), 7.52 (4H,d,J=8.3Hz), 8.21 (4H,d,J=8.5Hz)

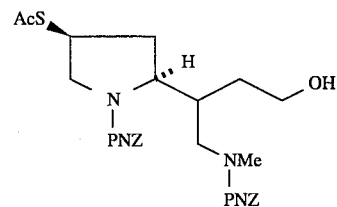
6)

The title compound (172 mg, yield: 89%) was obtained from the above compound (200 mg, 0.32 mmol) in the same manner as in REFERENCE EXAMPLE 1-6.

IR(KBr)cm⁻¹: 3450,2940,1700,1610,1520,1400,1345, 1200, 1110,855,765,735,630 NMR(CDCl₃) δ: 1.33 (1H,m), 1.56 (2H,m), 2.34 (3H,s), 2.52 (1H,m), 2.83 (2H,m), 3.01 (3H,s), 3.05 (1H,m), 3.16 (1H,m), 3.40 (1H,m), 3.65 (2H, m), 3.96 (2H,m), 4.23 (2H,m), 5.19 (2H,s), 5.20 (2H,s), 7.51 (4H,d,J=8.6Hz), 8.22 (4H,d,J=8.6Hz)

REFERENCE EXAMPLE 27

(2S,4S)-4-Mercapto-2-[(1R)-1-hydroxy-3-N-methylaminopropyl]pyrrolidine Dihydrochloride

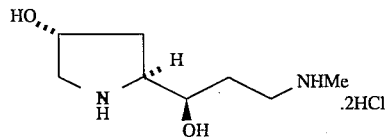
1)

To a solution of (2S,4R)-N-tert-butoxycarbonyl-4 -tert-butyldimethylsiloxy-2-[(1R)-1,3 -dihydroxypropyl]pyrrolidine diastereomer prepared in REFERENCE EXAMPLE 7-2 (76.1 g, 203 mmol) in methylene chloride (860 ml) were added triethylamine (112.3 ml, 809 mmol), dimethylaminopyridine (2.19 g, 18.0 mmol) and p-toluenesulfonyl chloride (61.2 g, 321 mmol) under cooling with ice under a nitrogen atmosphere. The mixture was stirred overnight at room temperature. The reaction mixture was washed sequentially with saturated aqueous sodium hydrogencarbonate, water, 10% aqueous citric acid, water and saturated aqueous sodium chloride, and dried over anhydrous magnesium sulfate. The solvent was removed in vacuo. The residue was dissolved in methanol (400 ml), and a solution of 40% methylamine in methanol (1 l) was added thereto. The mixture was stirred overnight at room temperature. The reaction solution was concentrated in vacuo. To the residue was added to methanol solution of 3.3N hydrochloric acid. The mixture was stirred overnight at room temperature. The reaction solution was concentrated in vacuo, and the obtained crystals were washed with ethanol and acetone to obtain (2S,4R)-4-hydroxy-2-[(1R)-1-hydroxy-3 -N-methylaminopropyl]pyrrolidine dihydrochloride (35.8 g, yield: 71%).

IR(KBr)cm$^{-1}$: 3410,2980,2800,1580,1420,1060,1010 NMR(D$_2$O) δ: 1.65–2.00 (2H,m), 2.07 (2H,dd,J=3.10Hz), 2.70 (3H,s), 3.10–3.50 (4H,m), 3.90–4.05 (1H,m), 4.10–4.20 (1H,m), 4.65 (1H,m)

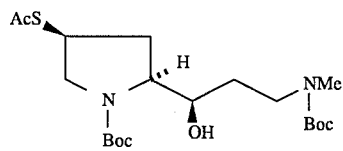
2)

The above compound (35.6 g, 144 mmol) was dissolved in water (150 ml) and dioxane (400 ml), and 5N aqueous sodium hydroxide was added to adjust the pH to 7. Then, di-tert-butyl-dicarbonate (63.0 g, 289 mmol) was added thereto, and the mixture was stirred at room temperature for 1 h. The reaction solution was adjusted to pH 10 with 5N aqueous sodium hydroxide, and di-tert-butyldicarbonate (12.6 g, 57.8 mmol) was added thereto. The mixture was stirred at room temperature for 30 minutes. To this reaction solution were added water and ethyl acetate. The organic layer was separated, washed with saturated aqueous sodium chloride and dried over anhydrous magnesium sulfate. The solvent was removed in vacuo, and the residue was dissolved in tetrahydrofuran (800 ml), and triethylamine (24 ml, 170 mmol) and methane-sulfonyl chloride (11.1 ml, 144 mmol) were added under cooling with ice. The mixture was stirred for 30 minutes, and ethyl acetate was added thereto. The mixture was washed successively with 10% aqueous citric acid, water and saturated aqueous sodium chloride, and dried over anhydrous magnesium sulfate. The solvent was removed in vacuo.

The residue thereby obtained was dissolved in N,N-dimethylformamide, and potassium thioacetate (24.7 g, 216 mmol) was added thereto. The mixture was stirred overnight at 70° C. To the reaction solution, ethyl acetate was added, and the mixture was washed successively with water and saturated aqueous sodium chloride, and dried over anhydrous magnesium sulfate. The solvent was removed in vacuo, and the residue was subjected to silica gel column chromatography (heptane-ethyl acetate) to give (2S,4S)-4-acetylthio-2-[[(1R)-1 -hydroxy-3-N-tert-butoxycarbonyl-N-methylamino]propyl]-N-tert-butoxycarbonylpyrrolidine (37.3 g, yield: 60%).

IR(KBr)cm$^{-1}$: 3420,2975,1690,1400,1365,1160 NMR(CDCl$_3$) δ: 1.20–1.40 (2H,m), 1.45 (18H,s), 1.50–1.75 (4H,m), 2.33 (3H,s), 2.84 (3H,s), 3.03 (1H,m), 3.70–4.00 (4H,m)

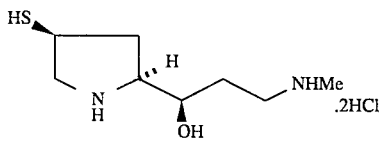
3)

To the above compound (34.5 g, 79.7 mmol), a methanol solution of 3.3N hydrochloric acid was added, and the mixture was stirred overnight at room temperature. The reaction solution was concentrated in vacuo, and after an addition of methanol, treated with active carbon. Then, the active carbon was filtered off, and the filtrate was concentrated to dryness. The residue was washed with a mixture of tetrahydrofuran and methanol to obtain (2S,4S)-4-mercapto-2-[(1R)-1-hydroxy-3 -N-methylaminopropyl]pyrrolidine dihydrochloride (17.0 g, yield: 81.1%).

IR(KBr)cm$^{-1}$: 3400,2950,1620,1580,1460,1400,1050 NMR(D$_2$O) δ: 1.60–2.00 (3H,m), 2.48–2.65 (1H,m), 2.70 (3H,s), 3.05–3.30 (3H,m), 3.45–3.85 (3H,m), 4.00–4.15 (1H,m)

REFERENCE EXAMPLE 28

(2R,4S)-4-Acetylthio-2-[(2 -p-nitrobenzyloxycarbonylamino)propyl]-N-(p-nitrobenzyloxycarbonyl)pyrrolidine Diastereomer A and Diastereomer B

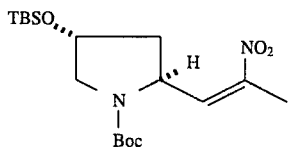
1)

To a solution of (2S,4R)-N-tert-butoxycarbonyl-4 -tert-butyldimethylsiloxy-2-formylpyrrolidine (16.5 g, 50 mmol) and nitroethane (14.2 ml, 200 mmol) in ethanol (20 ml) was added n-butylamine (0.5 ml, 5 mmol). This mixture was refluxed overnight under a nitrogen atmosphere, and the solvent was removed in vacuo. The residue thereby obtained was extracted with ethyl acetate (500 ml). This ethyl acetate solution was washed successively with dilute hydrochloric acid, saturated aqueous sodium hydrogencarbonate and saturated aqueous sodium chloride, and dried over anhydrous sodium sulfate. The solvent was removed in vacuo, and the residue was subjected to silica gel column chromatography (hexane-ethyl acetate) to give a lower polar isomer of (2S,4 R)-N-tert-butoxycarbonyl-4-tert-butyldimethylsiloxy-2-(2-nitropropylenyl)pyrrolidine (8.01 g, yield: 41%).

IR(KBr)cm$^{-1}$: 2950,1700,1520,1400,1250,1020,840,770 NMR(CDCl$_3$) δ: 0.08 (6H,s), 0.89 (9H,s), 1.40 (9H,s), 1.79 (1H,m), 2.10 (1H,m), 2.22 (3H,s), 3.49 (2H,m), 4.39 (1H, m), 4.55 (1H,m), 6.97 (1H,d,J=9.2Hz)

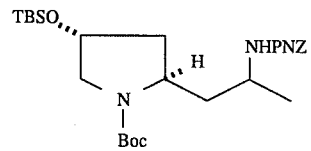
2)

A solution of the above compound (7.30 g, 18.9 mmol) in diethyl ether (25 ml) was dropwise added to a suspension of lithium aluminum hydride (2.15 g, 56.7 mmol) in diethyl ether (50 ml) under a nitrogen atmosphere under cooling with ice, and the mixture was stirred for 3 h at the same temperature. Water (5 ml) was dropwise added to the reaction solution to decompose an excess reagent, and then diethyl ether (200 ml) was added thereto. Insoluble material was filtered off. The insoluble material was further extracted with diethyl ether (200 ml). Diethyl ether extracts were put together and washed successively with water and saturated aqueous sodium chloride, and dried over anhydrous sodium sulfate. The solvent was removed in vacuo to obtain a crude amine. To a solution of this crude amine in dioxane (70 ml)

was added 4,6-dimethyl-2-(p-nitrobenzyloxycarbonylthio)pyrimidine (6.04 g, 18.9 mmol), and the mixture was stirred for 1 h at room temperature. The solvent was removed in vacuo, and the residue was extracted with ethyl acetate (300 ml). The extract was washed successively with 10% aqueous citric acid, saturated aqueous sodium hydrogencarbonate and saturated aqueous sodium chloride, and dried over anhydrous sodium sulfate. The solvent was removed in vacuo, and the residue was subjected to silica gel column chromatography (hexane-ethyl acetate) to give a mixture of isomers of (2R,4 R)-N-tert-butoxycarbonyl-4-tert-butyldimethylsiloxy-2-(2 -p-nitrobenzyloxycarbonylamino)propyl pyrrolidine (2.27 g, yield: 22%).

IR(KBr)cm$^{-1}$: 3320,2950,1700,1520,1400,1340,1250,1160, 840, 780 NMR(CDCl$_3$) δ: 0.05 (6H,s), 0.86 (9H,s), 1.24 (3H,d,J= 5.6Hz), 1.45 (9H,s), 1.66 (2H,m), 1.80–2.00 (2H,m), 3.20–3.30 (2H,m), 3.66 (1H,m), 4.01 (1H,br m), 4.31 (1H, m), 5.17 (2H,s), 5.51 (1H,br), 7.49 (2H,d,J=8.9Hz), 8.21 (2H,d,J=8.6Hz)

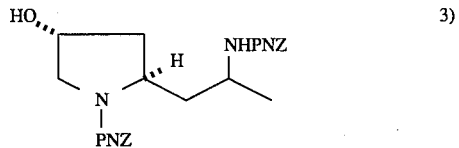

3)

To the above compound (2.27 g, 4.22 mmol) was added 2.7M hydrochloric acid-methanol (20 ml), and the mixture was stirred for 1.5 h at room temperature. The solvent was removed in vacuo to obtain a hydrochloride of crude amine. This crude amine was dissolved again in dioxane (50 ml) and water (50 ml), and 4,6-dimethyl-2 -(p-nitrobenzyloxycarbonylthio)pyrimidine (1.35 g, 4.22 mmol) was added thereto while maintaining the pH at 10 with 1N aqueous sodium hydroxide. The reaction solution was stirred for 1 h at room temperature and then concentrated in vacuo. The residue was extracted with ethyl acetate (100 ml). The organic layer was washed successively with 10% aqueous citric acid, water and saturated aqueous sodium chloride, and dried over anhydrous sodium sulfate. The solvent was removed in vacuo. The residue was subjected to silica gel column chromatography (chloroform-methanol) to give (2R,4R)-4-hydroxy-N-(p-nitrobenzyloxycarbonyl)- 2-[(2-p-nitrobenzyloxycarbonylamino)propyl]pyrrolidine diastereomer A (polar compound, 1.40 g, yield: 66%) and diastereomer B (less polar compound, 348 mg, yield: 16 %).

DIASTEREOMER A: IR(KBr)cm$^{-1}$: 3400,1700,1600,1520,1430,1400,1350,1240, 1110,850,740 NMR(CDCl$_3$) δ: 1.24 (3H,d,J=7.3Hz), 1.69 (1H,m), 1.70–2.10 (3H,m), 3.45 (1H,m), 3.70 (2H,m), 4.08 (1H,m), 4.45 (1H,s), 5.21 (5H,m), 7.48 (4H,d,J=8.6Hz), 8.18 (4H,d, J=8.6Hz)

DIASTEREOMER B: IR(KBr)cm$^{-1}$: 3400,1700,1600,1520,1350,850,740 NMR(CDCl$_3$) δ: 1.19 (3H,d,J=6.6Hz), 1.39 (1H,m), 1.80–2.30 (3H,m), 3.40–3.70 (3H,m), 4.04 (1H,m), 4.45 (1H,m), 5.21 (5H,m), 7.49 (4H, d,J=8.6Hz), 8.20 (4H,d,J=8.6Hz)

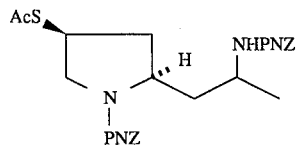

4)

A mesyl product was obtained from the above compound (diastereomer A, 1.51 g, 3.01 mmol) in the same manner as in REFERENCE EXAMPLE 1-5, and then the title compound (1.33 g, yield: 79%) was obtained in the same manner as in REFERENCE EXAMPLE 1-6.

IR(KBr)cm$^{-1}$: 3310,1700,1610,1523,1425,1350,1260, 1110,850, 740,626 NMR(CDCl$_3$) δ: 1.23 (3H,d,J=6.3Hz), 1.75 (2H,m), 2.15 (1H,m), 2.33 (3H,s), 2.55 (1H,m), 3.18 (1H,m), 3.71 (1H,m), 3.86 (1H,m), 3.94 (1H,m), 4.10 (1H, m), 5.16 (5H,m), 7.49 (4H,d,J=8.9Hz), 8.21 (4H,d,J=8.9Hz)

REFERENCE EXAMPLE 29

(2R,4S)-4-Acetylthio-N-(p-nitrobenzyloxycarbonyl)-2-[(2-p-nitrobenzyloxycarbonylamino)propyl]pyrrolidine Diastereomer B

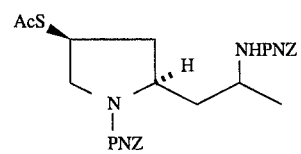

A mesyl product was obtained from (2R,4R)-4-hydroxy-N-(p-nitrobenzyloxycarbonyl)- 2-[(2-p-nitrobenzyloxycarbonylamino)propyl]pyrrolidine diastereomer B prepared in REFERENCE EXAMPLE 28-3 (378 mg, 0.75 mmol) in the same manner as in REFERENCE EXAMPLE 1-5, and then the title compound (250 mg, yield: 65%) was obtained in the same manner as in REFERENCE EXAMPLE 1-6.

IR(KBr) cm$^{-1}$: 3400,1700,1600,1520,1400,1350,1250, 1100, 850, 740,630 NMR(CDCl$_3$) δ: 1.19 (3H,d,J=6.3Hz), 1.64 (1H,m), 1.70–2.20 (2H,m), 2.34 (3H,s), 2.55 (1H,m), 3.23 (1H,m), 3.67 (1H,m), 3.92 (2H,m), 4.08 (1H,m), 5.16 (5H,m), 7.51 (4H,d,J=8.6Hz), 8.22 (4H,d,J=8.6Hz)

REFERENCE EXAMPLE 30

(2R,4S)-4-Acetylthio-2-[3-(N-methyl-N-p-nitrobenzyloxycarbonylamino)butyl]-N-p-nitrobenzyloxycarbonylpyrrolidine Diastereomer Mixture

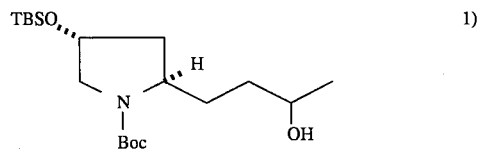

1)

A solution of methylene chloride (80 ml) and dimethyl sulfoxide (2.98 ml, 40 mmol) was cooled to −78° C., and oxalyl chloride (1.85 ml, 21.2 mmol) was dropwise added thereto. The mixture was stirred for 15 minutes at the same temperature, and then a solution of (2R,4R)-N-tert-butoxycarbonyl- 4-tert-butyldimethylsiloxy-2-(3 -hydroxypropyl)pyrrolidine (5 g, 13.9 mmol) in methylene chloride (70 ml) was dropwise added thereto over a period of 10 minutes. The mixture was stirred for 30 minutes, and then triethylamine (9.66 ml, 69.3 mmol) was added thereto. The mixture was heated to room temperature and stirred for 15 minutes. The reaction solution was concentrated in vacuo, and ethyl acetate (70 ml) was added thereto. The mixture was washed twice with 10% aqueous citric acid (30 ml) and further with saturated aqueous sodium chloride, and then dried over anhydrous magnesium sulfate. The solvent was removed in vacuo to obtain (2R,4R)-N-tert-butoxycarbonyl-4-tert-butyldimethylsiloxy- 2-(2-formylethyl)pyrrolidine (5.5 g, yield: 100%) as crude product. This compound was used for the subsequent reaction without purification.

The above compound was dissolved in tetrahydrofuran (70 ml), and the solution was cooled to −78° C. Then, a 1.6M methyl lithium-diethyl ether solution (15.7 ml, 25.1 mmol) was dropwise added thereto. The mixture was stirred for 1 h at the same temperature, and then ethyl acetate (70 ml) was added thereto. The mixture was washed with water, and the solvent was removed in vacuo. The residue was subjected to silica gel column chromatography (heptane-ethyl acetate) to give (2R,4 R)-N-tert-butoxycarbonyl-4-tert-butyldimethylsiloxy-2-(3 -hydroxybutyl)pyrrolidine (4.21 g, yield: 81.1%).

IR(KBr)cm$^{-1}$: 3450,2930,1695,1680 NMR(CDCl$_3$) δ: 0.05 (6H,s), 0.86 (9H,s), 1.18 (3H,d,J=6.0Hz), 1.40 (2H,m), 1.45 (9H,s), 1.70 (1H,m), 1.90 (2H,m), 3.37 (2H,m), 3.80–4.00 (2H,m), 4.85 (1H,m)

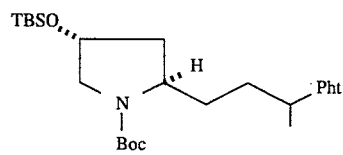
2)

The above compound (4.21 g, 11.27 mmol) was dissolved in tetrahydrofuran (70 ml) and cooled to 0° C. Then, triphenylphosphine (6.65 g, 25.4 mmol) and phthalimide (2.49 g, 16.9 mmol) were added thereto, and diethylazodicarboxylate (2.66 ml, 16.9 mmol) was further dropwise added thereto. The mixture was stirred for 17 h at room temperature. The reaction solution was concentrated, and the residue was subjected to silica gel column chromatography (ethyl acetate-heptane) to give (2R,4R)-N-tert-butoxycarbonyl-4-tert-butyldimethylsiloxy- 2-(3-phthalimido)butyl)pyrrolidine (4.73 g, yield: 83.3 %).

IR(KBr)cm$^{-1}$: 3400,2920,1720 NMR(CDCl$_3$) δ: 0.06 (6H,s), 0.86 (9H,s), 1.35 (3H,m), 1.45 (9H,s), 1.50 (2H,m), 1.60–2.15 (4H,m), 3.20–3.40 (2H,m), 3.80 (1H,m), 4.20–4.40 (2H,m), 7.68 (2H,m), 7.80 (2H,m)

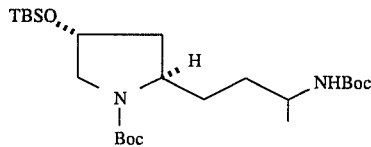
3)

The above compound (4.1 g, 8.16 mmol) was dissolved in a mixture of methylene chloride (40 ml) and methanol (4 ml), and hydrazine monohydrate (1.14 ml, 22.8 mmol) was dropwise added thereto under cooling with ice. The mixture was stirred for 1 h at the same temperature. The reaction solution was washed successively with 8% aqueous ammonia and water. The solvent was removed in vacuo, and the residue was dissolved in dioxane (40 ml). Then, 4,6-dimethyl-2-(tert-butoxycarbonylthio)pyrimidine (1.96 g, 8.16 mmol) was added thereto, and the mixture was stirred for 17 h at room temperature. To the reaction solution was added ethyl acetate (40 ml), and the mixture was washed successively with saturated aqueous sodium hydrogencarbonate, water and saturated aqueous sodium chloride, and dried over anhydrous magnesium sulfate. The solvent was removed in vacuo, and the residue was subjected to silica gel column chromatography (ethyl acetate-heptane) to give (2R,4R)-N-tert-butoxycarbonyl- 4-tert-butyldimethylsiloxy-2-[3 -(tert-butoxycarbonylamino)butyl]pyrrolidine (2.28 g, yield: 59.2%).

IR(KBr)cm$^{-1}$: 2920,1695,1470 NMR(CDCl$_3$) δ: 0.06 (6H,s), 1.10 (3H,d,J=6.6Hz), 1.37 (4H,m), 1.60–2.00 (2H, m), 3.30 (2H,m), 3.60 (1H,m), 3.80 (1H,m), 4.28 (1H,m)

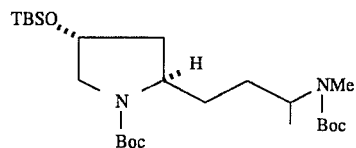
4)

A crude oil of (2R,4R)-N-tert-butoxycarbonyl-2-[3 -(N-tert-butoxycarbonyl-N-methylamino)butyl]-4-tert-butyldimethylsiloxypyrrolidine was obtained from the above compound (1.35 g, 2.86 mmol) in the same manner as in REFERENCE EXAMPLE 26-2, and this compound was used for the subsequent reaction without purification.

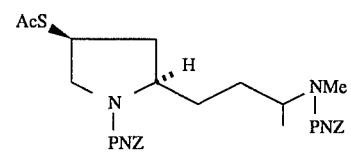

The title compound (1.23 g, yield: 94%) was obtained from the above compound (1.2 g, 2.54 mmol) in the same manner as in REFERENCE EXAMPLES 6-6, 6-7 and 6-8.

IR(KBr)cm$^{-1}$: 2950,1700,1600,1520 NMR(CDCl$_3$) δ: 1.15 (4H,m), 1.50 (2H,br s), 1.63 (2H,br s), 2.10–2.50 (2H,m), 2.3 (3H,s), 3.18 (1H,m), 3.72 (1H,m), 3.87 (1H,m), 4.12 (1H,m), 5.20 (4H,m), 7.50 (4H,m), 8.20 (4H,m)

REFERENCE EXAMPLE 31

(2R,4S)-4-Acetylthio-2-[2-fluoro-3-(N-methyl-N-p-nitrobenzyloxycarbonylamino)propyl]-N-p-nitrobenzyloxycarbonylpyrrolidine

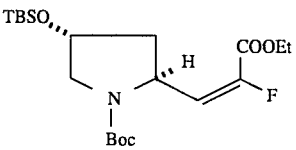
1)

A solution of triethyl 2-fluoro-2-phosphonoethanoate (6.7 g, 27.8 mmol) and dry tetrahydrofuran (140 ml) was cooled to 0° C., and 60% sodium hydride (1.11 g, 27.8 mmol) in oil was added thereto. The mixture was stirred for 1 h, and a mixture of (2S,4R)-N-tert-butoxycarbonyl- 4-tert-butyldimethylsiloxy-2-formylpyrrolidine (7.3 g, 23.2 mmol) and tetrahydrofuran (35 ml) was dropwise added thereto. The mixture was stirred at room temperature for 17 h. Ethyl acetate (100 ml) was added to the reaction solution, and the mixture was washed sequentially with water and saturated aqueous sodium chloride, and dried over anhydrous magnesium sulfate. The solvent was removed in vacuo, and the residue was subjected to silica gel column chromatography (ethyl acetate-heptane) to give 3-[(2S,4R)-N-tert-butoxycarbonyl-4-tert-butyldimethylsiloxypyrrolidin- 2-yl]-2-fluoroacrylic acid ethyl ester (8.0 g, yield: 82.8%).

IR(KBr)cm$^{-1}$: 2950,1695,1470 NMR(CDCl$_3$) δ: 0.06 (6H,s), 0.85 (9H,s), 1.35 (3H,q,J=6.0Hz), 1.40 (9H,br s), 1.87–2.20 (2H,m), 3.43 (2H,m), 4.30 (3H,m), 5.21 (1H,m), 5.8 (1H,m) MS: [M+H]$^+$=376

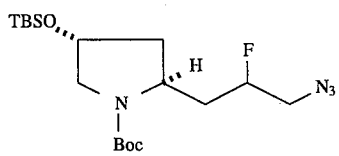

2)

The above compound (6.4 g, 15.3 mmol) was dissolved in ethanol (120 ml), and the solution was vigorously stirred for 2 h in a hydrogen atmosphere using 10% palladium-carbon as a catalyst. The catalyst was filtered off, and the solvent was removed in vacuo. Dry diethyl ether (60 ml) was added thereto, and the mixture was cooled to 0° C. Then, lithium aluminum hydride (1.73 g, 45.6 mmol) was slowly added thereto. The mixture was stirred at the same temperature for 1 h. After completion of the reaction, water (1 ml) and the 1N aqueous sodium hydroxide (45.6 ml, 45.6 mmol) were added thereto. The organic layer was washed twice each with water and saturated aqueous sodium chloride, and then dried over anhydrous magnesium sulfate. The solvent was removed in vacuo to obtain a crude oil of (2R,4 R)-N-tert-butoxycarbonyl-2-(2-fluoro-4-hydroxypropyl)-4 -tert-butyldimethylsiloxypyrrolidine. This oil was dissolved in tetrahydrofuran (60 ml) and cooled to 0° C. Then, triethylamine (3.2 ml, 22.9 mmol) and then methanesulfonyl chloride (1.78 ml, 22.9 mmol) were dropwise added, and the mixture was stirred at the same temperature for 1 h. Ethyl acetate (60 ml) was added to the reaction solution, and the mixture was washed with saturated aqueous sodium hydrogencarbonate, 10% aqueous citric acid and saturated aqueous sodium chloride, and dried over anhydrous magnesium sulfate. The solvent was removed in vacuo. The residue was dissolved in N,N-dimethylformamide (60 ml). Then, sodium azide (3.98 g, 61.2 mmol) was added thereto, and the mixture was heated to 80° C. and stirred for 17 h. After completion of the reaction, ethyl acetate (100 ml) was added thereto, and the mixture was washed three times with water (100 ml). Then, the solvent was removed in vacuo, and the residue was subjected to silica gel column chromatography (ethyl acetate-heptane) to give (2R,4R)-2-(3-azido-2 -fluoropropyl)-N-tert-butoxycarbonyl-4-(tert-butyldimethylsiloxy)pyrrolidine (5.14 g, yield: 83.3%).

IR(KBr)cm$^{-1}$: 2960,2250,1695,1470 NMR(CDCl$_3$) δ: 0.06 (6H,s), 0.85 (9H,s), 1.40 (9H,s), 1.42 (2H,br s), 1.60 (2H,s), 1.70–2.10 (2H,m), 3.30–3.40 (3H,m), 4.35 (1H,m), 4.55–4.9 (1H,m)

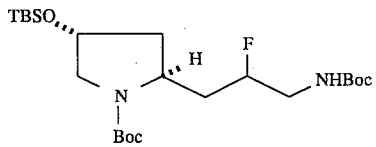

3)

The above compound (5.1 g, 12.7 mmol) was dissolved in methanol (75 ml), and the solution was stirred at 40° C. for 1 h under a hydrogen atmosphere using 10% palladium-carbon (2 g) as a catalyst. The catalyst was filtered off, and the solvent was removed in vacuo to obtain a crude amine.

The crude amine was dissolved in dioxane (50 ml), and di-tert-butyl-dicarbonate (2.76 g, 12.7 mmol) was added thereto. The mixture was stirred for 17 h at room temperature. This reaction solution was diluted with ethyl acetate and washed sequentially with 10% aqueous citric acid and water. Then, the solvent was removed in vacuo, and the residue was subjected to silica gel column chromatography (ethyl acetate-heptane) to give (2R,4 R)-N-tert-butoxycarbonyl-4-tert-butyldimethylsiloxy-2-(3 -tert-butoxycarbonylamino-2-fluorobutyl)pyrrolidine (5.86 g, yield: 97%).

NMR(CDCl$_3$) δ: 0.06 (6H,s), 0.85 (9H,s), 1.25 (2H,br s), 1.40 (18H,s), 1.80–2.05 (2H,s), 3.10–3.50 (4H,m), 4.00 (1H,m), 4.30 (1H,m), 4.50–4.80 (1H,m)

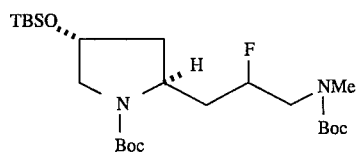

4)

(2R,4R)-N-tert-butoxycarbonyl-2-[3 -(N-tert-butoxycarbonyl-N-methylamino)-2-fluoropropyl]-4 -tert-butyldimethylsiloxypyrrolidine (1.45 g, yield: 98%) was obtained from the above compound (1.43 g, 3 mmol) in the same manner as in REFERENCE EXAMPLE 26-2.

NMR(CDCl$_3$) δ: 0.06 (6H,s), 0.85 (9H,s), 1.26 (2H,br s), 1.40 (18H,s), 1.80–2.05 (2H,s), 2.94 (3H,s), 3.10–3.50 (4H, m), 4.00 (1H,m), 4.30 (1H,m), 4.50–4.80 (1H,m)

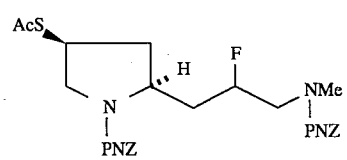

5)

The title compound (850 mg, yield: 67%) was obtained from the above compound (1.08 g, 226 mmol) in the same manner as in REFERENCE EXAMPLES 6-6, 6-7 and 6-8.

IR(KBr)cm$^{-1}$: 2950,1700,1600,1520 NMR(CDCl$_3$) δ: 1.60–1.80 (4H,m), 2.35 (3H,s), 2.05–2.6 (2H,m), 3.03 (3H, br s), 3.20 (1H,m), 3.15–3.70 (2H,m), 3.85 (1H,m), 4.10 (1H,m), 4.60–5.00 (1H,m), 5.20 (4H,s), 7.50 (4H,d,J= 9.0Hz), 8.23 (4H,d,J=9.0Hz)

REFERENCE EXAMPLE 32

(2S,4R)-4-tert-butyldimethylsiloxy-
N-tert-butoxycarbonyl-
2-[(1S)-2-methoxycarbonyl-1-hydroxyethyl]pyrrolidine
and (2S,4R)-4-tert-butyldimethylsiloxy-
N-tert-butoxycarbonyl-
2-[(1R)-2-methoxycarbonyl-1-hydroxyethyl]pyrrolidine

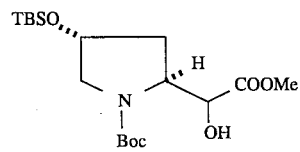

To a solution of (2S,4R)-4-tert-butyldimethylsiloxy-N-tert-butoxycarbonyl- 2-(2-methoxycarbonyl-1 -oxoethyl)pyrrolidine (402 mg, 1.0 mmol) in methanol (2 ml) was added sodium borohydride (19 mg, 0.5 mmol) under a nitrogen atmosphere under cooling with ice. The mixture was stirred for 30 minutes at the same temperature. To this reaction solution was added saturated aqueous ammonium chloride (about 2 ml). This mixture was poured into ethyl acetate-water (50 ml—50 ml) for liquid separation. The organic layer was washed successively with 10% aqueous citric acid and saturated aqueous sodium chloride, and dried over anhydrous magnesium sulfate. The solvent was removed in vacuo. The residue was purified by silica gel column chromatography [Wakogel™ C-300, heptane-ethyl acetate (3:1)] to obtain (2S,4R)-4-tert-butyldimethylsiloxy-N-tert-butoxycarbonyl- 2-[(1S)-2-methoxycarbonyl-1 -hydroxyethyl]pyrrolidine (113 mg, yield: 28%, less polar compound) and (2S,4R)-4-tert-butyldimethylsiloxy-N-tert-butoxycarbonyl- 2-[(1R)-2-methoxycarbonyl-1-hydroxyethyl]pyrrolidine (86 mg, yield: 21%, polar compound) and a mixture of the two (202 mg, yield: 50%, (1S)-form:(1R)-form=4:6).

(2S,4R)-4-tert-Butyldimethylsiloxy-N-tert-butoxycarbonyl- 2-[(1S)-2-methoxycarbonyl-1 -hydroxyethyl]pyrrolidine IR(KBr)cm⁻¹: 3450,2930,1740,1700,1670,1390,1360, 1250, 1160,1110 NMR(CDCl₃) δ: 0.06 (6H,s), 0.86 (9H,s), 1.46 (9H,s), 1.75 (1H,m), 1.95 (1H,m), 2.47 (2H,m), 3.26 (1H,dd,J=4.0,12.6Hz), 3.55 (1H,m), 3.71 (3H,s), 4.05 (2H, m), 4.35 (1H,m)

(2S,4R)-4-tert-Butyldimethylsiloxy-N-tert-butoxycarbonyl- 2-[(1R)-2-methoxycarbonyl-1 -hydroxyethyl]pyrrolidine IR(KBr)cm⁻¹: 3450,2930,1740,1700,1670,1400,1360,1250, 1160 1110 NMR(CDCl₃) δ: 0.07 (6H,s), 0.88 (9H,s), 1.48 (9H,s), 1.90 (2H,m), 2.39 (2H,m), 3.28 (1H,dd,J=3.8,11.4Hz), 3.40 (1H, m), 3.72 (3H,s), 4.12 (1H,m), 4.35 (2H,m)

REFERENCE EXAMPLE 33

(2S,4R)-N-tert-Butoxycarbonyl-4-tert-butyldimethylsiloxy-2-[(1-hydroxy-N-methylamino)propyl]pyrrolidine Borane Complex

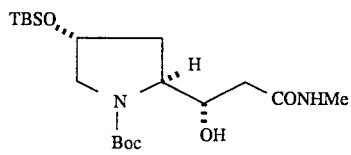
1)

(2S,4R)-N-tert-Butoxycarbonyl-4-tert-butyldimethylsiloxy- 2-[[(1R)-2-ethoxycarbonyl-1 -hydroxy]ethyl]pyrrolidine (4 g, 9.58 mmol) was dissolved in a 40% methylamine solution in methanol (40 ml), and the solution was sealed and stirred overnight at room temperature. The reaction solution was concentrated in vacuo to obtain a crude foam of (2S,4R)-N-tert-butoxycarbonyl- 4-tert-butyldimethylsiloxy-2-[[(1R)-1 -hydroxy-2-(N-methylcarbamoyl)]ethyl] pyrrolidine (3.83 g, yield: 99.3%).

IR(KBr)cm⁻¹: 2931,1676,1411,1165,1113,837,775 NMR(CDCl₃) δ: 0.06 (6H,s), 0.86 (9H,s), 1.46 (9H,s), 1.68–1.83 (1H,m), 1.91–2.05 (1H,m), 2.19–2.69 (2H,m), 2.81 (3H,d,J=4.8Hz), 3.25 (1H,dd,J=3.68,11.5Hz), 3.49 (1H, d,J=11.5Hz), 3.92–3.95 (1H,m), 4.11–4.21 (1H,m), 4.30 (1H,m), 5.66 (1H,d,J=8.0Hz), 7.24 (1H,br)

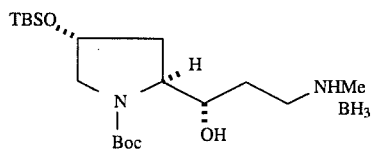
2)

To a solution of the crude foam of the above compound (500 mg, 1.24 mmol) in tetrahydrofuran (4 ml) was slowly dropwise added a borane dimethylsulfide complex (0.372 ml, 3.92 mmol) under stirring at room temperature. After the dropwise addition, the mixture was heated and refluxed for 3 h under stirring. The reaction mixture was cooled to room temperature, and methanol (2 ml) was slowly dropwise added thereto. The mixture was stirred for 1 h at room temperature and then concentrated in vacuo. Chloroform (15 ml) was added to the residue, and the organic layer was washed with water and saturated aqueous sodium chloride, and dried over anhydrous sodium sulfate. Then, the solvent was removed in vacuo. The residue was subjected to silica gel column chromatography [Wakogel™ C-300, 75 ml, heptane:ethyl acetate=100:0→1:2] to give the title compound (244 mg, yield: 48.8%) as a mixture of diastereomers.

MS: [M+H]⁺=403 IR(KBr)cm⁻¹: 3452,3220,2954,2364, 1672,1413,1167,1113,837, 777

NMR data of the diastereomers separated by column chromatography are shown below.

NMR(CDCl₃) δ: POLAR COMPOUND 0.06 (6H,s), 0.86 (9H,s), 1.47 (9H,s), 1.62–1.83 (2H,m), 1.89–2.18 (2H,m), 2.54 (3H,d,J=6.0Hz), 2.81–2.90 (2H,m), 3.24 (1H,dd,J=3.2, 12.0Hz), 3.53 (1H,d,J=12.0Hz), 3.82–3.91 (1H,m), 4.11–4.21 (1H,m), 4.28 (1H,m), 4.95 (1H,m), 5.18 (1H,m) LESS POLAR COMPOUND 0.05 (6H,s), 0.85 (9H,s), 1.45 (9H,s), 1.51–1.77 (3H,m), 1.89–2.03 (1H,m), 2.48 (3H,d,J= 5.6Hz), 2.70–2.90 (1H,m), 3.04–3.16 (1H,m), 3.22 (1H,dd, J=3.42,11.6Hz), 3.52 (1H,d,J=11.6Hz), 3.86 (1H,m), 4.14 (1H,m), 4.26 (1H,m), 4.82 (1H,m), 5.22 (1H,m)

REFERENCE EXAMPLE 34

(2S,4S)-2-[(1R)-3-(N,N-Dimethylamino)-1-hydroxypropyl]-N-p-nitrobenzyloxycarbonyl-4-tritylthiopyrrolidine

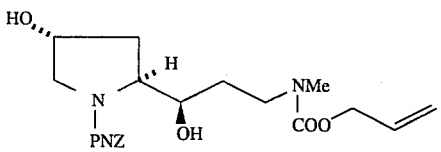
1)

To a 40% methylamine solution in methanol (240 ml) was added a solution of (2S,4R)-N-tert-butoxycarbonyl-4 -tert-butyldimethylsiloxy-2-[[(1R)-1-hydroxy-3 -p-toluenesulfonyloxy]propyl]pyrrolidine prepared in REFERENCE EXAMPLE 15-1 (16.7 g, 0.03 mol) in methanol (64 ml) at room temperature. The mixture was stirred overnight. The reaction solution was concentrated in vacuo, and methylene chloride (100 ml) was added to the residue. Then, triethylamine (6.3 ml, 0.05 mol) and allyl chloroformate (4.0 ml, 0.04 mol) were slowly dropwise added thereto under cooling with ice. The mixture was stirred for 30 minutes. Then, the reaction solution was poured into water and extracted three times with ethyl acetate. The extract was washed successively with 1N aqueous potassium hydrogen sulfate, water, saturated aqueous sodium hydrogencarbonate and saturated aqueous sodium chloride, and dried over anhydrous magnesium sulfate. Then, the solvent was removed in vacuo. The residue was subjected to the same reaction as in REFERENCE EXAMPLE 15-2 to obtain (2S,4R)-2-[(1R)-3 -(N-allyloxycarbonyl-N-methylamino)-1-hydroxypropyl]-4-hydroxy-N-(p-nitrobenzyloxycarbonyl)-pyrrolidine (11.4 g, yield: 93%).

IR(CHCl₃)cm⁻¹: 3620,3610,3020,1690,1525,1215,780, 755 NMR(CDCl₃) δ: 1.50–1.80 (4H,m), 1.95 (1H,m), 2.21 (1H,m), 2.80–2.90 (3H,m), 3.12 (1H,m), 3.40–3.90 (3H,m), 4.00–4.50 (2H,m), 4.50–4.60 (3H,m), 5.10–5.30 (4H,m), 5.90 (1H,m), 7.52 (2H,d,J=8.5Hz), 8.22 (2H,d,J=8.5Hz)

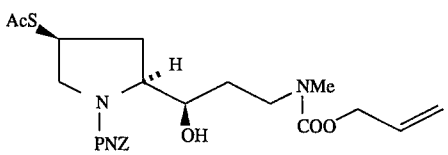

(2S,4S)-4-Acetylthio-2-[(1R)-3-(N-allyloxycarbonyl-N-methylamino)-1-hydroxypropyl]-N-p-nitrobenzyloxycarbonylpyrrolidine (9.8 g, yield: 80%) was obtained from the above compound (11.4 g, 25.8 mmol) in the same manner as in REFERENCE EXAMPLE 4-3.

IR(CHCl$_3$)cm$^{-1}$: 3790,3020,2400,1690,1520,1420,1215, 775,670 NMR(CDCl$_3$) δ: 1.57 (7H,s), 2.34 (3H,s), 2.80–3.20 (4H,m), 3.70–4.30 (5H,m), 4.58 (2H,d,J=5.1Hz), 5.10–5.40 (4H,m), 5.93 (1H,m), 7.25 (2H,d,J=8.6Hz), 8.23 (2H,d,J=8.9Hz)

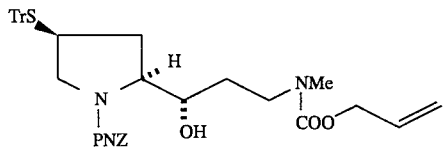

To a solution of the above compound (9.8 g, 19.6 mmol) in methanol (980 ml) was added 1N aqueous sodium hydroxide (19.6 ml, 19.6 mmol) at room temperature in a nitrogen atmosphere. The mixture was stirred for 30 minutes. To the reaction solution was added 1N hydrochloric acid (22 ml, 21.6 mmol). The mixture was concentrated in vacuo and diluted with ethyl acetate and washed successively with water and saturated aqueous sodium chloride. The solvent was removed in vacuo. To the residue were added N,N-dimethylformamide (65 ml) and chlorotriphenylmethane (645 mg, 2.3 mmol). The mixture was stirred overnight at 50° C. The reaction solution was poured into water (100 ml) and extracted with ethyl acetate. The organic layer was washed with saturated aqueous sodium hydrogencarbonate and dried over anhydrous sodium sulfate. The organic layer was concentrated in vacuo, and the residue was subjected to silica gel column chromatography (heptane-ethyl acetate) to give (2S,4S)-2-[(1R)-3-(N-allyloxycarbonyl-N-methylamino)-1-hydroxypropyl]-N-p-nitrobenzyloxycarbonyl-4-tritylthiopyrrolidine (10.4 g, yield: 73%).

IR(KBr)cm$^{-1}$: 3020,1690,1525,1215,760,670 NMR(CDCl$_3$) δ: 1.54 (9H,s), 2.60–3.00 (4H,m), 3.50–3.90 (2H,m), 4.50–4.60 (2H,m), 5.00–5.40 (4H,m), 5.80–6.00 (1H,br), 7.10–7.50 (17H,m), 8.10–8.30 (2H,m)

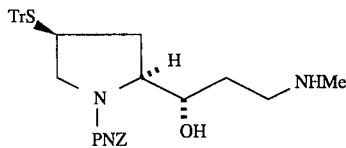

To a solution of the above compound (10.4 g, 14.9 mmol) in methylene chloride (50 ml) were added water (0.7 ml, 37 mmol), bis(triphenylphosphine)palladium(II) chloride (209 mg, 0.3 mmol) and tributyltin hydride (12 ml, 45 mmol) under cooling with ice. The mixture was stirred at room temperature for 30 minutes. The reaction solution was poured into saturated aqueous sodium hydrogencarbonate and extracted with methylene chloride. The organic layer was dried over anhydrous sodium sulfate and concentrated in vacuo. The residue was subjected to silica gel column chromatography (methanol-chloroform) to give (2S,4S)-2-[(1R)-1-hydroxy-3-(N-methylamino)propyl]-N-p-nitrobenzyloxycarbonyl-4-tritylthiopyrrolidine (11.8 g, yield: quantitative).

IR(KBr)cm$^{-1}$: 3435,3320,2925,1700,1525,1430,1345, 1200, 1100,745 NMR(CDCl$_3$) δ: 1.57 (6H,s), 2.39 (3H,s), 2.60–3.00 (4H,m), 3.50–3.80 (2H,m), 4.15 (1H,m), 5.00–5.30 (2H,m), 7.10–7.50 (17H,m), 8.10–8.30 (2H,m)

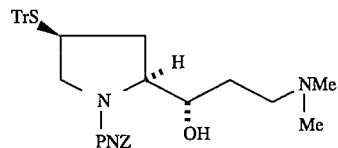

To a solution of the above compound (5.0 g, 7.9 mmol) in tetrahydrofuran (32 ml) were added 37% formalin (0.6 ml, 7.9 mmol), acetic acid (0.45 ml, 7.9 mmol) and sodium triacetoxyborohydride (32.5 g, 11.9 mmol) under cooling with ice. The mixture was stirred at room temperature for 6 h. The reaction solution was concentrated in vacuo, diluted with a saturated aqueous sodium hydrogencarbonate. It was extracted with methylene chloride. The solvent was removed in vacuo. The residue was subjected to silica gel column chromatography (methanol-chloroform) to give (2S,4S)-2-[(1R)-3-(N,N-dimethylamino)-1-hydroxypropyl]-N-p-nitrobenzyloxycarbonyl-4-tritylthiopyrrolidine (3.7 g, yield: 72%).

IR(KBr)cm$^{-1}$: 3455,2950,1700,1520,1345,1105,855 NMR(CDCl$_3$) δ: 1.20–2.50 (8H,m), 2.91 (6H,d,J=21.7Hz), 3.50–3.70 (2H,m), 4.15 (1H,m), 5.00–5.20 (2H,m), 7.10–7.60 (17H,m), 8.24 (2H,d,J=8.4Hz)

REFERENCE EXAMPLE 35

(2S,4R)-4-Hydroxy-2-[(R)-1-hydroxy-3-(N-methylamino)propyl]pyrrolidine Dihydrochloride

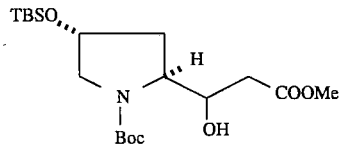

Hexamethyldisilazane (11.0 ml, 52.1 mmol) was dropwise added over a period of 20 minutes at a temperature of not higher than –60° C. to a solution containing a 1.6M n-butyl lithium hexane solution (33.8 ml, 54.1 mmol) in tetrahydrofuran (70 ml), in a nitrogen atmosphere. To this solution was dropwise added methyl acetate (4.14 ml, 52.1 mmol) over a period of 15 minutes at –60° C. This solution was stirred for 30 minutes. To the reaction solution was dropwise added a solution of (2S,4R)-N-tert-butoxycarbonyl-4-tert-butyldimethylsiloxyprolinal (13.2 g, 40.1 mmol) in tetrahydrofuran (23 ml) at a temperature of not higher than –60° C. for 1.5 h. The mixture was stirred at a temperature of not higher than –60° C. for 30 minutes. The reaction mixture was added to an aqueous solution (90 ml) of citric acid (9 g), and the mixture was stirred for 30 minutes and extracted with ethyl acetate (150 ml). The organic layer was washed with water (50 ml) and concentrated in vacuo at a temperature of not higher than 40° C. Ethyl acetate (15 ml) was added to the residue, and the mixture was concentrated in vacuo. Then, n-heptane (30 ml) was added to the residue. The same operation was repeated to obtain (2S,4R)-N-tert-butoxycarbonyl-4-tert-butyldimethylsiloxy-2-[(R,S)-1-hydroxy-2-(methoxycarbonyl)ethyl]pyrrolidine[(R)-isomer (polar compound):(S)-isomer (less polar compound)=75.6:24.4].

2)

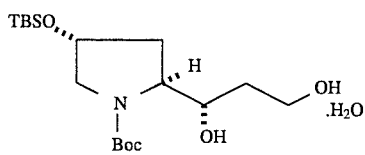

The above residue was dissolved in tetrahydrofuran (75 ml), and sodium borohydride (2.3 g, 60.8 mmol) was added thereto at room temperature. The mixture was stirred for 30 minutes, and then methanol (15 ml) was dropwise added over a period of 1 h at a temperature of from 60° to 65° C. The mixture was stirred for 1 h at the same temperature. The reaction solution was cooled to room temperature, and an aqueous solution (134 ml) containing citric acid (8.4 g) and ethyl acetate (150 ml) were added thereto. The organic layer was separated and washed with water (60 ml), and concentrated in vacuo at 40° C. Then, n-heptane (30 ml) was added to the crystal residue. The mixture was concentrated in vacuo. To the precipitated solid residue were added n-heptane (50 ml) and water (5 ml). This mixture was cooled to a temperature of not higher than 5° C. and stirred for 1 h. The precipitated crystals were collected by filtration and washed with n-heptane (35 ml) and dried in air to obtain a white powder of (2S,4R)-N-tert-butoxycarbonyl-4-tert-butyldimethylsiloxy-2-[(R,S)-1,3-dihydroxypropyl]pyrrolidine monohydrate [8.04 g, yield: 51%; (R)-isomer (polar compound):(S)-isomer (less polar compound)=94.7:2.7].

mp: 84.6° C. IR(KBr)cm$^{-1}$: 3510,3400,3300,3230,2950, 1660,1420,1360, 1170,1065,770 NMR(CDCl$_3$) δ: 0.06 (6H, s), 0.86 (9H,s), 1.46 (9H,s), 1.70–1.80 (1H,m), 1.90–2.00 (1H,m), 3.05 (1H,br s), 3.25 (1H,dd,J=4.0,12.0Hz), 3.51 (1H,d,J=12.0Hz), 3.85 (2H,d,J=4.0Hz), 4.00 (1H,m), 4.13 (1H,m), 4.30 (1H,s), 4.82 (1H,m)

3)

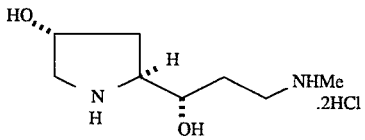

The above compound (12.35 g, 31.34 mmol) was dissolved in a mixture of methylene chloride (67 ml) and water (13 ml). The organic layer was separated and concentrated in vacuo. Ethyl acetate (15 ml) was added to the residue, and the mixture was concentrated. The residue was dissolved in methylene chloride (111 ml) and 4-dimethylaminopyridine (383 mg, 3.13 mmol) was added thereto at 7° C. The mixture was stirred for 15 minutes, and triethylamine (13.1 ml, 93.9 mmol) was added thereto at 5° C. The reaction mixture was stirred for 10 minutes. Then, tosyl chloride (7.18 g, 37.7 mmol) was added to the reaction mixture at 5° C. The mixture was stirred for 4 h at a temperature of from 10° to 20° C. To the reaction mixture was added an aqueous solution (75 ml) of sodium hydrogencarbonate (5 g) at a temperature of not higher than 10° C. The mixture was stirred for 15 minutes. The organic layer was separated, sequentially washed with 10 % aqueous citric acid (60 ml) and water (50 ml), and concentrated. To the residue were added methylene chloride (10 ml) and methanol (10 ml). The mixture was concentrated in vacuo to obtain a tosylate as an oily residue. This residue was dissolved in methanol (9 ml). This mixture was added to a solution of methylamine (26.3 g, 84.7 mmol) in methanol (44 ml). The mixture was stirred at room temperature for 18 h. Then, the reaction mixture was concentrated at 40° C. to a volume of 25 ml. Ethyl acetate (60 ml) was added to the residue. The mixture was washed with an aqueous solution (50 ml) containing sodium hydrogencarbonate (1.6 g) and water (30 ml), and then concentrated in vacuo. Ethyl acetate (7 ml) was added to the residue, and the moisture was distilled off together with the organic solvent. This operation was repeated five times.

The obtained residue was dissolved in hydrogen chloride (4.93 g)-methanol (50 ml) at 10° C. The mixture was stirred at room temperature for 16 h and then stirred at 14° C. for 1 h. Precipitated crystals were collected by filtration, and washed with methanol-diisopropyl ether (1:2, 15 ml) and dried in vacuo at 40° C. for 5.5 h to obtain the title compound as white crystals (6.41 g, yield: 83%). Further, from the mother liquor, secondary crystals (78 mg) were obtained.

mp: ca 194° C. IR(KBr)cm$^{-1}$: 3410,2980,2800,1580,1010 NMR(D$_2$O) δ: 1.75 (1H,m), 1.90 (1H,m), 2.05 (2H,m), 2.66 (3H,s), 3.12 (2H,m), 3.25 (1H,d,J=12.5Hz), 3.50 (1H,dd,J= 3.6,12.5Hz), 3.92 (1H,m), 4.10 (1H,m), 4.60 (1H,br s)

REFERENCE EXAMPLE 36

(2S,4R)-N-tert-Butoxycarbonyl-4-tert-butyldimethylsiloxy-2-[(S)-1-hydroxy-2-(N-methylcarbamoyl)ethyl]pyrrolidine

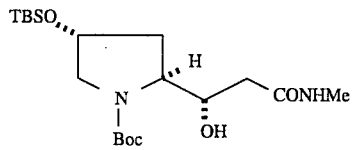

A 40% methylamine methanol solution (50 ml) was added to (2S,4R)-N-tert-butoxycarbonyl-4-tert-butyldimethylsiloxy-2-[(S)-1-hydroxyethyl-2-methoxycarbonyl]pyrrolidine (5.0 g, 12.4 mmol) prepared in REFERENCE EXAMPLE 32. The mixture was stirred overnight at room temperature. Then, the reaction solution was concentrated, and ethyl acetate (100 ml) was added thereto. This mixture was successively washed with dilute hydrochloric acid, saturated aqueous sodium hydrogencarbonate and saturated aqueous sodium chloride, dried over anhydrous sodium sulfate, and concentrated in vacuo. The residue was subjected to silica gel column chromatography (Wakogel™ C-300, heptane-ethyl acetate=1:1→1:3) to give the title compound (3.5 g, yield: 70%).

NMR(CDCl$_3$) δ: 0.05 (6H,s), 0.85 (9H,s), 1.46 (9H,s), 2.79 (3H,m), 3.26 (1H,m), 3.57 (1H,m), 3.80 (1H,m), 3.97 (1H,m), 4.27 (1H,m), 6.17 (1H,m), 6.92 (1H,m)

REFERENCE EXAMPLE 37

(2S,4R)-N-tert-Butoxycarbonyl-4-tert-butyldimethylsiloxy-2-[(R)-1-hydroxy-2-(N-methylcarbamoyl)ethyl]pyrrolidine

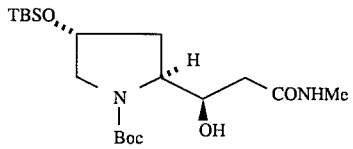

The title compound (4.5 g, yield: 90%) was obtained from (2S,4R)-N-tert-butoxycarbonyl-4-tert-butyldimethylsiloxy-2-[(R)-1-hydroxyethyl-2-methoxycarbonyl]pyrrolidine (5.0 g, 12.4 mmol) in the same manner as in REFERENCE EXAMPLE 36.

NMR(CDCl$_3$) δ: 0.06 (6H,s), 0.86 (9H,s), 1.46 (9H,s), 2.80 (3H,d,J=4.9Hz), 3.25 (1H,dd,J=3.9,11.7Hz), 3.47 (1H, m), 3.91 (1H,m), 4.13 (1H,m), 4.28 (1H,m), 5.63 (1H,m), 6.97 (1H,m)

REFERENCE EXAMPLE 38

(2S,4R)-N-tert-Butoxycarbonyl-4-methanesulfonyloxy-2-(2-methoxycarbonyl-1-oxoethyl)pyrrolidine

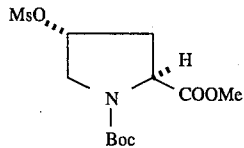
1)

To a solution of (2S,4R)-N-tert-butoxycarbonyl-4-hydroxyproline methyl ester (30.2 g, 123 mmol) in methylene chloride (300 ml) were dropwise added successively triethylamine (41.2 ml, 0.295 mmol) and methanesulfonyl chloride (17.1 ml, 0.221 mol) at 0° C. in a nitrogen atmosphere. The mixture was stirred at 0° C. for 2 h, and saturated aqueous sodium hydrogencarbonate was added. The mixture was extracted with ethyl acetate. The organic layer was washed with saturated aqueous sodium chloride, and dried over anhydrous magnesium sulfate. The solvent was removed in vacuo. The residue was subjected to silica gel flash column chromatography (heptane-ethyl acetate=5:5) to give (2S,4R)-N-tert-butoxycarbonyl-4-methanesulfonyloxyproline methyl ester (39.5 g, yield: 99.1%).

NMR(CDCl$_3$) δ: 1.42 & 1.47 (total 9H, each s), 2.21–2.31 (1H,m), 2.53–2.71 (1H,m), 3.06 (3H,s), 3.75 (3H,s), 3.70–3.90 (2H,m), 4.41 & 4.47 (total 1H, each dd,J=6.9, 6.9Hz), 5.24–5.30 (1H,m)

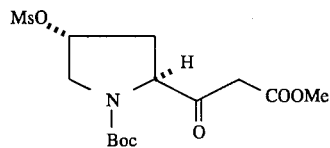
2)

To a solution of the above compound (1.03 g, 3.19 mmol) in methanol (6 ml) was added 1N aqueous sodium hydroxide (8 ml, 8.00 mmol) at room temperature. The mixture was stirred for 2 h at the same temperature, and then 1N hydrochloric acid (10 ml) was added thereto. The mixture was extracted with ethyl acetate. The organic layer was washed with saturated aqueous sodium chloride, and dried over anhydrous sodium sulfate. The solvent was removed in vacuo. The residue was dissolved in tetrahydrofuran (5 ml), and carbonyldiimidazole (672 mg, 4.15 mmol) was added thereto at 0° C. This solution was stirred at room temperature for 3 h to obtain a solution of an imidazolide. In a separate reactor, monomethyl malonate (1.40 g, 12.8 mmol) was dissolved in tetrahydrofuran, and magnesium chloride (7.29 mg, 7.66 mmol) and triethylamine (1.97 ml, 14.0 mmol) were successively added thereto at 0° C. The mixture was stirred at room temperature for 2 h. This reaction solution was cooled to 0° C., and the previously prepared imidazolide solution was dropwise added thereto. The reaction solution was stirred for 24 h at room temperature. To the reaction solution was added saturated aqueous ammonium chloride. The mixture was extracted with ethyl acetate. The organic layer was washed with saturated aqueous sodium chloride, and dried over anhydrous magnesium sulfate. The solvent was removed in vacuo. The residue was purified by silica gel column chromatography (heptane-ethyl acetate= 2:3) to obtain the title compound (945 mg, yield: 81.2%).

NMR(CDCl$_3$) δ: 1.46 (9H,s), 2.20–2.39 (1H,m), 2.48–2.7 (1H,m), 3.05 & 3.06 (total 3H, each s), 3,48–3.70 (3H,m), 3.73 & 3.75 (total 3H, each s), 3.80–4.01 (1H,m), 4.54 (dd,J$_1$=7.8,7.8Hz) & 4.62 (dd,J$_1$=8.1,8.1Hz)=(total 1H), 5.21–5.29 (1H,m)

REFERENCE EXAMPLE 39

(2S,4R)-N-tert-Butoxycarbonyl-4-tert-butyldimethylsiloxy-2-[2-(N-methylcarbamoyl)-1-oxoethyl]pyrrolidine

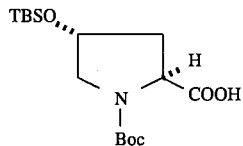
1)

(2S,4R)-N-tert-Butoxycarbonyl-4-tert-butyldimethylsiloxyproline methyl ester (5.9 g, 16.5 mmol) was dissolved in methanol (45 ml) and water (11 ml). Then, 2.5N aqueous sodium hydroxide (6.6 ml, 16.5 mmol) was added thereto. The mixture was stirred at room temperature for 6 h, and then the organic solvent was distilled off. The aqueous layer was washed with ethyl acetate, then adjusted to pH 2.5 with 1N hydrochloric acid, and extracted with ethyl acetate. The organic layer was washed with saturated aqueous sodium chloride, and concentrated in vacuo to obtain crude (2S,4R)-N-tert-butoxycarbonyl- 4-tert-butyldimethylsiloxyproline (5.1 g).

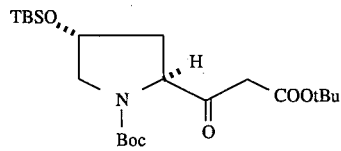
2)

The above compound (5.1 g) was dissolved in tetrahydrofuran, and a solution of 1,1'-carbonyldiimidazole (3.1 g, 19.1 mmol) in N,N-dimethylformamide (16 ml) was added thereto. This solution was stirred for 40 minutes to obtain a solution of an imidazolide.

To a suspension of mono tert-butyl malonate (6.4 g, 39.9 mmol) and magnesium chloride (2.3 g, 24.1 mmol) in tetrahydrofuran (90 ml) was dropwise added triethylamine (6.1 ml, 43.9 mmol) under cooling with ice. The mixture was stirred at room temperature for 80 minutes. To this suspension was added the previously prepared imidazolide solution. The mixture was stirred at room temperature for 4 days. Insoluble material was filtered off, and methylene chloride was added to the filtrate. The organic layer was washed successively with dilute hydrochloric acid, saturated aqueous sodium hydrogencarbonate and saturated aqueous sodium chloride, and concentrated in vacuo. The residue was subjected to silica gel column chromatography (Wakogel™ C-300, heptane-ethyl acetate=10:1) to give (2S,4R)-N-tert-butoxycarbonyl-4-tert-butyldimethylsiloxy-2-(2- tert-butoxycarbonyl-1-oxoethyl)pyrrolidine (5.6 g, yield: 79.2 %).

IR(KBr)cm$^{-1}$: 2977,2896,1747,1712,1473,1463,1456, 1253, 1162,1116,837,777 NMR(CDCl$_3$) δ: 0.08 (6H,s), 0.88 (9H,s), 1.43–1.58 (18H,m), 2.02–2.19 (2H,m), 3.33–3.54 (4H,m), 4.36–4.58 (2H,m)

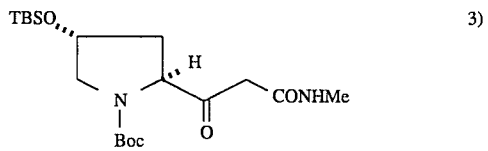

3)

A 11.8% methylamine toluene solution (8.9 ml) was added to a solution of the above compound (4.9 g, 11.0 mmol) in toluene (40 ml). This solution was stirred in a sealed tube at 100° C. for 3 h. Ethyl acetate was added to this reaction solution. The organic layer was washed successively with dilute hydrochloric acid and saturated aqueous sodium chloride, and dried over anhydrous magnesium sulfate. The solvent was distilled off in vacuo. The residue was subjected to silica gel column chromatography (Wakogel™ C-300, heptane-ethyl acetate=1:2) to give (2S,4R)-N-tert-butoxycarbonyl-4 -tert-butyldimethylsiloxy-2-[2-(N-methylcarbamoyl)-1 -oxoethyl]pyrrolidine (4.1 g, yield: 92.9%).

IR(KBr)cm$^{-1}$: 2883,2856,1695,1660,1558,1473,1456, 1253, 1160,1116,837,777 NMR(CDCl$_3$) δ: 0.06 (6H,s), 0.86 (9H,s), 1.39 & 1.45 (total 9H, each s), 1.82–2.17 (3H,m), 2.80–2.85 (3H,m), 3.36–3.57 (4H,m), 4.38–4.51 (2H,m), 7.11–7.14 (1H,br s)

REFERENCE EXAMPLE 40

(2S,4R)-N-tert-Butoxycarbonyl-4-tert-butyldimethylsiloxy-2-[(R,S)-1-hydroxy-(2-methoxycarbonyl)ethyl]pyrrolidine

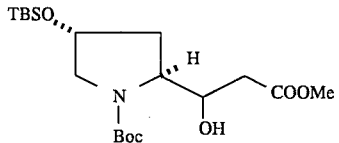

In an argon atmosphere, (1,5 -cyclooctadiene)ruthenium(II) chloride polymer (13 mg, 4.6×10$^{-2}$ mmol), (S)-(–)-bis(diphenylphosphino)-1,1'-binaphthyl (28 mg, 4.6×10$^{-2}$ mmol), triethylamine (0.1 ml, 6.5×10$^{-1}$ mmol) and toluene (5 ml) were stirred in a sealed tube at 140° C. for 4 h. The solvent was removed in vacuo from the obtained red solution. To the residue was added a solution of (2S,4R)-N-tert-butoxycarbonyl-4 -tert-butyldimethylsiloxy-2-(2-methoxycarbonyl-1 -oxoethyl)pyrrolidine (2.0 g, 5 mmol) in tetrahydrofuran (5 ml)—methanol (8 ml). The interior of the system was substituted twice with argon, and the mixture was stirred under a hydrogen pressure of 4 kg/cm$^2$ at 80° C. for two days. The reaction solution was concentrated, and the residue was subjected to silica gel column chromatography (Wakogel™ C-300, heptane-ethyl acetate=7:1→4:1) to give (2S,4R)-N-tert-butoxycarbonyl-4 -tert-butyldimethylsiloxy-2-(2-methoxycarbonyl-1 -oxoethyl)pyrrolidine (670 mg, recovery of starting material) and (2S,4R)-N-tert-butoxycarbonyl-4 -tert-butyldimethylsiloxy-[(R,S)-1-hydroxy-2-(2 -methoxycarbonyl)ethyl]pyrrolidine [1.24 g, yield: 62%; by high performance liquid column chromatography YMC PACKED COLUMN, A-001 S-5 120 A SIL, developer:hexane-2 -propanol=100:1, flow rate 2 ml/min, detection at 210 nm (R)-isomer (polar compound):(S)-isomer (less polar compound)=2.5:1].

NMR(CDCl$_3$) δ: 0.07 (6H,s), 0.88 (9H,s), 1.48 (9H,s), 1.90 (2H,m), 2.39 (2H,m), 3.28 (2H,dd,J=3.8,11.4Hz), 3.72 (3H,s), 4.12 (1H,m), 4.35 (2H,m)

REFERENCE EXAMPLE 41

(2S,4R)-N-tert-Butoxycarbonyl-4-tert-butyldimethylsiloxy-2-[(R,S)-1-hydroxy-(2-methoxycarbonyl)ethyl]pyrrolidine

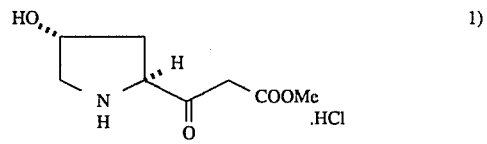

1)

To (2S,4R)-N-tert-butoxycarbonyl-4 -tert-butyldimethylsiloxy-2-(2-methoxycarbonyl-1 -oxoethyl)pyrrolidine (3.17 g, 7.9 mmol) was added a 3N hydrogen chloride—dioxane solution (30 ml). The mixture was stirred at room temperature for 2 h, and then concentrated in vacuo. Chloroform (20 ml) and methanol (20 ml) were added thereto, and the solvent was removed in vacuo. This operation was repeated twice, followed by being left overnight to obtain crude (2S,4R)-4-hydroxy-2 -(2-methoxycarbonyl-1-oxoethyl)pyrrolidine monohydrochloride (1.76 g).

NMR(D$_2$O) δ: 2.10–2.75 (3H,m), 3.45 (2H,s), 4.72 (1H, m), 5.01 (1H,m)

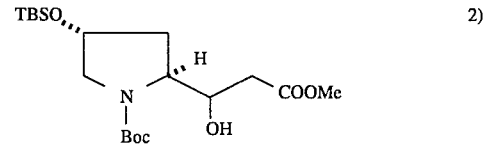

2)

Under an argon atmosphere, (1,5 -cyclooctadiene)ruthenium(II) chloride polymer (10 mg, 3.6×10$^{-2}$ mmol), (S)-(–)-bis(diphenylphosphino)-1,1'-binaphthyl (24 mg, 3.6×10$^{-2}$ mmol), triethylamine (0.1 ml, 6.5×10$^{-1}$ mmol) and toluene (5 ml) were stirred in a sealed tube at 140° C. for 6 h. The solvent was removed in vacuo from the obtained red solution. To the residue was added a methanol (8 ml)—tetrahydrofuran (5 ml) solution of (2S,4R)-4-hydroxy-2-(2-methoxycarbonyl-1 -oxoethyl)pyrrolidine monohydrochloride (1.76 g) obtained by the above reaction. This mixture was stirred under a hydrogen pressure of 4 kg/cm$^2$ at 80° C. for 22 h. Tetrahydrofuran (20 ml) was added to the reaction solution, and triethylamine (0.99 ml, 7.1 mmol) and di-tert-butyl dicarbonate (1.86 g, 8.5 mmol) were added thereto at 0° C. The mixture was stirred for 1 h. The precipitated solid was filtered off, and the organic layer was concentrated in vacuo. The residue was extracted with ethyl acetate, and the organic layer was washed successively with dilute hydrochloric acid, saturated aqueous sodium hydrogencarbonate and saturated aqueous sodium chloride, dried over anhydrous sodium sulfate and concentrated in vacuo. To a solution of the obtained oil in N,N-dimethylformamide (30 ml) were added chloro-tert-butyldimethylsilane (1.20 g, 7.9 mmol) and imidazole (540 mg, 7.9 mmol) at 0° C. The mixture was stirred overnight at room temperature. Ethyl acetate was added to the reaction mixture. The organic layer was washed successively with dilute hydrochloric acid, saturated aqueous sodium hydrogencarbonate and saturated aqueous sodium chloride, dried over anhydrous sodium sulfate and concentrated in vacuo. The obtained oil was subjected to silica gel column chromatography (Wakogel™ C-300, heptane-ethyl acetate) to give the title compound [1.3 g, yield: 45%; by high performance liquid column chromatography under the same conditions as in REFERENCE EXAMPLE 40 (R)-isomer (polar compound):(S)-isomer (less polar compound)=14.9:1].

NMR(CDCl$_3$) δ: 0.07 (6H,s), 0.88 (9H,s), 1.48 (9H,s), 1.90 (2H,m), 2.39 (2H,m), 3.28 (2H,dd,J=3.8,11.4Hz), 3.72 (3H,s), 4.12 (1H,m), 4.35 (2H,m)

REFERENCE EXAMPLE 42

(2S,4R)-N-tert-Butoxycarbonyl-2-[(R,S)-2-tert-butoxycarbonyl-1-hydroxyethyl]-4-tert-butyldimethylsiloxypyrrolidine

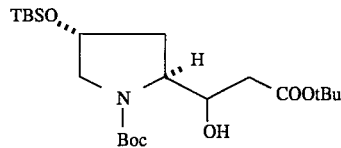

Under an argon atmosphere, (1,5-cyclooctadiene)ruthenium(II) chloride polymer (11 mg, 3.6×10$^{-2}$ mmol), (R)-(–)-bis(diphenylphosphino)-1,1'-binaphthyl (27 mg, 4.5×10$^{-2}$ mmol), triethylamine (0.1 ml, 6.5×10$^{-1}$ mmol) and toluene (5 ml) were stirred in a sealed tube at 140° C. for 4 h. The solvent was removed in vacuo from the obtained red solution. To the residue was added a tetrahydrofuran (5 ml)—tert-butanol (10 ml) solution of (2S,4R)-N-tert-butoxycarbonyl-2-(2-tert-butoxycarbonyl-1-oxoethyl)-4-tert-butyldimethylsiloxypyrrolidine (2.0 g, 5 mmol). The mixture was stirred under a hydrogen pressure of 4 kg/cm$^2$ at 80° C. for 22 h. Then, the reaction solution was concentrated. The residue was subjected to silica gel column chromatography (Wakogel™ C-300, heptane-ethyl acetate= 4:1) to give the title compound [1.48 g, yield: 97%; by high performance liquid column chromatography YMC PACKED COLUMN, A-001 S-5 120A SIL, developer:hexane-2-propanol 100:1, flow rate 2 ml/min, detection at 210 nm (R)-isomer (polar compound):(S)-isomer (less polar compound)=1:25].

NMR(CDCl$_3$) δ: 0.06 (6H,s), 0.87 (9H,s), 1.47 (9H,s), 2.38 (2H,m), 3.29 (1H,m), 3.56 (1H,m), 4.33 (1H,m)

REFERENCE EXAMPLE 43

(2S,4R)-N-tert-Butoxycarbonyl-4-tert-butyldimethylsiloxy-2-[1-hydroxy-2-(N-methylcarbamoyl)ethyl]pyrrolidine

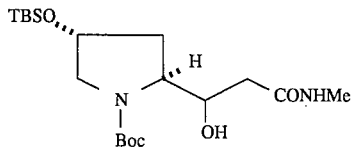

Under an argon atmosphere, (1,5-cyclooctadiene)ruthenium(II) chloride polymer (10 mg, 3.6×10$^{-2}$ mmol), (S)-(–)-bis(diphenylphosphino)-1,1'-binaphthyl (24 mg, 3.6×10$^{-2}$ mmol), triethylamine (0.1 ml, 6.5×10$^{-1}$ mmol) and toluene (5 ml) were stirred in a sealed tube at 140° C. for 6 h. The solvent was removed in vacuo from the obtained red solution. To the residue was added a tetrahydrofuran (5 ml)—ethanol (10 ml) solution of (2S,4R)-N-tert-butoxycarbonyl-4-tert-butyldimethylsiloxy-2-[2-(N-methylcarbamoyl)-1-oxoethyl]pyrrolidine (1.5 g, 3.9 mmol). The mixture was stirred under a hydrogen pressure of 4 kg/cm$^2$ at 80° C. for 22 h. Then, the reaction solution was concentrated. The residue was subjected to silica gel column chromatography (Wakogel™ C-300, heptane-ethyl acetate=3:1→1:3) to give the title compound [1.19 g, yield: 79%; by high performance liquid column chromatography YMC PACKED COLUMN, AQ-32 S-5 120A ODS, developer:acetonitrile—water 70:30, detection at 210 nm (R)-isomer (polar compound):(S)-isomer (less polar compound)=1.89:1].

NMR(CDCl$_3$) δ: 0.06 (6H,s), 0.87 (9H,s), 1.47 (9H,s), 1.75 (1H,m), 1.95 (1H,m), 2.81 (3H,d,J=3.6Hz), 3.26 (1H, dd,J=3.6,11.7Hz), 3.53 (1H,m), 3.75–4.40 (3H,m), 6.96 (1H, m)

REFERENCE EXAMPLE 44

(2S,4R)-N-tert-Butoxycarbonyl-4-tert-butyldimethylsiloxy-2-[1-hydroxy-2-(N-methylcarbamoyl)ethyl]pyrrolidine

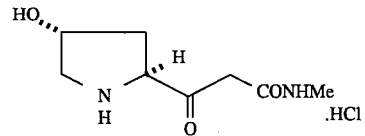

1)

To a solution of (2S,4R)-N-tert-butoxycarbonyl-4-tert-butyldimethylsiloxy-2-[2-(N-methylcarbamoyl)-1-oxoethyl]pyrrolidine (2.07 g, 5.3 mmol) in methanol (10 ml) was added a 5.5N hydrogen chloride—methanol solution (6 ml, 33 mmol). The mixture was stirred at room temperature for 6 h. The reaction solution was concentrated in vacuo. Tetrahydrofuran and ethanol were added to the obtained residue, and the precipitate was collected by filtration and washed with ethanol to obtain (2S,4R)-4-hydroxy-2-[2-(N-methylcarbamoyl)-1-oxoethyl]pyrrolidine monohydrochloride (737 mg, yield: 62 %).

NMR(D$_2$O) δ: 2.20–2.42 (2H,m),2.55–2.70 (2H,m), 2.78 (4H,s), 3.44 (2H,d,J=1Hz), 4.72 (1H,m), 4.93 (1H,m)

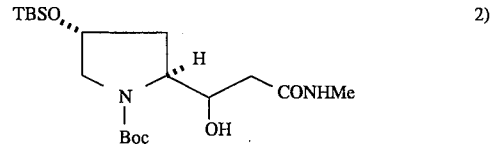

2)

Under an argon atmosphere, (1,5-cyclooctadiene)ruthenium(II) chloride polymer (10 mg, 3.6×10$^{-2}$ mmol), (S)-(–)-bis(diphenylphosphino)-1,1'-binaphthyl (24 mg, 3.6×10$^{-2}$ mmol), triethylamine (0.1 ml, 6.5×10$^{-1}$ mmol) and toluene (5 ml) were stirred in a sealed tube at 140° C. for 6 h. The solvent was removed in vacuo from the obtained red solution. To the residue were added a solution of (2S,4R)-4-hydroxy-2-[2-(N-methylcarbamoyl)-1-oxoethyl]pyrrolidine monohydrochloride (660 mg, 3.0 mmol) in methanol (10 ml) and tetrahydrofuran (5 ml). The mixture was stirred under a hydrogen pressure of 4 kg/cm$^2$ at 80° C. for 6 h. Then, the reaction solution was concentrated in vacuo. Dioxane (20 ml) and water (10 ml) were added to the residue, and 1N aqueous sodium hydroxide (5 ml) and di-tert-butyl dicarbonate (930 mg, 4.2 mmol) were added thereto at 0° C. The mixture was stirred overnight at room temperature. Then, the reaction solution was concentrated. The residue was extracted with chloroform (50 ml×5). The organic layer was dried over anhydrous sodium sulfate and concentrated in vacuo. The obtained oil (930 mg) was dissolved in N,N-dimethylformamide (10 ml), and chloro-tert-butyldimethylsilane (520 mg, 3.4 mmol) and imidazole (240 mg, 3.4 mmol) were added thereto at 0° C. The mixture was stirred at room temperature for 4 h. Then, ethyl acetate (100 ml) was added to the reaction solution. The mixture was washed successively with dilute hydrochloric acid, saturated aqueous sodium hydrogencarbonate and saturated aqueous sodium chloride, dried over anhydrous sodium sulfate and concentrated in vacuo. The obtained oil was subjected to silica gel column chromatography (Wakogel™ C-300, heptane-ethyl acetate) to give the title compound [602 mg, yield: 60%; by high performance liquid column chromatography under the same conditions as in REFERENCE EXAMPLE 43 (R)-isomer (polar compound):(S)-isomer (less polar compound)=149:1].

REFERENCE EXAMPLE 45

(2S,4R)-N-tert-Butoxycarbonyl-4-methanesulfonyloxyprolinal

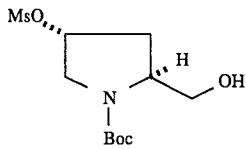
1)

To a solution of (2S,4R)-N-tert-butoxycarbonyl-4 -methanesulfonyloxyproline methyl ester (10.0 g, 30.9 mmol) in tetrahydrofuran—methanol (1:1, 100 ml) were successively added lithium chloride (3.93 g, 92.8 mmol) and sodium borohydride (3.51 g, 92.8 mmol). The reaction solution was stirred at room temperature for 11 h. Acetic acid (2 ml) was added to the reaction solution, and ethyl acetate and water were added thereto. The mixture was concentrated in vacuo. The residue was dissolved in water and ethyl acetate and extracted with ethyl acetate. The organic layer was washed with saturated aqueous sodium chloride, and dried over anhydrous magnesium sulfate. The solvent was removed in vacuo to obtain a residue of (2S,4R)-N-tert-butoxycarbonyl-2-hydroxymethyl-4 -methanesulfonyloxyproline (9.41 g).

NMR(CDCl$_3$) δ: 1.48 (9H,s), 1.84–1.97 (1H,m), 2.33–2.45 (1H,m), 3.05 (3H,s), 3.55–3.65 (2H,m), 3.74–3.93 (2H,m), 4.05–4.22 (1H,m), 4.43–4.60 (1H,m), 5.17–5.26 (1H, br)

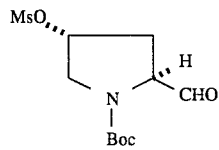
2)

A solution of oxalyl chloride (1.71 g, 13.5 mmol) in methylene chloride (50 ml) was cooled to −78° C. and a solution of dimethyl sulfoxide (2.18 g, 27.1 mmol) in methylene chloride (5 ml) was added thereto. This solution was stirred for 10 minutes. To this solution was added a solution of the alcohol crude product obtained by the above reaction in methylene chloride (10 ml). The mixture was stirred for 10 minutes, and then triethylamine (4.76 ml, 33.9 mmol) was dropwise added at the same temperature. The reaction solution was gradually warmed to 20° C. over a period of 2 h. To the reaction mixture was added saturated aqueous ammonium chloride, and the mixture was extracted with ethyl acetate. The organic layer was washed with saturated aqueous sodium chloride, and dried over anhydrous magnesium sulfate. The solvent was removed in vacuo. The residue was purified by silica gel column chromatography (heptane-ethyl acetate=1:4) to give the title compound (829 mg, yield: 84.5%).

NMR(CDCl$_3$) δ: 1.45 & 1.49 (total 9H, each s), 2.04–2.32 (1H,m), 2.36–2.61 (1H,m), 3.05 & 3.07 (total 3H, each s), 3.51–4.02 (2H,m), 4.23–4.49 (1H,m), 5.18–5.30 (1H,m), 9.47 & 9.59 (total 1H, each d,J=3.0Hz)

REFERENCE EXAMPLE 46

(2S,4R)-N-tert-Butoxycarbonyl-4-tert-butyldimethylsiloxy-2-[1-hydroxy-2-(methoxycarbonyl)ethyl]pyrrolidine

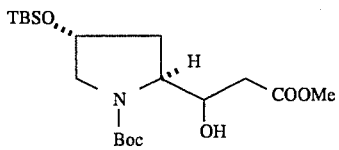

To tetrahydrofuran (5 ml) were successively dropwise added a 1.0M sodium hexamethyldisilazide—tetrahydrofuran solution (0.910 ml, 0.910 mmol) and methyl acetate (72.0 μl) at −78° C. The mixture was stirred for 30 minutes, and a tetrahydrofuran solution of (2S,4R)-N-tert-butoxycarbonyl-4-tert-butyldimethylsiloxyprolinal (200 mg, 0.607 mmol) was added thereto at the same temperature. This solution was stirred for 30 minutes. Saturated aqueous ammonium chloride was added to the reaction solution, and the mixture was extracted with ethyl acetate. The organic layer was washed with saturated aqueous sodium chloride, and dried over anhydrous magnesium sulfate. The solvent was removed in vacuo. The residue was purified by silica gel column chromatography (heptane-ethyl acetate=3:1) to give the title compound [232 mg, yield: 94.7%; (R)-isomer (polar compound):(S)-isomer (less polar compound)=6.27:1].

NMR(CDCl$_3$) δ: 0.05 (6H,s), 0.86 & 0.88 (total 9H, each s), 1.46 & 1.45 (total 9H, each s), 1.78–2.06 (2H,m), 2.34–2.49 (2H,m), 3.27 (dd,J=4.2,11.4Hz) & 3.23–3.30 (m)= (total 1H), 3.4–3.65 (1H,m), 3.696 & 3.704 (total 3H, each s), 3.8–4.26 (2H,m), 4.23–4.39 (2H,br)

REFERENCE EXAMPLE 47

(2S,4R)-N-tert-Butoxycarbonyl-4-tert-butyldimethylsiloxy-2-[1-hydroxy-2-(methoxycarbonyl)ethyl]pyrrolidine

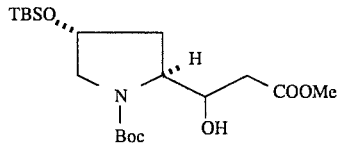

To a mixture of tetrahydrofuran (45 ml) and tetraethylethylenediamine (1.5 ml) were successively added a 1.0M sodium hexamethyldisilazide—tetrahydrofuran solution (0.892 ml) and methyl acetate (71.2 μl) at −78° C. The mixture was stirred for 30 minutes, and then a tetrahydrofuran solution of (2S,4R)-N-tert-butoxycarbonyl- 4-(tert-butyldimethylsiloxy)prolinal (196 mg) was added thereto. This solution was stirred for 30 minutes. Saturated aqueous ammonium chloride was added to the reaction solution. The mixture was extracted with ethyl acetate. The organic layer was washed with saturated aqueous sodium chloride, and dried over anhydrous magnesium sulfate. The solvent was removed in vacuo. The residue was purified by silica gel column chromatography (heptane-ethyl acetate=3:1) to obtain the title compound [209 mg, yield: 87.1%; (R)-isomer (polar compound):(S)-isomer (less polar compound)= 1.82:1].

NMR(CDCl$_3$) δ: 0.05 (6H, s), 0.86 & 0.88 (total 9H, each s), 1.46 & 1.45 (total 9H, each s), 1.78–2.06 (2H,m), 2.34–2.49 (2H,m), 3.27 (dd,J=4.2,11.4Hz) & 3.23–3.30 (m)=(total 1H), 3.4–3.65 (1H,m), 3.696 & 3.704 (total 3H, each s), 3.8–4.26 (2H,m), 4.23–4.39 (2H,br)

REFERENCE EXAMPLE 48

(2S,4R)-N-tert-Butoxycarbonyl-2 -(2-tert-butoxycarbonyl-1-oxoethyl)-4-methanesulfonyloxypyrrolidine

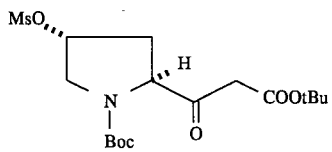

To a solution of (2S,4R)-N-tert-butoxycarbonyl-2-(2 -tert-butoxycarbonyl-1-oxoethyl)-4-tert-butyldimethylsiloxypyrrolidine (3.39 g, 7.64 mmol) in tetrahydrofuran (35 ml) was added a 1M tetrabutylammonium fluoride—tetrahydrofuran solution (8.41 ml, 8.41 mmol). This solution was stirred at room temperature for 8 h. Saturated aqueous ammonium chloride was added thereto. The mixture was extracted with ethyl acetate. The organic layer was washed successively with water and saturated aqueous sodium chloride, and dried over anhydrous magnesium sulfate. The solvent was removed in vacuo. The residue was dissolved in methylene chloride (50 ml), and triethylamine (3.22 ml, 22.9 mmol) and methanesulfonyl chloride (1.18 ml, 15.3 mmol) were successively dropwise added thereto at 0° C. The mixture was stirred at the same temperature for 2 h. Then, saturated aqueous ammonium chloride was added thereto. The mixture was extracted with ethyl acetate. The organic layer was washed successively with 1N hydrochloric acid, saturated aqueous sodium hydrogencarbonate and saturated aqueous sodium chloride, and dried over anhydrous magnesium sulfate. The solvent was removed in vacuo. The residue was purified by silica gel column chromatography (heptane-ethyl acetate=1:1) to obtain the title compound (2.33 g, yield: 74.8%).

NMR(CDCl$_3$) δ: 1.45 & 1.47 (total 18H, each s), 2.22–2.41 (1H,m), 2.48–2.72 (1H,m), 3.05 (3H,s), 3.40 (d,J=16.2Hz) & 3.49 (d,J=16.2Hz) & 3.54 (d,J=15.8Hz) & 3.61 (d,J=15.8Hz)=(total 2H), 3.62–3.69 (1H,m), 3.81–4.00 (1H,m), 4.52 (dd,J=8.6,8.6Hz) & 4.61 (dd,J=8.0,8.0Hz)=(total 1H), 5.20–5.28 (1H,m)

REFERENCE EXAMPLE 49

(2S,4R)-N-tert-Butoxycarbonyl-4-methanesulfonyloxy-2 [(R)-1-hydroxy-2-(N-methylcarbamoyl) ethyl]pyrrolidine

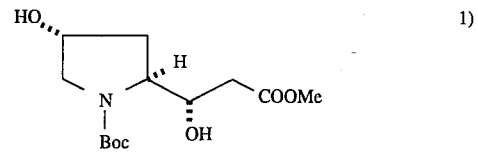
1)

To a solution of (2S,4R)-1-tert-butoxycarbonyl-4 -tert-butyldimethylsiloxy-2-[(R)-1-hydroxy-2 -(methoxycarbonyl)ethyl]pyrrolidine (2.40 g, 5.95 mmol) in tetrahydrofuran (24 ml) was dropwise added a 1M tetrabutylammonium fluoride—tetrahydrofuran solution (7.14 ml) at room temperature. The mixture was stirred at the same temperature for 4 h. The reaction solution was washed with saturated aqueous sodium chloride, and dried over anhydrous magnesium sulfate. The solvent was removed in vacuo. The residue was purified by silica gel column chromatography (heptane-ethyl acetate=3:7) to obtain (2S,4R)-N-tert-butoxycarbonyl-4-hydroxy-2-[(R)-1 -hydroxy-2-(methoxycarbonyl)ethyl]pyrrolidine diastereomer B (1.22 g, yield: 70.9%).

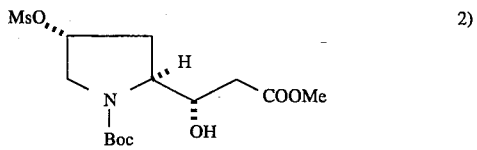
2)

The above compound (1.22 g, 4.22 mmol) was dissolved in methylene chloride (12 ml), and triethylamine (0.647 ml, 4.64 mmol) and methanesulfonyl chloride (0.359 ml) were successively dropwise added thereto at 0° C. The mixture was stirred at 0° C. for 1 h. Then, saturated aqueous ammonium chloride was added thereto. The mixture was extracted with ethyl acetate. The organic layer was washed with saturated aqueous sodium chloride, and dried over anhydrous magnesium sulfate. Then, the solvent was removed in vacuo. The residue was purified by silica gel column chromatography (heptane-ethyl acetate=2:3) to obtain (2S,4R)-N-tert-butoxycarbonyl-4 -methanesulfonyloxy-2-[(R)-1-hydroxy-2 -(methoxycarbonyl)ethyl]pyrrolidine (947 mg, yield: 43.3 %).

NMR(CDCl$_3$) δ: 1.48 (9H,s), 2.21–2.62 (4H,m), 3.04 (3H,s), 3.45–3.62 (1H,m), 3.72 (3H,s), 3.82–4.23 (3H,m), 4.39–4.48 (1H,m), 5.20–5.30 (1H,m)

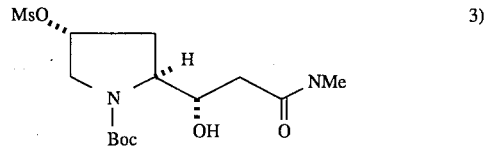
3)

The above compound (724 mg, 1.97 mmol) was dissolved in a 40% methylamine—methanol solution (4 ml). The solution was stirred at room temperature for 14 h. The reaction solution was concentrated in vacuo. The residue was diluted with ethyl acetate. The solution was washed successively with saturated aqueous sodium chloride, saturated aqueous copper sulfate and saturated aqueous sodium sulfate, and dried over anhydrous magnesium sulfate. The solvent was removed in vacuo to obtain a crude product of the title compound (400 mg, yield: 55.4 %).

NMR(CDCl₃) δ: 1.47 (9H,s), 2.10–2.36 (4H,m), 2.81 (3H,d,J=4.6Hz), 3.04 (3H,s), 3.52 (dd,J=4.1,12.8Hz) & 3.48–3.59 (m)=(total 1H), 3.85–3.99 (1H,m), 4.06–4.16 (2H,m), 5.03–5.16 & 5.18–5.29 (total 2H, each br), 6.51–6.63 (1H,br).

REFERENCE EXAMPLE 50

(2S,4R)-N-tert-Butoxycarbonyl-4-tert-butyldimethylsiloxy-2-[(R,S)-2-ethoxycarbonyl-1-hydroxyethyl]pyrrolidine

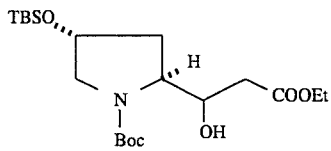

A solution of (2S,4R)-N-tert-butoxycarbonyl-4-tert-butyldimethylsiloxyprolinal (1.0 g, 3.04 mmol) and ethyl trimethylsilyl acetate (1.0 ml, 5.47 mmol) in tetrahydrofuran (7.5 ml) was added to a 0.1M tetrabutylammonium fluoride—tetrahydrofuran solution (45.6 ml) under a nitrogen atmosphere at −35° C. The mixture was stirred at a temperature of from −25° to −35° C. for 40 minutes. To the reaction solution was added a solution of dl-camphor sulfonic acid (2.12 g, 9.13 mmol) in tetrahydrofuran (10 ml) at the same temperature, and the mixture was stirred for 15 minutes. The reaction mixture was extracted with ethyl acetate (100 ml). The organic layer was washed successively with water, saturated aqueous sodium hydrogencarbonate and saturated aqueous sodium chloride, dried over anhydrous magnesium sulfate, and concentrated in vacuo. The residue was subjected to silica gel column chromatography (Wakogel™ C-300, hexane-ethyl acetate=2:1) to give the title compound [820 mg, yield: 64.7%; (R)-isomer (polar compound):(S)-isomer (less polar compound)=9.56:1].

REFERENCE EXAMPLE 51

(2S,4R)-N-tert-Butoxycarbonyl-4-tert-butyldimethylsiloxy-2-(3-hydroxy-1-oxopropyl)pyrrolidine

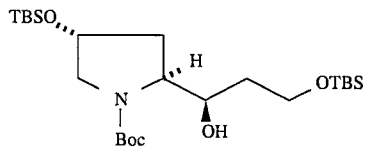

To a solution of (2S,4R)-1-tert-butoxycarbonyl-4-tert-butyldimethylsiloxy-2-[(S)-1,3-dihydroxypropyl]pyrrolidine (16.95 g, 45.2 mmol) in methylene chloride (200 ml) were successively added tert-butylchlorodimethylsilane (6.81 g, 45.2 mmol), 4-N,N-dimethylaminopyridine (0.55 g, 4.5 mmol) and imidazole (3.08 g, 45.2 mmol) in a nitrogen atmosphere under cooling with ice under stirring. The mixture was stirred at room temperature for 1 h. Then, the reaction solution was poured into water (200 ml). The organic layer was washed with water, dried over anhydrous sodium sulfate, and concentrated in vacuo. The residue was subjected to silica gel column chromatography (Wakogel™ C-300, heptane-ethyl acetate=9:1→4:1) to give (2S,4 R)-N-tert-butoxycarbonyl-4-tert-butyldimethylsiloxy-2-[(S)-3-tert-butyldimethylsiloxy-1-hydroxypropyl]pyrrolidine (20.36 g, yield: 92.0%).

NMR(CDCl₃) δ: 0.05 (6H,s), 0.86 (9H,s), 1.47 (9H,s), 1.91–2.03 (2H,m), 3.24–3.31 (1H,m), 3.48–3.86 (5H,m), 3.97–4.09 (1H,m), 4.30 (1H,br s), 4.96 (1H,br s)

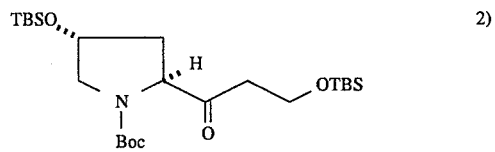

A solution of oxalyl chloride (3.06 ml) in methylene chloride (100 ml) was cooled to a temperature of not higher than −70° C. under a nitrogen atmosphere, and a solution of dimethyl sulfoxide (6.24 ml) in methylene chloride (20 ml) was gradually dropwise added thereto. The mixture was stirred at the same temperature for 30 minutes. Then, a solution of the compound obtained by the above reaction (14.68 g, 30.0 mmol) in methylene chloride (100 ml) was dropwise added thereto over a period of 5 minutes. The mixture was stirred at −70° C. for 30 minutes. Then, triethylamine (19.61 ml) was dropwise added thereto, and the mixture was stirred at the same temperature for 1 h. The reaction mixture was heated to room temperature and concentrated in vacuo. Ethyl acetate (100 ml) and water (100 ml) were added to the residue. The organic layer was dried over anhydrous sodium sulfate, and concentrated in vacuo. The residue was subjected to silica gel column chromatography (Wakogel™ C-300, heptane-ethyl acetate=1:1) to give (2S,4R)-N-tert-butoxycarbonyl-4-tert-butyldimethylsiloxy-2-(3-tert-butyldimethylsiloxy-1-oxopropyl)pyrrolidine (14.31 g, yield: 97.9%) as an oil.

NMR(CDCl₃) δ: 0.05 (6H,s), 0.86 (9H,s), 1.40 (9H,s), 1.93–2.07 (2H,m), 2.59–2.73 (2H,m), 3.50–3.54 (2H,m), 3.85–3.92 (2H,m), 4.32–4.46 (2H,m)

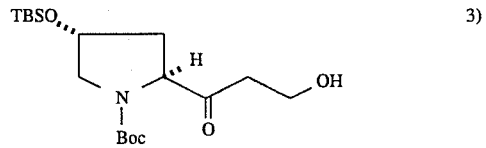

To a solution of the above compound (4.87 g, 10 mmol) in tetrahydrofuran (12.0 ml) were added water (28 ml) and acetic acid (52 ml) at room temperature. The mixture was stirred at room temperature for 24 h. Then, the reaction mixture was concentrated in vacuo. The residue was subjected to silica gel column chromatography (Wakogel™ C-300, heptane-ethyl acetate=1:1) to give the title compound (2.50 g, yield: 67.0%).

NMR(CDCl₃) δ: 0.06 (6H,s), 0.87 (9H,s), 1.44 (9H,s), 1.81–1.91 (1H,m), 2.04–2.16 (1H,m), 2.63–2.88 (2H,m), 3.37–3.60 (2H,m), 3.84–3.95 (2H,m), 4.33–4.60 (2H,m)

REFERENCE EXAMPLE 52

(2S,4R)-4-Hydroxy-2-(3-hydroxy-1-oxopropyl)pyrrolidine Monohydrochloride

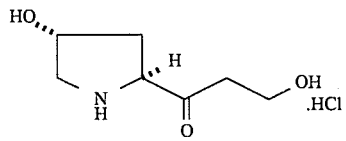

(2S,4R)-N-tert-Butoxycarbonyl-4-tert-butyldimethylsiloxy- 2-(3-tert-butyldimethylsiloxy-1 -oxopropyl)pyrrolidine (4.87 g, 10.0 mmol) was dissolved in a 3.3N hydrogen chloride—methanol solution (16.5 ml). The solution was stirred at room temperature for 24 h, and then concentrated in vacuo to obtain the title compound (2.29 g).

NMR(D₂O) δ: 2.06–2.21 (1H,m), 2.53–2.65 (1H,m), 2.84–2.95 (2H,m), 3.39–3.43 (2H,m), 3.72–3.91 (2H,m), 4.66–4.76 (1H,m), 4.82–4.88 (1H,m)

REFERENCE EXAMPLE 53

(2S,4R)-N-tert-Butoxycarbonyl-4-(tert-butyldimethylsiloxy)- 2-[(R,S)-2-cyano-1-hydroxyethyl]pyrrolidine

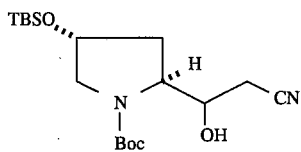

Under a nitrogen atmosphere, acetonitrile (87 µl, 1.67 mmol) was dropwise added at −78° C. to a solution comprising a 2.0M lithium diisopropylamide—tetrahydrofuran solution (835 µl, 1.67 mmol) and tetrahydrofuran (15 ml). The mixture was stirred at −78° C. for 10 minutes, and then a solution of (2S,4 R)-N-tert-butoxycarbonyl-4-tert-butyldimethylsiloxyprolinal (500 mg, 1.52 mmol) in tetrahydrofuran (1 ml) was dropwise added thereto. The reaction mixture was stirred for 20 minutes. Then, acetic acid was added to the reaction mixture. The reaction mixture was poured into a mixture of ethyl acetate—water. The organic layer was washed with saturated aqueous sodium chloride, dried over anhydrous sodium sulfate and concentrated in vacuo. The obtained oily residue was subjected to silica gel column chromatography (heptane-ethyl acetate=3:1) to give the title compound [467 mg, yield: 83%, (R)-isomer (polar compound):(S)-isomer (less polar compound)=2.99:1].

NMR(CDCl₃) δ: 0.06 (6H,s), 0.85 (9H,s), 1.45 (9H,s), 1.81–2.09 (2H,m), 2.37–2.56 (2H,m), 3.20–3.36 (1H,m), 3.50–3.64 (1H,m), 4.03–4.41 (3H,m)

REFERENCE EXAMPLE 54

(2S,4R)-N-tert-Butoxycarbonyl-4-tert-butyldimethylsiloxy-2-[1-hydroxy-2-(N-methylcarbamoyl)ethyl]pyrrolidine

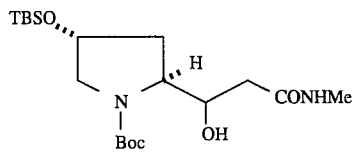

Under a nitrogen atmosphere, a solution of N-methylacetamide (116 µl, 1.52 mmol) in tetrahydrofuran (2 ml) and then hexamethylphosphoric triamide (555 µl, 3.19 mmol) were dropwise added at −78° C. to a solution comprising 2.0M lithium diisopropylamide—tetrahydrofuran (1.6 ml, 3.19 mmol) and tetrahydrofuran (10 ml). The mixture was stirred at −78° C. for 30 minutes. Then, a solution of (2S,4R)-N-tert-butoxycarbonyl- 4-tert-butyldimethylsiloxyprolinal (500 mg, 1.52 mmol) in tetrahydrofuran (2 ml) was dropwise added. The reaction mixture was stirred at room temperature for 2 h. Water was added to the reaction mixture. Then, the reaction mixture was poured into a mixture of ethyl acetate-water. The organic layer was washed with saturated aqueous sodium chloride, dried over anhydrous sodium sulfate, and concentrated in vacuo. The obtained oily residue was subjected to silica gel column chromatography (chloroform—methanol=20:1) to give the title compound (158 mg, yield: 25.9%).

NMR(CDCl₃) δ: 0.06 (6H,s), 0.87 (9H,s), 1.46 (9H,s), 1.90–2.32 (2H,m), 2.62 & 2.65 (total 3H, each s), 2.80 (2H,m), 3.20–3.28 (1H,m), 3.45–3.60 (1H,m), 3.78–4.32 (3H,m), 6.93 (1H,m)

REFERENCE EXAMPLE 55

(2S,4R)-N-tert-Butoxycarbonyl-2-[2-(N-tert-butoxycarbonyl-N-methylcarbamoyl)-1-hydroxyethyl]-4-tert-butyldimethylsiloxypyrrolidine

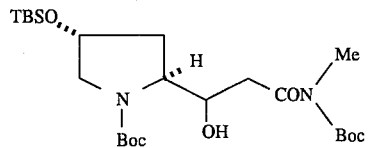

Under a nitrogen atmosphere, a solution of N-tert-butoxycarbonyl-N-methylacetamide (289 mg, 1.67 mmol) in tetrahydrofuran (1.0 ml) and then hexamethylphosphoric triamide (290 µl, 1.67 mmol) were dropwise added at −78° C. to a solution comprising a 2.0M lithium diisopropylamide—tetrahydrofuran solution (835 µl, 1.67 mmol) and tetrahydrofuran (10 ml). The mixture was stirred at −78° C. for 20 minutes, and a solution of (2S,4 R)-N-tert-butoxycarbonyl-4-tert-butyldimethylsiloxyprolinal (500 mg, 1.52 mmol) in tetrahydrofuran (2 ml) was dropwise added thereto. The reaction mixture was stirred at the same temperature for 30 minutes. Saturated aqueous ammonium chloride was added to the reaction mixture, and then the reaction mixture was poured into a mixture of ethyl acetate—water. The organic layer was washed with saturated aqueous sodium chloride, dried over anhydrous sodium sulfate, and concentrated in vacuo. The obtained oily residue was subjected to silica gel column chromatography (heptane-ethyl acetate=1:2) to give the title compound (288.8 mg, yield: 37.8%).

NMR(CDCl₃) δ: 0.06 (6H,s), 0.84 (9H,s), 1.46 (18H,s), 1.82–2.11 (2H,m), 2.36–2.51 (2H,m), 2.77 & 2.80 (total 3H, each s), 3.27–3.50 (2H,m), 3.97–4.44 (2H,m), 5.32–5.46 (1H,m)

REFERENCE EXAMPLE 56

(2S,4R)-2-[2-(N-Benzyl-N-methylcarbamoyl)-1-hydroxyethyl]-4-tert-butyldimethylsiloxypyrrolidine

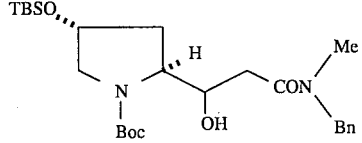

Under a nitrogen atmosphere, a solution of N-benzyl-N-methylacetamide (280 mg, 1.67 mmol) in tetrahydrofuran (1 ml) was dropwise added at −78° C. to a solution comprising a 2.0M lithium diisopropylamide—tetrahydrofuran solution (835 µl, 1.67 mmol) and tetrahydrofuran (15 ml). The mixture was stirred at −78° C. for 10 minutes, and then a solution of (2S,4 R)-N-tert-butoxycarbonyl-4-tert-butyldimethylsiloxyprolinal (500 mg, 1.52 mmol) in tetrahydrofuran (1 ml) was dropwise added thereto. The reaction mixture was stirred at the same temperature for 10 minutes. Saturated aqueous ammonium chloride was added to the reaction mixture, and then the reaction mixture was poured into a mixture of ethyl acetate—water. The organic layer was washed with saturated aqueous sodium chloride, dried over anhydrous sodium sulfate and concentrated in vacuo. The obtained oily residue was subjected to silica gel column chromatography (heptane-ethyl acetate=2:1) to give the title compound (549 mg, yield: 73.6%).

NMR(CDCl₃) δ: 0.06 (6H,s), 0.86 (9H,s), 1.41 (9H,s), 1.79–2.21 (2H,s), 2.34–2.61 (2H,m), 2.91 (3H,m), 3.23–3.51 (2H,m), 3.98–4.86 (3H,m)

REFERENCE EXAMPLE 57

(2S,4S)-2-[(R)-1-Hydroxy-3-(N-methylamino)propyl]-4- mercaptopyrrolidine Hydrochloride

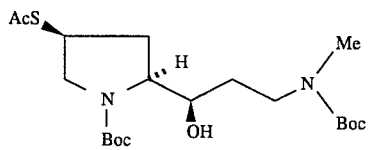
1)

To a solution of (2S,4R)-N-tert-butoxycarbonyl-2 -[(R)-3-(N-tert-butoxycarbonyl-N-methylamino)-1 -hydroxypropyl]-4-hydroxypyrrolidine (1.0 g, 2.67 mmol, intermediate prepared in REFERENCE EXAMPLE 27-2) in tetrahydrofuran (10 ml) were successively added triphenylphosphine (842 mg, 3.21 mmol) and diethyl azodicarboxylate (0.505 ml, 3.21 mmol) under a nitrogen atmosphere under cooling with ice. The mixture was stirred at the same temperature for 10 minutes, and then thioacetic acid (0.25 ml, 0.35 mmol) was dropwise added thereto. The reaction solution was stirred at the same temperature for 2.5 h and then concentrated in vacuo. A mixture (10 ml) of hexane-ethyl acetate (5:1) was added to the residue. The precipitate was filtered off, and the filtrate was concentrated in vacuo. The residue was subjected to silica gel column chromatography (Wakogel™ C-300, hexane-ethyl acetate=5:1) to give (2S,4 R)-N-tert-butoxycarbonyl-4-acetylthio-2-[(R)-3 -(N-tert-butoxycarbonyl-N-methylamino)-1-hydroxypropyl]pyrrolidine (1.03 g, yield: 89.2%). The data of this compound agreed with those of the compound prepared in REFERENCE EXAMPLE 27-2.

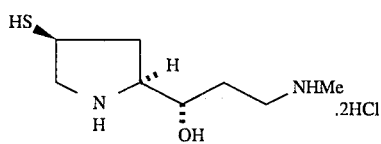
2)

To a solution of the above compound (1.03 g, 2.38 mmol) in methanol (10 ml) was added a 5.5N hydrogen chloride—methanol solution (2.4 ml). The reaction solution was refluxed for 1 h and concentrated in vacuo. A tetrahydrofuran—methanol (3:1) solution and seed crystals were added to the residue, and the mixture was left to stand overnight under cooling with ice. Precipitated crystals were collected by filtration and dried to obtain the title compound (486 mg, yield: 77.1 %).

REFERENCE EXAMPLE 58

(2S,4S)-2-[(R)-1-Hydroxy-3-(N-methylamino)propyl]-4 -mercaptopyrrolidine Dihydrochloride

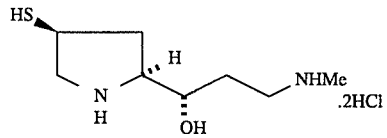

Diisopropyl azodicarboxylate (63.2 ml, 320.9 mmol) was dropwise added over a period of 30 minutes to a solution of (2S,4R)-N-tert-butoxycarbonyl-2-[(R)-3 -(N-tert-butoxycarbonyl-N-methylamino)-1-hydroxypropyl]-4 -hydroxypyrrolidine (100 g, 267.4 mmol) and triphenylphosphine (84.2 g, 320.9 mmol) in tetrahydrofuran (1 l) under a nitrogen atmosphere under cooling with ice under stirring. The mixture was stirred for 10 minutes under cooling with ice, and then thioacetic acid (22.9 ml, 320.9 mmol) was dropwise added thereto over a period of 30 minutes. The reaction solution was stirred for 1 h and 15 minutes and then concentrated in vacuo. The obtained oily residue was dissolved in a heptane-ethyl acetate mixture (1:1, 200 ml). This mixture was stirred for 1 h under cooling with ice. The precipitate was filtered off, and the filtrate was concentrated in vacuo. To the obtained residue was added a 3.4N hydrogen chloride—methanol solution (600 ml). The mixture was stirred at room temperature for 18 h. This mixture was concentrated in vacuo. To the obtained oily residue was added ethanol (350 ml), and the mixture was left to stand to obtain crystals of the title compound (43.07 g, yield: 61.2%).

NMR(D₂O) δ: 1.88–2.06 (3H,m), 1.58–1.64 (1H,m), 2.79 (3H,s), 3.16–3.32 (3H,m), 3.58–3.88 (3H,m), 4.09–4.18 (1H,m)

REFERENCE EXAMPLE 59

(2S,4R)-N-Formyl-4-methanesulfonyloxyproline Methyl Ester

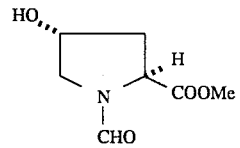
1)

To a suspension of (2S,4R)-4-hydroxyproline methyl ester hydrochloride (9.08 g, 50.0 mmol) in methyl formate (90.0 ml) was added triethylamine (11.85 ml, 85.0 mmol). The mixture was refluxed for 5 h. The precipitate was filtered off, and the filtrate was concentrated in vacuo. The residue was subjected to silica gel column chromatography (Wakogel™ C-300, heptane-ethyl acetate=4:1→3:2) to give (2S,4R)-N-formyl-4-hydroxyproline methyl ester (6.70 g, yield: 77.4%).

NMR(CDCl₃) δ: 2.05–2.45 (2H,m), 3.43–3.72 (5H,m), 4.56–4.64 (2H,m), 8.25 (1H,s)

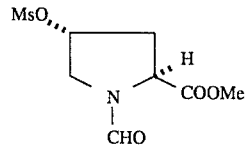
2)

To a solution of the above compound (0.866 g, 5.0 mmol) in methylene chloride (20 ml) were successively added methanesulfonyl chloride (0.387 ml, 5.0 mmol) and triethylamine (0.697 ml, 5.0 mmol) under a nitrogen atmosphere under cooling with ice under stirring. The mixture was stirred for 1 h at the same temperature. Then, the reaction solution was washed with water, dried over anhydrous sodium sulfate and concentrated in vacuo. The residue was subjected to silica gel column chromatography (Wakogel™ C-300, ethyl acetate) to give the title compound (1.070 g, yield: 85.2%).

NMR(CDCl₃) δ: 2.23–2.74 (3H,m), 3.06 (3H,s), 3.80 (3H,s), 4.12 (1H,m), 4.64 (1H,m), 5.32 (1H,m), 8.27 (1H,s)

REFERENCE EXAMPLE 60

(2S,4R)-4-tert-Butyldimethylsiloxy-N-formylproline Methyl Ester

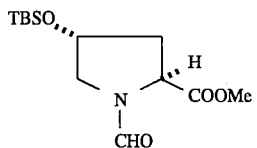

To a solution of (2S,4R)-1-formyl-4-hydroxyproline methyl ester (3.46 g, 20.0 mmol) in N,N-dimethylformamide (10 ml) and methylene chloride (20 ml) were successively added tert-butylchlorodimethylsilane (3.20 g, 21.2 mmol) and imidazole (1.47 g, 21.6 mmol) under a nitrogen atmosphere under cooling with ice under stirring. The mixture was stirred at room temperature for 4 h. Then, the reaction solution was washed with water, dried over anhydrous sodium sulfate and concentrated in vacuo. The residue was subjected to silica gel column chromatography (Wakogel™ C-300, heptane-ethyl acetate=1:1) to give the title compound (5.54 g, yield: 96.3%).

NMR(CDCl₃) δ: 0.06 (6H,s), 0.85 (9H,s), 2.03–2.26 (2H,m), 3.43–3.76 (5H,m), 4.42–4.59 (2H,m), 8.23 (1H,s)

We claim:

1. A compound of the formula:

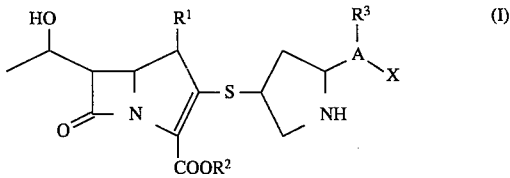

wherein $R^1$ is a hydrogen atom or a methyl group, $R^2$ is a hydrogen atom or a negative charge, $R^3$ is a halogen atom, a hydroxyl group, a lower alkoxy group, a lower alkanoyloxy group, an amino group, an N-lower alkylamino group, an N,N-di-lower alkylamino group, a lower alkanoylamino group, an aroylamino group, a (lower alkylsulfonyl)amino group, a sulfamoylamino group, a cyano group, a nitro group, a group of —COOR⁴ (wherein $R^4$ is a hydrogen atom or a lower alkyl group) or a group of —CON(R⁵)R⁶ (wherein each of $R^5$ and $R^6$ which may be the same or different, is a hydrogen atom or a lower alkyl group, or $R^5$ and $R^6$ form together with the adjacent nitrogen atom a heterocyclic group selected from the group consisting of an aziridinyl group, an azetidinyl group, a pyrrolidinyl group, a piperidyl group, a piperazinyl group, a 4-lower alkyl piperazinyl group and a morpholino group), A is a linear or branched lower alkylene group, X is a group of —N(R⁷)R⁸ (wherein each of $R^7$ and $R^8$ which may be the same or different, is a hydrogen atom or a lower alkyl group) or a group of —N⁺(R⁹)(R¹⁰)R¹¹ (wherein each of $R^9$, $R^{10}$ and $R^{11}$ which may be the same or different, is a lower alkyl group); or a pharmaceutically acceptable salt or ester thereof.

2. The compound according to claim 1, which is represented by the formula:

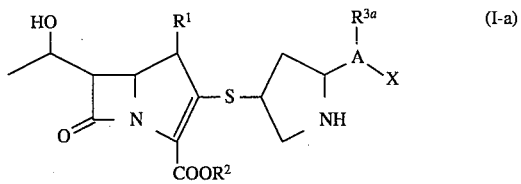

wherein $R^1$ is a hydrogen atom or a methyl group, $R^2$ is a hydrogen atom or a negative charge, $R^{3a}$ is a halogen atom, a hydroxyl group, a lower alkoxy group, a lower alkanoyloxy group, an amino group, an N-lower alkylamino group, a lower alkanoylamino group, a (lower alkylsulfonyl)amino group, a cyano group or a carbamoyl group, A is a linear or branched lower alkylene group, X is a group of —N(R⁷)R⁸ (wherein each of $R^7$ and $R^8$ which may be the same or different, is a hydrogen atom or a lower alkyl group) or a group of —N⁺(R⁹)(R¹⁰)R¹¹ (wherein each of $R^9$, $R^{10}$ and $R^{11}$ which may be the same or different, is a lower alkyl group); or a pharmaceutically acceptable salt or ester thereof.

3. The compound according to claim 1, which is represented by the formula:

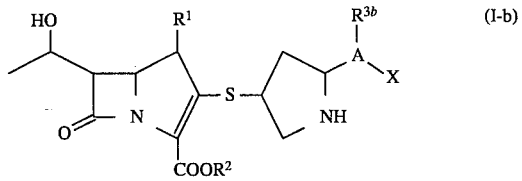

wherein $R^1$ is a hydrogen atom or a methyl group, $R^2$ is a hydrogen atom or a negative charge, $R^{3b}$ is a hydroxyl group, an amino group, a lower alkanoylamino group, a (lower alkylsulfonyl)amino group, a cyano group or a carbamoyl group, A is a linear or branched lower alkylene group, X is a group of —N(R⁷)R⁸ (wherein each of $R^7$ and $R^8$ which may be the same or different, is a hydrogen atom or a lower alkyl group) or a group of —N⁺(R⁹)(R¹⁰)R¹¹ (wherein each of $R^9$, $R^{10}$ and $R^{11}$ which may be the same or different, is a lower alkyl group); or a pharmaceutically acceptable salt or ester thereof.

4. The compound according to claim 1, which is represented by the formula:

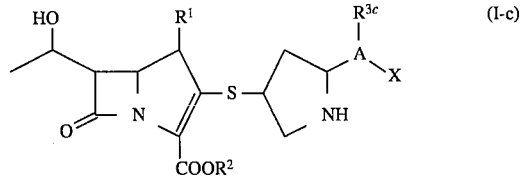

wherein $R^1$ is a hydrogen atom or a methyl group, $R^2$ is a hydrogen atom or a negative charge, $R^{3c}$ is a halogen atom, a lower alkoxy group, an N-lower alkylamino group or a lower alkanoyloxy group, A is a linear or a branched lower alkylene group, X is a group of —N(R⁷)R⁸ (wherein each of $R^7$ and $R^8$ which may be the same or different, is a hydrogen atom or a lower alkyl group) or a group of —N⁺(R⁹)(R¹⁰)R¹¹ (wherein each of $R^9$, $R^{10}$ and $R^{11}$ which may be the same or different, is a lower alkyl group), provided that when A is a linear lower alkylene group, $R^{3c}$ is other than a hydrogen atom; or a pharmaceutically acceptable salt or ester thereof.

5. The compound according to claim 1, wherein A is a branched lower alkylene group.

6. The compound according to claim 1, wherein $R^3$ is a hydroxyl group.

7. The compound according to claim 1, wherein A is a branched lower alkylene group, and $R^3$ is a hydroxyl group or a carbamoyl group.

8. The compound according to claim 1, wherein A is a linear lower alkylene group, and $R^3$ is a halogen atom, a hydroxyl group, a lower alkoxy group, a lower alkanoyloxy group, an amino group, a lower alkanoylamino group, a (lower alkylsulfonyl)amino group, a cyano group or a carbamoyl group.

9. The compound according to claim 1, which has a steric configuration of (5R,6S,8R) or (1R,5S,6S,8R).

10. The compound according to claim 1, wherein $R^1$ is a methyl group.

11. The compound according to claim 1, which is:
(5R,6S)-2-[(2S,4S)-2-(1-aminomethyl-2-carbamoylethyl)pyrrolidin- 4-ylthio]-6-[(1R)-1-hydroxyethyl]-1-carbapen-2-em- 3-carboxylic acid,
(1R,5S,6S)-2-[(2S,4S)-2-(1-aminomethyl-2-carbamoylethyl)pyrrolidin- 4-ylthio]-6-[(1R)-1-hydroxyethyl]-1-methyl-1-carbapen-2-em-3-carboxylic acid,
(5R,6S)-2-[(2R,4S)-2-(2-amino-2-carbamoylethyl)-pyrrolidin-4 -ylthio]-6-[(1R)-1-hydroxyethyl]-1-carbapen-2-em-3-carboxylic acid,
(1R,5S,6S)-2-[(2R,4S)-2-(2-amino-2-carbamoylethyl)-pyrrolidin- 4-ylthio]-6-[(1R)-1-hydroxyethyl]-1-methyl-1-carbapen-2-em -3 -carboxylic acid,
(5R,6S)-2-[(2S,4S)-2-(1-acetamido-2-aminoethyl)-pyrrolidin-4 -ylthio]-6-[(1R)-1-hydroxyethyl]-1-carbapen-2-em-3-carboxylic acid,
(1R,5S,6S)-2-[(2S,4S)-2-(1-acetamido-2-aminoethyl)-pyrrolidin- 4-ylthio]-6-[(1R)-1-hydroxyethyl]-1-methyl-1-carbapen -2-em-3 -carboxylic acid,
(5R,6S)-6-[(1R)-1-hydroxyethyl]-2-[(2S,4S)-2-(1 -methanesulfonylamido-2-aminoethyl)pyrrolidin-4-ylthio]-1-carbapen-2-em-3-carboxylic acid,
(1R,5S,6S)-6-[(1R)-1-hydroxyethyl]-1-methyl-2-[(2S,4S)-2-(1 -methanesulfonylamido-2-aminoethyl)pyrrolidin-4-ylthio]-1 -carbapen-2-em-3-carboxylic acid,
(5R,6S)-2-[(2S,4S)-2-(1-amino-1-cyanomethyl)pyrrolidin-4-ylthio]-6-[(1R)-1-hydroxyethyl]-1-carbapen-2-em-3-carboxylic acid,
(1R,5S,6S)-2-[(2S,4S)-2-(1-amino-1-cyanomethyl)-pyrrolidin-4 -ylthio]-6-[(1R)-1-hydroxyethyl]-1-methyl-1-carbapen-2-em 3 -carboxylic acid,
(1R,5S,6S)-2-[(2R,4S)-2-[(3-amino-2-methyl)propyl]-pyrrolidin- 4-ylthio]-6-[(1R)-1-hydroxyethyl]-1-methyl-1-carbapen-2-em -3 -carboxylic acid,
(5R,6S)-2-[(2S,4S)-2-[(3-amino-1-hydroxy)propyl]-pyrrolidin-4 -ylthio]-6-[(1R)-1-hydroxyethyl]-1-carbapen-2-em-3-carboxylic acid,
(1R,5S,6S)-2-[(2S,4S)-2-[(3-amino-1-hydroxy) propyl]pyrrolidin-4-ylthio]-6-[(1R)-1-hydroxyethyl]-1-methyl-1-carbapen-2-em-3-carboxylic acid,
(5R,6S)-2-[(2S,4S)-2-(1,3-diaminopropyl)pyrrolidin-4-ylthio]-6-[(1R)-1-hydroxyethyl]-1-carbapen-2-em-3-carboxylic acid,
(1R,5S,6S)-2-[(2S,4S)-2-(1,3-diaminopropyl)pyrrolidin-4-ylthio]-6-[(1R)-1-hydroxyethyl]-1-methyl-1-carbapen-2-em-3-carboxylic acid,
(5R,6S)-2-[(2S,4S)-2-[(2-amino-1-hydroxy)ethyl]-pyrrolidin-4-ylthio]-6-[(1R)-1-hydroxyethyl]-1-carbapen-2-em-3-carboxylic acid,
(1R,5S,6S)-2-[(2S,4S)-2-[(2-amino-1-hydroxy)ethyl]-pyrrolidin- 4-ylthio]-6-[(1R)-1-hydroxyethyl]-1-methyl-1-carbapen-2-em-3 -carboxylic acid,
(5R,6S)-2-[(2S,4S)-2-[(1-aminomethyl-3-hydroxy)propyl] pyrrolidin-4-ylthio]-6-[(1R)-1-hydroxyethyl]-1-carbapen-2-em- 3-carboxylic acid,
(1R,5S,6S)-2-[(2S,4S)-2-[(1-aminomethyl-3-hydroxy)propyl]pyrrolidin -4-ylthio]-6-[(1R)-1-hydroxyethyl]-1-methyl- 1-carbapen-2-em-3-carboxylic acid,
(5R,6S)-2-[(2S,4S)-2-[(1R)-1-methoxy-3-(N-methylamino) propyl]pyrrolidin-4-ylthio]-6-[(1R)-1-hydroxyethyl]-1-carbapen-2-em-3-carboxylic acid,
(1R,5S,6S)-2-[(2S,4S)-2-[(1R)-1-methoxy-3 -(N-methylamino)propyl]pyrrolidin-4-ylthio]-6-[(1R)-1 -hydroxyethyl]-1-methyl-1-carbapen-2-em-3-carboxylic acid,
(5R,6S)-2-[(2S,4S)-2-[(1S)-1-hydroxy-3-(N-methylamino) propyl]pyrrolidin-4-ylthio]-6-[(1R)-1-hydroxyethyl]-1-carbapen-2-em-3-carboxylic acid,
(1R,5S,6S)-2-[(2S,4S)-2-[(1R)-1-hydroxy-3 -(N-methylamino)propyl]pyrrolidin-4-ylthio]-6-[(1R)-1 -hydroxyethyl]-1-methyl-1-carbapen-2-em-3-carboxylic acid,
(5R,6S)-2-[(2S,4S)-2-[(1R)-1-hydroxy-3-(N-methylamino) propyl]pyrrolidin-4-ylthio]-6-[(1R)-1-hydroxyethyl]-1-carbapen-2-em-3-carboxylic acid,
(1R,5S,6S)-2-[(2S,4S)-2-[(1R)-1-hydroxy-3 -(N-methylamino)propyl]pyrrolidin-4-ylthio]-6-[(1R)-1-hydroxyethyl]-1-methyl-1-carbapen-2-em-3-carboxylic acid,
(5R,6S)-2-[(2S,4S)-2-[(1S)-1-hydroxy-2-(N-methylamino)ethyl]pyrrolidin-4-ylthio]-6-[(1R)-1-hydroxyethyl]-1-carbapen-2-em-3-carboxylic acid,
(1R,5S,6S)-2-[(2S,4S)-2-[(1S)-1-hydroxy-2 -(N-methylamino)ethyl]pyrrolidin-4-ylthio]-6-[(1R)-1-hydroxyethyl]-1-methyl-1-carbapen-2-em-3-carboxylic acid,
(5R,6S)-2-[(2S,4S)-2-[(1R)-1-hydroxy-2-(N-methylamino) ethyl]pyrrolidin-4-ylthio]-6-[(1R)-1-hydroxyethyl]-1-carbapen- 2-em-3-carboxylic acid,
(1R,5S,6S)-2-[(2S,4S)-2-[(1R)-1-hydroxy-2 -(N-methylamino)ethyl]pyrrolidin-4-ylthio]-6-[(1R)-1-hydroxyethyl]-1-methyl-1-carbapen -2-em-3-carboxylic acid,
(5R,6S)-2-[(2R,4S)-2-[3-hydroxy-2-(N-methylamino)propyl]pyrrolidin-4-ylthio]-6-[(1R)-1-hydroxyethyl]-1 -carbapen-2-em-3-carboxylic acid,
(1R,5S,6S)-2-[(2R,4S)-2-[3-hydroxy-2-(N-methylamino) propyl]pyrrolidin-4-ylthio]-6-[(1R)-1-hydroxyethyl]-1-methyl- 1-carbapen-2-em-3-carboxylic acid,
(5R,6S)-2-[(2S,4S)-2-[(1-aminomethyl-3-hydroxy)propyl] pyrrolidin-4-ylthio]-6-[(1R)-1-hydroxyethyl]-1-carbapen-2-em- 3-carboxylic acid,
(1R,5S,6S)-2-[(2S,4S)-2-[(1-aminomethyl-3-hydroxy)propyl]pyrrolidin-4-ylthio]-6-[(1R)-1-hydroxyethyl]-1-methyl- 1-carbapen-2-em-3-carboxylic acid,
(5R,6S)-2-[(2S,4S)-2-[[1-(2-aminoethyl)-3-hydroxy]propyl]pyrrolidin-4-ylthio]-6-[(1R)-1-hydroxyethyl]-1 -carbapen-2-em-3-carboxylic acid,
(1R,5S,6S)-2-[(2S,4S)-2-[[1-(2-aminoethyl)-3-hydroxy] propyl]pyrrolidin-4-ylthio]-6-[(1R)-1-hydroxyethyl]-1-methyl- 1-carbapen-2-em-3-carboxylic acid,
(5R,6S)-2-[(2R,4S)-2-(3-amino-2-hydroxypropyl)pyrrolidin-4 -ylthio]-6-[(1R)-1-hydroxyethyl]-1-carbapen-2-em-3-carboxylic acid,
(1R,5S,6S)-2-[(2R,4S)-2-(3-amino-2-hydroxypropyl)-pyrrolidin- 4-ylthio]-6-[(1R)-1-hydroxyethyl]-1-methyl-1-carbapen-2-em -3 -carboxylic acid,
(5R,6S)-2-[(2R,4S)-2-(2-acetoxy-3-aminopropyl)pyrrolidin-4 -ylthio]-6-[(1R)-1-hydroxyethyl]-1-carbapen-2-em-3-carboxylic acid, (1R,5S,6S)-2-[(2R,4S)-2-(2-acetoxy-3-aminopropyl)pyrrolidin- 4-ylthio]-6-[(1R)-1-hydroxyethyl]-1-methyl-1-carbapen-2-em-3 -carboxylic acid, (5R,6S)-2-[(2R,4S)-2-[[2-fluoro-3-(N-methylamino)]propyl]pyrrolidin-4-ylthio]-6-[(1R)-1-hydroxyethyl]-1 -carbapen-2-em-3-carboxylic acid, (1R,5S,6S)-2-[(2R,4S)-2-[[2-fluoro-3-(N-methylamino)] propyl]pyrrolidin-4-ylthio]-6-[(1R)-1-hydroxyethyl]-1-methyl- 1-carbapen-2-em-3-carboxylic acid, (5R,6S)-2-[(2S,4S)-2-[(1R)-3-(N,N-dimethyl)amino-1 -hydroxypropyl]pyrrolidin-4-ylthio]-6-[(1R)-1-hydroxyethyl]-1 -carbapen-2-em-3-carboxylic acid or (1R,5S,6S)-2-[(2S,4S)-2-[(1R)-3-(N,N-dimethyl)amino-1-hydroxypropyl]pyrrolidin -4-ylthio]-6-[(1R)-1-hydroxyethyl]-1 -methyl-1-carbapen-2-em-3-carboxylic acid.

12. The compound according to claim 1, which is (1R, 5S,6S)-2-[(2S,4S)-2-[(1R)-1-hydroxy-3 -(N-methylamino)propyl]pyrrolidin-4-ylthio]-6-[(1R)-1 -hydroxyethyl]-1-methyl-1-carbapen-2-em-3-carboxylic acid.

13. An antibacterial agent comprising an antibacterially effective amount of the compound of the formula:

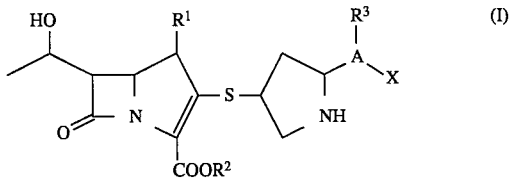

wherein $R^1$ is a hydrogen atom or a methyl group, $R^2$ is a hydrogen atom or a negative charge, $R^3$ is a hydrogen atom, a hydroxyl group, a lower alkoxy group, a lower alkanoyloxy group, an amino group, an N-lower alkylamino group, an N,N-di-lower alkylamino group, a lower alkanoylamino group, an aroylamino group, a (lower alkylsulfonyl)amino group, a sulfamoylamino group, a cyano group, a nitro group, a group of —$COOR^4$ (wherein $R^4$ is a hydrogen atom or a lower alkyl group) or a group of —$CON(R^5)R^6$ (wherein each of $R^5$ and $R^6$ which may be the same or different, is a hydrogen atom or a lower alkyl group, or $R^5$ and $R^6$ form together with the adjacent nitrogen atom a heterocyclic group selected from the group consisting of an aziridinyl group, an azetidinyl group, a pyrrolidinyl group, a piperidyl group, a piperazinyl group, a 4-lower alkyl piperazinyl group and a morpholino group), A is a linear or branched lower alkylene group, X is a group of —$N(R^7)R^8$ (wherein each of $R^7$ and $R^8$ which may be the same or different, is a hydrogen atom or a lower alkyl group) or a group of —$N^+(R^9)(R^{10})R^{11}$ (wherein each of $R^9$, $R^{10}$ and $R^{11}$ which may be the same or different, is a lower alkyl group); or a pharmaceutically acceptable salt or ester thereof, and a pharmaceutically acceptable carrier or diluent.

14. The antibacterial agent according to claim 13 which is effective against pseudomonads.

15. The antibacterial agent according to claim 13 which is effective against methicillin resistant *Staphylococcus aureus* species.

16. An antibacterial agent which comprises an antibacterially effective amount of the compound of claim 1 and a pharmaceutically acceptable carrier or diluent.

17. A method for treating disease caused by the infection bacteria which comprises administering to a subject in need of treatment an antibacterially effective amount of a compound of the formula:

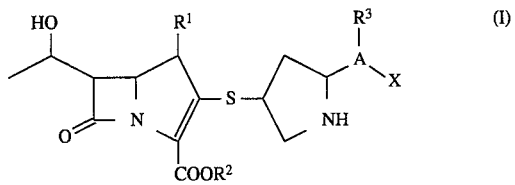

wherein $R^1$ is a hydrogen atom or a methyl group, $R^2$ is a hydrogen atom or a negative charge, $R^3$ is a halogen atom, a hydroxyl group, a lower alkoxy group, a lower alkanoyloxy group, an amino group, an N-lower alkylamino group, an N,N-di-lower alkylamino group, a lower alkanoylamino group, an aroylamino group, a (lower alkylsulfonyl)amino group, a sulfamoylamino group, a cyano group, a nitro group, a group of —$COOR^4$ (wherein $R^4$ is a hydrogen atom or a lower alkyl group) or a group of —$CON(R^5)R^6$ (wherein each of $R^5$ and $R^6$ which may be the same or different, is a hydrogen atom or a lower alkyl group, or $R^5$ and $R^6$ form together with the adjacent nitrogen atom a heterocyclic group selected from the group consisting of an aziridinyl group, an azetidinyl group, a pyrrolidinyl group, a piperidyl group, a piperazinyl group, a 4-lower alkyl piperazinyl group and a morpholino group), A is a linear or branched lower alkylene group, X is a group of —$N(R^7)R^8$ (wherein each of $R^7$ and $R^8$ which may be the same or different, is a hydrogen atom or a lower alkyl group) or a group of —$N^+(R^9)(R^{10})R^{11}$ (wherein each of $R^9$, $R^{10}$ and $R^{11}$ which may be the same or different, is a lower alkyl group); or a pharmaceutically acceptable salt or ester thereof.

18. The method according to claim 17, wherein the compound is used against pseudomonads.

19. The method according to claim 17, wherein the compound is used against methicillin resistant *Staphylococcus aureus* species.

20. The method according to claim 14, which comprises administering to the subject in need of treatment an antibacterially effective amount of the compound according to claim 1.

21. The compound of claim 1, wherein $R^3$ is a hydroxyl group, $R^7$ is a hydrogen atom and $R^8$ is a lower alkyl group.

* * * * *